United States Patent
Dragovich et al.

(10) Patent No.: US 11,576,979 B2
(45) Date of Patent: Feb. 14, 2023

(54) PYRROLOBENZODIAZEPINE PRODRUGS AND ANTIBODY CONJUGATES THEREOF

(71) Applicant: GENENTECH, INC., South San Francisco, CA (US)

(72) Inventors: Peter Dragovich, South San Francisco, CA (US); Zhonghua Pei, South San Francisco, CA (US); Thomas Pillow, South San Francisco, CA (US); Jack Sadowsky, South San Francisco, CA (US); Vishal Verma, South San Francisco, CA (US); Donglu Zhang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 473 days.

(21) Appl. No.: 16/689,286

(22) Filed: Nov. 20, 2019

(65) Prior Publication Data

US 2020/0085965 A1    Mar. 19, 2020

Related U.S. Application Data

(60) Division of application No. 16/271,549, filed on Feb. 8, 2019, now Pat. No. 10,532,108, which is a (Continued)

(51) Int. Cl.
*A61K 47/68* (2017.01)
*A61P 35/00* (2006.01)
*A61K 31/5517* (2006.01)

(52) U.S. Cl.
CPC ...... *A61K 47/6803* (2017.08); *A61K 31/5517* (2013.01); *A61K 47/6849* (2017.08); (Continued)

(58) Field of Classification Search
None
See application file for complete search history.

(56) References Cited

U.S. PATENT DOCUMENTS

2019/0175749 A1    6/2019    Dragovich et al.

FOREIGN PATENT DOCUMENTS

WO      2013055987    *    4/2013
WO      2014057113 A1      4/2014
(Continued)

OTHER PUBLICATIONS

Dragovich, P., et al., "Design, synthesis, and biological evaluation of pyrrolobenzodiazepinecontaining hypoxia-activated prodrugs", Bioorganic & Medicinal Chemistry Letters 27, 5300-5304 (2017).
(Continued)

*Primary Examiner* — Karl J Puttlitz
(74) *Attorney, Agent, or Firm* — Viksnins Harris Padys Malen LLP

(57) ABSTRACT

The invention relates generally to pyrrolobenzodiazepine monomer and dimer prodrugs having a glutathione-activated disulfide prodrug moiety, a DT-diaphorase-activated quinone prodrug moiety or a reactive oxygen species-activated aryl boronic acid or aryl boronic ester prodrug moiety. The invention further relates to pyrrolobenzodiazepine prodrug dimer-antibody conjugates.

10 Claims, 29 Drawing Sheets

| | Compound | IC50 potency (nM) |
|---|---|---|
| ----- | PBD monomer control 1 | 330.11 |
| --- — | PBD monomer disulfide prodrug 1 | 323.84 |
| —— | PBD monomer disulfide prodrug 3 | 356.69 |
| — · — | PBD monomer disulfide prodrug 2 | 497.33 |
| ----- | PBD monomer disulfide prodrug 4 | >10000 |

Related U.S. Application Data continuation of application No. PCT/US2017/046102, filed on Aug. 9, 2017.

(60) Provisional application No. 62/373,740, filed on Aug. 11, 2016.

(52) U.S. Cl.
CPC ...... *A61K 47/6851* (2017.08); *A61K 47/6889* (2017.08); *A61P 35/00* (2018.01)

(56) References Cited

FOREIGN PATENT DOCUMENTS

| | | | |
|---|---|---|---|
| WO | 2015052322 A1 | 4/2015 |
| WO | 2015052532 A1 | 4/2015 |
| WO | 2015052533 A1 | 4/2015 |
| WO | 2015052534 A1 | 4/2015 |
| WO | 2015052535 A1 | 4/2015 |
| WO | 2015089344 A1 | 6/2015 |
| WO | 2015155345 A1 | 10/2015 |
| WO | 2015159076 A1 | 10/2015 |
| WO | 2015179658 A2 | 11/2015 |
| WO | 2016040723 A1 | 3/2016 |
| WO | 2016044560 A1 | 3/2016 |
| WO | 2017059289 A1 | 4/2017 |
| WO | 2017064675 A1 | 4/2017 |
| WO | 2017137555 A1 | 8/2017 |
| WO | 2017172930 A1 | 10/2017 |

OTHER PUBLICATIONS

Kamal, A., et al., "Pyrrolo[2,1-c][1,4]benzodiazepine-β-glucuronide prodrugs with a potential for selective therapy of solid tumors by PMT and ADEPT strategies", Bioorganic & Medicinal Chemistry Letters 18(13), 3769-3773 (2008).

Patent Cooperation Treaty, International Searching Authority, Search Report and Written Opinion for PCT/US2017/046102, 24 pages, dated Jan. 4, 2018.

Pei, Z., et al., "Exploration of Pyrrolobenzodiazepine (PBD)-Dimers Containing Disulfide-Based Prodrugs as Payloads for Antibody-Drug Conjugates", Mol Pharmaceutics 15, 3979-3996 (2018).

Pillow, T., et al., "Decoupling stability and release in disulfide bonds with antibody-small molecule conjugates", Chem Sci 8, 366-370 (2017).

Pillow, T., et al., "Modulating Therapeutic Activity and Toxicity of Pyrrolobenzodiazepine Antibody-Drug Conjugates with Self-Immolative Disulfide Linkers", Mol Cancer Ther 16(5), 871-878 (2017).

Sadowsky, J., et al., "Development of Efficient Chemistry to Generate Site-Specific Disulfide-Linked Protein- and Peptide-Payload Conjugates: Application to THIOMAB Antibody-Drug Conjugates", Bioconjugate Chem 28, 2086-2098 (2017).

Sagnou, M., et al., "Design and synthesis of novel pyrrolobenzodiazepine (PBD) prodrugs for ADEPT and GDEPT", Bioorganic & Medicinal Chemistry Letters 10(18), 2083-2086 (2000).

Su, D., et al., "Modulating Antibody-Drug Conjugate Payload Metabolism by Conjugation Site and Linker Modification", Bioconjugate Chem 29, 1155-1167 (2018).

Zhang, D., et al., "Chemical Structure and Concentration of Intratumor Catabolites Determine Efficacy of Antibody Drug Conjugates", Drug Metabolism and Disposition 44(9), 1517-1523 (2016).

Zhang, D., et al., "Intratumoral Payload Concentration Correlates with the Activity of Antibody-Drug Conjugates", Mol Cancer Ther 17(3), 677-685 (2018).

Zhang, D., et al., "Linker Immolation Determines Cell Killing Activity of Disulfide-Linked Pyrrolobenzodiazepine Antibody-Drug Conjugates", ACS Med Chem Lett 7, 988-993 (2016).

* cited by examiner

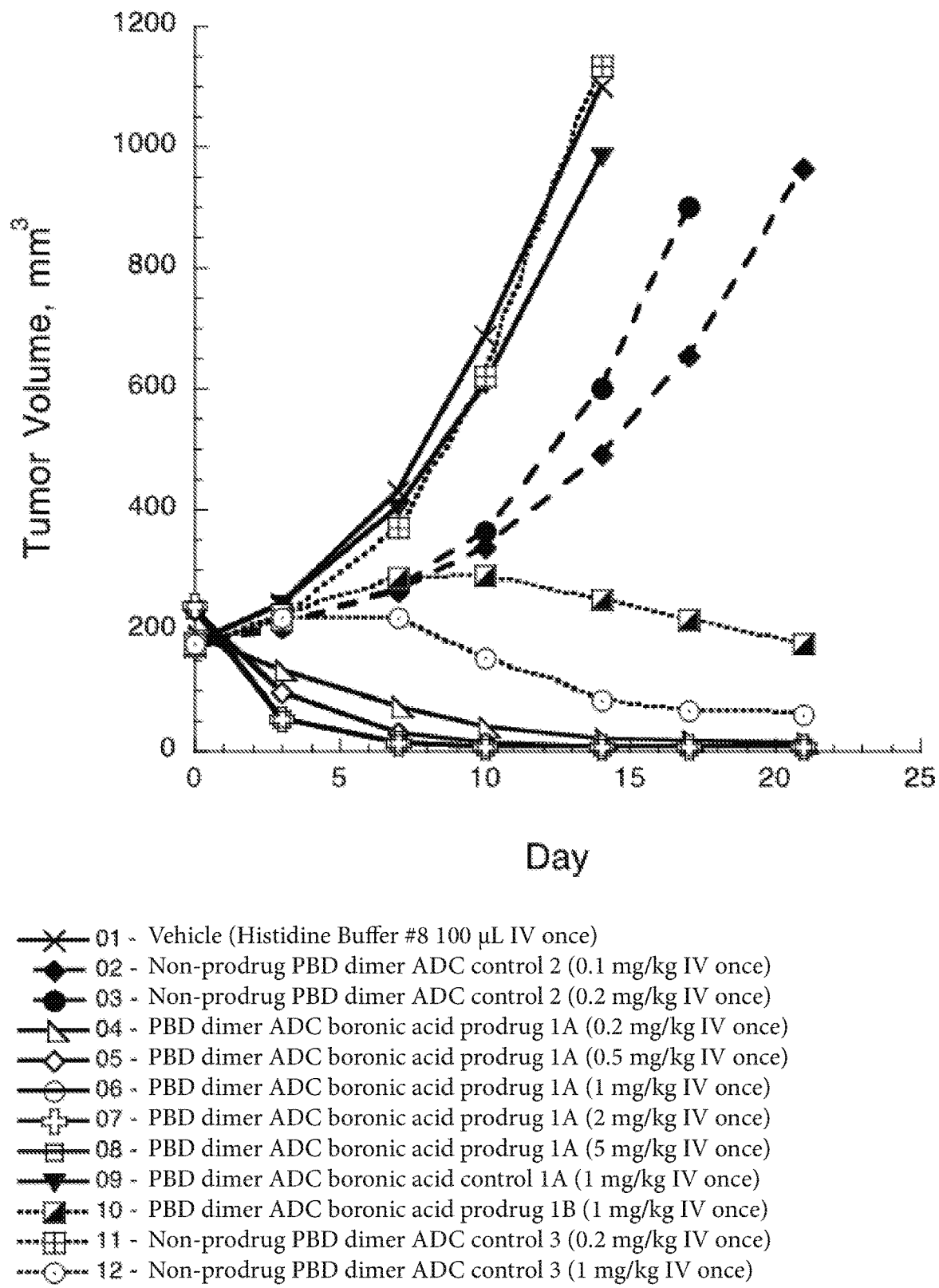

- 01 - Vehicle (Histidine Buffer #8 100 μL IV once)
- 02 - Non-prodrug PBD dimer ADC control 2 (0.1 mg/kg IV once)
- 03 - Non-prodrug PBD dimer ADC control 2 (0.2 mg/kg IV once)
- 04 - PBD dimer ADC boronic acid prodrug 1A (0.2 mg/kg IV once)
- 05 - PBD dimer ADC boronic acid prodrug 1A (0.5 mg/kg IV once)
- 06 - PBD dimer ADC boronic acid prodrug 1A (1 mg/kg IV once)
- 07 - PBD dimer ADC boronic acid prodrug 1A (2 mg/kg IV once)
- 08 - PBD dimer ADC boronic acid prodrug 1A (5 mg/kg IV once)
- 09 - PBD dimer ADC boronic acid control 1A (1 mg/kg IV once)
- 10 - PBD dimer ADC boronic acid prodrug 1B (1 mg/kg IV once)
- 11 - Non-prodrug PBD dimer ADC control 3 (0.2 mg/kg IV once)
- 12 - Non-prodrug PBD dimer ADC control 3 (1 mg/kg IV once)

FIG. 23

PYRROLOBENZODIAZEPINE PRODRUGS AND ANTIBODY CONJUGATES THEREOF

CROSS-REFERENCE TO RELATED APPLICATION

This divisional application claims the benefit of priority of U.S. application Ser. No. 16/271,549 filed 8 Feb. 2019 which is a continuation of International Application No. PCT/US2017/046102 filed Aug. 9, 2017, and claims priority benefit of U.S. Provisional Application Ser. No. 62/373,740 filed on Aug. 11, 2016, each of which are incorporated by reference herein and in their entirety.

FIELD OF THE DISCLOSURE

The field of the disclosure relates generally to pyrrolobenzodiazepine prodrugs having a disulfide trigger, a cyclic dione trigger, or an aryl boronic acid or aryl boronic ester trigger, and antibody conjugates thereof.

BACKGROUND

Pyrrolobenzodiazepines (PBD) and dimers thereof are known to interact with DNA and are effective cancer chemotherapy agents. Problematically, side effects associated with some PBDs, such as cardiotoxicity and acute tissue necrosis have limited use, dosage and effectiveness.

Conjugates comprising a selective carrier-linker-PBD structure (e.g., an antibody-PBD conjugate (ADC)), are attractive selective chemo-therapeutic molecules, as they combine ideal properties of selectivity to a target cell and cytotoxic drugs. By directing potent cytotoxic drugs to a target cell, the desired therapeutic effect may be improved in the target cell while minimizing the effect on non-targeted cells. Examples of such improvements include reduced dose required to achieve a therapeutic effect, targeted delivery, and improved bloodstream stability. Nonetheless, PBD ADCs may still present adverse side effects that limit use and/or dosage.

A need therefore exists for PBD compounds and formulations that provided for reduced toxicity and improved bioefficacy.

SUMMARY

In some embodiments, a PBD prodrug dimer-antibody conjugate composition of formula (I) comprising a first PBD prodrug monomer M1 and a second PBD-antibody monomer M2 is provided:

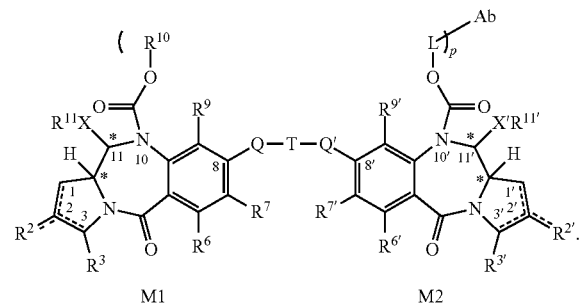

(I)

M1 is a PBD monomer. $R^2$ is selected from —H, =$CH_2$, —CN, —R, =CH—R, aryl, heteroaryl, bicyclic ring and heterobicyclic ring. $R^3$ is H. $R^6$, $R^7$ and $R^9$ are independently selected from H, R, OH, OR, halo, amino, nitro, SH and SR. X is selected from S, O and NH. $R^{10}$ is a prodrug moiety comprising (i) a glutathione-activated disulfide, (ii) a DT-diaphorase-activated quinone, or (iii) a reactive oxygen species-activated aryl boronic acid or aryl boronic ester. $R^{11}$ is selected from (i) H and R when X is O or NH, and (ii) H, R and $O_zU$ when X is S, wherein z is 2 or 3 and U is a monovalent pharmaceutically acceptable cation. R is selected from a lower alkyl group having 1 to 10 carbon atoms and an arylalkyl group of up to 12 carbon atoms, (i) wherein the alkyl group optionally contains one or more carbon-carbon double or triple bonds, or an arylalkyl, of up to 12 carbon atoms and (ii) wherein R is optionally substituted by one or more halo, hydroxy, amino, or nitro groups, and optionally contains one or more hetero atoms. M1 contains an optional double bond, as indicated by the dashed line, between one of: (i) $C_1$ and $C_2$; (ii) $C_2$ and $C_3$; and (iii) $C_2$ and $R^2$.

M2 is a PBD monomer. $R^{2'}$, $R^{3'}$, $R^{6'}$, $R^{7'}$, $R^{9'}$, $R^{11'}$ and X' correspond to, and are defined in the same way as, $R^2$, $R^3$, $R^6$, $R^7$, $R^9$, $R^{11}$ and X, respectively. L is a self-immolative linker comprising a disulfide moiety, a peptide moiety or a peptidomimetic moiety. M2 contains an optional double bond, as indicated by the dashed line, between one of: (i) $C_{1'}$ and $C_{2'}$; (ii) $C_{2'}$ and $C_{3'}$; and (iii) $C_{2'}$ and $R^{2'}$.

M1 and M2 are bound at the C8 position by a moiety -Q-T-Q'-, wherein Q and Q' are independently selected from O, NH and S, and wherein T is an optionally substituted $C_{1-12}$ alkylene group that is further optionally interrupted by one or more heteroatoms and/or aromatic rings. Ab is an antibody, and p is an integer having a value of 1, 2, 3, 4, 5, 6, 7 or 8, and represents the number of PBD prodrug dimers that may be conjugated or bound to the antibody. Each asterisk independently represents a chiral center of racemic or undefined stereochemistry.

In some other embodiments, a PBD monomer prodrug composition of formula (II) is provided.

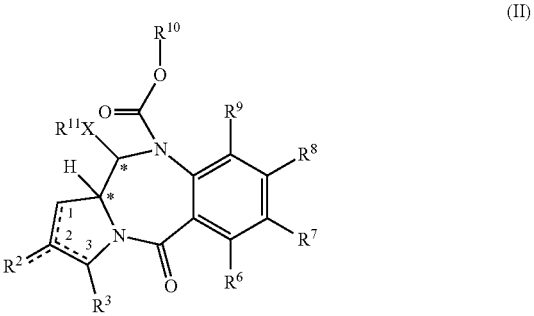

(II)

$R^2$ is selected from —H, =$CH_2$, —CN, —R, =CH—R, aryl, heteroaryl, bicyclic ring and heterobicyclic ring. $R^3$ is H. $R^6$, $R^7$, $R^8$ and $R^9$ are independently selected from H, R, OH, OR, halo, amino, nitro, SH and SR, or $R^7$ and $R^8$ together with the carbon atoms to which they are bound form a group —O—$(CH_2)_n$—O—, where n is 1 or 2. X is selected from S, O and NH. $R^{10}$ is a prodrug moiety comprising a (i) glutathione-activated disulfide, (ii) a DT-diaphorase-activated quinone or (iii) a reactive oxygen species-activated aryl boronic acid or aryl boronic ester. $R^{11}$ is selected from (i) H and R when X is O or NH, and (ii) H, R and $O_zU$ when X is S, wherein z is 2 or 3 and U is a monovalent pharmaceutically acceptable cation. R is selected from a lower alkyl group having 1 to 10 carbon atoms and an arylalkyl group of up to 12 carbon atoms, (i) wherein the alkyl group optionally contains one or more carbon-carbon double or triple bonds, or an aryl group, of up to 12 carbon atoms and (ii) wherein R is optionally substituted by one or more halo, hydroxy, amino, or nitro groups, and optionally contains one or more hetero atoms. The PBD monomer prodrug contains an optional double bond, as indicated by the dashed line, between one of: (i) $C_1$ and $C_2$; (ii) $C_2$ and $C_3$; and (iii) $C_2$ and $R^2$. Each asterisk independently represents a chiral center of racemic or undefined stereochemistry.

In some other embodiments, a PBD prodrug dimer compound of formula (VIII) comprising a first PBD prodrug monomer M1 and a second PBD monomer M2 is provided:

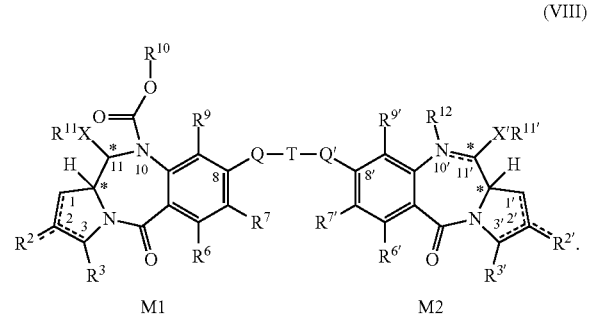

(VIII)

M1 is a PBD monomer. $R^2$ is selected from —H, =$CH_2$, —CN, —R, =CH—R, aryl, heteroaryl, bicyclic ring and heterobicyclic ring. $R^3$ is H. $R^6$, $R^7$ and $R^9$ are independently selected from H, R, OH, OR, halo, amino, nitro, SH and SR. X is selected from S, O and NH. $R^{10}$ is a prodrug moiety comprising (i) a glutathione-activated disulfide, (ii) a DT-diaphorase-activated quinone or (iii) a reactive oxygen species-activated aryl boronic acid or aryl boronic ester. $R^{11}$ is selected from (i) H and R when X is O or NH, and (ii) H, R and $O_zU$ when X is S, wherein z is 2 or 3 and U is a monovalent pharmaceutically acceptable cation. R is selected from a lower alkyl group having 1 to 10 carbon atoms and an arylalkyl group of up to 12 carbon atoms, (i) wherein the alkyl group optionally contains one or more carbon-carbon double or triple bonds, or an aryl group, of up to 12 carbon atoms and (ii) wherein R is optionally substituted by one or more halo, hydroxy, amino, or nitro groups, and optionally contains one or more hetero atoms. M1 contains an optional double bond, as indicated by the dashed line, between one of: (i) $C_1$ and $C_2$; (ii) $C_2$ and $C_3$; and (iii) $C_2$ and $R^2$.

M2 is a PBD monomer. $R^{2'}$, $R^{3'}$, $R^{6'}$, $R^{7'}$, $R^{9'}$, $R^{11'}$ and X' correspond to $R^2$, $R^3$, $R^6$, $R^7$, $R^9$, $R^{11}$ and X, respectively. M2 contains an optional double bond, as indicated by the dashed line, between one of: (i) $C_{1'}$ and $C_{2'}$; (ii) $C_{2'}$ and $C_{3'}$; and (iii) $C_{2'}$ and $R^{2'}$. $R^{12}$ is absent when the bond between N10' and C11' is a double bond, or is selected from —C(O)O-L and —C(O)O—$R^{10}$.

L is a self-immolative linker comprising at least one of a disulfide moiety, a peptide moiety and a peptidomimetic moiety. M1 and M2 are bound at the C8 position by a moiety -Q-T-Q'-, wherein Q and Q' are independently selected from O, NH and S, and wherein T is an optionally substituted $C_{1-12}$ alkylene group that is further optionally interrupted by one or more heteroatoms and/or aromatic rings.

Each asterisk independently represents a chiral center of racemic or undefined stereochemistry.

In some other embodiments, a pharmaceutical composition comprising the PBD prodrug dimer-antibody conjugate compound previously described and a pharmaceutically acceptable diluent, antibody or excipient is provided.

In some other embodiments, a method of treating cancer comprising administering to a patient a pharmaceutical composition as previously described is provided.

In other embodiments, a use of an antibody-drug conjugate compound as previously described in the manufacture of a medicament for the treatment of cancer in a mammal is provided.

In still other embodiments, an antibody-drug conjugate compound as previously described for use in a method for treating cancer is provided.

In other embodiments, an article of manufacture comprising a pharmaceutical composition as previously described, a container, and a package insert or label indicating that the pharmaceutical composition can be used to treat cancer is provided.

BRIEF DESCRIPTION OF THE DRAWINGS

FIG. 17 further depicts a table of PBD dimer diaphorase prodrug and control IC$_{50}$ potency and IC$_{50}$ ratio against the KPL-4 cells. The IC$_{50}$ ratio is based on the prodrug IC$_{50}$ value relative to the PBD dimer control.

FIG. 18 further depicts a table of PBD dimer diaphorase prodrug and control IC$_{50}$ potency and IC$_{50}$ ratio against the KPL-4 cells. The IC$_{50}$ ratio is based on the prodrug IC$_{50}$ value relative to the PBD dimer control.

FIG. 19 further depicts a table of PBD dimer diaphorase prodrug and control IC$_{50}$ potency and IC$_{50}$ ratio against the KPL-4 cells. The IC$_{50}$ ratio is based on the prodrug IC$_{50}$ value relative to the PBD dimer control.

FIG. 20 further depicts a table of PBD dimer diaphorase prodrug and control IC$_{50}$ potency and IC$_{50}$ ratio against the WSU cells. The IC$_{50}$ ratio is based on the prodrug IC$_{50}$ value relative to the PBD dimer control.

FIG. 23 depicts a plot of tumor volume (mm³) versus days after treatment for SCID mice with BJAB-luc human Burkitt's lymphoma with: (i) histidine buffer vehicle; (ii) non-prodrug anti-CD22 HC-A118C PBD dimer ADC; (iii) anti-CD22 LC-K149C PDB dimer boronic acid prodrug ADC; (iv) anti-Ly6E LC-K149C PDB dimer boronic acid prodrug ADC; (v) non-prodrug anti-CD22 LC-K149C PDB dimer ADC; and (vi) non-prodrug anti-Her2 HC-A118C PBD dimer ADC.

DETAILED DESCRIPTION OF EXEMPLARY EMBODIMENTS

Figure 1:
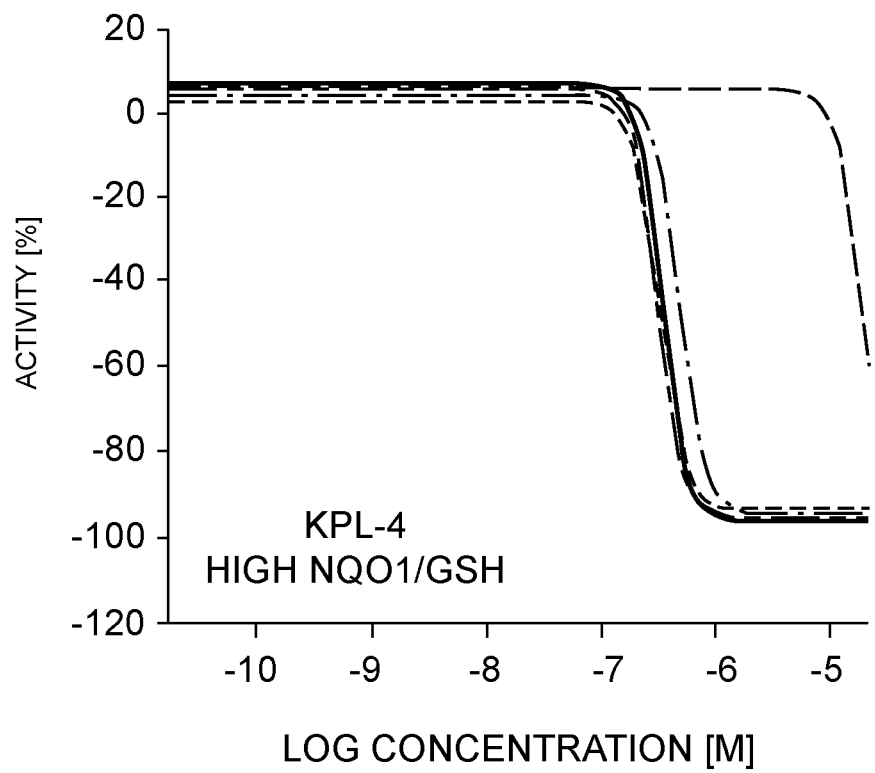
FIG. 1 depicts a plot of PBD monomer disulfide prodrug Activity [%] against KPL-4 cells versus the log of prodrug concentration in moles per liter and further depicts a table of PBD monomer $IC_{50}$ potency against the KPL-4 cells.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

In some embodiments, the present disclosure is generally directed to PBD monomer prodrug compounds of formula (II):

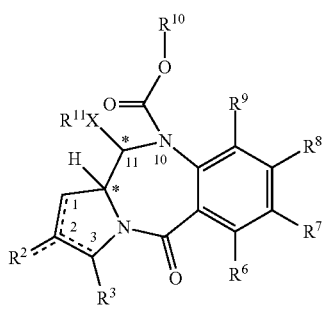

(II)

where $R^2$, $R^3$, $R^6$, $R^7$, $R^8$, $R^9$, X, $R^{10}$, $R^{11}$ and * are defined in more detail elsewhere herein.

In some embodiments, the present disclosure is directed to PBD dimer prodrug compounds comprising a first PBD monomer having $R^{10}$ at the N10 position. The dimer additionally comprises a second PBD monomer having at the N10 position: (1) no substitution; (2) $R^{10}$; or (3) a linker. The PBD dimer is generally one of the following two structures:

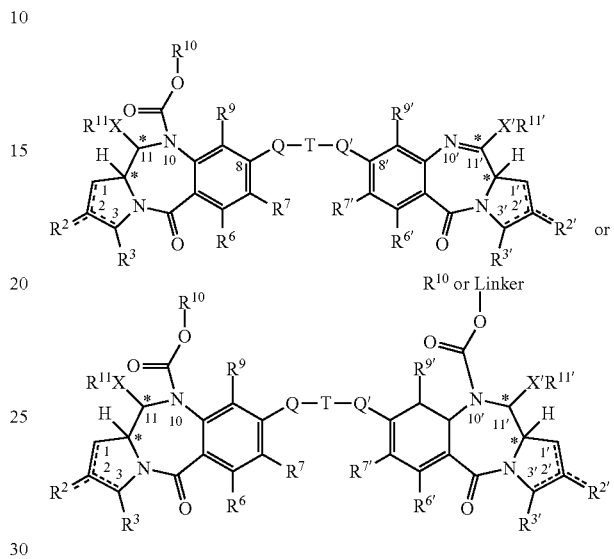

where $R^2$, $R^{2'}$, $R^3$, $R^{3'}$, $R^6$, $R^{6'}$, $R^7$, $R^{7'}$, $R^9$, $R^{9'}$, X, $R^{10}$, $R^{11}$, $R^{11'}$, Q, Q', T, *, and the linker are defined in more detail elsewhere herein.

In some embodiments, the present disclosure is directed to PBD dimer prodrug compounds comprising a first PBD monomer having at the N10 position: (i) a protecting group comprising a GSH-activated disulfide trigger, (ii) a protecting group comprising a DTD-activated quinone trigger, or (iii) a protecting group comprising a ROS-activated aryl boronic acid or aryl boronic ester trigger. The dimer additionally comprises a second PBD monomer having a linker conjugated to an antibody sulfhydryl moiety at the N10 position. The PBD dimer is as generally follows:

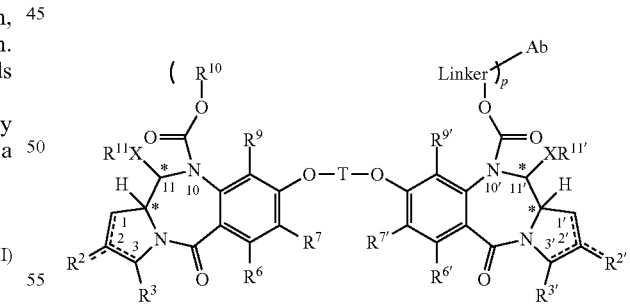

where $R^2$, $R^{2'}$, $R^3$, $R^{3'}$, $R^6$, $R^{6'}$, $R^7$, $R^{7'}$, $R^9$, $R^{9'}$, X, $R^{10}$, $R^{11}$, $R^{11'}$, T, *, the linker, the antibody, and p are defined in more detail elsewhere herein.

I. Definitions

Unless defined otherwise, technical and scientific terms used herein have the same meaning as commonly understood by one of ordinary skill in the art to which this disclosure belongs, and are consistent with: Singleton et al. (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

A "prodrug" as defined herein is a PBD substituted at the N10 position with a protecting group comprising a trigger, wherein the protecting group masks drug toxicity. The protecting group is enzymatically or chemically activated (cleaved) to generate the active drug by the application of stimulus to the trigger, such as an enzyme (e.g., DTD), ROS or GSH. In some embodiments the trigger is a disulfide, a cyclic dione (e.g., a quinone), or an aryl boronic acid or an aryl boronic ester.

A "protecting group" as defined herein refers to a moiety introduced into a drug molecule by chemical modification of a functional group that blocks or protects a particular functionality.

"DTD" refers to DT-diaphorase; "ROS" refers to a reactive oxygen species; and "GSH" refers to glutathione.

A "linker" (L) is a bifunctional or multifunctional moiety that can be used to link one or more drug moieties (D) to an antibody (Ab) to form an antibody-linker-drug conjugate of the general formula:

Antibody-[L-D]$_p$ wherein p may be 1, 2, 3, 4, 5, 6, 7 or 8. The linker generally comprises a connection to the antibody (Ab), an optional antibody spacer unit, an optional trigger unit to provide for immolation, an optional drug (D) spacer unit, and a connection to the drug, and is of the general structure:

Ab-[Ab connection]-[Ab spacer]$_{opt}$-[Trigger]$_{opt}$-[D spacer]$_{opt}$-[D connection]-D.

In some embodiments, antibody-D conjugates can be prepared using a linker having reactive functionalities for covalently attaching to the drug and to the antibody. For example, in some embodiments, the cysteine thiol of a cysteine-engineered antibody (Ab) can form a bond with a reactive functional group of a linker or a drug-linker intermediate to make an ADC. In one embodiment, a linker has a functionality that is capable of reacting with a free cysteine present on an antibody to form a covalent disulfide bond (See, e.g., the conjugation method at page 766 of Klussman, et al (2004), *Bioconjugate Chemistry* 15(4):765-773, and the Examples herein, incorporated herein by reference in its entirety). In some embodiments, the linker may comprise a cleavable immolative moiety such as a peptide, peptidomimetic or disulfide trigger. A linker may optionally comprise one or more "spacer" units between an immolative moiety and the drug moiety (such asp-amino-benzyl ("PAB")) and/or between an immolative moiety and the antibody (such as a moiety derived from caproic acid). Non-limiting examples of spacers include valine-citrulline ("val-cit" or "vc"), alanine-phenylalanine ("ala-phe"), and p-aminobenzyloxycarbonyl (a "PABC"). In some embodiments the spacer may be immolating.

"Immolating" and "immolative" refer to a moiety, such as a linker, spacer and/or prodrug trigger, that is cleavable in vivo and/or in vitro such as by an enzyme (e.g. a protease or DTD), GSH, a ROS, and/or pH change. Examples of immolative moieties include disulfides, peptides, and peptidomimetics.

"Peptide" refers to short chains of two or more amino acid monomers linked by amide (peptide) bonds. The amino acid monomers may be naturally occurring and/or non-naturally occurring amino acid analogs.

"Peptidomimetic" refers to a group or moiety that has a structure that is different from the general chemical structure of an amino acid or peptide, but functions in a manner similar to a naturally occurring amino acid or peptide.

"Hindered linker" refers to a linker having a carbon atom bearing a sulfur capable of forming a disulfide bond wherein the carbon atom is substituted with at least one substituent other than H, and more particularly is substituted with a hydrocarbyl or a substituted hydrocarbyl moiety as further detailed herein below.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

"Cell Targeting Moiety" refers to an antibody having binding affinity for a target expressing an antigen.

"Predominantly Comprises" refers to at least 50%, at least 75%, at least 90%, at least 95% or at least 99% of a referenced component on a recited basis, such as for instance and without limitation, w/w %, v/v %, w/v %, mole % or equivalent % basis. "Consisting essentially of" generally limits a feature, compound, composition or method to the recited elements and/or steps, but does not exclude the possibility of additional elements and/or steps that do not materially affect the function, compound, composition and/or characteristics of the recited feature, compound, composition or method.

The terms "antibody" and "Ab" herein are used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al. (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one embodiment, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) Nature, 352:624-628; Marks et al. (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267: 7246-7256; US 2005/0048572; US 2004/0229310).

A "cysteine engineered antibody" or "cysteine engineered antibody variant" is an antibody in which one or more residues of an antibody are substituted with cysteine residues. In accordance with the present disclosure, the thiol group(s) of the cysteine engineered antibodies can be conjugated to prodrugs of the disclosure to form a THIOMAB™ ADC (i.e., a THIOMAB™ drug conjugate (TDC)). In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. For example, a THIOMAB™ antibody may be an antibody with a single mutation of a non-cysteine native residue to a cysteine in the light chain (e.g., G64C, K149C or R142C according to Kabat numbering) or in the heavy chain (e.g., D101C or V184C or T205C according to Kabat numbering). In specific examples, a THIOMAB™ antibody has a single cysteine mutation in either the heavy or light chain such that each full-length antibody (i.e., an antibody with two heavy chains and two light chains) has two engineered cysteine residues. Cysteine engineered antibodies and preparatory methods are disclosed by US 2012/0121615 A1 (incorporated by reference herein in its entirety).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds. In some embodiments, the particular site on an antigen molecule to which an antibody binds is determined by hydroxyl radical footprinting.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "leaving group," as used herein, refers to a moiety that leaves in the course of a chemical reaction involving the groups as described herein.

The term "hydrocarbyl" as used herein describes organic compounds or radicals consisting exclusively of the elements carbon and hydrogen. These moieties include, without limitation, alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms, 1 to 10 carbon atoms or 1 to 6 carbon atoms.

The term "alkyl", as used herein, by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Unless otherwise indicated, the alkyl groups described herein are preferably lower alkyl containing from one to ten or one to eight carbon atoms in the principal chain. They may be straight or branched chain or cyclic including, but not limited to, methyl, ethyl, propyl, isopropyl, allyl, benzyl, hexyl and the like. The alkyl moieties may optionally comprise one or more hetero atoms selected from O, S and N and are referred to as "heteroalkyl".

The terms "carbocycle", "carbocyclyl", "carbocyclic ring" and "cycloalkyl" refer to a monovalent non-aromatic, saturated or partially unsaturated ring having 3 to 12 carbon atoms ($C_{3-12}$) as a monocyclic ring or 7 to 12 carbon atoms as a bicyclic ring. Bicyclic carbocycles having 7 to 12 atoms can be arranged, e.g., as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The carbocycle and cycloalkyl moieties may optionally comprise one or more hetero atoms selected from O, S and N.

The term "alkoxy" refers to those alkyl groups attached to the remainder of the molecule via an oxygen atom. The alkoxy moieties may optionally comprise one or more hetero atoms selected from O, S and N and are referred to as "heteroalkoxy".

The term "alkylene" by itself or as part of another substituent means a divalent radical derived from an alkane, such as —$CH_2CH_2CH_2CH_2CH_2$—.

Unless otherwise indicated, the alkynyl groups described herein are preferably lower alkynyl containing from two to eight carbon atoms in the principal chain and up to 20 carbon atoms. They may be straight or branched chain including, but not limited to, ethynyl, propynyl, butynyl, isobutynyl, hexynyl, and the like.

The term "aryl" as used herein alone or as part of another group denotes optionally substituted homocyclic aromatic groups, preferably monocyclic or bicyclic groups containing from 5 to 20 carbons, from 5 to 10 carbons, or from 5 to 6 carbons in the ring portion, including, but not limited to, phenyl, biphenyl, naphthyl, substituted phenyl, substituted biphenyl or substituted naphthyl. The aryl moieties may optionally comprise one or more hetero atoms selected from O, S and N and are referred to as "heteroaryl" or "heterobicyclic". Such heteroaromatics may comprise 1 or 2 nitrogen atoms, 1 or 2 sulfur atoms, 1 or 2 oxygen atoms, and combinations thereof, in the ring, wherein the each hetero atom is bonded to the remainder of the molecule through a carbon. Non limiting exemplary groups include pyridine, pyrazine, pyrimidine, pyrazole, pyrrole, imidazole, thiopene, thiopyrrilium, parathiazine, indole, purine, benzimidazole, quinolone, phenothiazine. Non-limiting exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The term "arylalkyl" as used herein refers to an aryl moiety substituted with at least one alkyl, and optionally further substituted. One example of arylalkyl is phenylmethyl, also referred to as benzyl ($C_6H_5CH_3$) or benzylene (—$C_6H_4CH_2$—).

The "substituted" moieties described herein are moieties such as hydrocarbyl, alkyl, heteroaryl, bicyclic and heterobicyclic which are substituted with at least one atom other than carbon, including moieties in which a carbon chain atom is substituted with a hetero atom such as nitrogen, oxygen, silicon, phosphorous, boron, sulfur, or a halogen atom. These substituents include, but are not limited to, halogen, heterocyclo, alkoxy, alkenoxy, alkynoxy, aryloxy, hydroxy, keto, acyl, acyloxy, nitro, tertiary amino, amido, nitro, cyano, thio, sulfinate, sulfonamide, ketals, acetals, esters and ethers.

The terms "halogen" and "halo" as used herein alone or as part of another group refer to chlorine, bromine, fluorine, and iodine.

The term "cyclic dione" refers to cyclic and heterocyclic compounds having an even number of —C(O)— groups. In some embodiments, the cyclic compounds are aryl (quinones). In some embodiments, the heterocyclic compounds heteroaryl. A non-exclusive listing of cyclic diones includes naphthoquinone and indole dione.

The term "pharmaceutically acceptable cation", denoted as U, refers to a monovalent cation. Examples of pharmaceutically acceptable monovalent cations are discussed in Berge, et al., J Pharm. Sci., 66, 1-19 (1977), which is incorporated herein by reference. In some aspects, the pharmaceutically acceptable cation is inorganic, including but not limited to, alkali metal ions (e.g., sodium or potassium ions) and ammonia. For instance, in some aspects, the moiety $SO_zU$ may be $SO_3Na$, $SO_3K$ or $SO_3NH_4$.

Certain compounds of the present disclosure may possess asymmetric carbon atoms (optical centers) or double bonds. Such compounds have the same molecular formula but differ in the nature or sequence of bonding of their atoms or the arrangement of their atoms in space, and are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer. The compounds of the present disclosure encompass racemates, diastereomers, geometric isomers, regioisomers and individual isomers thereof (e.g., separate enantiomers), and all are intended to be encompassed within the scope of the present disclosure.

II. Prodrug Monomers, Dimers and Conjugates

In some embodiments, the drug is a PBD monomer or a PBD dimer. In some embodiments, PDB dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466). Each reference cited in this paragraph is incorporated by reference herein in its entirety.

PBD monomers and PBD dimers within the scope of the present disclosure are known. See, for instance, US 2010/0203007, WO 2009/016516, US 2009/304710, US 2010/047257, US 2009/036431, US 2011/0256157, WO 2011/130598), WO 00/12507, WO 2005/085250 and WO 2005/023814, each of which is incorporated by reference herein in its entirety. PBD dimers within the scope of the present disclosure are formed from two PBD monomers linked at the C8 carbon atom of each PBD monomer.

A. Conjugates

In some embodiments, PBD prodrug dimer-antibody conjugates are of formula (I) comprising a first PBD prodrug monomer M1 and a second PBD-antibody monomer M2:

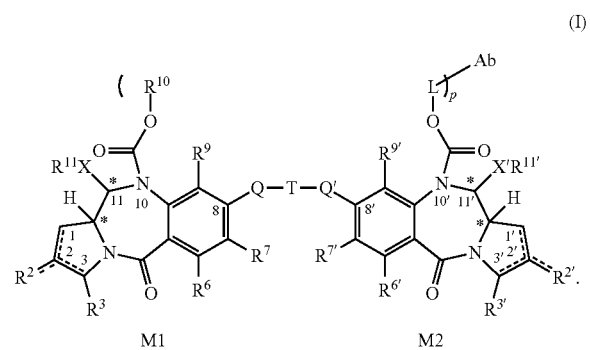

M1 is a PBD monomer wherein the dashed lines represent an optional double bond between one of: (i) $C_1$ and $C_2$; (ii) $C_2$ and $C_3$; and (iii) $C_2$ and $R^2$. In some embodiments, the bond between $C_1$ and $C_2$ is a single bond, the bond between $C_2$ and $C_3$ is a single bond, and the bond between $C_2$ and $R^2$ is a double bond.

$R^2$ is selected from —H, =$CH_2$, —CN, —R, =CHR, aryl, heteroaryl, bicyclic ring and heterobicyclic ring. In some embodiments, $R^2$ is =$CH_2$,

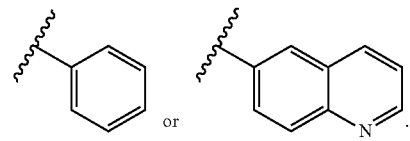 [SMILES: *c1ccccc1 ; *c1ccc2ncccc2c1]

$R^3$ is hydrogen; X is selected from S, O, and NH; and $R^{11}$ is selected from (i) H and R when X is O or NH, and (ii) H, R and $O_zU$ when X is S, wherein z is 2 or 3 and U is a monovalent pharmaceutically acceptable cation.

$R^6$, $R^7$ and $R^9$ are independently selected from H, R, OH, OR, halo, amino, nitro, SH and SR. In some embodiments, $R^6$ and $R^9$ are H. In some embodiments, $R^7$ is $OCH_3$.

$R^{10}$ is a prodrug moiety, described in more detail elsewhere herein, comprising (i) a glutathione-activated disulfide, (ii) a DT-diaphorase-activated quinone or (iii) a reactive oxygen species-activated aryl boronic acid or aryl boronic ester.

R is selected from a lower alkyl group having 1 to 10 carbon atoms and an arylalkyl group of up to 12 carbon atoms, (i) wherein the alkyl group optionally contains one or more carbon-carbon double or triple bonds, or an aryl group, of up to 12 carbon atoms, and (ii) wherein R is optionally substituted by one or more halo, hydroxy, amino, or nitro groups, and optionally contains one or more hetero atoms.

M2 is a PBD monomer wherein the dashed lines represent an optional double bond between one of: (i) $C_{1'}$ and $C_{2'}$; (ii) $C_{2'}$ and $C_{3'}$; and (iii) $C_{2'}$ and $R^{2'}$. In some embodiments, the bond between $C_{1'}$ and $C_{2'}$ is a single bond, the bond between $C_{2'}$ and $C_{3'}$ is a single bond, and the bond between $C_{2'}$ and $R^{2'}$ is a double bond.

$R^{2'}$, $R^{3'}$, $R^{6'}$, $R^{7'}$, $R^{9'}$, $R^{11'}$ and X' correspond to, and are defined in the same way as, $R^2$, $R^3$, $R^6$, $R^7$, $R^9$, $R^{11}$ and X, respectively.

L is a self-immolative linker comprising at least one of a disulfide moiety, a peptide moiety and a peptidomimetic moiety. In some embodiments, the linker comprises a disulfide moiety or a peptide moiety.

Each asterisk independently represents a chiral center of racemic or undefined stereochemistry.

M1 and M2 are bound at the C8 position by a moiety -Q-T-Q'-, wherein Q and Q' are independently selected from O, NH and S, and wherein T is an optionally substituted $C_{1-12}$ alkylene group that is further optionally interrupted by one or more heteroatoms and/or aromatic rings. In some embodiments, Q and Q' are O, and T is $C_3$ alkylene or $C_5$ alkylene.

Ab is an antibody as defined elsewhere herein. In some embodiments, the antibody comprises at least one cysteine sulfhydryl moiety, wherein the antibody binds to one or more tumor-associated antigens or cell-surface receptors selected from: (1) BMPR1B (bone morphogenetic protein receptor-type IB); (2) E16 (LAT1, SLC7A5); (3) STEAP1 (six transmembrane epithelial antigen of prostate); (4) MUC16 (0772P, CA125); (5) MPF (MPF, MSLN, SMR, megakaryocyte potentiating factor, mesothelin); (6) Napi2b (NAPI-3B, NPTIIb, SLC34A2, solute carrier family 34 (sodium phosphate), member 2, type II sodium-dependent phosphate transporter 3b); (7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B); (8) PSCA hlg (2700050C12Rik, C530008016Rik, RIKEN cDNA 2700050C12, RIKEN cDNA 2700050C12 gene); (9) ETBR (Endothelin type B receptor); (10) MSG783 (RNF124, hypothetical protein FLJ20315); (11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein); (12) TrpM4 (BR22450, FLJ20041, TRPM4, TRPM4B, transient receptor potential cation channel, subfamily M, member 4); (13) CRIPTO (CR, CR1, CRGF, CRIPTO, TDGF1, teratocarcinoma-derived growth factor); (14) CD21 (CR2 (Complement receptor 2) or C3DR (C3d/Epstein Barr virus receptor) or Hs 73792); (15) CD79b (CD79B, CD79β, IGb (immunoglobulin-associated beta), B29); (16) FcRH2 (IFGP4, IRTA4, SPAP1A (SH2 domain containing phosphatase anchor protein 1a), SPAP1B, SPAP1C); (17) HER2; (18) NCA; (19) MDP; (20) IL20Rα; (21) Brevican; (22) EphB2R; (23) ASLG659; (24) PSCA; (25) GEDA; (26) BAFF-R (B cell-activating factor receptor, BLyS receptor 3, BR3); (27) CD22 (B-cell receptor CD22-B isoform); (28) CD79a (CD79A, CD79α, immunoglobulin-associated alpha); (29) CXCR5 (Burkitt's lymphoma receptor 1); (30) HLA-DOB (Beta subunit of MHC class II molecule (Ia antigen)); (31) P2X5 (Purinergic receptor P2x ligand-gated ion channel 5); (32) CD72 (B-cell differentiation antigen CD72, Lyb-2); (33) LY64 (Lymphocyte antigen 64 (RP105), type I membrane protein of the leucine rich repeat (LRR) family); (34) FcRH1 (Fc receptor-like protein 1); (35) FcRH5 (IRTA2, Immunoglobulin superfamily receptor translocation associated 2); (36) TENB2 (putative transmembrane proteoglycan); (37) PMEL17 (silver homolog; SILV; D12S53E; PMEL17; SI; SIL); (38) TMEFF1 (transmembrane protein with EGF-like and two follistatin-like domains 1; Tomoregulin-1); (39) GDNF-Ra1 (GDNF family receptor alpha 1; GFRA1; GDNFR; GDNFRA; RETL1; TRNR1; RET1L; GDNFR-alpha1; GFR-ALPHA-1); (40) Ly6E (lymphocyte antigen 6 complex, locus F; Ly67,RIG-E,SCA-2,TSA-1); (41) TMEM46 (shisa homolog 2 (*Xenopus laevis*); SHISA2); (42) Ly6G6D (lymphocyte antigen 6 complex, locus G6D; Ly6-D, MEGT1); (43) LGR5 (leucine-rich repeat-containing G protein-coupled receptor 5; GPR49, GPR67); (44) RET (ret proto-oncogene; MEN2A; HSCR1; MEN2B; MTC1; PTC; CDHF12; Hs.168114; RET51; RET-ELE1); (45) LY6K (lymphocyte antigen 6 complex, locus K; LY6K; HSJ001348; FLJ35226); (46) GPR19 (G protein-coupled receptor 19; Mm.4787); (47) GPR54 (KISS1 receptor; KISS1R; GPR54; HOT7T175; AXOR12); (48) ASPHD1 (aspartate beta-hydroxylase domain containing 1; LOC253982); (49) Tyrosinase (TYR; OCAIA; OCA1A; tyrosinase; SHEP3); (50) TMEM118 (ring finger protein, transmembrane 2; RNFT2; FLJ14627); (51) GPR172A (G protein-coupled receptor 172A; GPCR41; FLJ11856; D15Ertd747e); (52) CD33; and (53) CLL-1. In some embodiments, the antibody is engineered for conjugation. In some embodiments, the antibody is a cysteine-engineered antibody comprising LC K149C, HC A118C, HC A140C or LC V205C as the site of linker conjugation. In some embodiments, the antibody or cysteine-engineered antibody is selected from anti-HER2, anti-CD22, anti-CD33, anti-Napi2b, anti-Ly6E, and anti-CLL-1.

The integer p is 1, 2, 3, 4, 5, 6, 7 or 8. In some embodiments, p is 1, 2, 3 or 4. In some embodiments, a composition comprising a mixture of PBD prodrug dimer-antibody conjugates is provided wherein the average drug loading per antibody in the mixture of conjugate compounds is about 2 to about 5.

In some embodiments, $R^7$ and $R^{7'}$ are $-OCH_3$; $R^3$, $R^{3'}$, $R^6$, $R^{6'}$, $R^9$ and $R^{9'}$ are H; and $R^2$ and $R^{2'}$ are $=CH_2$,

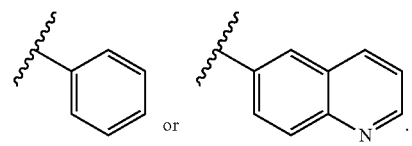 [SMILES: *c1ccccc1 ; *c1ccc2ncccc2c1]

In some embodiments, the bond between $C_1$ and $C_2$ of M1 is a single bond; the bond between $C_2$ and $C_3$ of M1 is a single bond; the bond between $C_{1'}$ and $C_{2'}$ of M2 is a single bond; the bond between $C_{2'}$ and $C_{3'}$ of M2 is a single bond; $C_3$ of M1 is substituted with two $R^3$ groups, each of which is H; $C_{3'}$ of M2 is substituted with two $R^{3'}$ groups, each of which is H; the bond between $C_2$ and $R^2$ of M1 is a double bond; and the bond between $C_{2'}$ and $R^{2'}$ of M2 is a double bond.

In some embodiments, the PBD prodrug dimer-antibody conjugate compound is of formula (Ia):

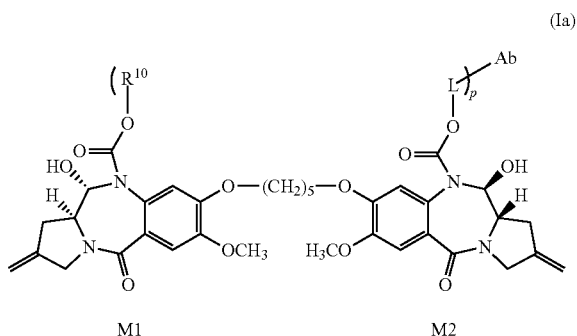

(Ia)

wherein $R^{10}$, L, p and Ab are as defined elsewhere herein.

B. Monomers

In some embodiments, PBD monomer compounds are of formula (II):

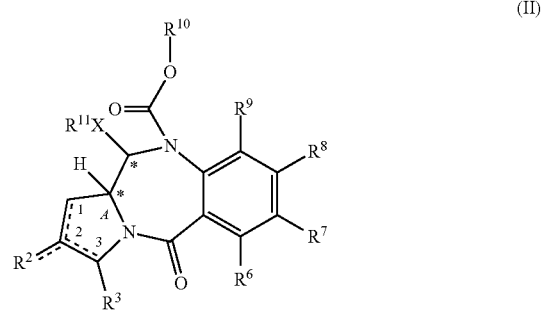

(II)

wherein $R^2$, $R^3$, $R^6$, $R^7$, $R^8$, $R^9$, $R^{10}$, $R^{11}$, X, *, and the bonding scheme in pyrrolidine ring A are as described elsewhere herein in connection with the PBD dimers.

In some embodiments, the PBD monomer compound is of formula (IIa):

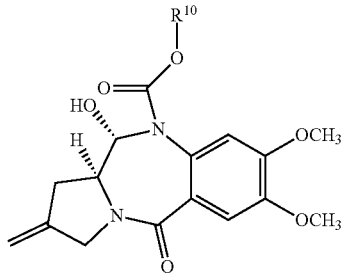

(IIa)

wherein $R^{10}$ is as defined elsewhere herein.

C. Dimers

In some embodiments, PBD prodrug dimer compounds are of formula (VIII) comprising a first PBD prodrug monomer M1 and a second PBD monomer M2:

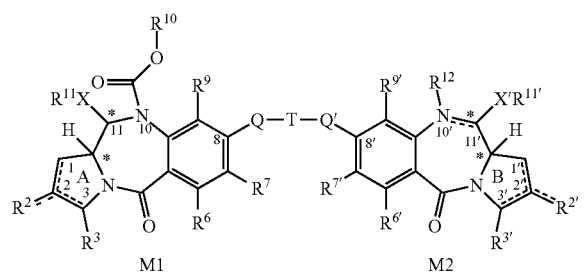

(VIII)

wherein $R^2$, $R^{2'}$, $R^3$, $R^{3'}$, $R^6$, $R^{6'}$, $R^7$, $R^{7'}$, $R^9$, $R^{9'}$, $R^{10}$, $R^{11}$, $R^{11'}$, X, X', Q, Q', T, *, and the bonding schemes in pyrrolidine rings A and B are as described elsewhere herein in connection with the PBD dimers.

In some embodiments, $R^{12}$ is absent and the bond between N10' and $C_{11'}$ is a double bond. In some embodiments, $R^{12}$ is selected from —C(O)O-L and —C(O)O—$R^{10}$ where $R^{10}$ is a prodrug moiety as described elsewhere herein. L is as defined elsewhere herein.

In some embodiments, the PBD prodrug dimer compounds are of formula (VIIIa):

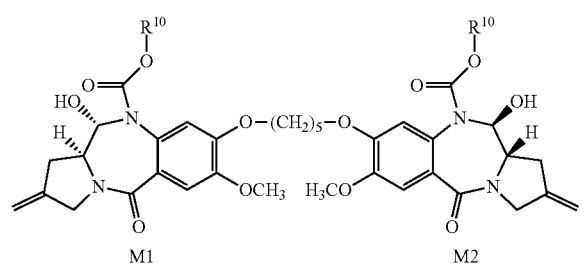

(VIIIa)

wherein $R^{10}$ is as defined elsewhere herein.

In some embodiments, the PBD prodrug dimer compounds are of formula (VIIb):

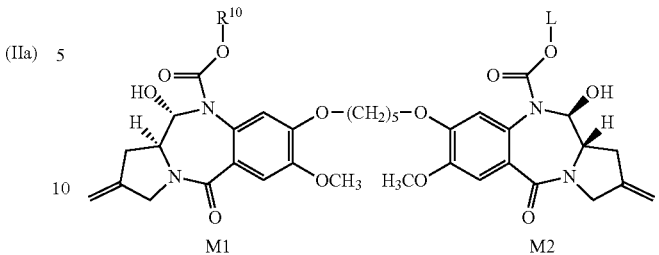

(VIIIb)

wherein $R^{10}$ and L are as defined elsewhere herein.

III. Prodrug Protecting Group-Trigger

Prodrug protecting groups comprising a trigger within the scope of the present disclosure include disulfides, cyclic diones, aryl boronic acids and aryl boronic esters. Prodrug protecting groups comprising a trigger are conjugated to PBDs at the N10 position by a carbamate moiety. The protecting group is enzymatically or chemically cleaved to generate the active drug by the application of stimulus, such as an enzyme (e.g., DTD), ROS or GSH.

A. Disulfide Protecting Group-Triggers

Disulfide protection group-trigger $R^{10}$ moieties of the present disclosure are of the general formula (V):

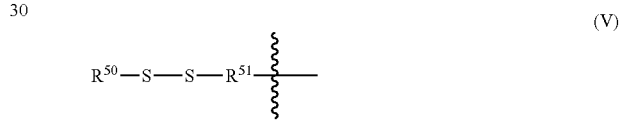

(V)

wherein the wavy line indicates the point of attachment to the PBD N10 position

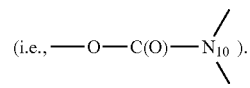

(i.e., —O—C(O)—$N_{10}$ ).

$R^{50}$ is selected from optionally substituted $C_{1-8}$ alkyl or $C_{2-6}$ alkyl, optionally substituted $C_{1-8}$ or $C_{2-6}$ heteroalkyl, optionally substituted cycloalkyl comprising from 2 to 6 carbon atoms, and optionally substituted heterocycloalkyl comprising from 2 to 6 carbon atoms. In some particular embodiments, $R^{50}$ is selected from —$CH_2$—$CH_3$, —CH$(CH_3)_2$, —C$(CH_3)_3$, —$CH_2$—$CH_2OH$, —$CH_2$—$CH_2$—C(O)OH, —$CH_2$—$CH_2$—O—$CH_3$, and a 3- to 6-membered cycloalkyl or a heterocycloalkyl. In some embodiments, cycloalkyl and heterocycloalkyl $R^{50}$ moieties are selected from:

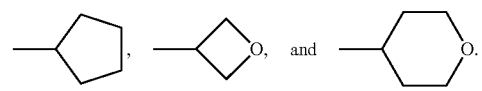

In some embodiments, $R^{50}$ is selected from $CH_3CH_2$—, $(CH_3)_2CH$— and $(CH_3)_3C$—.

$R^{51}$ is optionally substituted $C_2$ alkylene or optionally substituted benzylene. In some such embodiments, $R^{51}$ is of the formula:

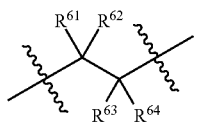
(Va)

In some embodiments, $R^{61}$ and $R^{62}$ are independently selected from H and optionally substituted $C_{1-6}$ alkyl, and optionally substituted $C_{1-6}$ heteroalkyl. In some particular embodiments, $R^{61}$ and $R^{62}$ are independently selected from H and optionally substituted $C_{1-4}$ alkyl, and optionally substituted $C_{1-4}$ ether or tertiary amine. In some other particular embodiments, one of $R^{61}$ and $R^{62}$ is H. In yet other particular embodiments, one of $R^{61}$ and $R^{62}$ is H and the other of $R^{61}$ and $R^{62}$ is —$CH_3$, $C_{1-4}$ ether or C tertiary amine. In some other particular embodiments, $R^{61}$ and $R^{62}$ are each H or $R^{61}$ and $R^{62}$ are each $CH_3$.

In some embodiments, $R^{61}$ and $R^{62}$ together with the carbon atom to which they are bound form an optionally substituted cycloalkyl, optionally substituted heterocycloalkyl, optionally substituted aryl or optionally substituted heteroaryl moiety, each ring substitution comprising from 2 to 6 carbon atoms.

In some embodiments, $R^{63}$ and $R^{64}$ are independently selected from H and $CH_3$. In some other particular embodiments, $R^{63}$ and $R^{64}$ are H.

A non-limiting listing of exemplary $R^{51}$ moieties is as follows:

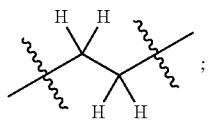
(Vb)

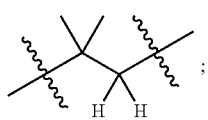
(Vc)

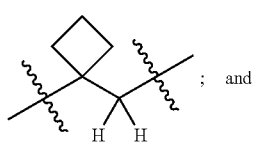
(Vd) ; and

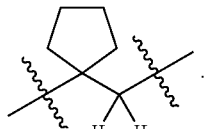
(Ve)

In some alternative embodiments, $R^{51}$ is an arylalkyl. In one such embodiment, $R^{51}$ is:

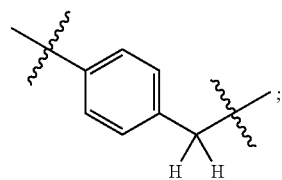
(Vf)

A non-limiting listing of exemplary disulfide protection group-trigger moieties is as follows:

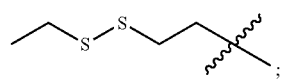

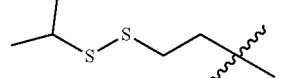

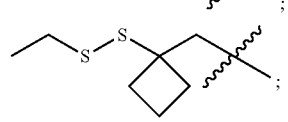

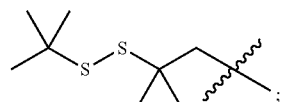

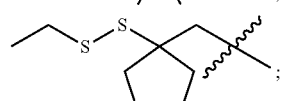

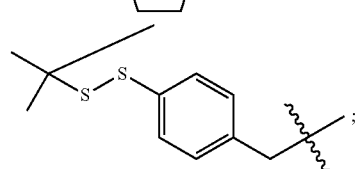

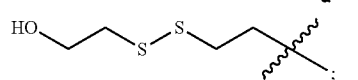

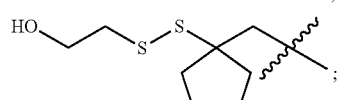

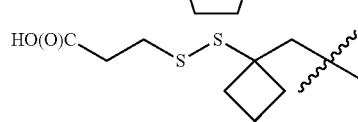

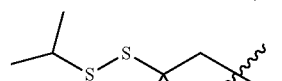

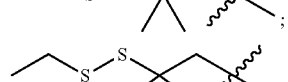

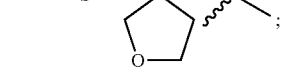

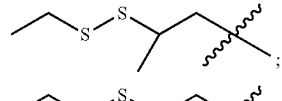

-continued

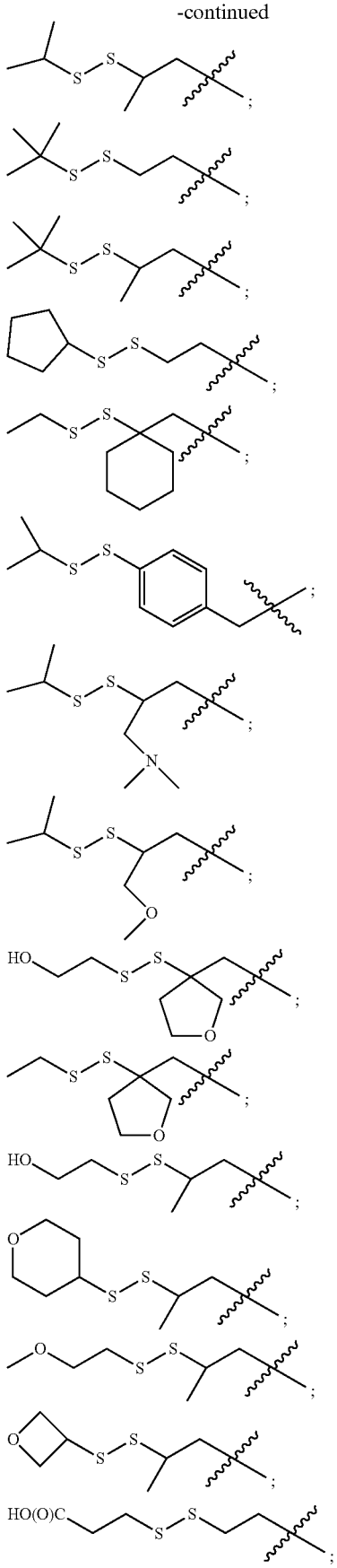

-continued

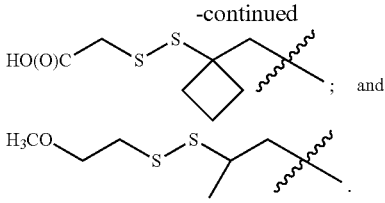

In accordance with the present disclosure and based on in vitro experimental evidence to-date, it has been discovered that disulfide protection group-triggers of the present disclosure are cleaved intracellularly in proliferating cells, such as cancer cells, expressing elevated GSH, and are generally stable in non-proliferating cells expressing normal GSH levels as well as in whole blood/plasma. More particularly, blood concentration of GSH is known to be very low, such as in the micromolar range, whereas intracellular GSH concentration is typically up to three orders of magnitude greater, such as in the millimolar range. It is further believed that GSH concentration in cancer cells is even greater, due to increased activity of reductive enzymes.

It has been further discovered that differences between intracellular reduction potential (expressed in mV) between proliferating and non-proliferating cells may be exploited to effect disulfide trigger activation and drug release in proliferating cells, while providing for prodrug stability in non-proliferating cells, whole blood and plasma. More particularly, it is believed that the ratio of reduced GSH to oxidized GSH (also termed GSH disulfide or "GSSG") in the GSH/GSSG redox couple is correlated with reduction potential, typically expressed in mV. Certain GSH/GSSG ratios are further believed to be characteristic of proliferating cells. Reduction potential negativity increases as the ratio of GSH/GSSG increases (i.e., as the relative concentration of GSH increases). Typical GSH/GSSG reduction potentials are presented in the table below:

|  | Cytoplasm Reduction Potential (mV) |
| --- | --- |
| Blood/plasma | −140 |
| Proliferating cell | −260 to −230 |
| Growth arrest cell | −220 to −190 |
| Apoptotic cell | −170 to −150 |

The reduction potential of the cysteine (Cys) and cysteine disulfide (CySS) redox couple may also effect intracellular drug release from disulfide prodrugs where the blood/plasma Cys/CySS reduction potential is typically −80 mV to 0 mV and the Cys/CySS reduction potential in the cytoplasm is typically about −160 mV.

B. Cyclic Dione Protecting Group-Triggers

In some embodiments, $R^{10}$ cyclic dione protecting group-triggers are 1,4- or 1,2-quinones of the general formulae:

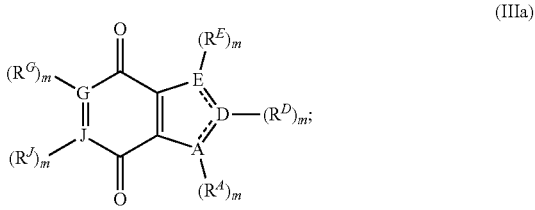

(IIIa)

-continued

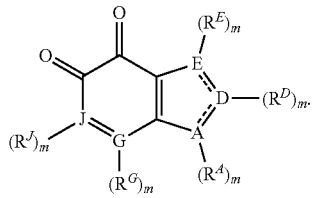
(IIIb)

A, D, E, G and J are independently selected from C and N wherein N is a secondary amine, a tertiary amine or an imine (=N—). Each m is independently selected from 0 and 1. The dashed lines represent an optional double bond between either E-D or D-A. $R^A$, $R^D$, $R^E$, $R^G$ and $R^J$, when present, are independently selected from H, OH, optionally substituted $C_{1-4}$ alkyl or heteroalkyl, $C_{1-4}$ alkoxy or heteroalkoxy, and halogen, with the proviso that at least one of $R^A$, $R^D$, $R^E$, $R^G$ and $R^J$ is a $C_{1-4}$ optionally substituted alkyl or heteroalkyl linker that is covalently bound to the oxygen atom of a carbamate moiety at the PBD N10 position. In some embodiments, one of $R^A$, $R^D$ and $R^E$ is the $C_{1-4}$ optionally substituted alkyl or heteroalkyl linker. In some other embodiments, one of A-$(R^A)_m$, D-$(R^D)_m$ and E-$(R^E)_m$ is

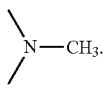

In some other embodiments, A-$(R^A)_m$ is

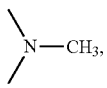

D is C and $R^D$ is a $C_1$ linker, E-$(R^E)_m$ is

where the bond between D and E is a double bond. In other embodiments, G and J are C (carbon). In other embodiments, G and J are C, and one of $R^G$ and $R^J$ is —O—CH$_3$. In some embodiments, the cyclic dione is a 1,4-cyclic dione.

In some embodiments, the cyclic dione prodrug moiety is a quinone selected from the following:

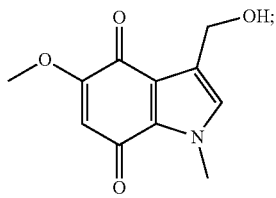

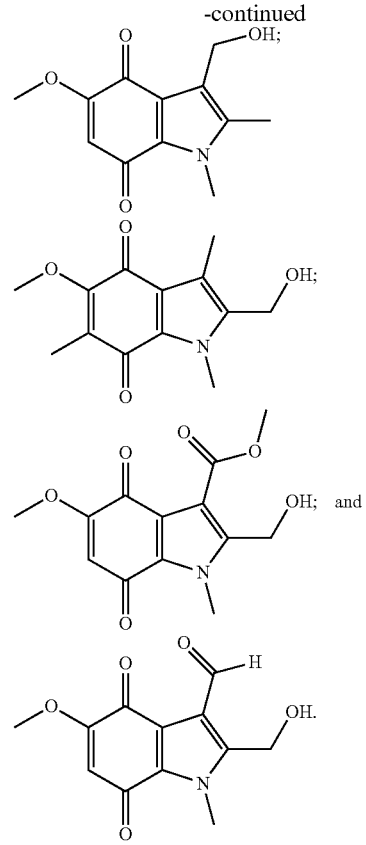

wherein the hydroxyl moiety provides the point of attachment to the PBD.

In some particular embodiments, the cyclic dione is an indole dione of one of the following formulae:

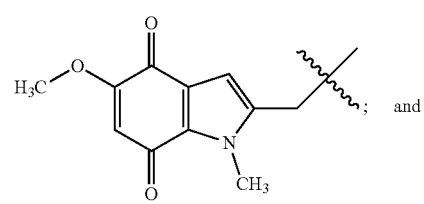
(IIIc)

(IIId)
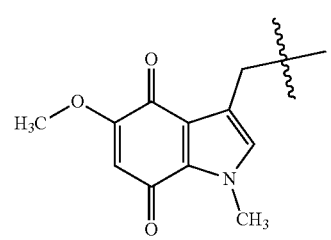

wherein the wavy line indicates the point of attachment to the oxygen atom at the PBD N10 position (i.e., —O—C(O)—N$_{10}$ ).

In some embodiments, $R^{10}$ cyclic dione protecting group-triggers are 1,4- or 1,2-cyclic diones of the following formulae:

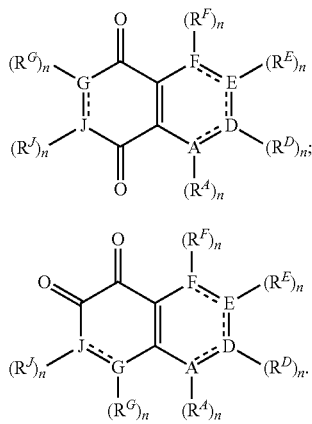

(IIIe)

(IIIf)

A, D, E, F, G and J are independently selected from C and N, wherein at least one of A, D, E and F is C and at least one of G and J is C, and wherein N is a secondary amine, a tertiary amine or an imine (=N—). Each n is independently selected from 0 and 1. The dashed lines represent optional double bonds. $R^A$, $R^D$, $R^E$, $R^F$, $R^G$ and $R^J$, when present, are independently selected from H, OH and optionally substituted $C_{1-4}$ alkyl or heteroalkyl, $C_{1-4}$ alkoxy or heteroalkoxy, and halogen, with the proviso that at least one of $R^A$, $R^D$, $R^E$, $R^F$, $R^G$ and $R^J$ is present and is a $C_{1-4}$ optionally substituted alkyl or heteroalkyl linker that is covalently bound to the oxygen atom of a carbamate moiety at the PBD N10 position. In some embodiments, one of $R^A$, $R^D$, $R^E$ and $R^F$ is the $C_{1-4}$ optionally substituted alkyl or heteroalkyl linker. In some embodiments, D-$R^D$ or E-$R^E$ is a moiety having a carbon atom bound to the $C_{1-4}$ optionally substituted alkyl or heteroalkyl linker, and at least one of A, F and the other of D and E is N. In some embodiments, one of $R^A$, $R^E$ and $R^F$ are independently selected from H, optionally substituted $C_{1-4}$ alkyl or heteroalkyl and optionally substituted $C_{1-4}$ alkoxy or heteroalkoxy, and wherein D is C and $R^D$ is a $C_1$ linker. In some other embodiments, at least one of G-$(R^G)_n$ and J-$(R^J)_n$ is

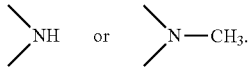

In some other embodiments, one of G-$R^G$ and J-$R^J$ is C—O—$CH_3$, the other of G-$R^G$ and J-$R^J$ is CH, where the bond between G and J is a double bond. In some other embodiments, the ring formed from A, D, E and F is unsaturated or partially saturated. In other embodiments, the ring formed from A, B, D and E is unsaturated or partially saturated.

Prodrugs having a cyclic dione protecting group-trigger may be activated with a DTD two-electron reducing enzyme that is believed to be over-expressed in many human tumors and in the endothelial cells of blood vessels. DTD is a NAD(P)H:quinone oxidoreductase type I (NQO1) enzyme (EC 1.6.99.2) that catalyzes the direct two-electron transfer of quinones using NADH or NADPH as a cofactor (see, e.g., Mendoza, et al., "Human NAD(P)H:quinone oxidoreductase type I (HNQO1) activation of quinone propionic acid trigger groups", *Biochemistry*, 2012 Oct. 9; 51(40): 8014-8026, incorporated by reference herein). It is believed that DTD is a prodrug activator under both aerobic and hypoxic conditions.

Human breast and lung cancers are known to express high DTD levels. For instance, NQO1 expression in nRPKM (where nRPKM refers to normalized reads per Kb of transcript length per million mapped read) is on the order of 30 to 2000 as compared to blood and lymph cancers that typically have nRPKM values in the range of from about 0.5 to about 20. As disclosed in the table below, DTD is over-expressed in many cancers relative to normal tissue (see S. Danson, et al., "DT-diaphorase: a target for new anticancer drugs", *Cancer Treatment Reviews* (2004) 30, 437-449) where "NS" refers to not significant:

| Cell | DTD ratio to normal tissue |
| --- | --- |
| Human colon carcinoma primary | 2.5 to 3.9 |
| Human colon carcinoma metastasis | 47 |
| Human breast carcinoma | NS to 9.5 |
| Human NSCLC | 8.2 to 19.2 |
| Human liver carcinoma | 3.8 to 50 |

Without being bound to any particular theory, the intracellular prodrug release mechanism is believed to generally proceed according to the following mechanism, as represented by one quinone species, wherein the prodrug quinone trigger activation and drug release is mediated by DTD two-electron reduction:

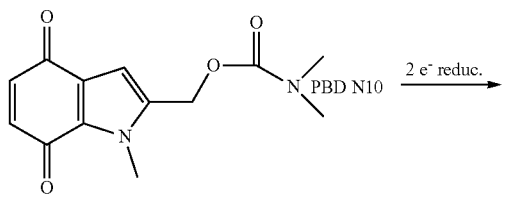

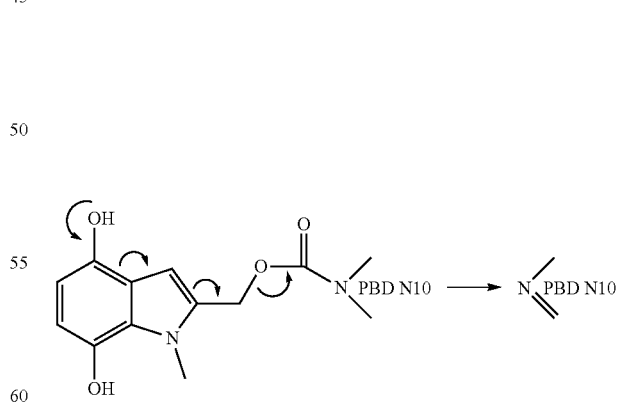

C. Aryl Boronic Acid and Aryl Boronic Ester Protecting Group-Triggers

Aryl boronic acid and aryl boronic ester protection group-trigger $R^{10}$ moieties of the present disclosure are of the general formula (IVa):

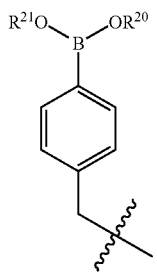

(IVa)

wherein the wavy line indicates the point of attachment to the oxygen atom at the PBD N10 position (i.e., —O—C(O)—N$_{10}$<PBD). R$^{20}$ and R$^{21}$ are independently selected from H, optionally substituted alkyl or heteroalkyl, optionally substituted cycloalkyl or heterocycloalkyl, and optionally substituted aryl or heteroaryl. Alternatively, R$^{20}$ and R$^{21}$ together are an optionally substituted moiety —(CH$_2$)$_n$—, wherein n is 2 or 3, said moiety together with the O atoms to which they are attached and the B atom form a heterocycloalkyl ring. The heterocycloalkyl ring may optionally comprise a fused heteroalkyl ring, a fused aryl ring or a fused heteroaryl ring. The wavy line indicates the point of attachment to the PBD N10 position.

In some embodiments, aryl boronic acid and aryl boronic ester triggers are of the formulae:

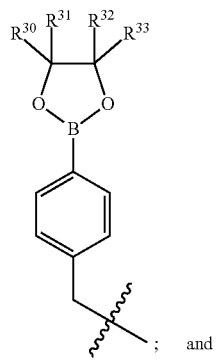

(IVb)

; and

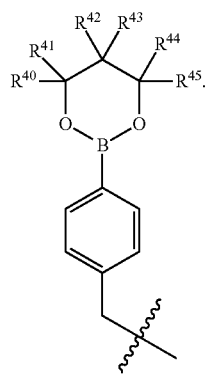

(IVc)

R$^{30}$, R$^{31}$, R$^{32}$, R$^{33}$, R$^{40}$, R$^{41}$, R$^{42}$, R$^{43}$, R$^{44}$ and R$^{45}$ are independently selected from H, halogen, —CN, —OH, —NH$_2$, —COOH, —CONH$_2$, —NO$_2$, —SH, —SO$_2$Cl, —SO$_3$H, —S$_4$H, —SO$_2$NH$_2$, —NHNH$_2$, —ONH$_2$, —NHC═(O)NHNH$_2$, optionally substituted C$_{1-8}$ alkyl or heteroalkyl, optionally substituted cycloalkyl or heterocycloalkyl comprising from 2 to 7 carbon atoms, optionally substituted aryl or heteroaryl. In some embodiments, (i) one of R$^{30}$ or R$^{31}$ and one of R$^{32}$ or R$^{33}$, (ii) one of R$^{40}$ or R$^{41}$ and one of R$^{42}$ or R$^{43}$, and/or (iii) one of R$^{42}$ or R$^{43}$ and one of R$^{44}$ or R$^{45}$ form an optionally substituted fused cycloalkyl ring, fused heterocycloalkyl ring, fused aryl ring or fused heteroaryl ring having from 2 to 7 carbon atoms. The wavy line indicates the point of attachment to the PBD N10 position.

A non-limiting listing of exemplary aryl boronic acid and aryl boronic ester protecting group-triggers is as follows:

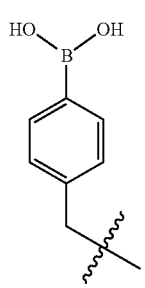

(IVd)

;

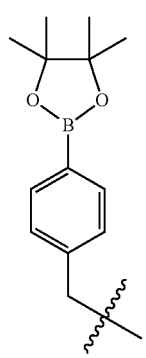

(IVe)

;

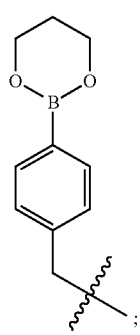

(IVf)

;

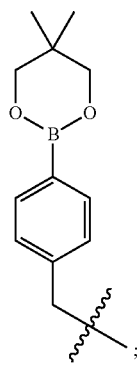

(IVg)

;

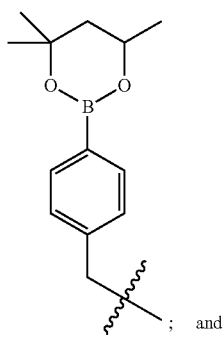
and

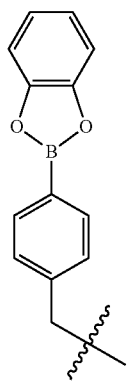
;

In one embodiment, the protecting group-trigger is aryl boronic acid, i.e., where $R^{20}$ and $R^{21}$ are H.

Prodrugs having an aryl boronic acid or an aryl boronic ester protecting group-trigger may be activated with a ROS, such as $H_2O_2$. (See, for instance, Kuang, Y., et al., "Hydrogen Peroxide Inducible DNA Cross-Linking Agents: Targeted Anticancer Prodrugs", J. Am. Chem. Soc. (2011), 133(48), 19278-19281; Peng, X., et al., "ROS-activated anticancer prodrugs: a new strategy for tumor-specific damage", Ther Deliv. (2012), 3(7), 823-833; and Chen, W., et al., "Reactive Oxygen Species (ROS) Inducible DNA Cross-Linking Agents and Their Effect on Cancer Cells and Normal Lymphocytes", J. Med. Chem. (2014), 57, 4498-4510, each of which is incorporated by reference herein in its entirety.)

Cancer cells are believed to exhibit increased oxidative stress as compared to normal, non-cancerous, cells and are believed to have increased cellular concentrations of ROS, such as $H_2O_2$, wherein $H_2O_2$ concentration may be elevated in cancer cells by ten-fold, such as up to 0.5 nmol/$10^4$ cells/h. (See, e.g., Peng; Chen; Zieba, M., et al., "Comparison of hydrogen peroxide generation and the content of lipid peroxidation products in lung cancer tissue and pulmonary parenchyma", Respiratory Medicine (2000), 94, 800-805; Szatrowski, T. et al., "Production of Large Amounts of Hydrogen Peroxide in Human Tumor Cells", Cancer Research (1991), 51, 794-798, each of which is incorporated by reference herein.) It is believed that the high ROS concentration in cancer cells, and concomitant ROS signaling, is a major factor in tumor formation, development, proliferation and survival through DNA mutation, metastasis, angiogenesis and reduced sensitivity to therapeutic agents (see, e.g., Peng).

Without being bound to any particular theory, the ROS-activated intracellular prodrug release mechanism is believed to proceed according to the following mechanism:

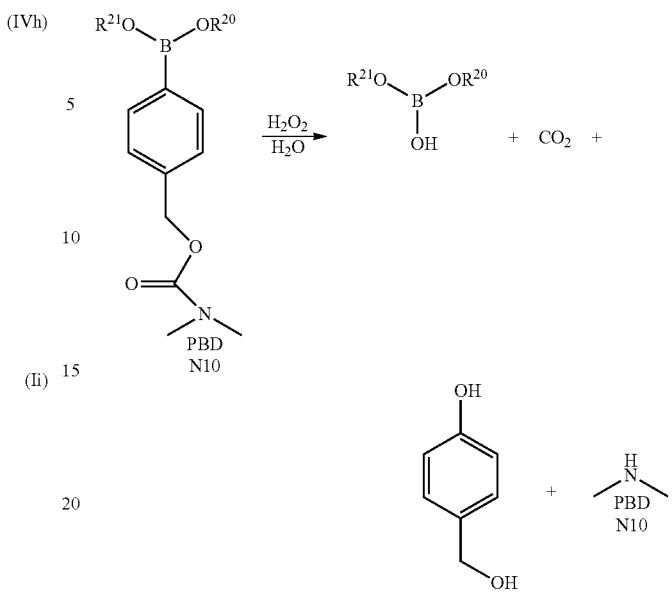

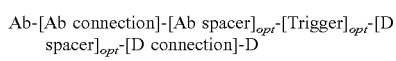

IV. Linkers

The linkers of the present disclosure are bifunctional chemical moieties that are capable of covalently linking together an antibody and a drug ("D") into a tripartite molecule. Linkers within the scope of the present disclosure are not narrowly limited and are of the general structure:

Ab-[Ab connection]-[Ab spacer]$_{opt}$-[Trigger]$_{opt}$-[D spacer]$_{opt}$-[D connection]-D and comprise an Ab connection, an optional Ab spacer unit, an optional immolative (trigger) unit, and optional drug spacer, and a drug connection.

In some embodiments, the linker comprises a self-immolative moiety (trigger). Non-limiting examples of self-immolative moieties within the scope of the present disclosure include peptides, peptidomimetics and disulfides.

In some embodiments, the linker comprises an immolative peptide unit allowing for enzymatic cleavage of the linker, such as by a protease, thereby facilitating release of the drug from the immunoconjugate upon exposure to intracellular proteases, such as lysosomal enzymes (Doronina et al. (2003) Nat. Biotechnol. 21:778-784). Exemplary peptide units include, but are not limited to, dipeptides, tripeptides, tetrapeptides, and pentapeptides. Exemplary dipeptides include, but are not limited to, valine-citrulline (vc or val-cit), valine-alanine (va or val-ala), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). A peptide unit may comprise amino acid residues that occur naturally and/or minor amino acids and/or non-naturally occurring amino acid analogs, such as citrulline. Peptide units can be designed and optimized for enzymatic cleavage by a particular enzyme, for example, a tumor-associated protease, cathepsin B, C and D, or a plasmin protease.

In some embodiments, the linker comprises an immolative peptidomimetic unit allowing for cleaving of the linker. Exemplary peptidomimetic units include, but are not limited to, triazoles, cyclobutane-1-1-dicarbaldehyde, cyclobutane-1-1-dicarbaldehyde-citrulline, alkenes, haloalkenes, and isoxazoles. Some peptidomimentic unit examples include the following where the wavy line at the left side of the peptidomimetic unit is the point of connection to a spacer or an antibody connection moiety and the wavy line at the right side of the peptidomimetic unit is the point of connection to a spacer or a drug connection moiety:

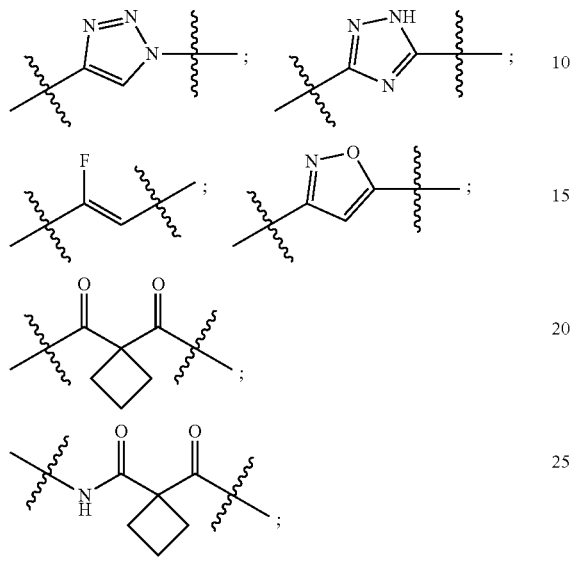

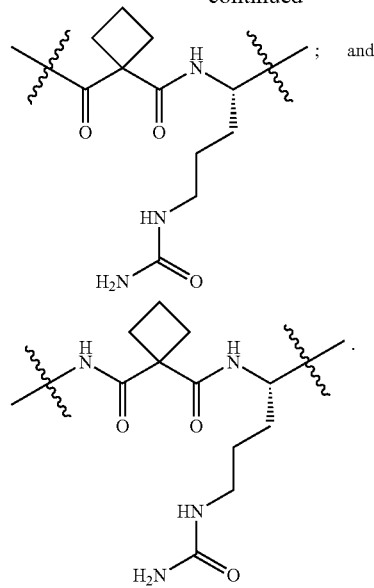

Examples of some Ab-[peptidomimetic linker unit]-Drug groups within the scope of the present disclosure are as follows, where "AA" refers to an amino acid, where AA1 and AA2 may be the same, or different, naturally occurring or non-naturally occurring amino acid:

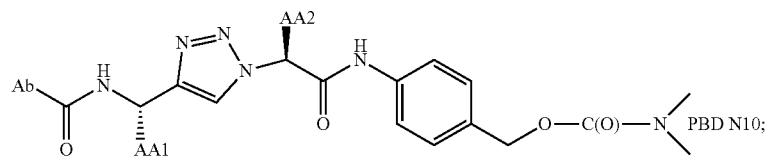

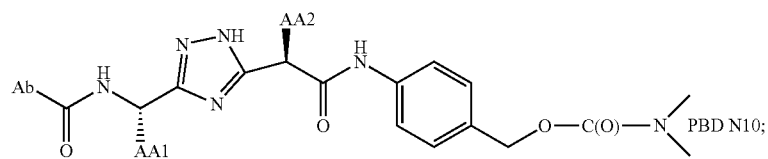

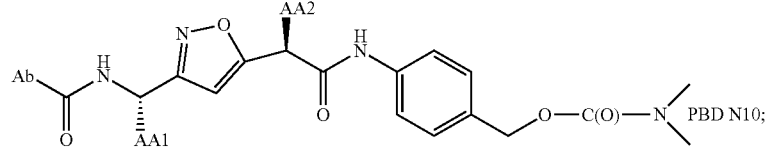

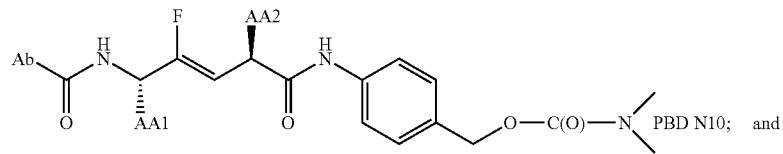

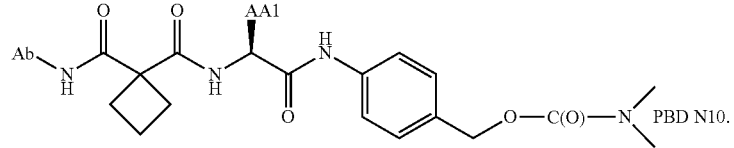

In some embodiments, the linker comprises an immolative disulfide unit allowing for cleavage of the linker. Disulfide linkers generally are of the formula:

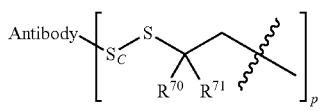

wherein: $S_C$ is an antibody cysteine sulfur atom; $R^{70}$ and $R^{71}$ are independently selected from H and $C_{1-3}$ alkyl, wherein only one of $R^{70}$ and $R^{71}$ can be H, or $R^{70}$ and $R^{71}$ together with the carbon atom to which they are bound form a four- to six-membered ring optionally comprising an oxygen heteroatom; and, the wavy line indicates the point of attachment to the oxygen atom of the carbamate moiety at a PBD N10 position. In some other embodiments, $R^{70}$ and $R^{71}$ are independently selected from H, —$CH_3$ and —$CH_2CH_3$, wherein only one of $R^{70}$ and $R^{71}$ can be H, or $R^{70}$ and $R^{71}$ together with the carbon atom to which they are bound form a ring selected from cyclobutyl, cyclopentyl, cyclohexyl, tetrahydrofuran and tetrahydropyran.

In some embodiments, the linker may comprise a spacer unit. In some embodiments, the spacer unit is p-aminobenzyloxycarbonyl (PAB). In some such embodiments, a p-aminobenzyl alcohol spacer unit is attached to an amino acid unit via an amide bond, and a carbamate, methylcarbamate, or carbonate connection is made between the benzyl alcohol and the drug (Hamann et al. (2005) Expert Opin. Ther. Patents (2005) 15:1087-1103). In other embodiments, the linker-antibody moiety is attached to the oxygen atom of the carbamate moiety at the PBD N10 position as follows:

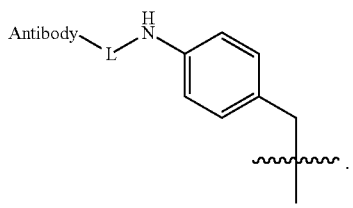

In some other embodiments, spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals.

In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the alpha-carbon of a glycine residue is another example of a spacer that may be useful (Kingsbury et al (1984) J. Med. Chem. 27:1447). In some aspects, the spacer unit is self-immolative.

The linker comprises a reactive group suitable for covalent conjugation to an antibody. In some embodiments, the antibody comprises at least one reactive sulfhydryl moiety and the linker comprises a reactive sulfur atom, a maleimide, a bromacetamide, and iodoacetamide, or an alkene, wherein the antibody is conjugated to the linker by a covalent bond formed by the reaction of the antibody reactive sulfhydryl with the linker reactive sulfur atom, maleimide, bromacetamide, iodoacetamide, or alkene according to methods known to those skilled in the art.

Non-limiting examples of schemes for conjugating an antibody having a reactive sulfhydryl moiety to a Drug-Linker moiety are indicated as follows:

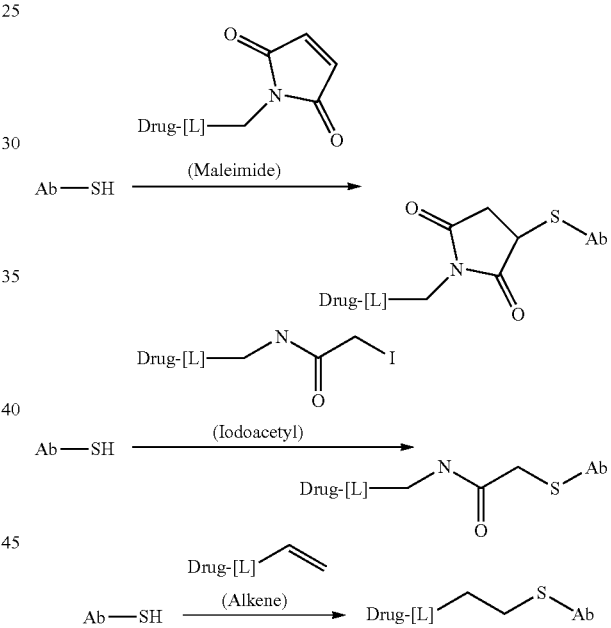

Examples of some particular Drug-[L] conjugates are as follows, where x is from 1 to 8 and where [Conj] refers to a reactive group as described elsewhere herein:

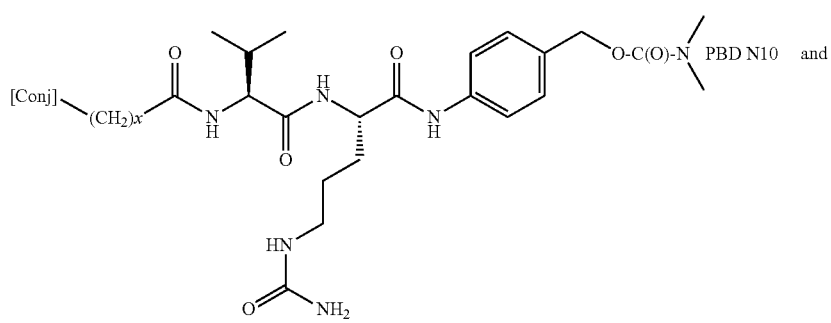

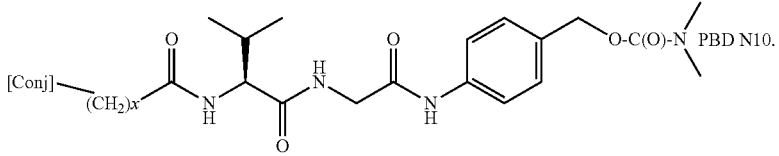

In embodiments comprising an immolative disulfide, conjugation to the Ab may be done according to the methods described in Application No. PCT/CN2015/092084, incorporated herein by reference in its entirety. In general, an activated leaving group-disulfide-drug compound of the following formula:

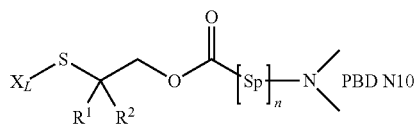

is contacted with an antibody having at least one sulfhydryl moiety, the leaving group ($X_L$) is displaced, and the sulfur atom is covalently bound to the sulfhydryl sulfur atom to form a disulfide. In the above formula: $X_L$ is a thiol leaving group; the leaving group and the linker are bound via a disulfide bond; $R^{70}$ and $R^{71}$ are as defined elsewhere herein; and, Sp is an optional spacer as described elsewhere herein, wherein n is 0 or 1. The linker may be considered to be a hindered linker because only one of $R^{70}$ and $R^{71}$ may be H.

In some embodiments, the leaving group may suitably be selected from the following:

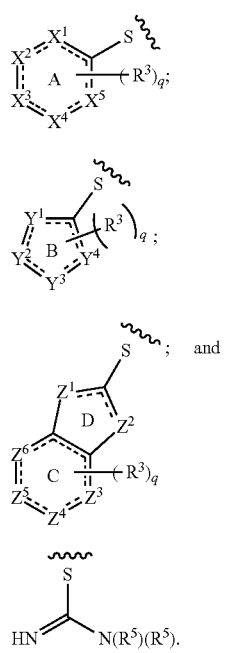

Leaving Group 1

Leaving Group 2

Leaving Group 3

Leaving Group 4

In such embodiments, the wavy lines indicate the point of attachment of the leaving group to the hindered linker S atom thereby forming a disulfide bond. $X^1$, $X^2$, $X^3$, $X^4$ and $X^5$ are independently C, N, S or O, provided at least one of $X^1$ to $X^5$ is N, the dashed lines represent optional double bonds, and A denotes a six-membered ring. $Y^1$, $Y^2$ $Y^3$ and $Y^4$ are independently C, N, S or O, provided at least one of $Y^1$ to $Y^4$ is N, the dashed lines represent optional double bonds, and B denotes a five-membered ring. $Z^1$, $Z^2$, $Z^3$, $Z^4$, $Z^5$ and $Z^6$ are independently C, N, S or O, provided at least one of $Z^1$ and $Z^2$ is N, the dashed lines represent optional double bonds, C denotes a six-membered ring, and D denotes a fused five-membered ring. Each $R^3$ is independently selected from —$NO_2$, —$NH_2$, —C(O)OH, $R^5$S(O)(O)—, —C(O)N($R^5$)($R^5$), —Cl, —F, —CN and —Br. Each $R^5$ is independently selected from H, optionally substituted $C_{1-6}$ hydrocarbyl, optionally substituted $C_{5-6}$ carbocycle, and optionally substituted $C_{5-6}$ heterocycle, and q is 1, 2 or 3. Each carbon atom in the ring structure of leaving group 1, leaving group 2, leaving group 3 and/or leaving group 4 is optionally substituted with $R^5$. Each nitrogen atom in the ring structure of leaving group 1, leaving group 2, leaving group 3 and/or leaving group 4 is optionally substituted with $R^5$ to form a tertiary amine or a quaternary amine.

In some particular such embodiments, $X^1$, $X^2$, $X^3$, $X^4$ and $X^5$ are independently C or N, no more than two of $X^1$ to $X^5$ are N, and ring A is unsaturated. In other particular embodiments, $Y^1$, $Y^2$ $Y^3$ and $Y^4$ are independently C or N, and B ring is unsaturated. In yet other particular embodiments, $Z^1$ is N, $Z^2$ is selected from N, S and O, $Z^3$ to $Z^6$ are selected from C and N, no more than two of $Z^3$ to $Z^6$ are N, and ring C is unsaturated. In still other particular embodiments, Each $R^3$ is independently selected from —$NO_2$, —$NH_2$, —C(O)OH, $H_3$CS(O)(O)— and —C(O)N($CH_3$)$_2$.

In some embodiments, the leaving group is

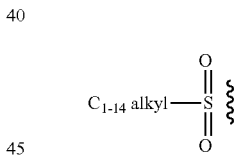

wherein the wavy line indicates the point of attachment of the leaving group to the hindered linker S atom thereby forming a disulfide bond. In some particular embodiments $C_{1-4}$ alkyl is methyl.

Some examples of leaving groups of the present disclosure are illustrated below:

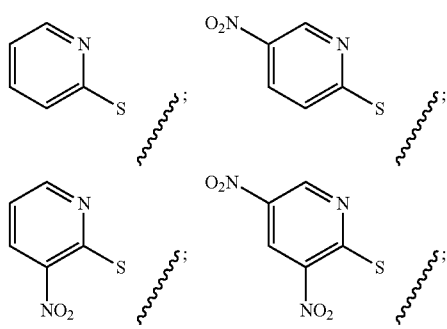

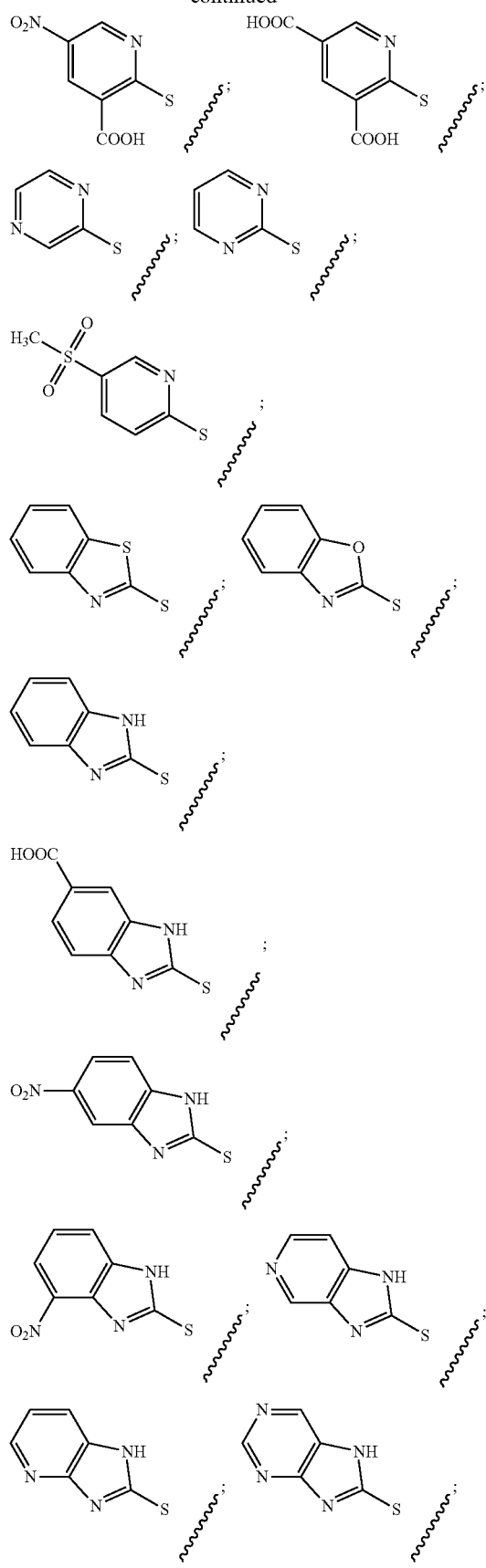
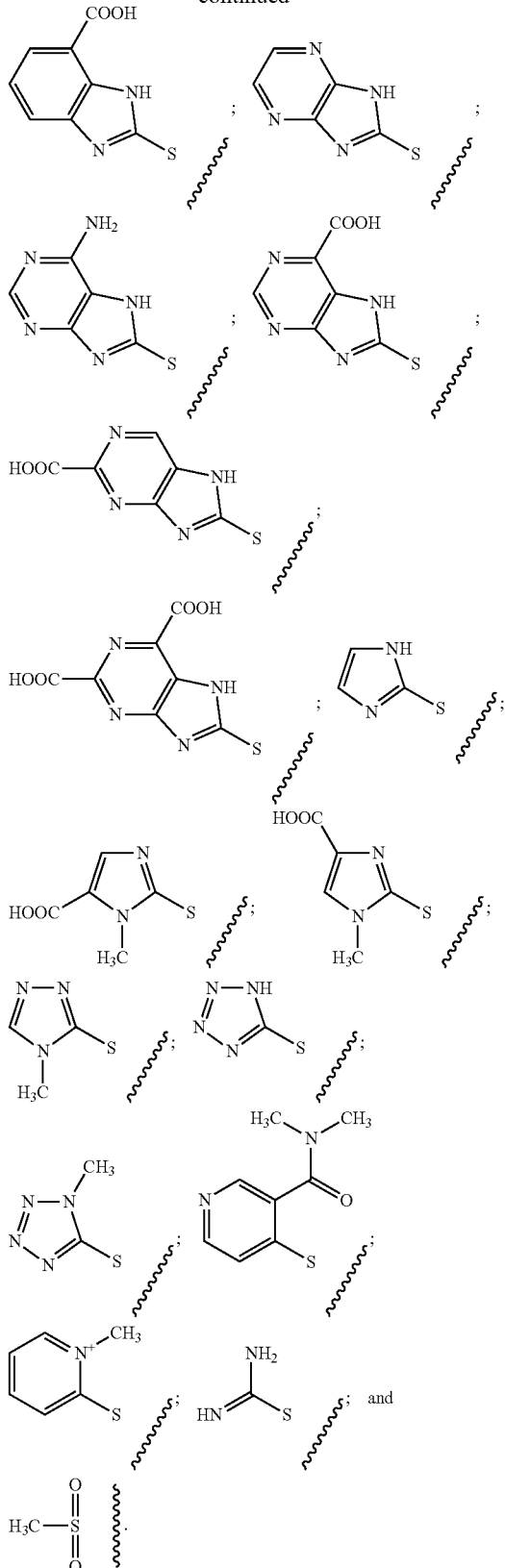
Examples of hindered disulfide linkers are as follows where the wavy line at the sulfur atom refers to the point of attachment to a leaving group as defined elsewhere herein and wherein the wavy line at the carbonyl moiety refers to the point of attachment to a PBD N10 atom:

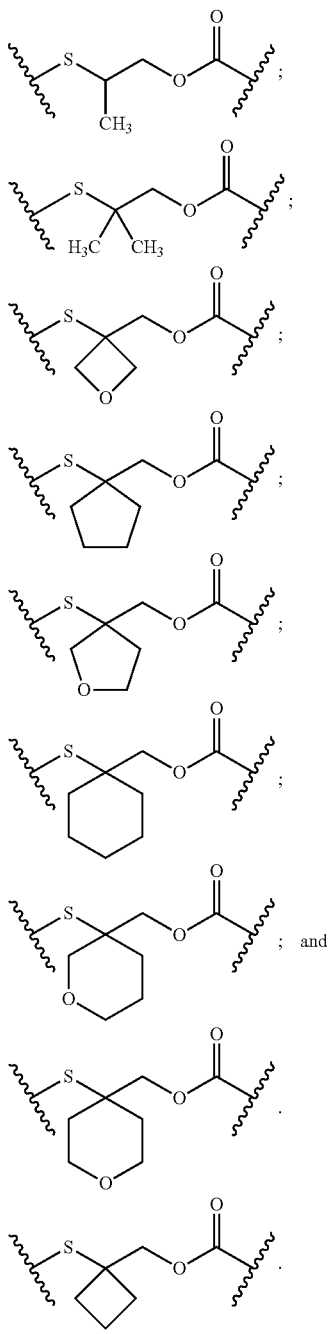

V. Antibodies

The antibodies of the present disclosure are any cell-targeting biologic compound that binds to one or more tumor-associated antigens or to cell-surface receptors, the antibodies comprising at least one reactive cysteine sulfhydryl moiety suitable for conjugation to a linker.

Certain types of cells, such as cancer cells, express surface molecules (antigens) that are unique as compared to surrounding tissue. Cell targeting moieties that bind to these surface molecules enable the targeted delivery of a drug described elsewhere herein specifically to the target cells. For instance and without limitation, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cell.

A. Tumor Associated Antigens

In some particular embodiments of the disclosure, the target cells are cancer cells that express tumor-associated antigens (TAA) or that comprise cell-surface receptors. Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4:
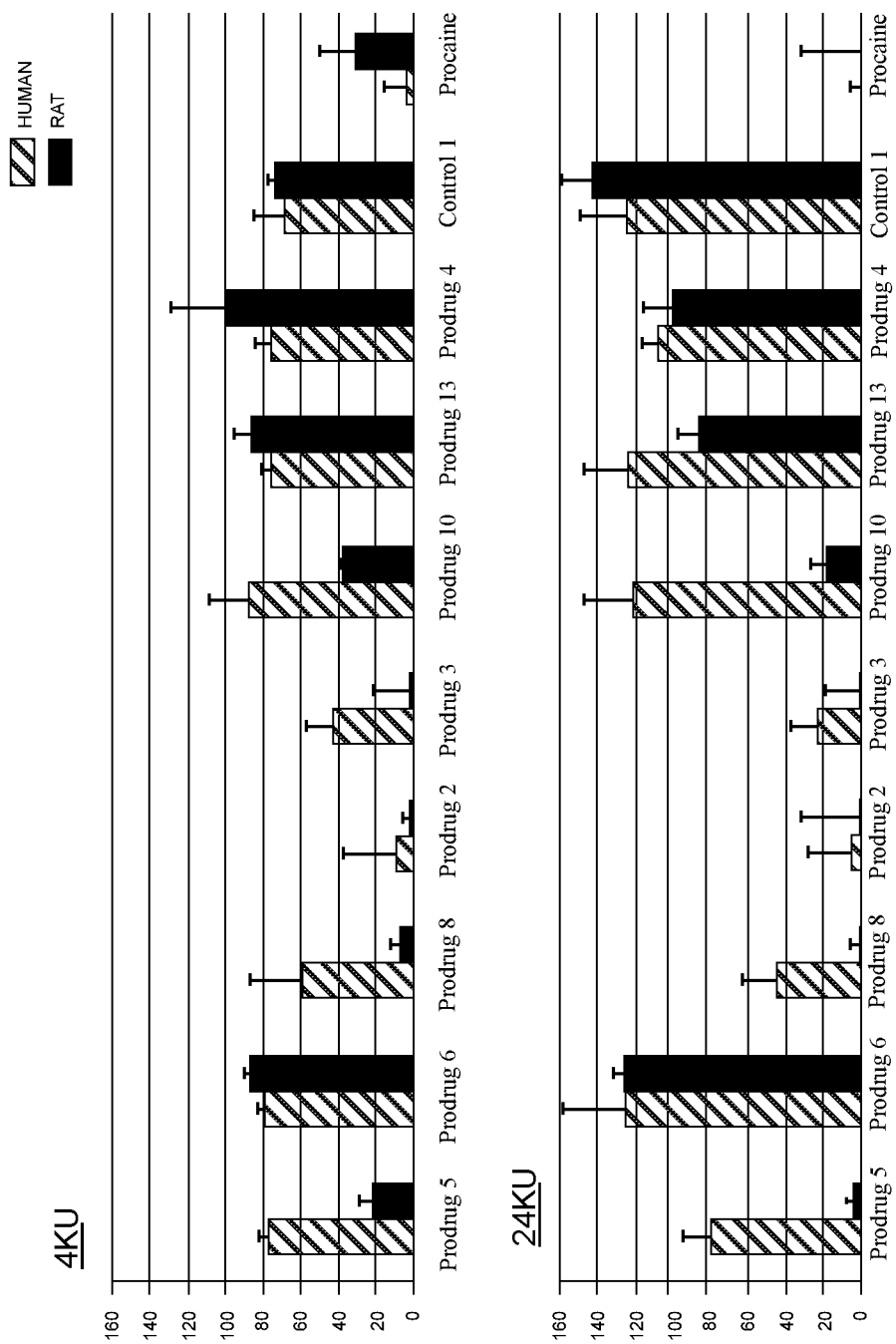
FIG. 4 depicts a plot of PBD monomer disulfide prodrug stability in human and rat whole blood evaluated at 4- and 24-hour intervals where the results are presented as percent of the parent compound remaining relative to time zero.

(1) BMPR1B (bone morphogenetic protein receptor-type IB, Genbank accession no. NM_001203) ten Dijke, P., et al. Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377(Page 349-350); WO200230268 (claim 27; Page 376); WO200148204 (Example; FIG. 4) NP_001194 bone morphogenetic protein receptor, type IB/pid=NP_001194.1-Cross-references: MIM:603248; NP_001194.1; AY065994.

Figure 3:
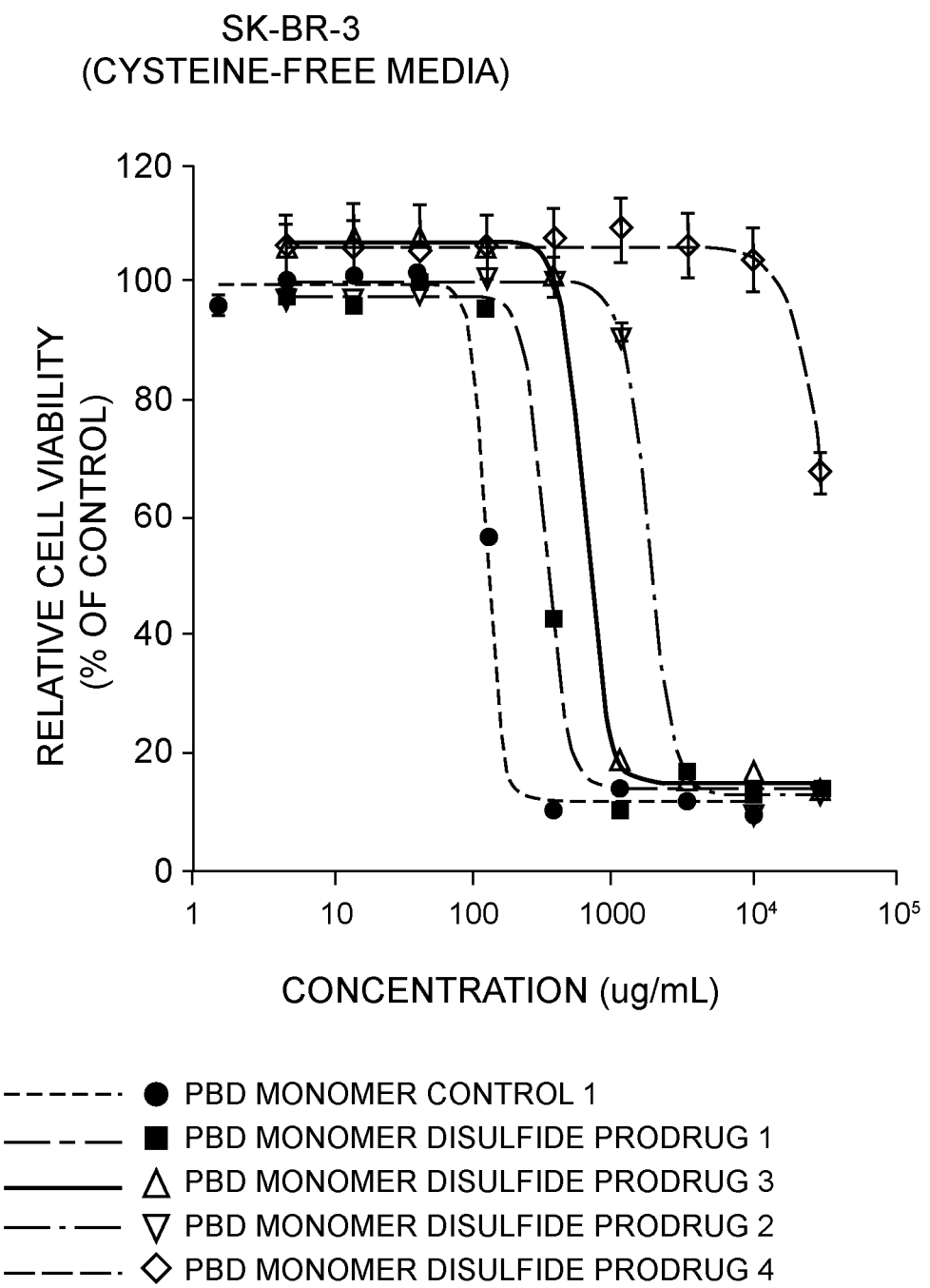
FIG. 3 depicts a plot of SK-BR-3 cell viability (% of control) versus PBD monomer disulfide prodrug concentration on a µg/mL basis.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al. (1992) J. Biol. Chem. 267 (16):11267-11273); WO2004048938 (Example 2); WO2004032842 (Example IV); WO2003042661 (claim 12); WO2003016475 (claim 1); WO200278524 (Example 2);

WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+ system), member 5/pid=NP_003477.3— *Homo sapiens* Cross-references: MIM:600182; NP_003477.3; NM_015923; NM_003486_1.

Figure 2:
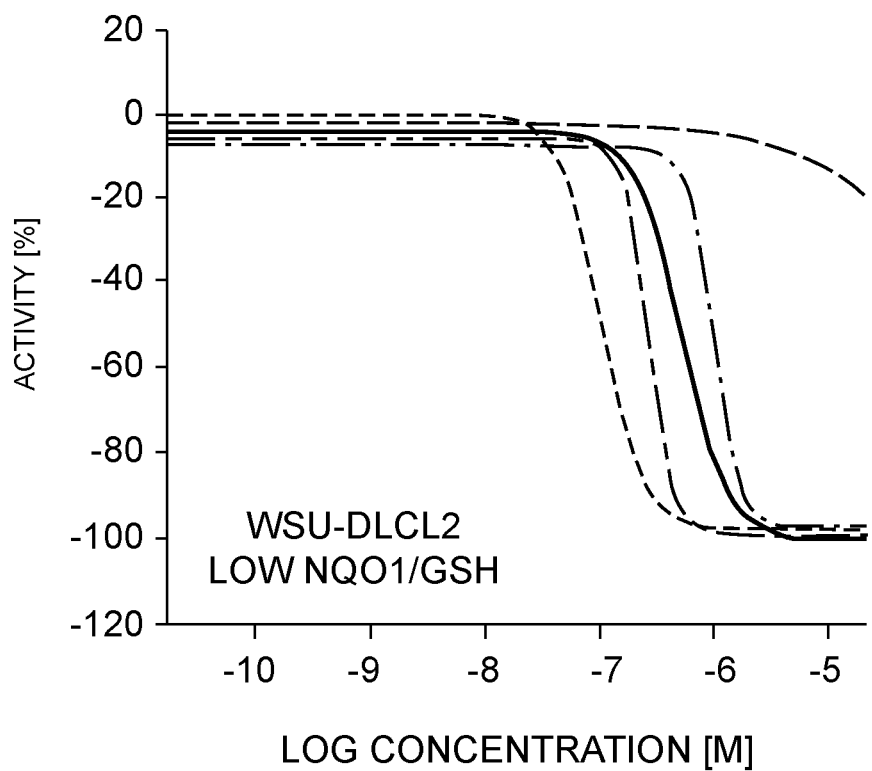
FIG. 2 depicts a plot of PBD monomer disulfide prodrug Activity [%] against WSU-DLCL2 cells versus the log of prodrug concentration in moles per liter and further depicts a table of PBD monomer $IC_{50}$ potency against the WSU-DLCL2 cells.

(3) STEAP1 (six transmembrane epithelial antigen of prostate, Genbank accession no. NM_012449) Cancer Res. 61 (15), 5857-5860 (2001), Hubert, R. S., et al. (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM: 604415; NP_036581.1; NM_012449_1.

Figure 12:
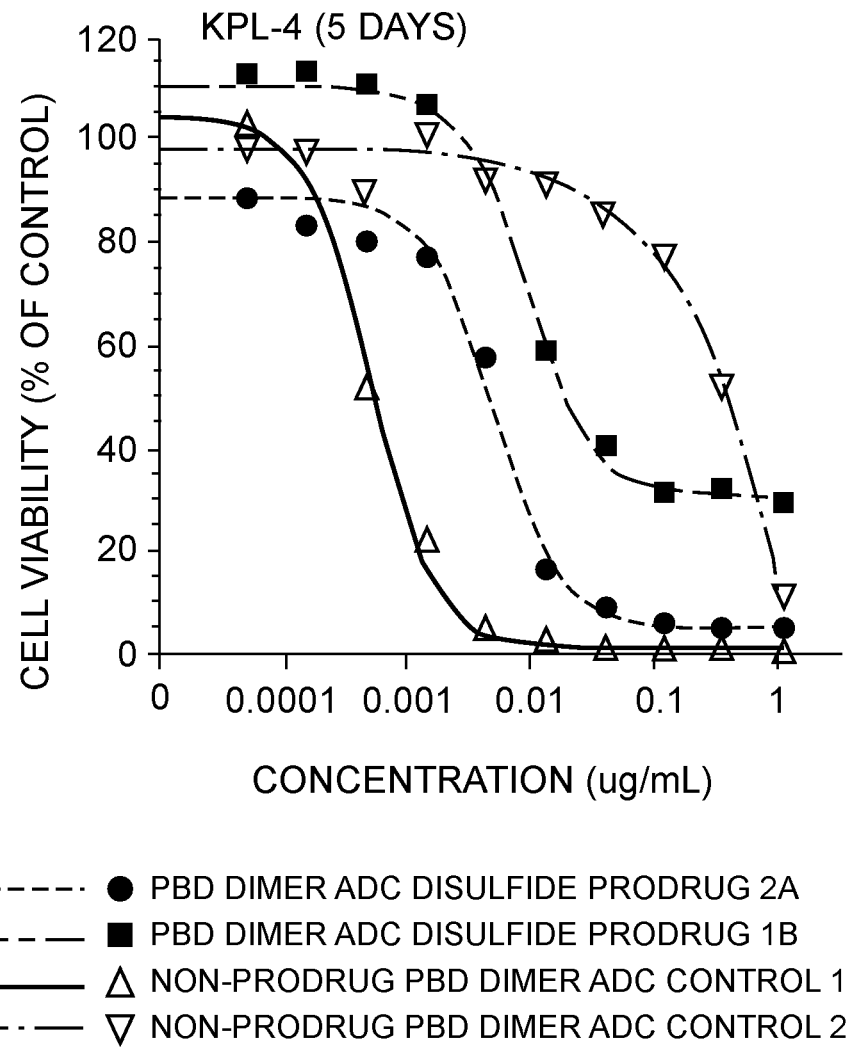
FIG. 12 depicts a plot of KPL-4 cell viability (% of control) versus the concentration of (i) a 7C2 HC A140C peptide-linked disulfide cyclopentyl prodrug ADC PBD dimer, (ii) a 7C2 LC K149C peptide-linked disulfide thiophenol prodrug ADC PBD dimer, (iii) a 7C2 HC A140C ADC PBD dimer not having a prodrug moiety, and (iv) a CD22 HC A140C ADC PBD dimer not having a prodrug moiety.

(4) 0772P (CA125, MUC16, Genbank accession no. AF361486) J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); US 798959. Cross-references: GI:34501467; AAK74120.3; AF361486_1.

(5) MPF (MPF, MSLN, SMR, megakaryocyte potentiating factor, mesothelin, Genbank accession no. NM_005823) Yamaguchi, N., et al. Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MIM:601051; NP_005814.2; NM_005823 1.

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al. (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140); Cross-references: MIM:604217; NP_006415.1; NM_006424_1.

(7) Sema 5b (FLJ10372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)Nagase T., et al. (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: Q9P283; EMBL; AB040878; BAA95969.1. Genew; HGNC:10737.

(8) PSCA hlg (2700050C12Rik, C530008016Rik, RIKEN cDNA 2700050C12, RIKEN cDNA 2700050C12 gene, Genbank accession no. AY358628); Ross et al. (2002) Cancer Res. 62:2546-2553; US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1.

Figure 6:
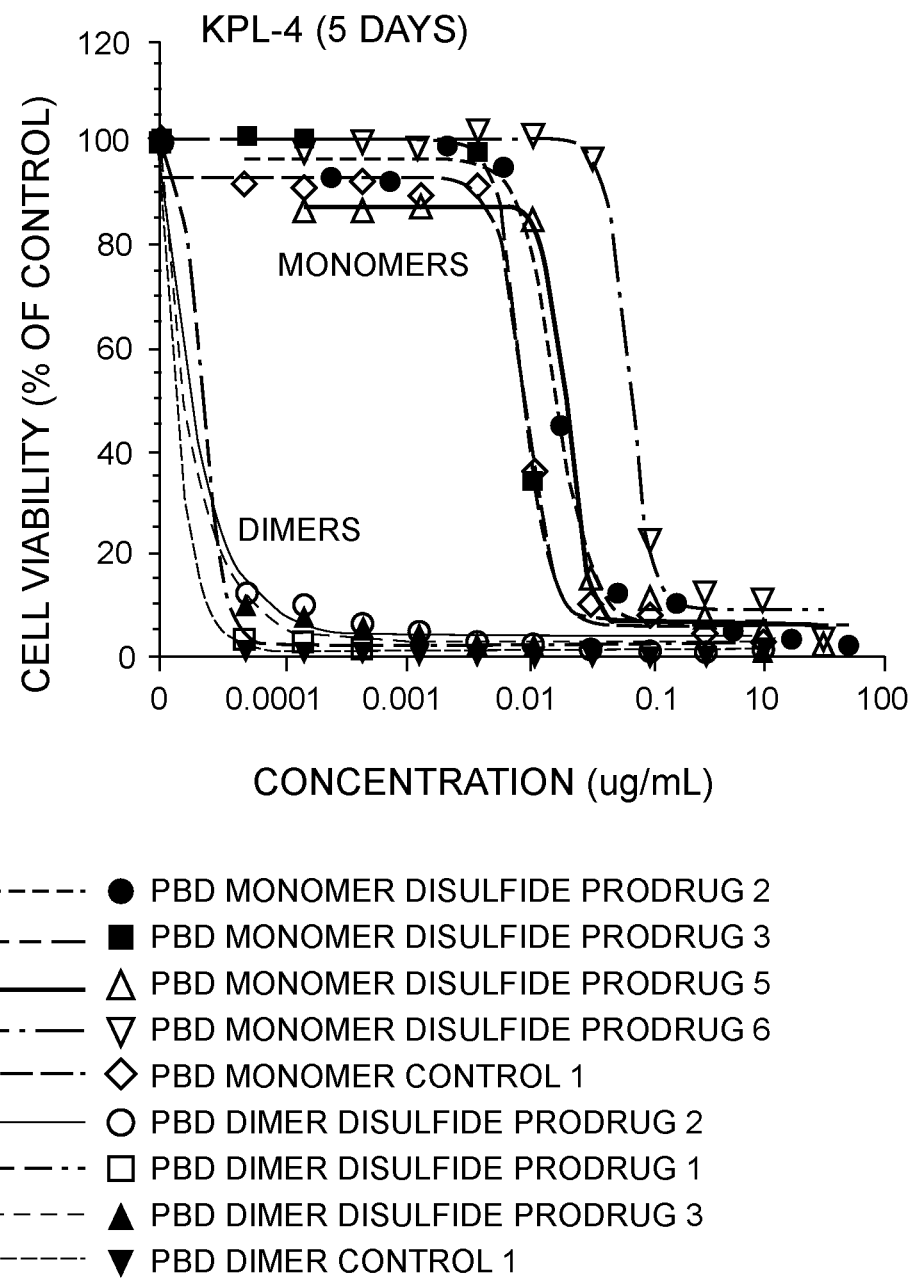
FIG. 6 depicts a plot of KPL-4 cell viability (% of control) versus PBD monomer disulfide prodrug concentration in micromoles and PBD dimer disulfide prodrug concentration in µg/mL.

(9) ETBR (Endothelin type B receptor, Genbank accession no. AY275463); Nakamuta M., et al. Biochem. Biophys. Res. Commun. 177, 34-39, 1991; Ogawa Y., et al. Biochem. Biophys. Res. Commun. 178, 248-255, 1991; Arai H., et al. Jpn. Circ. J. 56, 1303-1307, 1992; Arai H., et al. J. Biol. Chem. 268, 3463-3470, 1993; Sakamoto A., Yanagisawa M., et al. Biochem. Biophys. Res. Commun. 178, 656-663, 1991; Elshourbagy N. A., et al. J. Biol. Chem. 268, 3873-3879, 1993; Haendler B., et al. J. Cardiovasc. Pharmacol. 20, s1-S4, 1992; Tsutsumi M., et al. Gene 228, 43-49, 1999; Strausberg R. L., et al. Proc. Natl. Acad. Sci. U.S.A. 99, 16899-16903, 2002; Bourgeois C., et al. J. Clin. Endocrinol. Metab. 82, 3116-3123, 1997; Okamoto Y., et al. Biol. Chem. 272, 21589-21596, 1997; Verheij J. B., et al. Am. J. Med. Genet. 108, 223-225, 2002; Hofstra R. M. W., et al. Eur. J. Hum. Genet. 5, 180-185, 1997; Puffenberger E. G., et al. Cell 79, 1257-1266, 1994; Attie T., et al., Hum. Mol. Genet. 4, 2407-2409, 1995; Auricchio A., et al. Hum. Mol. Genet. 5:351-354, 1996; Amiel J., et al. Hum. Mol. Genet. 5, 355-357, 1996; Hofstra R. M. W., et al. Nat. Genet. 12, 445-447, 1996; Svensson P. J., et al. Hum. Genet. 103, 145-148, 1998; Fuchs S., et al. Mol. Med. 7, 115-124, 2001; Pingault V., et al. (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (claim 1a; Col 31-34); WO2004001004.

(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1.

Figure 10:
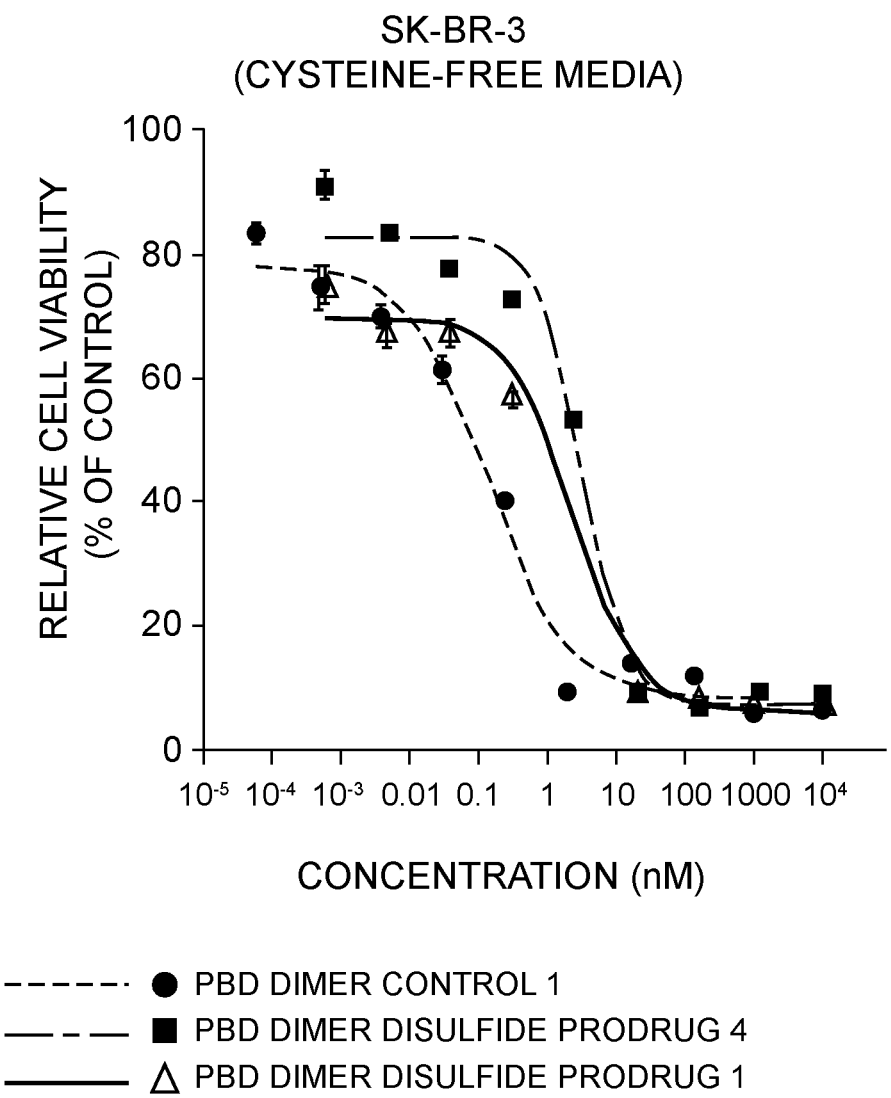
FIG. 10 depicts a plot of SK-BR3 relative cell viability (% of control) versus the concentration in nM of (i) PBD dimer non-prodrug, (ii) a PBD dimer having a disulfide prodrug a one PBD monomer N10 position and not having a prodrug at the other PBD monomer, and (iii) a PBD dimer having a disulfide prodrug at the N10 position of both PBD monomers.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1.

(12) TrpM4 (BR22450, FLJ20041, TRPM4, TRPM4B, transient receptor potential cation channel, subfamily M, member 4, Genbank accession no. NM_017636) Xu, X. Z., et al. Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D); Cross-references: MIM:606936; NP_060106.2; NM_017636_1.

(13) CRIPTO (CR, CR1, CRGF, CRIPTO, TDGF1, teratocarcinoma-derived growth factor, Genbank accession no. NP_003203 or NM_003212) Ciccodicola, A., et al. EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1.

Figure 9:
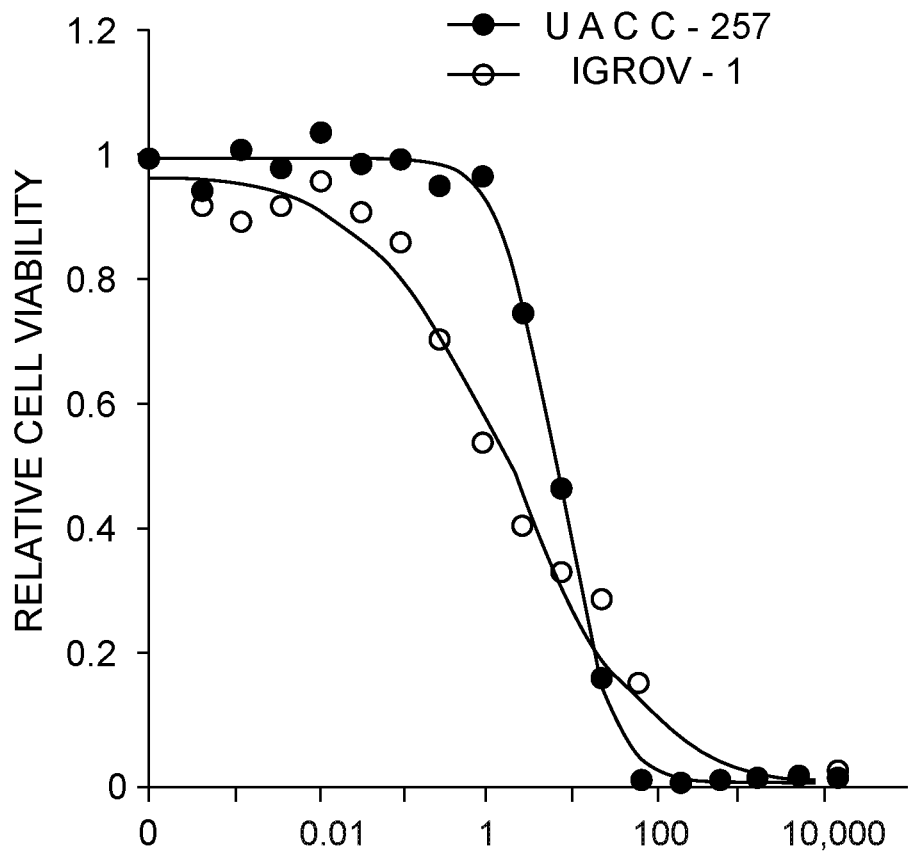
FIG. 9 depicts a plot of UACC-257 and IGROV-1 relative cell viability (% of control) versus the concentration in nM of a PBD dimer having a disulfide prodrug at the N10 position of both PBD monomers and further depicts a table of PBD dimer $IC_{50}$ potency and $IC_{50}$ ratio for an indicated GSH concentration against the UACC-257 and IGROV-1. The IC$_{50}$ ratio is determined relative to the data for the PBD dimer non-prodrug control depicted in FIG. 7.

(14) CD21 (CR2 (Complement receptor 2) or C3DR (C3d/Epstein Barr virus receptor) or Hs.73792 Genbank accession no. M26004) Fujisaku et al. (1989) J. Biol. Chem. 264 (4):2118-2125); Weis J. J., et al. J. Exp. Med. 167, 1047-1066, 1988; Moore M., et al. Proc. Natl. Acad. Sci. U.S.A. 84, 9194-9198, 1987; Barel M., et al. Mol. Immunol. 35, 1025-1031, 1998; Weis J. J., et al. Proc. Natl. Acad. Sci. U.S.A. 83, 5639-5643, 1986; Sinha S. K., et al. (1993) J. Immunol. 150, 5311-5320; WO2004045520 (Example 4); US2004005538 (Example 1); WO2003062401 (claim 9); WO2004045520 (Example 4); WO9102536 (FIG. 9.1-9.9); WO2004020595 (claim 1); Accession: P20023; Q13866; Q14212; EMBL; M26004; AAA35786.1.

(15) CD79b (CD79B, CD7913, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al. (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1.

Figure 18:
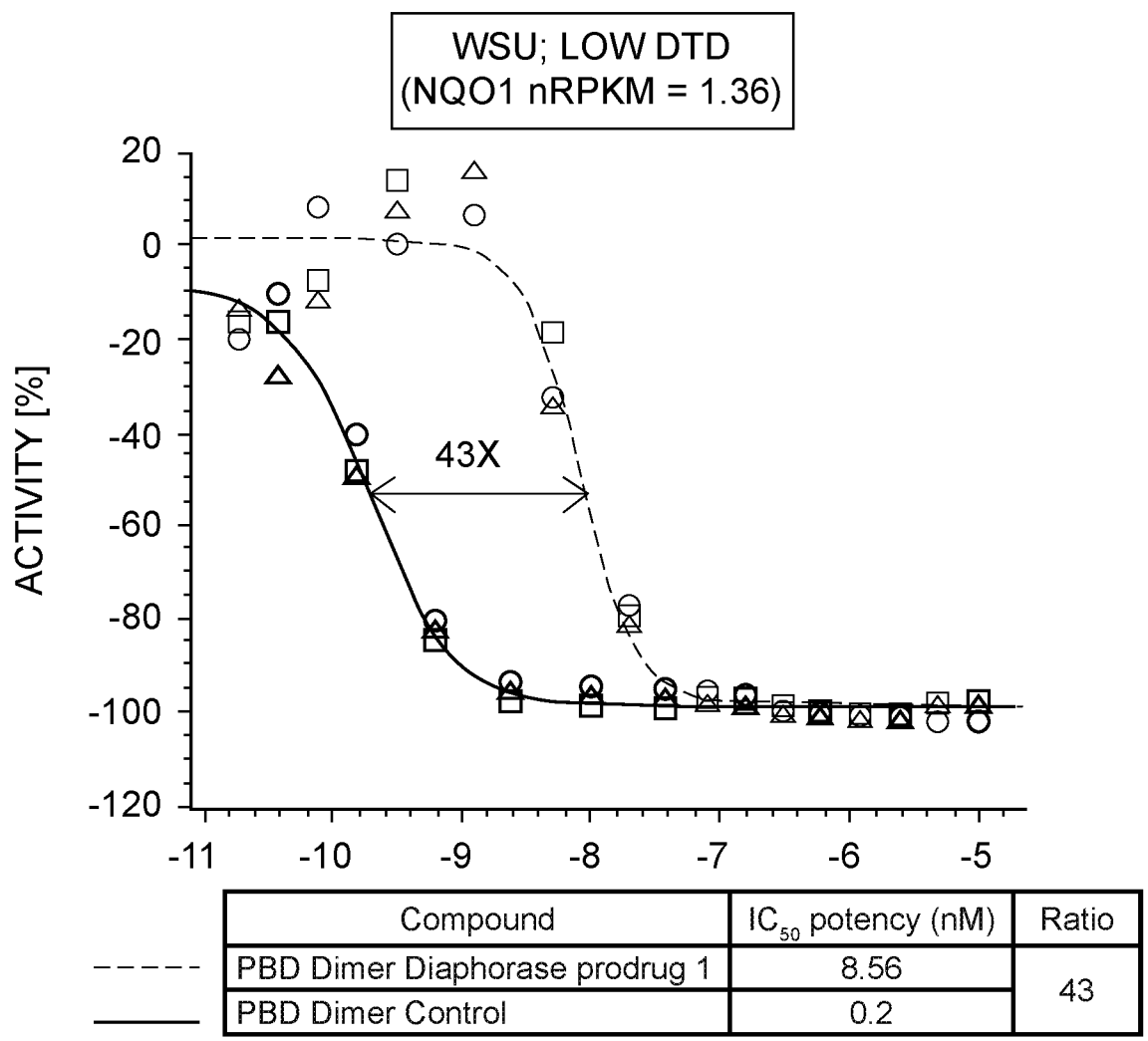
FIG. 18 depicts a plot of the Activity [%] against WSU cells versus the concentration in M of (i) a PBD dimer having a quinone prodrug at the N10 position of one PBD monomer and no prodrug or linker at the N10 position of the other PBD monomer and (ii) a PBD dimer not having a prodrug or a linker.
Figure 19:
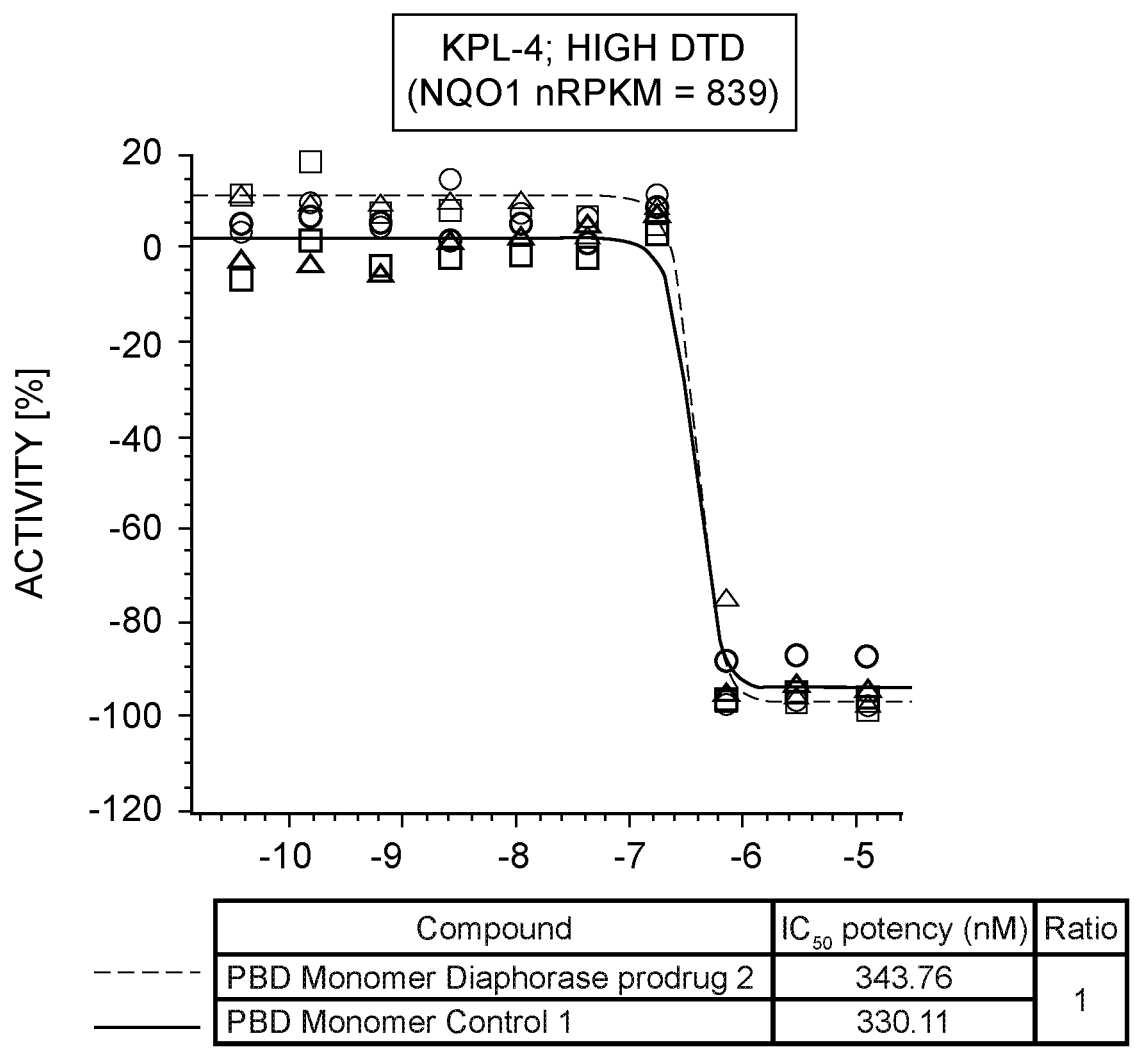
FIG. 19 depicts a plot of the Activity [%] against KPL-4 cells versus the concentration in M of (i) a PBD monomer having a quinone prodrug at the N10 and (ii) a PBD monomer not having a prodrug or a linker.
Figure 20:
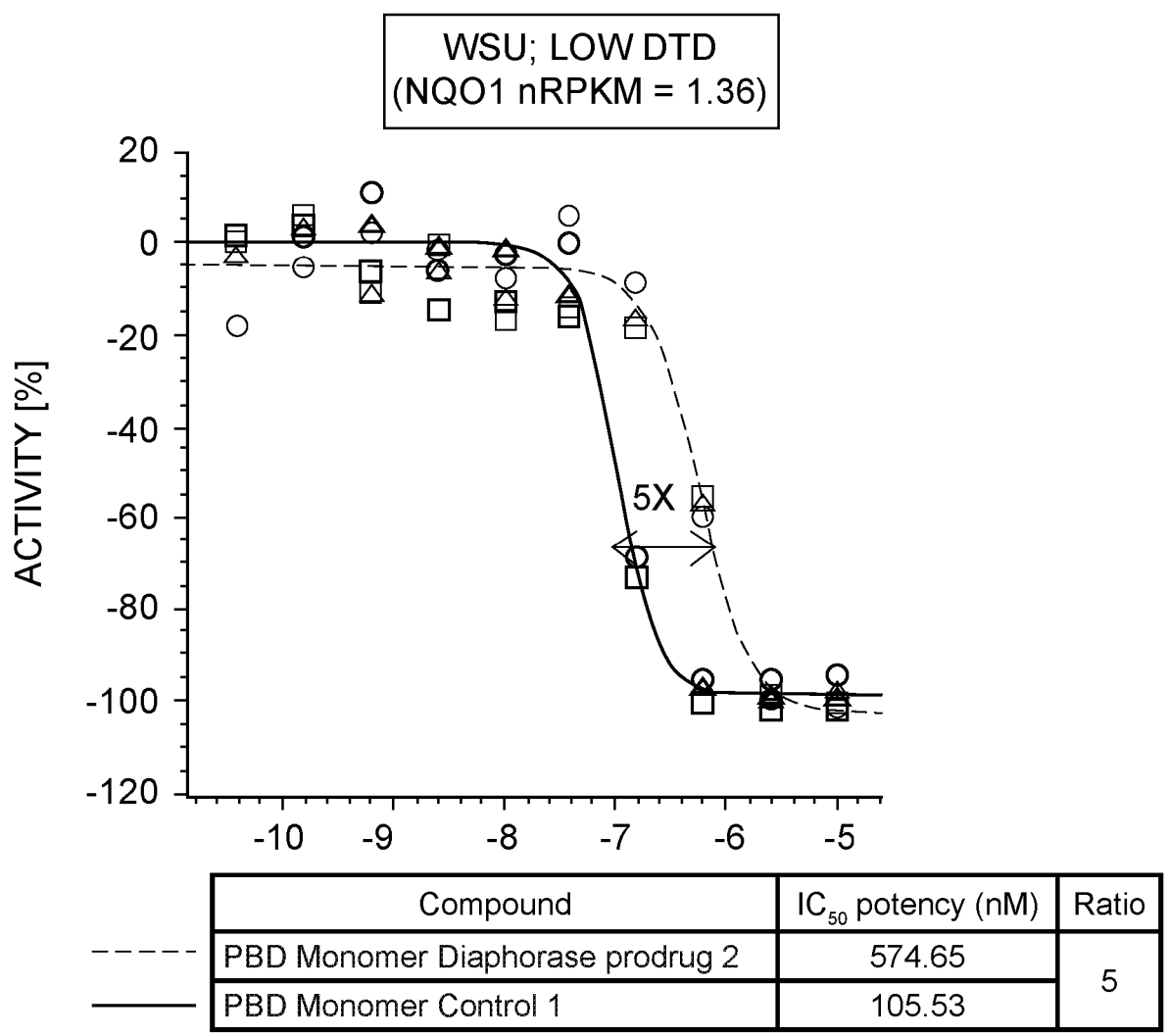
FIG. 20 depicts a plot of the Activity [%] against WSU cells versus the concentration in M of (i) a PBD monomer having a quinone prodrug at the N10 and (ii) a PBD monomer not having a prodrug or a linker.

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al. (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25); Cross-references: MIM:606509; NP_110391.2; NM_030764_1.

Figure 7:
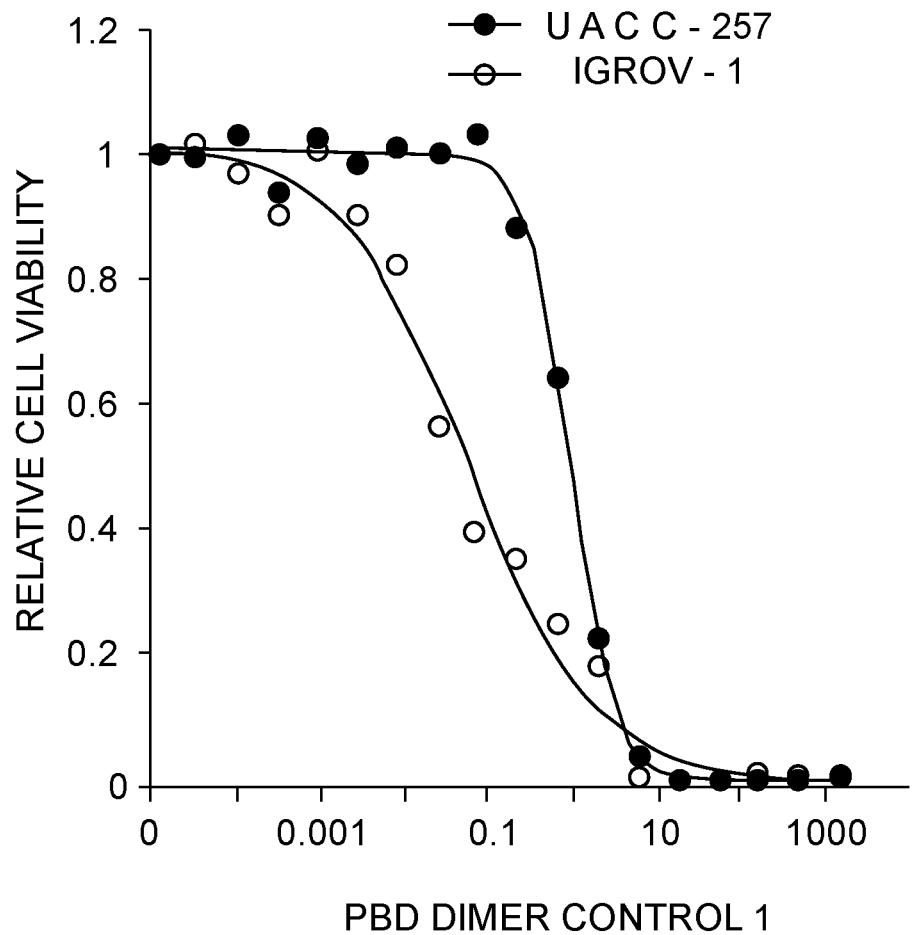
FIG. 7 depicts a plot of UACC-257 and IGROV-1 relative cell viability (% of control) versus a PBD dimer non-prodrug control concentration in nM and further depicts a table of PBD dimer $IC_{50}$ potency against the UACC-257 and IGROV-1 cells.

(17) HER2 (ErbB2, Genbank accession no. M11730) Coussens L., et al. Science (1985) 230(4730):1132-1139); Yamamoto T., et al. Nature 319, 230-234, 1986; Semba K., et al. Proc. Natl. Acad. Sci. U.S.A. 82, 6497-6501, 1985; Swiercz J. M., et al. J. Cell Biol. 165, 869-880, 2004; Kuhns J. J., et al. J. Biol. Chem. 274, 36422-36427, 1999; Cho H.-S., et al. Nature 421, 756-760, 2003; Ehsani A., et al. (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al. Genomics 3, 59-66, 1988; Tawaragi Y., et al. Biochem. Biophys. Res. Commun. 150, 89-96, 1988; Strausberg R. L., et al. Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2); Accession: P40199; Q14920; EMBL; M29541; AAA59915.1. EMBL; M18728.

Figure 8:
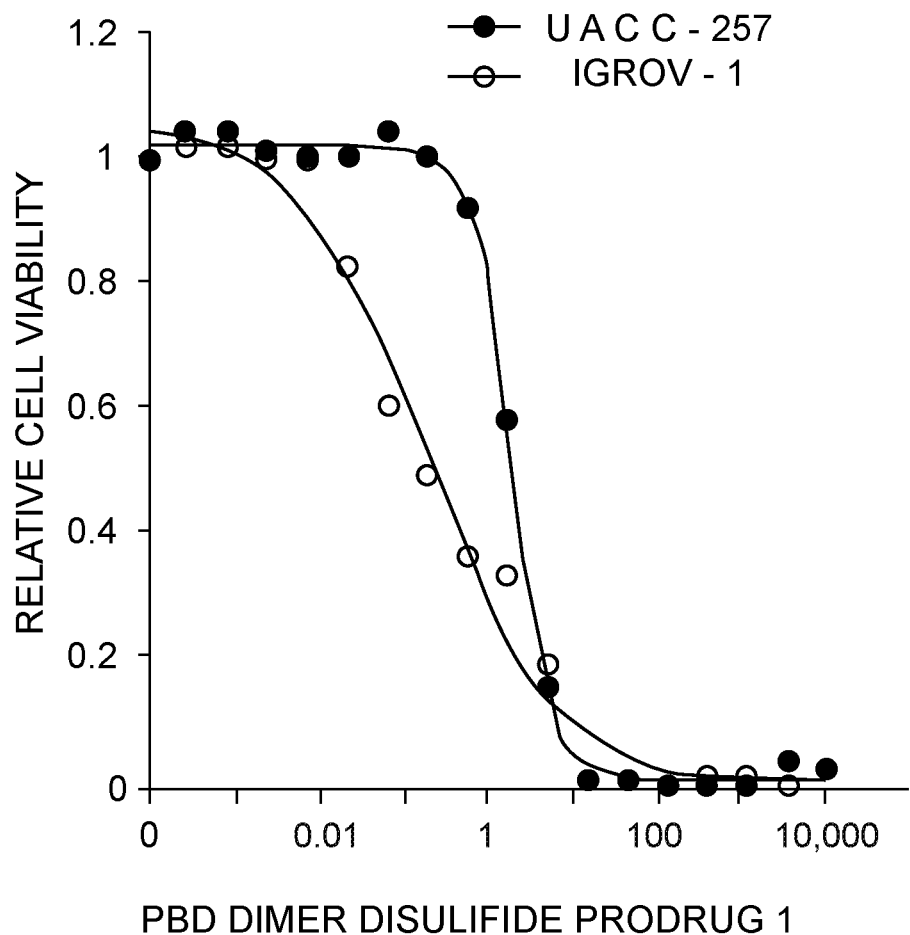
FIG. 8 depicts a plot of UACC-257 and IGROV-1 relative cell viability (% of control) versus the concentration in nM of a PBD dimer having a disulfide prodrug a one PBD monomer N10 position and not having a prodrug at the other PBD monomer and further depicts a table of PBD dimer $IC_{50}$ potency and $IC_{50}$ ratio for an indicated GSH concentration against the UACC-257 and IGROV-1 cells. The $IC_{50}$ ratio is determined relative to the data for the PBD dimer non-prodrug control depicted in FIG. 7.

(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1.

(20) IL20Rα (IL20Ra, ZCYTOR7, Genbank accession no. AF184971); Clark H. F., et al. Genome Res. 13, 2265-2270, 2003; Mungall A. J., et al. Nature 425, 805-811, 2003; Blumberg H., et al. Cell 104, 9-19, 2001; Dumoutier L., et al. J. Immunol. 167, 3545-3549, 2001; Parrish-Novak J., et al. J. Biol. Chem. 277, 47517-47523, 2002; Pletnev S., et al. (2003) Biochemistry 42:12617-12624; Sheikh F., et al. (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al. Gene 256, 139-147, 2000; Clark H. F., et al. Genome Res. 13, 2265-2270, 2003; Strausberg R. L., et al. Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1).

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1.

(23) ASLG659 (B7h, Genbank accession no. AX092328) US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318.

Figure 17:
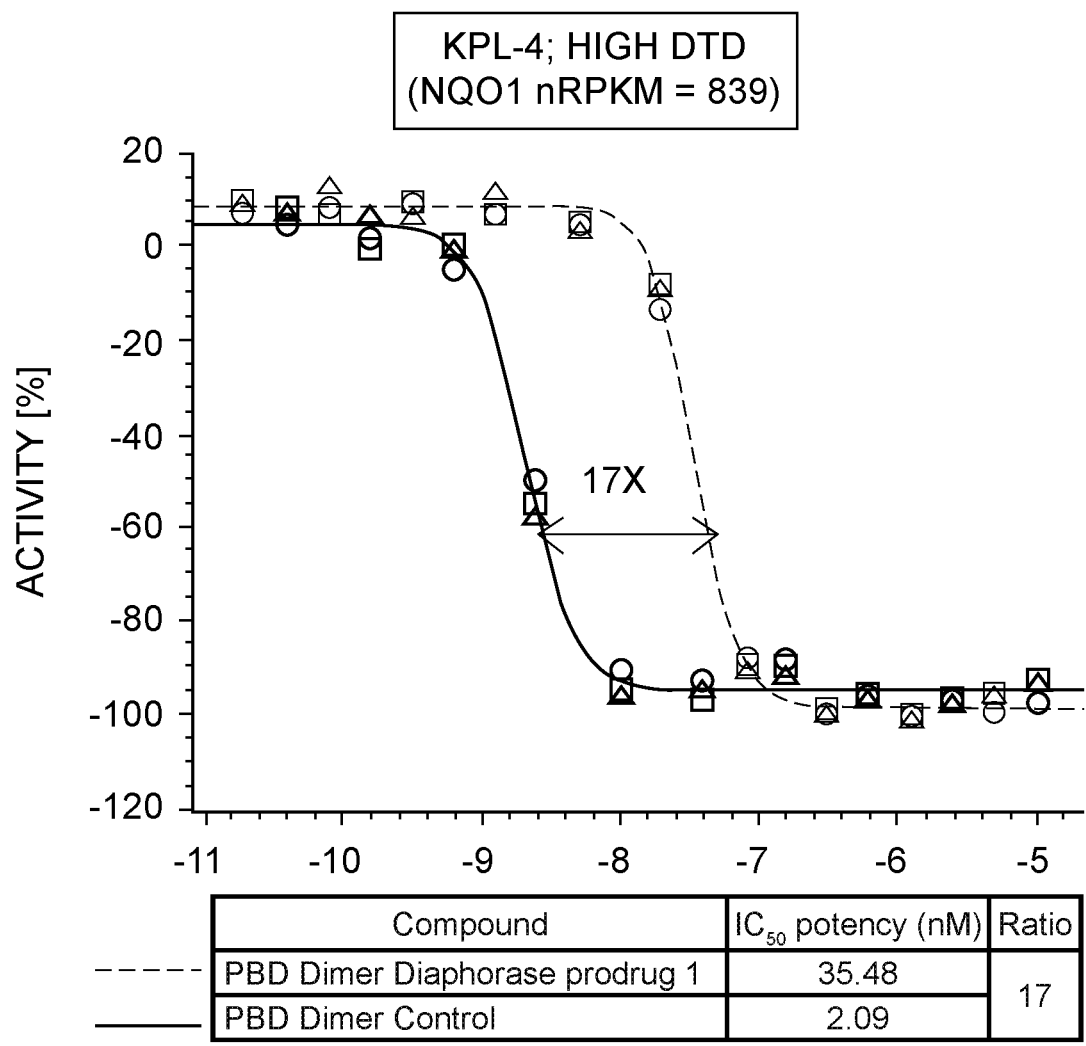
FIG. 17 depicts a plot of the Activity [%] against KPL-4 cells versus the concentration in M of (i) a PBD dimer having a quinone prodrug at the N10 position of one PBD monomer and no prodrug or linker at the N10 position of the other PBD monomer and (ii) a PBD dimer not having a prodrug or a linker.

(24) PSCA (Prostate stem cell antigen precursor, Genbank accession no. AJ297436) Reiter R. E., et al. Proc. Natl. Acad. Sci. U.S.A. 95, 1735-1740, 1998; Gu Z., et al. Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (claim 20); WO2003000842 (claim 1); WO2003023013 (Example 3, claim 20); US2003194704 (claim 45); Cross-references: GI:30102449; AAP14954.1; AY260763_1.

(26) BAFF-R (B cell-activating factor receptor, BLyS receptor 3, BR3, Genbank accession No. AF116456); BAFF receptor/pid=NP_443177.1—*Homo sapiens* Thompson, J. S., et al. Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP_443177.1; NM_052945 1; AF132600.

(27) CD22 (B-cell receptor CD22-B isoform, BL-CAM, Lyb-8, Lyb8, SIGLEC-2, FLJ22814, Genbank accession No. AK026467); Wilson et al. (1991) J. Exp. Med. 173:137-146; WO2003072036 (claim 1; FIG. 1); Cross-references: MIM: 107266; NP_001762.1; NM_001771_1.

Figure 16:
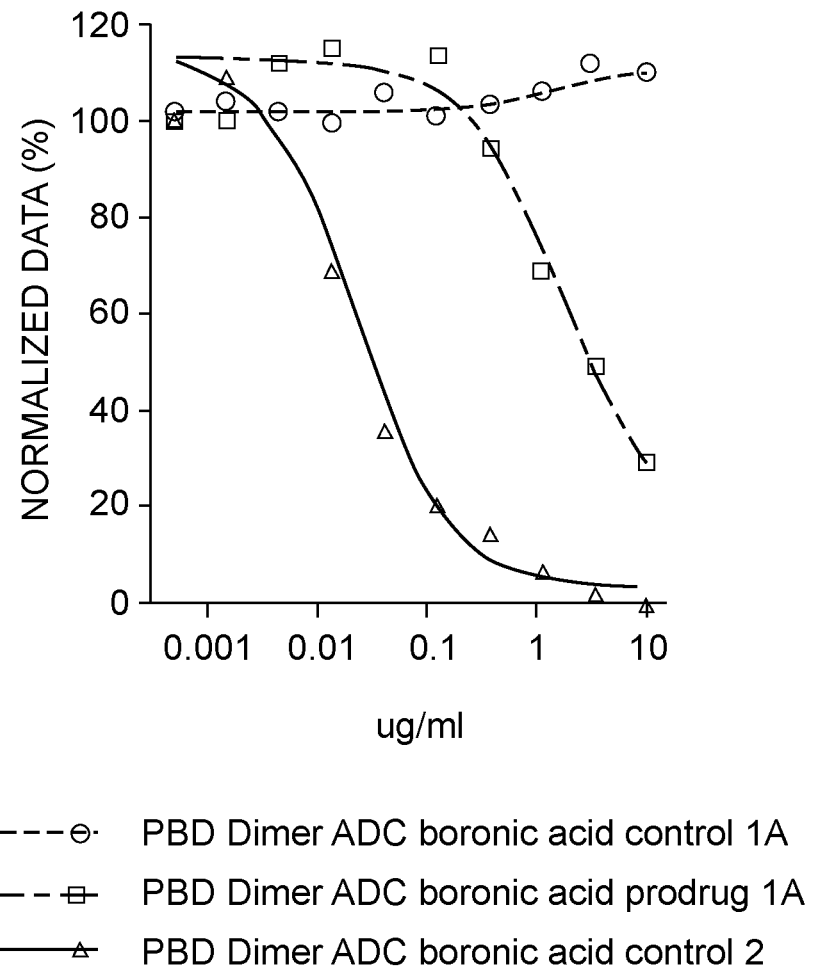
FIG. 16 depicts a plot of BJAB normalized percent of viable cells after 3 days as compared to the number of cells at time zero versus the concentration of (i) a CD22 antibody ADC PBD dimer having a benzyl formate ($C_6H_5$—$CH_2$—O—C(O)—) moiety at the N10 position of one PBD monomer (negative control), (ii) a CD22 antibody ADC PBD dimer aryl boronic acid prodrug (($OH)_2B$—$C_6H_4$—$CH_2$—O—C(O)—), and (iii) a CD22 antibody ADC PBD dimer not having a prodrug moiety (positive control).

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al. (1992) J. Immunol. 148(5):1526-1531; Mueller et al. (1992) Eur. J. Biochem. 22:1621-1625; Hashimoto et al. (1994) Immunogenetics 40(4):287-295; Preud'homme et al. (1992) Clin. Exp. Immunol. 90(1):141-146; Yu et al. (1992) J. Immunol. 148(2) 633-637; Sakaguchi et al. (1988) EMBO J. 7(11): 3457-3464.

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al. (1992) Eur. J. Immunol. 22:2795-2799; Barella et al. (1995) Biochem. J. 309:773-779.

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1) Tonnelle et al. (1985) EMBO J. 4(11):2839-2847; Jonsson et al. (1989) Immunogenetics 29(6):411-413; Beck et al. (1992) J. Mol. Biol. 228:433-441; Strausberg et al. (2002) Proc. Natl. Acad. Sci USA 99:16899-16903; Servenius et al. (1987) J. Biol. Chem. 262:8759-8766; Beck et al. (1996) J. Mol. Biol. 255:1-13; Naruse et al. (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al. (1989) Immunogenetics 30(1):66-68; Larhammar et al. (1985) J. Biol. Chem. 260(26):14111-14119.

(31) P2X5 (Purinergic receptor P2x ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2) Le et al. (1997) FEBS Lett. 418(1-2):195-199; WO2004047749; WO2003072035 (claim 10); Touchman et al. (2000) Genome Res. 10:165-173; WO200222660 (claim 20); WO2003093444 (claim 1); WO2003087768 (claim 1); WO2003029277 (page 82).

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al. (1990) J. Immunol. 144(12):4870-4877; Strausberg et al. (2002) Proc. Natl. Acad. Sci USA 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al. (1996) Genomics 38(3):299-304; Miura et al. (1998) Blood 92:2815-2822; WO2003083047; WO9744452 (claim 8, pages 57-61); WO200012130 (pages 24-26).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al. (2001) Proc. Natl. Acad. Sci USA 98(17):9772-9777; WO2003089624 (claim 8); EP1347046 (claim 1); WO2003089624 (claim 7).

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085;

Mouse:AK089756, AY158090, AY506558; NP_112571.1. WO2003024392 (claim 2, FIG. 97); Nakayama et al. (2000) Biochem. Biophys. Res. Commun. 277(1):124-127; WO2003077836; WO200138490 (claim 3, FIG. 18B-1-18B-2).

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al. (2000) Genomics 67:146-152; Uchida et al. (1999) Biochem. Biophys. Res. Commun. 266:593-602; Liang et al. (2000) Cancer Res. 60:4907-12; Glynne-Jones et al. (2001) Int J Cancer. October 15; 94(2): 178-84.

(37) PMEL17 (silver homolog; SILV; D12S53E; PMEL17; SI; SIL); ME20; gp100) BC001414; BT007202; M32295; M77348; NM_006928; McGlinchey, R. P. et al. (2009) Proc. Natl. Acad. Sci. U.S.A. 106 (33), 13731-13736; Kummer, M. P. et al. (2009) J. Biol. Chem. 284 (4), 2296-2306.

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al. (2003) Oncogene 22 (18):2723-2727.

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al. (2009) Mol. Cell. Biol. 29 (8), 2264-2277; Treanor, J. J. et al. (1996) Nature 382 (6586):80-83.

(40) Ly6E (lymphocyte antigen 6 complex, locus E; Ly67, RIG-E,SCA-2,TSA-1); NP_002337.1; NM_002346.2; de Nooij-van Dalen, A. G. et al. (2003) Int. J. Cancer 103 (6), 768-774; Zammit, D. J. et al. (2002) Mol. Cell. Biol. 22 (3):946-952.

(41) TMEM46 (shisa homolog 2 (Xenopus laevis); SHISA2); NP_001007539.1; NM_001007538.1; Furushima, K. et al. (2007) Dev. Biol. 306 (2), 480-492; Clark, H. F. et al. (2003) Genome Res. 13 (10):2265-2270.

(42) Ly6G6D (lymphocyte antigen 6 complex, locus G6D; Ly6-D, MEGT1); NP_067079.2; NM_021246.2; Mallya, M. et al. (2002) Genomics 80 (1):113-123; Ribas, G. et al. (1999) J. Immunol. 163 (1):278-287.

(43) LGR5 (leucine-rich repeat-containing G protein-coupled receptor 5; GPR49, GPR67); NP_003658.1; NM_003667.2; Salanti, G. et al. (2009) Am. J. Epidemiol. 170 (5):537-545; Yamamoto, Y. et al. (2003) Hepatology 37 (3):528-533.

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al. (2009) Cancer Sci. 100 (10):1895-1901; Narita, N. et al. (2009) Oncogene 28 (34):3058-3068.

(45) LY6K (lymphocyte antigen 6 complex, locus K; LY6K; HSJ001348; FLJ35226); NP_059997.3; NM_017527.3; Ishikawa, N. et al. (2007) Cancer Res. 67 (24):11601-11611; de Nooij-van Dalen, A. G. et al. (2003) Int. J. Cancer 103 (6):768-774.

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al. (1996) FEBS Lett. 394 (3):325-329.

(47) GPR54 (K1SS1 receptor; KISS1R; GPR54; HOT7T175; AXOR12); NP_115940.2; NM_032551.4; Navenot, J. M. et al. (2009) Mol. Pharmacol. 75 (6):1300-1306; Hata, K. et al. (2009) Anticancer Res. 29 (2):617-623.

(48) ASPHD1 (aspartate beta-hydroxylase domain containing 1; LOC253982); NP_859069.2; NM_181718.3; Gerhard, D. S. et al. (2004) Genome Res. 14 (10B):2121-2127.

(49) Tyrosinase (TYR; OCAIA; OCA1A; tyrosinase; SHEP3); NP_000363.1; NM_000372.4; Bishop, D. T. et al. (2009) Nat. Genet. 41 (8):920-925; Nan, H. et al. (2009) Int. J. Cancer 125 (4):909-917.

(50) TMEM118 (ring finger protein, transmembrane 2; RNFT2; FLJ14627); NP_001103373.1; NM_001109903.1; Clark, H. F. et al. (2003) Genome Res. 13 (10):2265-2270; Scherer, S. E. et al. (2006) Nature 440 (7082):346-351.

(51) GPR172A (G protein-coupled receptor 172A; GPCR41; FLJ11856; D15Ertd747e); NP_078807.1; NM_024531.3; Ericsson, T. A. et al. (2003) Proc. Natl. Acad. Sci. U.S.A. 100 (11):6759-6764; Takeda, S. et al. (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al. (2005) Cancer Res. 64 (22):8443-50; Marshall A S, et al. (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

In any of the antibody embodiments of the disclosure, an antibody is humanized. In one embodiment, an antibody comprises HVRs as in any of the embodiments of the disclosure, and further comprises a human acceptor framework, e.g. a human immunoglobulin framework or a human consensus framework. In certain embodiments, the human acceptor framework is the human VL kappa I consensus (VLKI) framework and/or the VH framework VH1. In certain embodiments, the human acceptor framework is the human VL kappa I consensus (VLKI) framework and/or the VH framework VH1 comprising any one of the following mutations.

In another embodiment, the antibody comprises a VH as in any of the embodiments provided herein, and a VL as in any of the embodiments provided herein.

In a further embodiment of the disclosure, an antibody according to any of the embodiments herein is a monoclonal antibody, including a human antibody. In one embodiment, an antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein. In some particular embodiments, the antibody is selected from anti-HER2, anti-CD22, anti-CD33, anti-Napi2b, and anti-CLL-1.

In a further embodiment, an antibody according to any of the embodiments herein may incorporate any of the features, singly or in combination, as described herein.

B. Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$M. (e.g. $10^{-8}$M or less, e.g. from $10^{-8}$M to $10^{-13}$M, e.g., from $10^{-9}$M to $10^{-13}$M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™, Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000, BIACORE®-T200 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) and/or HBS-P (0.01 M Hepes pH7.4, 0.15M NaCl, 0.005% Surfactant P20) before injection at a flow rate of 5 µl/minute and/or 30 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay describe herein, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

C. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described herein. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

D. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

E. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described herein.

F. Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self- and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

G. Multispecific Antibodies

In certain embodiments, an antibody provided herein is a multispecific antibody, e.g. a bispecific antibody. The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). In some embodiments, multispecific antibodies are monoclonal antibodies that have binding specificities for at least two different sites. In some embodiments, an antigen-binding domain of a multispecific antibody (such as a bispecific antibody) comprises two VH/VL units, wherein a first VH/VL unit specifically binds to a first epitope and a second VH/VL unit specifically binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further herein.

In certain embodiments, a multispecific antibody provided herein may be a bispecific antibody. The term "bispecific antibody" is used in the broadest sense and covers a multispecific antibody comprising an antigen-binding domain that is capable of specifically binding to two different epitopes on one biological molecule or is capable of specifically binding to epitopes on two different biological molecules. A bispecific antibody may also be referred to herein as having "dual specificity" or as being "dual specific." Bispecific antibodies can be prepared as full length antibodies or antibody fragments. The term "biparatopic antibody" as used herein, refers to a bispecific antibody where a first antigen-binding domain and a second antigen-binding domain bind to two different epitopes on the same antigen molecule or it may bind to epitopes on two different antigen molecules.

In some embodiments, the first antigen-binding domain and the second antigen-binding domain of the biparatopic antibody may bind the two epitopes within one and the same antigen molecule (intramolecular binding). For example, the first antigen-binding domain and the second antigen-binding domain of the biparatopic antibody may bind to two different epitopes on the same antibody molecule. In certain embodiments, the two different epitopes that a biparatopic antibody binds are epitopes that are not normally bound at the same time by one monospecific antibody, such as e.g. a conventional antibody or one immunoglobulin single variable domain.

In some embodiments, the first antigen-binding domain and the second antigen-binding domain of the biparatopic antibody may bind epitopes located within two distinct antigen molecules.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168), WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, and Zhu et al., 1997, Protein Science 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W. In some embodiments, a hole mutation in an IgG1 constant region comprises one or more mutations selected from T366S, L368A and Y407V. In some embodiments, a hole mutation in an IgG1 constant region comprises T366S, L368A and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (Hollinger et al., *Proc. Natl. Acad. Sci. USA,* 90:6444-6448 (1993)); and using single-chain Fv (sFv) dimers (Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (US 2006/0025576A1, and Wu et al. (2007) *Nature Biotechnology*).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056 which is incorporated by reference in its entirety). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581 which is incorporated by reference in its entirety).

In certain embodiments Pro329 of a wild-type human Fc region is substituted with glycine or arginine or an amino acid residue large enough to destroy the proline sandwich within the Fc/Fcγ receptor interface, that is formed between the proline329 of the Fc and tryptophan residues Trp 87 and Trp 110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region (U.S. Pat. No. 8,969,526 which is incorporated by reference in its entirety).

In certain embodiments, a polypeptide comprises the Fc variant of a wild-type human IgG Fc region wherein the polypeptide has Pro329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU index of Kabat (U.S. Pat. No. 8,969,526 which is incorporated by reference in its entirety). In certain embodiments, the polypeptide comprising the P329G, L234A and L235A substitutions exhibit a reduced affinity to the human FcγRIIIA and FcγRIIA, for down-modulation of ADCC to at least 20% of the ADCC induced by the polypeptide comprising the wild type human IgG Fc region, and/or for down-modulation of ADCP (U.S. Pat. No. 8,969,526 which is incorporated by reference in its entirety).

In a specific embodiment the polypeptide comprising an Fc variant of a wild type human Fc polypeptide comprises a triple mutation: an amino acid substitution at position Pro329, a L234A and a L235A mutation (P329/LALA) (U.S. Pat. No. 8,969,526 which is incorporated by reference in its entirety). In specific embodiments, the polypeptide comprises the following amino acid substitutions: P329G, L234A, and L235A.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

H. Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. In certain embodiments, any one or more of the following residues may be substituted with cysteine: V205 (Kabat numbering) of the light chain; K149 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In some embodiments, a THIOMAB™ antibody comprises one of the heavy or light chain cysteine substitutions listed in Table A below.

TABLE A

| Chain (HC/LC) | Residue | Screening Mutation Site # | GNE Mutation Site # | Kabat Mutation Site # |
|---|---|---|---|---|
| LC | T | 22 | 22 | 22 |
| LC | K | 39 | 39 | 39 |
| LC | Y | 49 | 49 | 49 |
| LC | Y | 55 | 55 | 55 |
| LC | T | 85 | 85 | 85 |
| LC | T | 97 | 97 | 97 |
| LC | I | 106 | 106 | 106 |
| LC | R | 108 | 108 | 108 |
| LC | R | 142 | 142 | 142 |
| LC | K | 149 | 149 | 149 |
| LC | V | 205 | 205 | 205 |
| HC | T | 117 | 114 | 110 |
| HC | A | 143 | 140 | 136 |
| HC | L | 177 | 174 | 170 |
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In other embodiments, a THIOMAB™ antibody comprises one of the heavy chain cysteine substitutions listed in Table B.

TABLE B

| Chain (HC/LC) | Residue | Screening Mutation Site # | GNE Mutation Site # | Kabat Mutation Site # |
|---|---|---|---|---|
| HC | T | 117 | 114 | 110 |
| HC | A | 143 | 140 | 136 |
| HC | L | 177 | 174 | 170 |

TABLE B-continued

| Chain (HC/LC) | Residue | Screening Mutation Site # | GNE Mutation Site # | Kabat Mutation Site # |
|---|---|---|---|---|
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In some other embodiments, a THIOMAB™ antibody comprises one of the light chain cysteine substitutions listed in Table C.

TABLE C

| Chain (HC/LC) | Residue | Screening Mutation Site # | GNE Mutation Site # | Kabat Mutation Site # |
|---|---|---|---|---|
| LC | I | 106 | 106 | 106 |
| LC | R | 108 | 108 | 108 |
| LC | R | 142 | 142 | 142 |
| LC | K | 149 | 149 | 149 |

In some other embodiments, a THIOMAB™ antibody comprises one of the heavy or light chain cysteine substitutions listed in Table D.

TABLE D

| Chain (HC/LC) | Residue | Screening Mutation Site # | GNE Mutation Site # | Kabat Mutation Site # |
|---|---|---|---|---|
| LC | K | 149 | 149 | 149 |
| HC | A | 143 | 140 | 136 |
| HC | A | 121 | 118 | 114 |

Cysteine engineered antibodies which may be useful in the antibody-drug conjugates (ADC) of the disclosure in the treatment of cancer include, but are not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

VI. Prodrug Preparation

Methods for the preparation of PBD monomer prodrugs and PBD dimer prodrugs within the scope of the present disclosure are described elsewhere herein.

VII. Linker-Drug Conjugation

Conjugation of the linker to a PBD amine may suitably be done according to the methods of WO 2013/055987, WO 2015/023355 and WO 2015/095227, each of which is incorporated by reference herein in its entirety.

In some such embodiments, an activated linker as described elsewhere herein is combined with a solution of PBD monomer or dimer to form a linker-PBD conjugate. Generally, any solvent capable of providing a solution comprising from about 0.05 to about 1 mole per liter PBD is suitable. In some embodiments, the solvent is DCM. In some other linker-PBD conjugation embodiments, a solution of PBD, a stoichiometric excess of triphosgene (or diphosgene or phosgene), and a base (e.g., 4-dimethylaminopyridine) is formed in a solvent (e.g., dry DCM). The linker intermediate having an alcohol moiety (as described elsewhere herein) is combined with the PBD solution to form a reaction mixture that is stirred until the reaction is complete to form a product mixture comprising the linker-PBD conjugate. The reaction mixture may suitably comprise from about 0.005 moles per liter to about 0.5 moles per liter of PBD, from about 2 to about 10 equivalents of linker intermediate per equivalent of PBD, and from about 0.02 to about 0.5 equivalents of base. After reaction completion, the linker-PBD conjugate may be isolated, such as by solvent evaporation, and purified by methods known in the art such as one or more of extraction, reverse phase high pressure liquid chromatography, ion exchange chromatography or flash chromatography.

VIII. Preparation of Disulfide Conjugate Compounds

In some embodiments, disulfide conjugate compounds of the disclosure of formula:

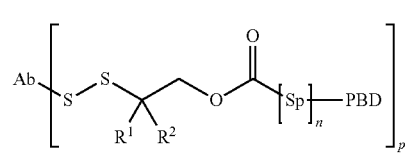

may be prepared by forming a reaction mixture comprising (1) a solvent system comprising water, (2) a source of an antibody comprising at least one cysteine having a sulfhydryl moiety, and (3) a stoichiometric excess of a source of a linker-PBD conjugate of the following formula:

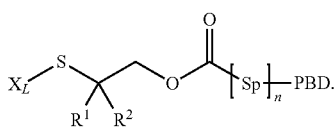

The antibody, $X_L$, $R^1$, $R^2$, Sp, n and D are as described elsewhere herein. The reaction mixture is reacted to form a mixture comprising the disulfide conjugate compound of formula (II), wherein p is 1, 2, 3, 4, 5, 6, 7 or 8. Although the individual disulfide conjugate compounds in a mixture may have a p value of from 1 to 8, and some antibody molecules in such a mixture may be unconjugated (p=0), the PBD to antibody ratio for a plurality of formed disulfide conjugate compounds in the product mixture, expressed as the ratio of PBD equivalents to antibody equivalents, is from about 1 to about 5, from about 1.5 to about 3, from about 1.5 to about 2.5, from about 1.7 to about 2.3, from about 1.8 to about 2.2, or about 2.

In any of the various embodiments of such embodiments, the source of the antibody may be provided in solution in an aqueous buffer. In some such embodiments, the buffer may suitably be N-(2-Acetamido)-aminoethanesulfonic acid ("ACES"); acetate salt; N-(2-Acetamido)-iminodiacetic acid ("ADA"); 2-Aminoethanesulfonic acid, Taurine ("AES"); 2-Amino-2-methyl-1-propanol ("AMP"); 2-Amino-2-methyl-1,3-propanediol, Ammediol ("AMPD"); N-(1,1-Dimethyl-2-hydroxyethyl)-3-amino-2-hydroxypropanesulfonic acid ("AMPSO"); N,N-Bis-(2-hydroxyethyl)-2-aminoethanesulfonic acid ("BES"); N,N'-Bis(2-hydroxyethyl)-glycine ("Bicine"); [Bis-(2-hydroxyethyl)-imino]-tris-(hydroxymethylmethane) ("BIS-Tris"); 1,3-Bis[tris(hydroxymethyl)-methylamino]propane ("BIS-Tris-Propane"); Dimethylarsinic acid ("Cacodylate"); 3-(Cyclohexylamino)-2-hydroxy-1-propanesulfonic acid ("CAPSO"); Cyclohexylaminoethanesulfonic acid ("CHES"); citric acid salt; 3-[N-Bis(hydroxyethyl)amino]-2-hydroxypropanesulfonic acid ("DIPSO"); N-(2-Hydroxyethyl)-piperazine-N'-ethanesulfonic acid ("HEPES"); N-(2-Hydroxyethyl)-piperazine-N'-3-propanesulfonic acid ("HEPPS, EPPS"); N-(2-Hydroxyethyl)-piperazine-N'-2-hydroxypropanesulfonic acid ("HEPPSO"); 2-(N-Morpholino)-ethanesulfonic acid ("MES"); 3-(N-Morpholino)-propanesulfonic acid ("MOPS"); 3-(N-Morpholino)-2-hydroxypropanesulfonic acid ("MOPSO"); Piperazine-N,N'-bis(2-ethanesulfonic acid) ("PIPES"); Piperazine-N,N'-bis(2-hydroxypropanesulfonic acid) ("POPSO"); salt of succinic acid; 3-{[Tris(hydroxymethyl)-methyl]-amino}-propanesulfonic acid ("TAPS"); 3-[N-Tris(hydroxymethyl)-methylamino]-2-hydroxypropanesulfonic acid ("TAPSO"); 2-Aminoethanesulfonic acid, AES ("Taurine"); Triethanolamine ("TEA"); 2-[Tris(hydroxymethyl)-methylamino]-ethanesulfonic acid ("TES"); N-[Tris(hydroxymethyl)-methyl]-glycine ("Tricine"); Tris(hydroxymethyl)-aminomethane ("TRIS"). In some such embodiments, the buffer may be succinate or tris. The buffer concentration is suitably about 5 mM, about 10 mM, about 15 mM, about 20 mM, about 50 mM, about 100 mM, or about 150 nM, such as from about 5 mM to about 150 mM, from about 5 mM to about 30 mM, from about 5 mM to about 20 mM, from about 5 mM to about 10 mM, or from about 50 mM to about 100 nM. The concentration of the antibody in the buffer may be about 1 mg/mL, about 5 mg/mL, about 10 mg/mL or more. The pH of the antibody solution is suitably from about 4 to about 8, from about 4 to about 6, or about 5.

In any of the various embodiments of such embodiments, the source of a linker-PBD conjugate compound ("activated linker-PBD conjugate") may generally be formed by dissolving an activated hindered linker-PBD conjugate in a solvent comprising at least one polar aprotic solvent selected from acetonitrile, tetrahydrofuran, ethyl acetate, acetone, N,N-dimethylformamide, dimethyl acetamide, dimethylsulfoxide, propylene glycol, ethylene glycol and dichloromethane. In some embodiments, the solvent comprises, predominantly comprises, or consists essentially of N,N-dimethylformamide and/or dimethyl acetamide.

The source of the antibody and the source of the activated linker-PBD conjugate may suitably be admixed to form a reaction mixture. The antibody concentration in the reaction mixture is suitably about 1 mg/mL, about 5 mg/mL, about 10 mg/mL, about 15 mg/mL, about 20 mg/mL, or about 25 mg/mL, and ranges thereof, such as from about 1 mg/mL to about 25 mg/mL, from about 1 mg/mL to about 20 mg/mL, from about 1 mg/mL to about 15 mg/mL, from about 1 mg/mL to about 10 mg/mL, from about 5 mg/mL to about 25 mg/mL, from about 5 mg/mL to about 20 mg/mL or from about 5 mg/mL to about 15 mg/mL. The equivalent ratio of activated linker-PBD conjugate to the antibody is suitably about 2:1, about 3:1, about 5:1, about 10:1, about 15:1 or about 20:1, and ranges thereof, such as from about 2:1 to about 20:1, from about 3:1 to about 15:1, from about 3:1 to about 10:1, or from about 5:1 to about 10:1. In some embodiments of the present disclosure, the reaction mixture solvent system predominantly comprises water. In some other embodiments, the reaction mixture solvent system may generally comprise at least 75 v/v % of a buffer as described elsewhere herein and about 5 v/v %, about 10 v/v %, about 15 v/v %, about 20 v/v %, about 25 v/v % or about 30 v/v %, and ranges thereof, such as from about 5 v/v % to about 30 v/v %, from about 5 v/v % to about 20 v/v %, from about 5 v/v % to about 15 v/v %, or about 10 v/v % of a polar aprotic solvent as described elsewhere herein. In some other embodiments, the reaction mixture solvent system may generally comprise at least 50 v/v % of a buffer as described elsewhere herein and between about 10 v/v % and about 50 v/v %, such as about 10 v/v %, about 20 v/v %, about 30 v/v % about 40 v/v % or above 50 v/v % propylene glycol or ethylene glycol. Alternatively stated, the reaction mixture solvent system may comprise, about 50 v/v %, about 60 v/v %, about 70 v/v %, 75 v/v %, about 80 v/v %, about 85 v/v %, about 90 v/v % or about 95 v/v % water to about 95 v/v %, and ranges thereof, such as from about 50 v/v % to about 95 v/v % water, from about 75 v/v % to about 95 v/v % water, from about 80 v/v % to about 95 v/v % water or from about 85 v/v % to about 95 v/v % water. The pH of the reaction mixture is suitably about 5.0, about 5.5, about 6.0, about 6.5, about 7.0, about 7.5, about 8.0, about 8.5 or about 9.0, and ranges thereof, such as from about 5.0 to about 9.0, from about 5.0 to about 9.0, from about 6.0 to about 9.0, from about 6.5 to about 9.0, or from about 7.0 to about 9.0, or from about 7.5 to about 8.5.

The reaction mixture is incubated at about 10° C., about 15° C., about 20° C., about 25° C., about 30° C., about 35° C., about 40° C., about 45° C. or about 50° C., and ranges thereof such as from about 10° C. to about 50° C., from about 15° C. to about 45° C., from about 15° C. to about 40° C., from about 20° C. to about 40° C., from about 20° C. to about 35° C., or from about 20° C. to about 30° C. for about 0.5 hours, about 1 hour, about 4 hours, about 8 hours, about 12 hours, about 18 hours about 24 hours, about 36 hours or about 48 hours, and ranges thereof, such as from about 0.5 hours to about 48 hours, or from about 1 hour to about 24 hours to form a product mixture comprising the disulfide conjugate compound of formula (II).

The product mixture may comprise at least 60 A % antibody-linker-PBD conjugate as determined by MS/LC, at least 65 area %, at least 70 area %, at least 75 area %, at least 80 area %, at least 85 area %, or at least 90 area %. The product mixture may further comprise at least one leaving group byproduct species. In some embodiments, the area percentage of total leaving group byproduct species as compared to the area percentage of formed disulfide conjugate compound as measured by MS/LC is less than 10 area %, less than 5 area %, less than 4 area %, less than 3 area %, less than 2 area %, less than 1 area %, less than 0.5 area %. In the case of antibodies, and based on experimental evidence to date, the leaving group byproduct species may comprise:

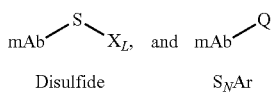

wherein $X_L$ is as defined elsewhere herein and wherein Q refers to an $X_L$ moiety not having a sulfur linking atom. Exemplary X and corresponding Q are illustrated below:

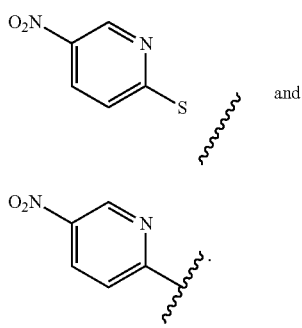

The reaction mixture may further comprise unconjugated antibody compounds comprising (i) unconjugated antibody monomer species comprising at least one disulfide bond formed by the reaction of two cysteine sulfhydryl moieties, (ii) unconjugated antibody dimer species comprising at least one disulfide bond formed by the reaction of two cysteine sulfhydryl moieties, and (iii) a combination of unconjugated antibody monomer species and unconjugated antibody dimer species. In some embodiments, the total concentration of unconjugated antibody compounds compared to the area percentage of formed disulfide conjugate compounds as measured by MS/LC is less than 10 area %, less than 5 area %, less than 4 area %, less than 3 area %, less than 2 area %, less than 1 area %, less than 0.5 area %, less than 0.3 area %, less than 0.1 area %, or is not detectable.

IX. PBD Prodrug Methods of Treatment

It is contemplated that the PBD prodrug conjugate compounds of the present disclosure may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In one embodiment, a PBD prodrug conjugate compounds provided herein is used in a method of inhibiting proliferation of a cancer cell, the method comprising exposing the cell to the antibody-prodrug conjugate under conditions permissive for binding of the antibody or antibody-prodrug conjugates to a tumor-associated antigen on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) J. Immunol. Meth. 160:81-88, U.S. Pat. No. 6,602, 677. The assay may be conducted in 96- or 384-well format, making it amenable to automated high-throughput screening (HTS). See Cree et al. (1995) AntiCancer Drugs 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another embodiment, a PBD prodrug conjugate compound for use as a medicament is provided. In further embodiments, a PBD prodrug conjugate compound for use in a method of treatment is provided. In certain embodiments, a PBD prodrug conjugate compound for use in treating cancer is provided. In certain embodiments, the disclosure provides a PBD prodrug conjugate compound for use in a method of treating an individual comprising administering to the individual an effective amount of the PBD prodrug conjugate compound.

PBD prodrug conjugate compounds of the disclosure can be used either alone or in combination with other agents in a therapy. For instance, an antibody or immunoconjugate of the disclosure may be co-administered with at least one additional therapeutic agent. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is 5-azacytidine or decitabine.

Such combination therapies noted herein encompass combined administration (where two or more therapeutic agents are included in the same or separate formulations), and separate administration, in which case, administration of the compounds of the disclosure can occur prior to, simultaneously, and/or following, administration of the additional therapeutic agent and/or adjuvant. Compounds of the disclosure can also be used in combination with radiation therapy.

Compounds of the disclosure (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Compounds of the disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Compounds of the disclosure need not be, but are optionally formulated with one or more agents currently used to prevent or treat the disorder in question. The effective amount of such other agents depends on the amount of the compound of the disclosure present in the formulation, the type of disorder or treatment, and other factors discussed herein. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of the disclosure (when used alone or in combination with one or more other additional therapeutic agents) will depend on the type of disease to be treated, the type of compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g. 0.1 mg/kg-10 mg/kg) of a compound of the disclosure can be an initial candidate dosage for administration to the patient, whether, for example, by one or more separate administrations, or by continuous infusion. One typical daily dosage might range from about 1 µg/kg to 100 mg/kg or more, depending on the factors mentioned herein. For repeated administrations over several days or longer, depending on the condition, the treatment would generally be sustained until a desired suppression of disease symptoms occurs. One exemplary dosage of the compound would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Intracellular release of the drug from the PBD prodrug conjugate compound in a target cell is believed to result from a combination of linker immolation and (i) GSH-activation of a disulfide trigger, (ii) DTD-activation of an quinone trigger or (iii) ROS-activation of an aryl boronic acid or an aryl boronic ester trigger.

In connection with linkers comprising a disulfide moiety, GSH-mediated release provides for advantages as compared to certain linkers known in the prior art, such as acid-labile hydrazine linkers. More particularly, blood concentration of GSH is known to be very low, such as in the micromolar range, whereas intracellular GSH concentration is typically up to three orders of magnitude greater, such as in the millimolar range. It is further believed that GSH concentration in cancer cells is even greater due to increased activity of reductive enzymes. It is yet further believed that steric hindrance at the linker carbon atom bearing a sulfur atom provides for improved blood stream stability and improved intracellular release. Therefore, it is believed that the disulfide conjugate compounds of the present disclosure provide for improved stability in the bloodstream and for improved intracellular release rates.

In connection with PBD prodrugs, GSH-, DTD- or ROS-activation of PBD N10 protecting groups masks toxicity in the blood stream and in plasma and provides for selective toxicity advantages as compared to PBD drugs not comprising a protecting prodrug moiety. More particularly, blood concentration of GSH, DTD and ROS are known to be low as compared to cancer cells. Therefore, it is believed that the PBD prodrug conjugate compounds of the present disclosure provide for reduced toxicity in the bloodstream and targeted intracellular activation to PBD.

X. Articles of Manufacture

In another embodiment of the disclosure, an article of manufacture containing materials useful for the treatment, prevention and/or diagnosis of the disorders described herein is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is a PBD prodrug conjugate compound of the disclosure. The label or package insert indicates that the composition is used for treating the condition of choice. Moreover, the article of manufacture may comprise (a) a first container with a composition contained therein, wherein the composition comprises a PBD prodrug conjugate compound of the disclosure; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compounds of the disclosure. It is understood that various other embodiments may be practiced, given the general description provided herein.

The structures of PBD monomer and dimer compounds disclosed in the examples are depicted below along with corresponding reference tags wherein the asterisk refers to a chiral center of racemic or undefined stereochemistry.

| Reference Tag | Compound Structure |
|---|---|
| PBD monomer control 1. Examples 6-9, 13 and 15. | 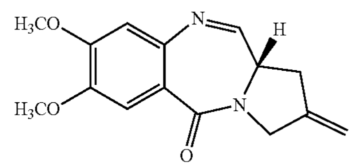 [SMILES: C=C1C[C@H]2C=Nc3cc(OC)c(OC)cc3C(=O)N2C1] |
| PBD monomer control 2. Examples 6, 9, 13 and 17. | 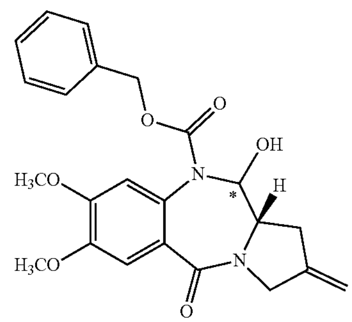 [SMILES: C=C1C[C@H]2C(O)N(C(=O)OCc3ccccc3)c3cc(OC)c(OC)cc3C(=O)N2C1] |
| PBD monomer disulfide prodrug 1. Examples 6, 9, 17 and 19K. | 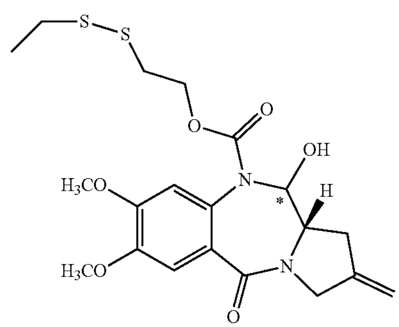 [SMILES: C=C1C[C@H]2C(O)N(C(=O)OCCSSCC)c3cc(OC)c(OC)cc3C(=O)N2C1] |
| PBD monomer disulfide prodrug 2. Examples 6, 9, 17 and 19E. | 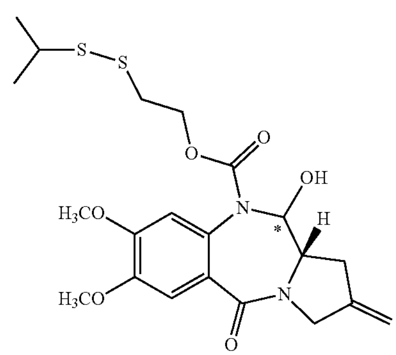 [SMILES: C=C1C[C@H]2C(O)N(C(=O)OCCSSC(C)C)c3cc(OC)c(OC)cc3C(=O)N2C1] |
| PBD monomer disulfide prodrug 3. Examples 6, 9, 17 and 19Q. | 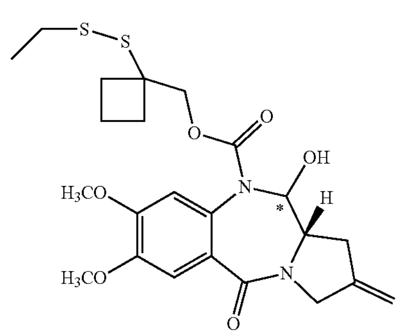 [SMILES: C=C1C[C@H]2C(O)N(C(=O)OCC3(SSCC)CCC3)c3cc(OC)c(OC)cc3C(=O)N2C1] |

| Reference Tag | Compound Structure |
| --- | --- |
| PBD monomer disulfide prodrug 4. Examples 6, 9, 17 and 19Q. | 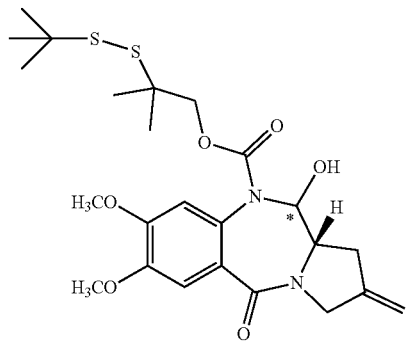 [SMILES: C=C1C[C@H]2C(O)N(C(=O)OCC(C)(C)SSC(C)(C)C)c3cc(OC)c(OC)cc3C(=O)N2C1] |
| PBD monomer disulfide prodrug 5. Examples 6, 9, 17 and 19R. | 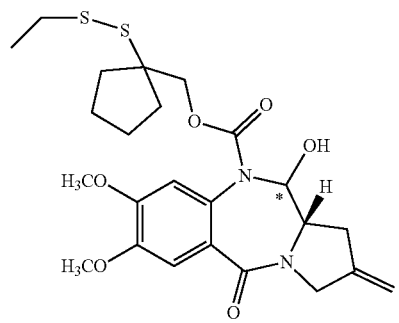 [SMILES: C=C1C[C@H]2C(O)N(C(=O)OCC3(SSCC)CCCC3)c3cc(OC)c(OC)cc3C(=O)N2C1] |
| PBD monomer disulfide prodrug 6. Examples 6, 9 add 17. | 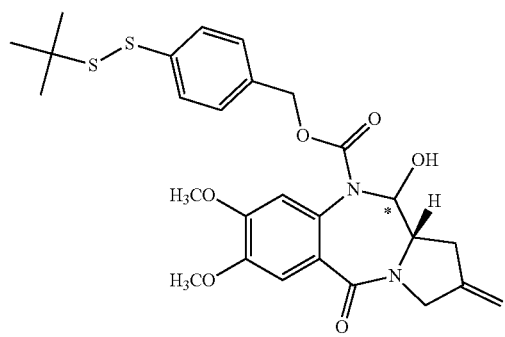 [SMILES: C=C1C[C@H]2C(O)N(C(=O)OCc3ccc(SSC(C)(C)C)cc3)c3cc(OC)c(OC)cc3C(=O)N2C1] |
| PBD monomer disulfide prodrug 7. Examples 9, 17 and 19J. | 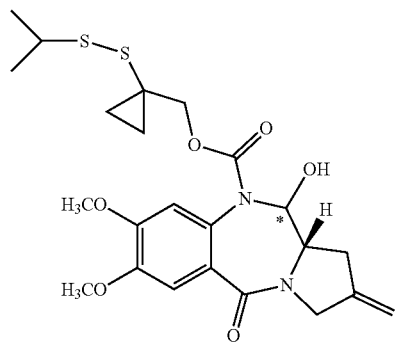 [SMILES: C=C1C[C@H]2C(O)N(C(=O)OCC3(SSC(C)C)CC3)c3cc(OC)c(OC)cc3C(=O)N2C1] |

-continued
| Reference Tag | Compound Structure |
|---|---|
| PBD monomer disulfide prodrug 8. Examples 9 and 17. | 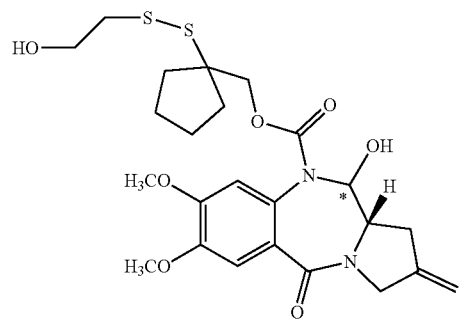 [SMILES: C=C1C[C@H]2C(O)N(C(=O)OCC3(SSCCO)CCCC3)c3cc(OC)c(OC)cc3C(=O)N2C1] |
| PBD monomer disulfide prodrug 9. Examples 9 and 17. | 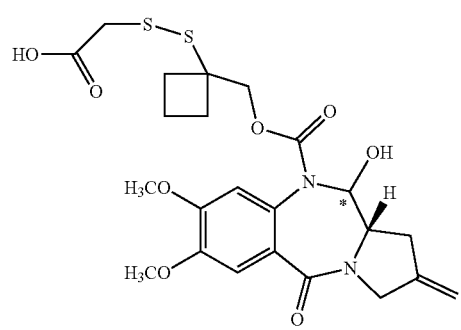 [SMILES: C=C1C[C@H]2C(O)N(C(=O)OCC3(SSCC(=O)O)CCC3)c3cc(OC)c(OC)cc3C(=O)N2C1] |
| PBD monomer disulfide prodrug 10. Examples 9, 17 and 19A. | 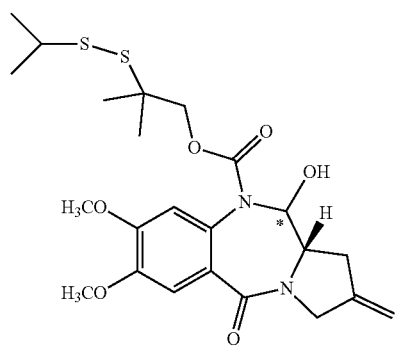 [SMILES: C=C1C[C@H]2C(O)N(C(=O)OCC(C)(C)SSC(C)C)c3cc(OC)c(OC)cc3C(=O)N2C1] |
| PBD monomer disulfide prodrug 11. Examples 9, 17 and 19S. | 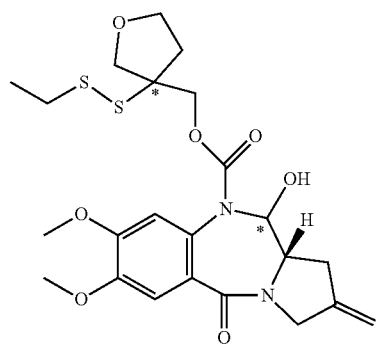 [SMILES: C=C1C[C@H]2C(O)N(C(=O)OCC3(SSCC)CCOC3)c3cc(OC)c(OC)cc3C(=O)N2C1] |

| Reference Tag | Compound Structure |
|---|---|
| PBD monomer disulfide prodrug 30. PBD monomer disulfide prodrug 11 and PBD monomer disulfide prodrug 30 are diastereomers having a different configuration at one or more of the chiral centers designated with the asterisk. Examples 9, 17 and 19S. | 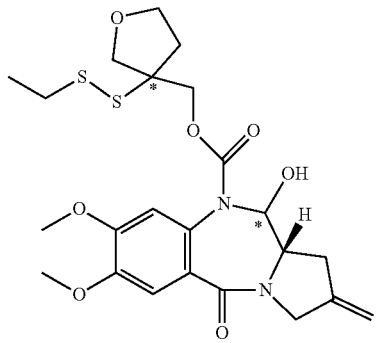 [SMILES: C=C1C[C@H]2C(O)N(C(=O)OCC3(SSCC)CCOC3)c3cc(OC)c(OC)cc3C(=O)N2C1] |
| PBD monomer disulfide prodrug 12. Examples 0, 17 and 19P. | 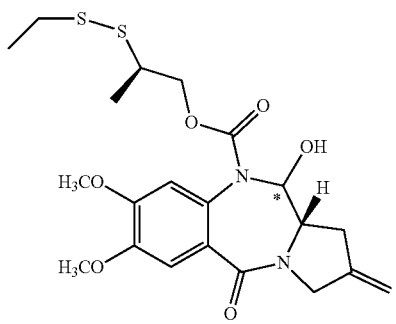 [SMILES: C=C1C[C@H]2C(O)N(C(=O)OC[C@@H](C)SSCC)c3cc(OC)c(OC)cc3C(=O)N2C1] |
| PBD monomer disulfide prodrug 14. Example 17. | 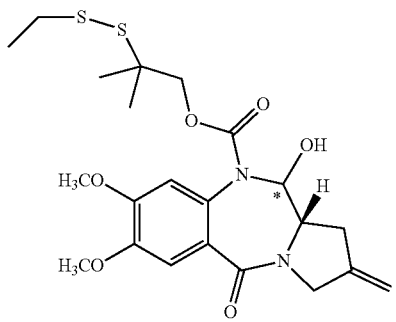 [SMILES: C=C1C[C@H]2C(O)N(C(=O)OCC(C)(C)SSCC)c3cc(OC)c(OC)cc3C(=O)N2C1] |
| PBD monomer disulfide prodrug 15. Examples 9, 17 and 19C. | 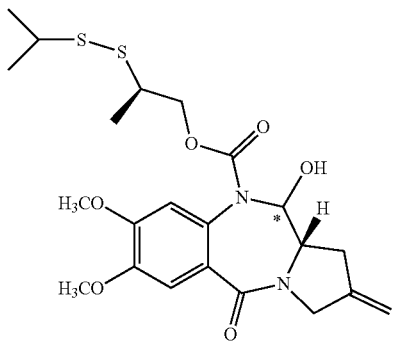 [SMILES: C=C1C[C@H]2C(O)N(C(=O)OC[C@@H](C)SSC(C)C)c3cc(OC)c(OC)cc3C(=O)N2C1] |

-continued
| Reference Tag | Compound Structure |
|---|---|
| PBD monomer disulfide prodrug 16. Examples 9, 17 and 19F. | 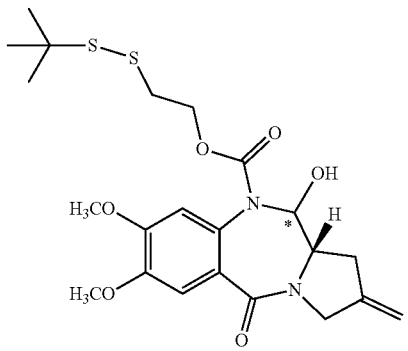 [SMILES: C=C1C[C@H]2C(O)N(C(=O)OCCSSC(C)(C)C)c3cc(OC)c(OC)cc3C(=O)N2C1] |
| PBD monomer disulfide prodrug 13. Examples 9, 17 and 19D. | 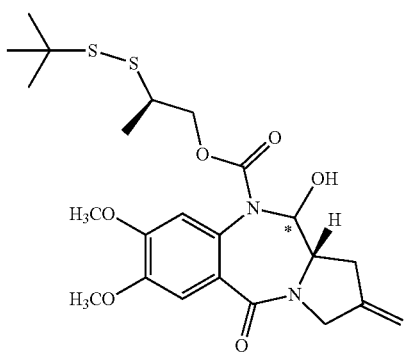 [SMILES: C=C1C[C@H]2C(O)N(C(=O)OC[C@@H](C)SSC(C)(C)C)c3cc(OC)c(OC)cc3C(=O)N2C1] |
| PBD monomer disulfide prodrug 17. Example 17. | 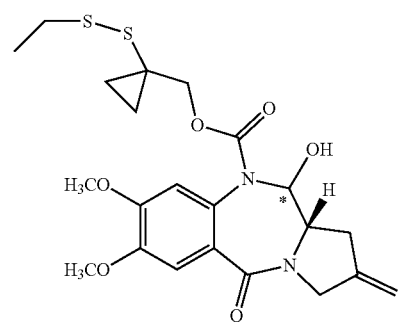 [SMILES: C=C1C[C@H]2C(O)N(C(=O)OCC3(SSCC)CC3)c3cc(OC)c(OC)cc3C(=O)N2C1] |
| PBD monomer disulfide prodrug 18. Example 17. | 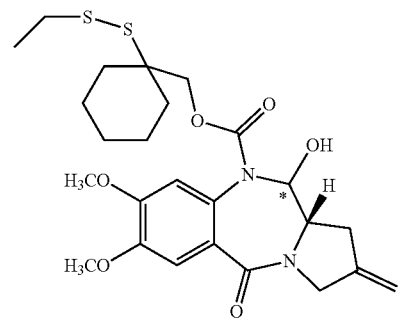 [SMILES: C=C1C[C@H]2C(O)N(C(=O)OCC3(SSCC)CCCCC3)c3cc(OC)c(OC)cc3C(=O)N2C1] |

-continued
| Reference Tag | Compound Structure |
|---|---|
| PBD monomer disulfide prodrug 19. Examples 6 and 17. | 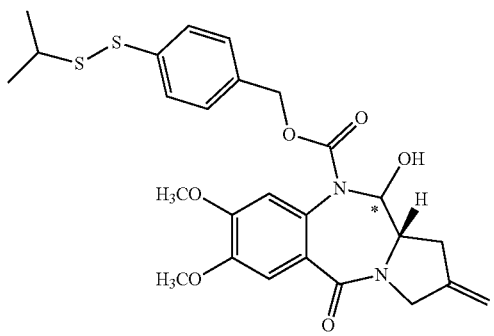 [SMILES: C=C1C[C@H]2C(O)N(C(=O)OCc3ccc(SSC(C)C)cc3)c3cc(OC)c(OC)cc3C(=O)N2C1] |
| PBD monomer disulfide prodrug 20. Example 17. | 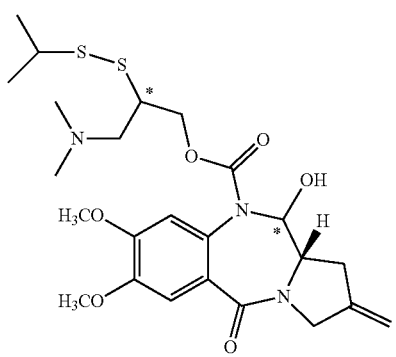 [SMILES: C=C1C[C@H]2C(O)N(C(=O)OCC(CN(C)C)SSC(C)C)c3cc(OC)c(OC)cc3C(=O)N2C1] |
| PBD monomer disulfide prodrug 21. Example 17. | 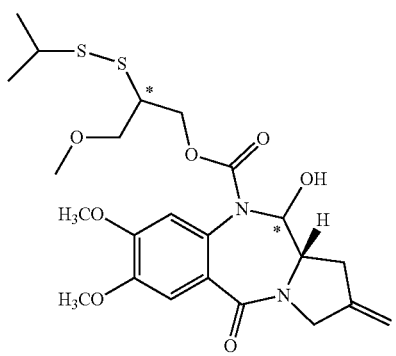 [SMILES: C=C1C[C@H]2C(O)N(C(=O)OCC(COC)SSC(C)C)c3cc(OC)c(OC)cc3C(=O)N2C1] |
| PBD monomer disulfide prodrug 22. Examples 9 and 17. | 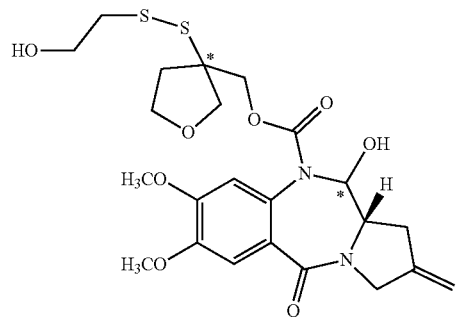 [SMILES: C=C1C[C@H]2C(O)N(C(=O)OCC3(SSCCO)CCOC3)c3cc(OC)c(OC)cc3C(=O)N2C1] |

| Reference Tag | Compound Structure |
|---|---|
| PBD monomer disulfide prodrug 23. Examples 9, 17 and 19O. | 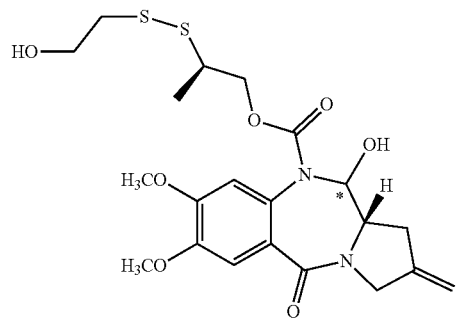 [SMILES: C=C1C[C@H]2C(O)N(C(=O)OC[C@@H](C)SSCCO)c3cc(OC)c(OC)cc3C(=O)N2C1] |
| PBD monomer disulfide prodrug 24. Examples 9, 17 and 19N. | 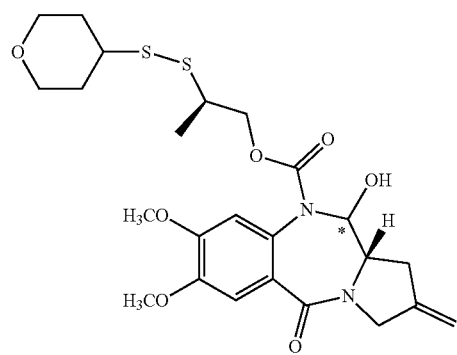 [SMILES: C=C1C[C@H]2C(O)N(C(=O)OC[C@@H](C)SSC3CCOCC3)c3cc(OC)c(OC)cc3C(=O)N2C1] |
| PBD monomer disulfide prodrug 25. Examples 9, 17 and 19M. | 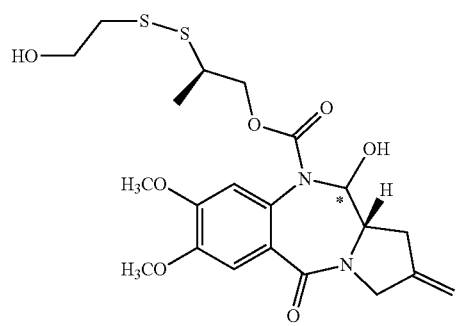 [SMILES: C=C1C[C@H]2C(O)N(C(=O)OC[C@@H](C)SSCCO)c3cc(OC)c(OC)cc3C(=O)N2C1] |
| PBD monomer disulfide prodrug 26. Examples 9, 17 and 19L. | 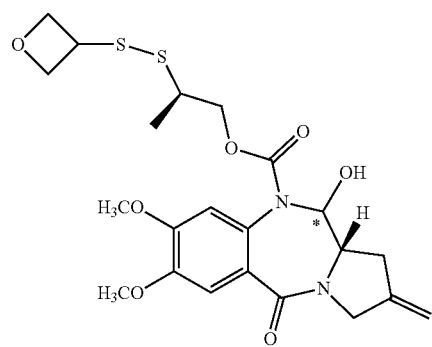 [SMILES: C=C1C[C@H]2C(O)N(C(=O)OC[C@@H](C)SSC3COC3)c3cc(OC)c(OC)cc3C(=O)N2C1] |

-continued
| Reference Tag | Compound Structure |
|---|---|
| PBD monomer disulfide prodrug 27. Examples 9, 17 and 19I. | 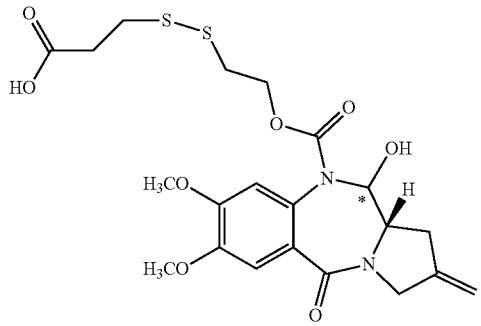 [SMILES: C=C1C[C@H]2C(O)N(C(=O)OCCSSCCC(=O)O)c3cc(OC)c(OC)cc3C(=O)N2C1] |
| PBD monomer disulfide prodrug 28. Examples 9, 17 and 19H. | 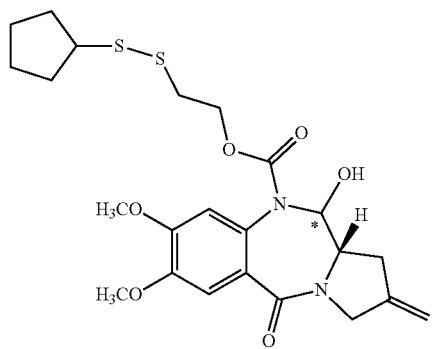 [SMILES: C=C1C[C@H]2C(O)N(C(=O)OCCSSC3CCCC3)c3cc(OC)c(OC)cc3C(=O)N2C1] |
| PBD monomer disulfide prodrug 29. Examples 9, 17 and 19G. | 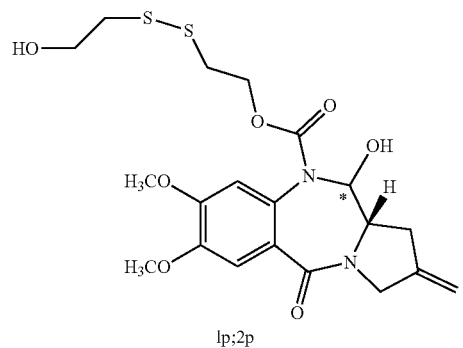<br>1p;2p |
| PBD Dimer control 1. Examples 7, 9, 15, 17 and 19E. | 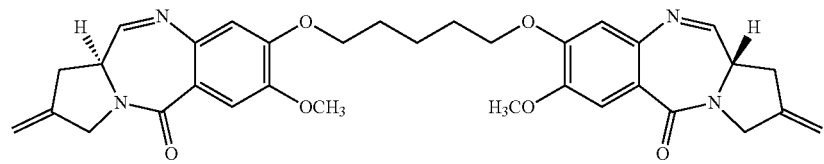 |
| PBD Dimer control 2. Examples 9, 17 and 19F. | 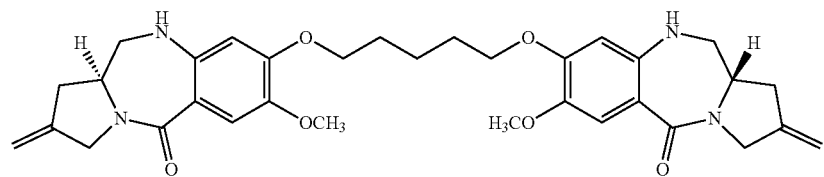 |

| Reference Tag | Compound Structure |
|---|---|
| PBD Dimer Disulfide Prodrug 1. Examples 7, 9, 17, 20B and 21D. | 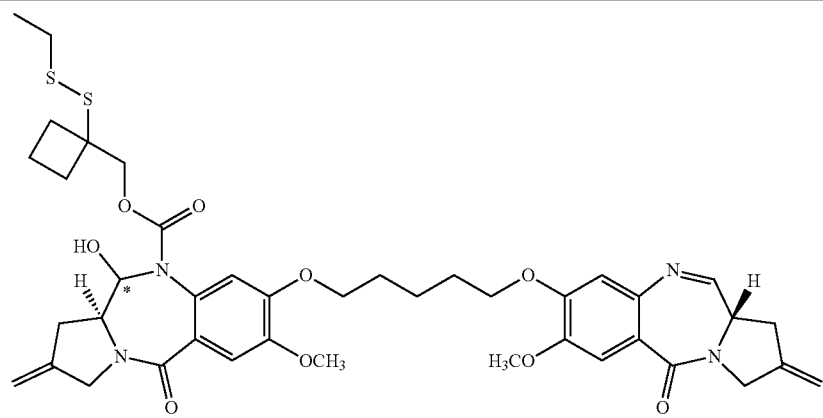 |
| PBD Dimer Disulfide Prodrug 4. Examples 7, 9, 20A and 21C. | 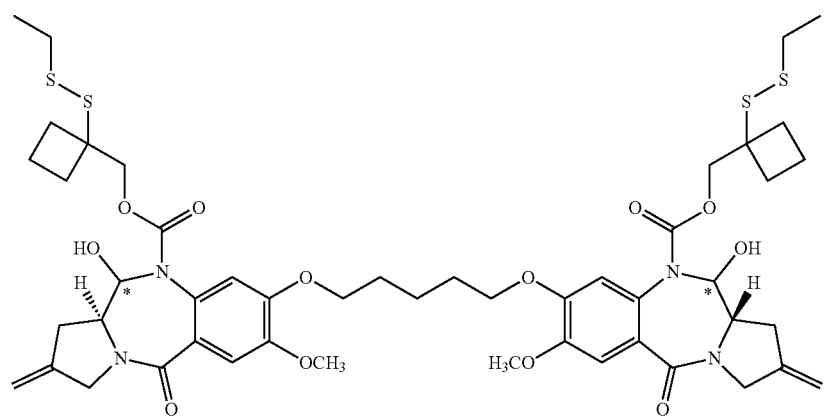 |
| PBD Dimer Disulfide Prodrug 2. Examples 9, 20C and 21B. | 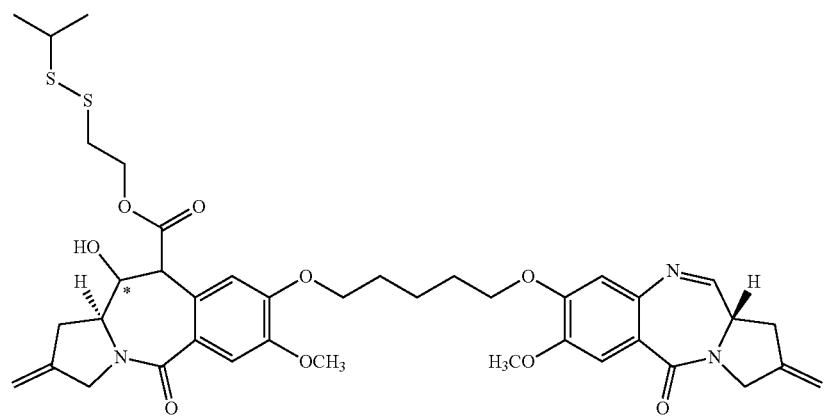 |

| Reference Tag | Compound Structure |
|---|---|
| PBD Dimer Disulfide Prodrug 3. Examples 9, 20D and 21A. | 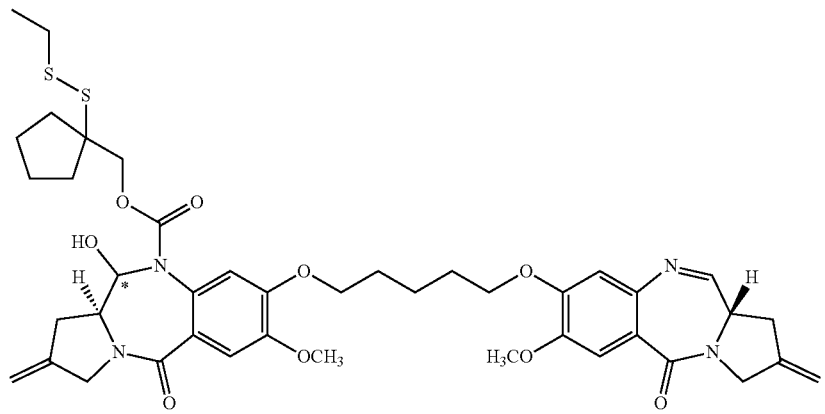 |
| Non-prodrug PBD dimer ADC controls 1 to 5, wherein an antibody sulfhydryl moiety is conjugated to the maleimide moiety<br>Non-prodrug PBD dimer ADC control 1: 7C2 HC A140C (Her2). Examples 10 and 14.<br>Non-prodrug PBD dimer ADC control 2: HC A118C (CD22). Examples 10 and 13.<br>Non-prodrug PBD dimer ADC control 3: 4D5 HC A118C (Her2). Examples 10 and 14.<br>Non-prodrug PBD dimer ADC control 4: 4D5 LC V205C (Her2). Example 10.<br>Non-prodrug PBD dimer ADC control 5: 4D5 HC A118C (Her2). Example 16. | 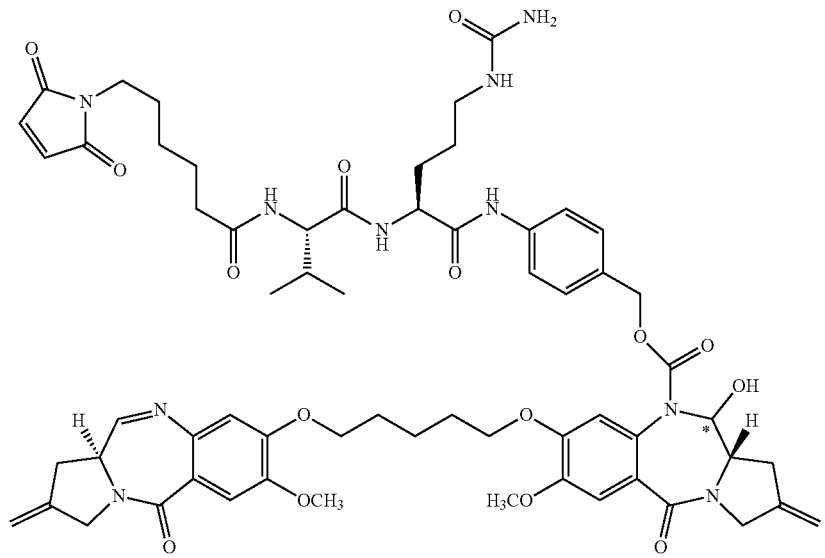 |
| PBD dimer ADC disulfide prodrug 1A (Her2) and PBD dimer. Examples 10 and 21D. ADC disulfide prodrug 1B (Examples 13 and 24D) each comprise a 7C2 LC K149C (Her2) antibody conjugated to the maleimide moiety | 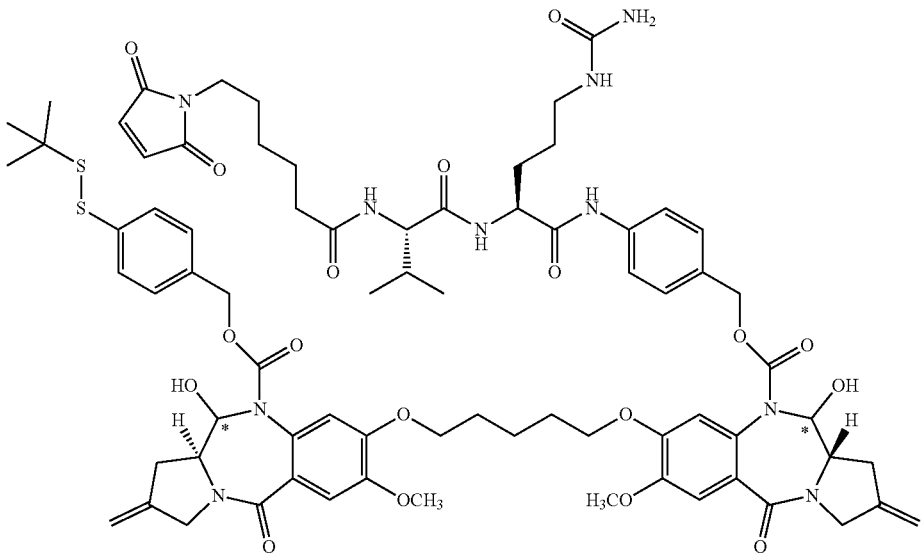 [SMILES: C=C1C[C@H]2C(O)N(C(=O)OCc3ccc(NC(=O)[C@H](CCCNC(N)=O)NC(=O)[C@@H](NC(=O)CCCCCN4C(=O)C=CC4=O)C(C)C)cc3)c3cc(OCCCCCOc4cc5c(cc4OC)C(=O)N4CC(=C)C[C@H]4C(O)N5C(=O)OCc4ccc(SSC(C)(C)C)cc4)c(OC)cc3C(=O)N2C1] |

| Reference Tag | Compound Structure |
|---|---|
| PBD dimer ADC disulfide prodrug 2A wherein a 7C2 HC A140C (Her2) antibody is conjugated to the maleimide moiety (Examples 8, 10 and 21B) and PBD dimer ADC disulfide prodrug 2B wherein a 7C2 LC K149C (Her2) antibody is conjugated to the maleimide moiety (Examples 8, 10, 21 and 21B) | 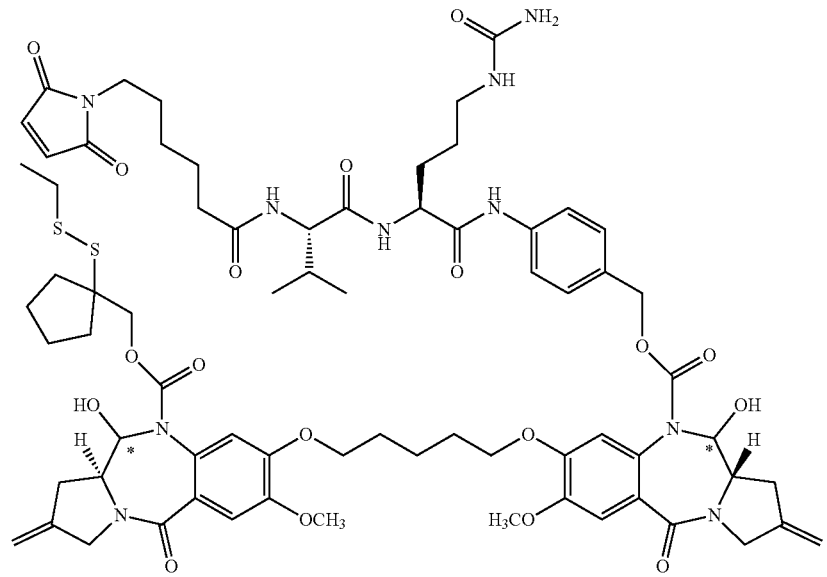 |
| PBD dimer ADC disulfide prodrug 3 wherein a 7C2 LC K149C antibody is conjugated to the maleimide moiety. Examples 8, 10 and 21A. | 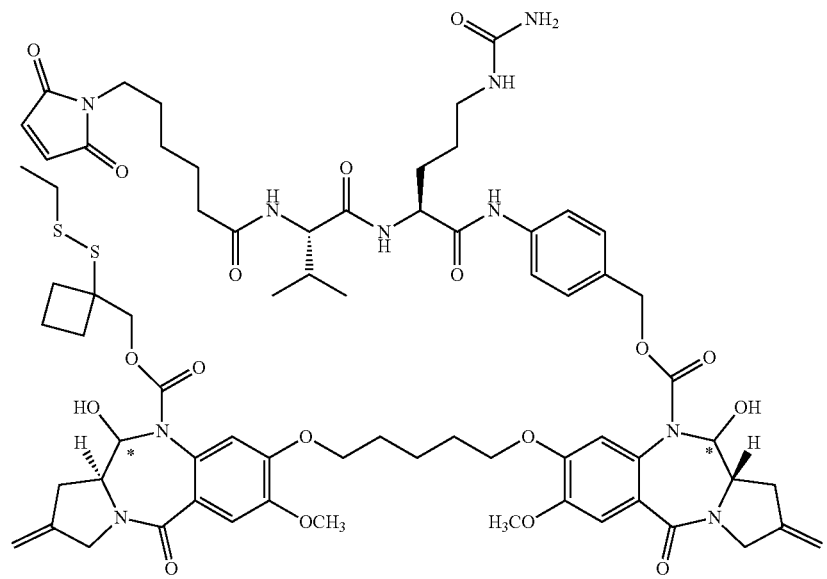 |

| Reference Tag | Compound Structure |
|---|---|
| PBD dimer ADC disulfide prodrug 4 wherein a 7C2 LC K149C antibody is conjugated to the maleimide moiety. Examples 8, 10 and 21C. | 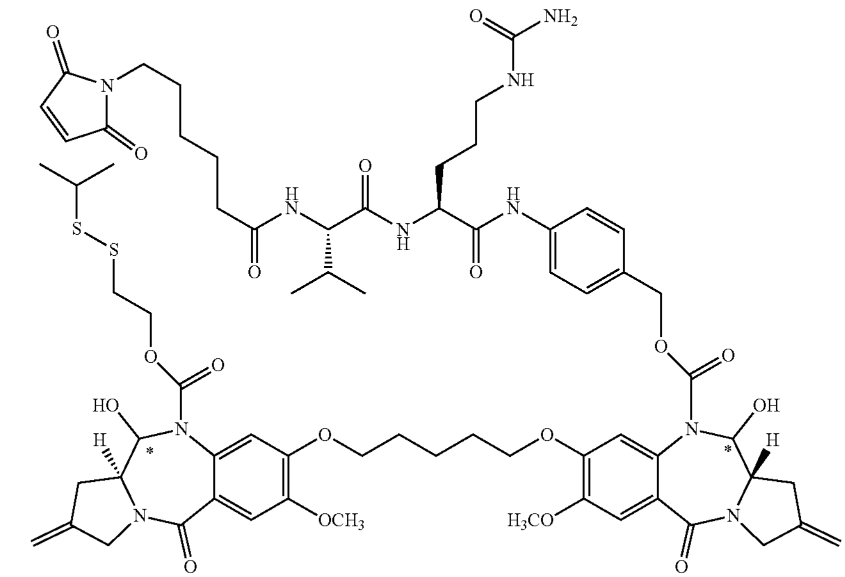 |
| PBD dimer ADC disulfide prodrug 5. Examples 8 and 21E. | 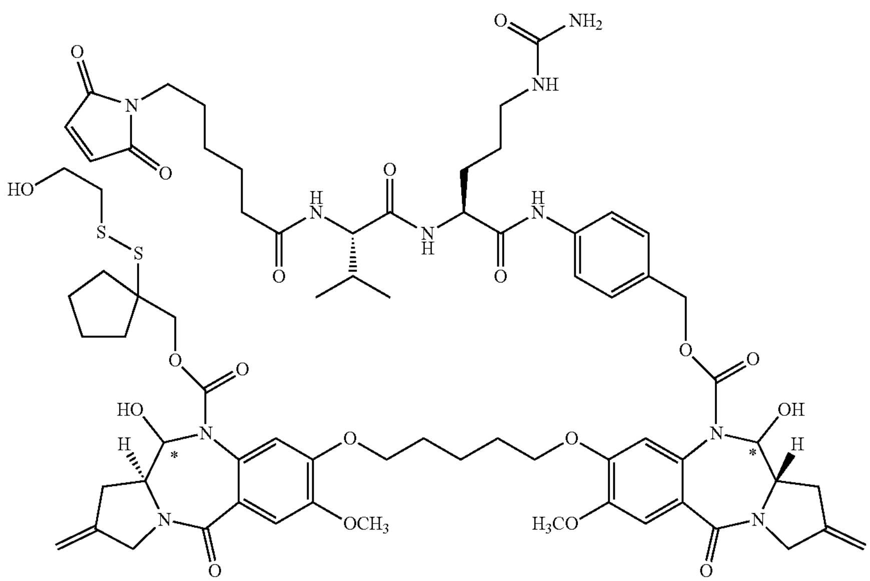 [SMILES: C=C1C[C@H]2C(O)N(C(=O)OCc3ccc(NC(=O)[C@H](CCCNC(N)=O)NC(=O)[C@@H](NC(=O)CCCCCN4C(=O)C=CC4=O)C(C)C)cc3)c3cc(OCCCCCOc4cc5c(cc4OC)C(=O)N4CC(=C)C[C@H]4C(O)N5C(=O)OCC4(SSCCO)CCCC4)c(OC)cc3C(=O)N2C1] |
| PBD monomer boronic acid prodrug 1. Example 13. | 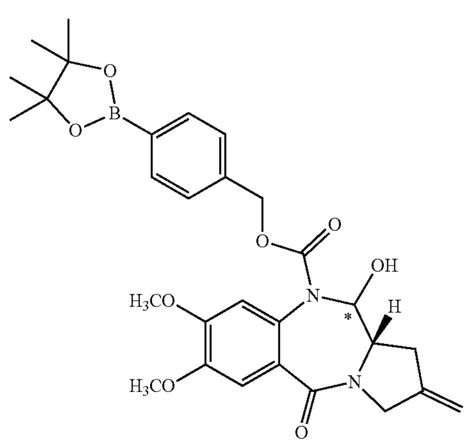 |

| Reference Tag | Compound Structure |
| --- | --- |
| PBD Dimer ADC boronic acid control 1A wherein a 10 F4v3; LC K149C antibody is conjugated to the maleimide moiety (Examples 13 and 22B) PBD Dimer ADC boronic acid control 1B wherein a Ly6 antibody; 9B12v.12; LC K149C is conjugated to the maleimide moiety (Example 22B) | 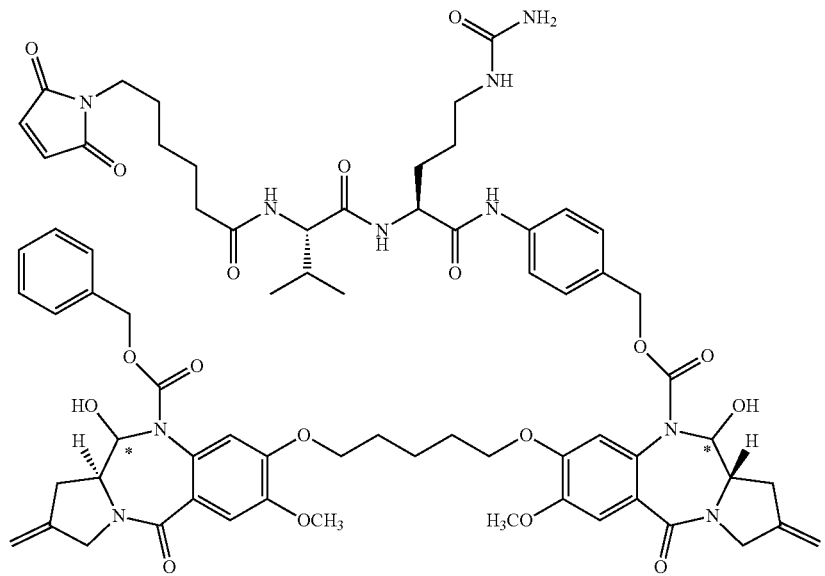 |
| PBD Dimer ADC boronic acid control 2 (positive control) wherein a LC K149C (CD22) antibody is conjugated to the maleimide moiety. Example 13. | 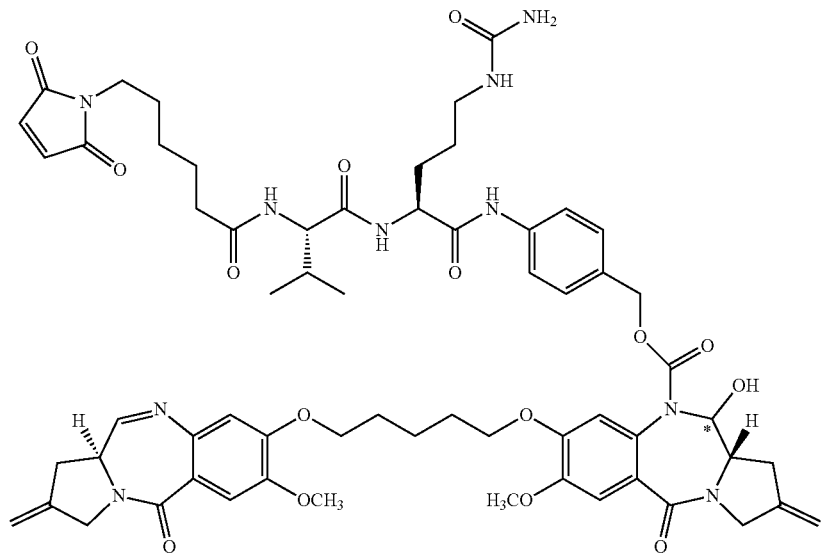 |

| Reference Tag | Compound Structure |
|---|---|
| PBD Dimer ADC boronic acid prodrug 1A wherein a LC K149C (CD22) antibody is conjugated to the maleimide moiety (Examples 13, 14 and 22A)<br>PBD Dimer ADC boronic acid prodrug 1B wherein a LC K149C (Ly6E) antibody is conjugated to the maleimide moiety (Example 13 and 22A) | 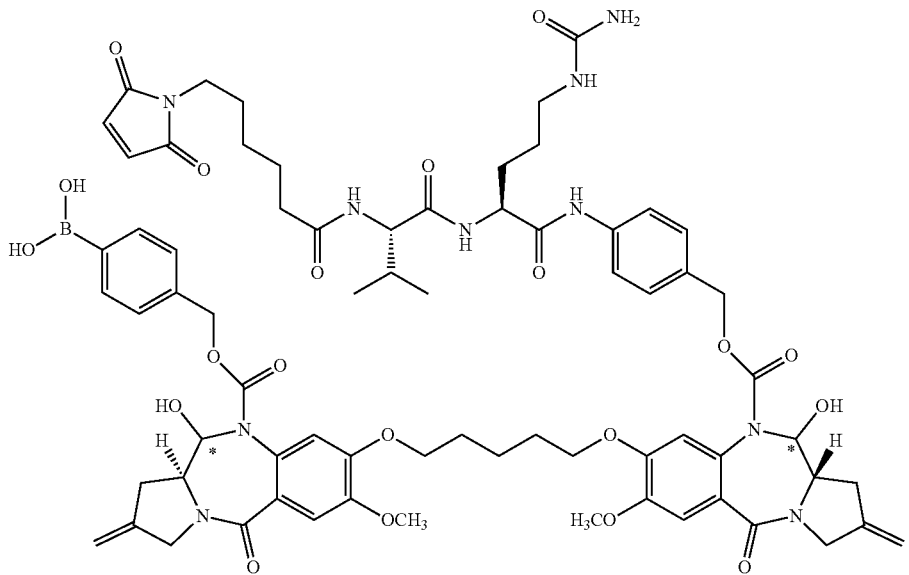 [SMILES: C=C1C[C@H]2C(O)N(C(=O)OCc3ccc(NC(=O)[C@H](CCCNC(N)=O)NC(=O)[C@@H](NC(=O)CCCCCN4C(=O)C=CC4=O)C(C)C)cc3)c3cc(OCCCCCOc4cc5c(cc4OC)C(=O)N4CC(=C)C[C@H]4C(O)N5C(=O)OCc4ccc(B(O)O)cc4)c(OC)cc3C(=O)N2C1] |
| PBD Dimer Diaphorase prodrug 1. Examples 6, 15, 23B and 25. | 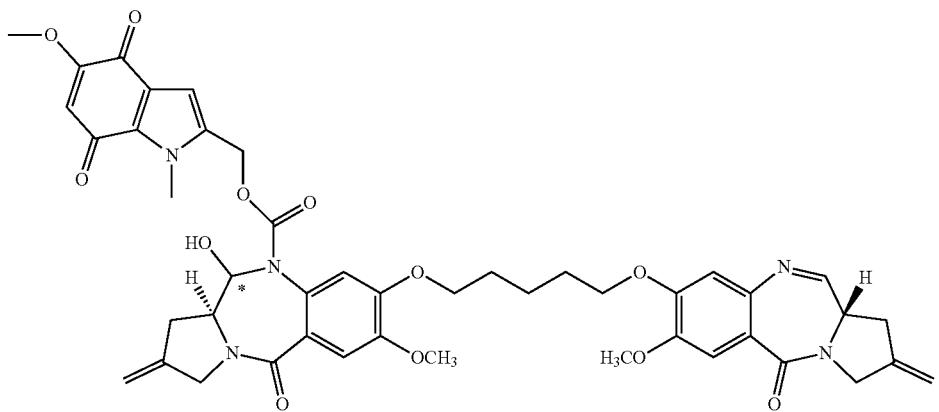 |
| PBD Monomer Diaphorase prodrug 2. Examples 6, 15, 18 and 23A. | 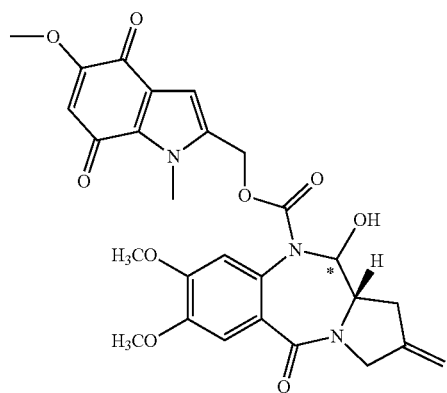 |

| Reference Tag | Compound Structure |
|---|---|
| PBD monomer diaphorase prodrug 3. Examples 6, 18 and 23C. | 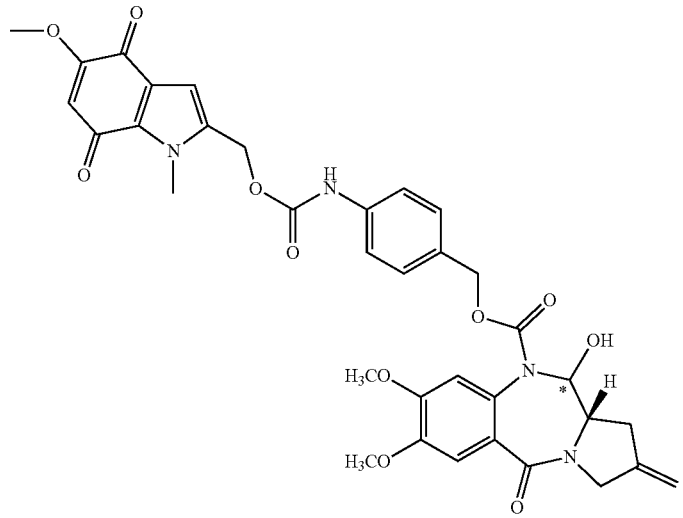 |
| PBD dimer diaphorase prodrug 2. Examples 6 and 23D. | 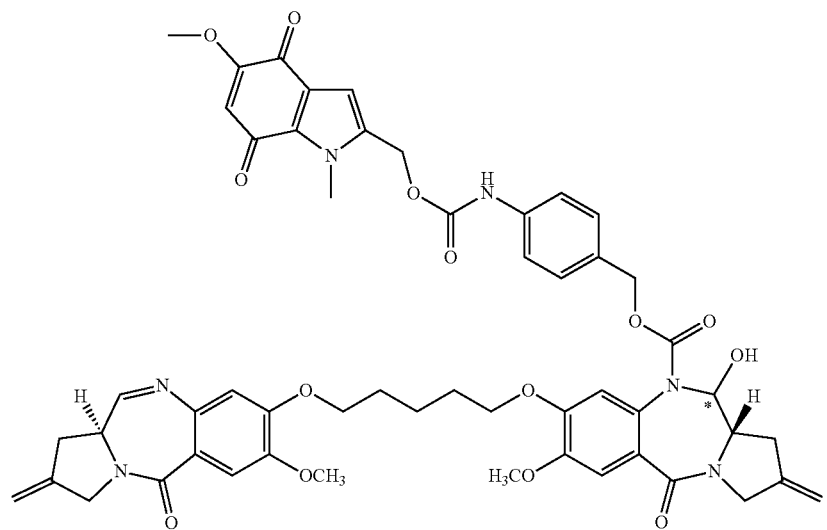 |
| PBD dimer diaphorase prodrug 3. Examples 6 and 23E. | 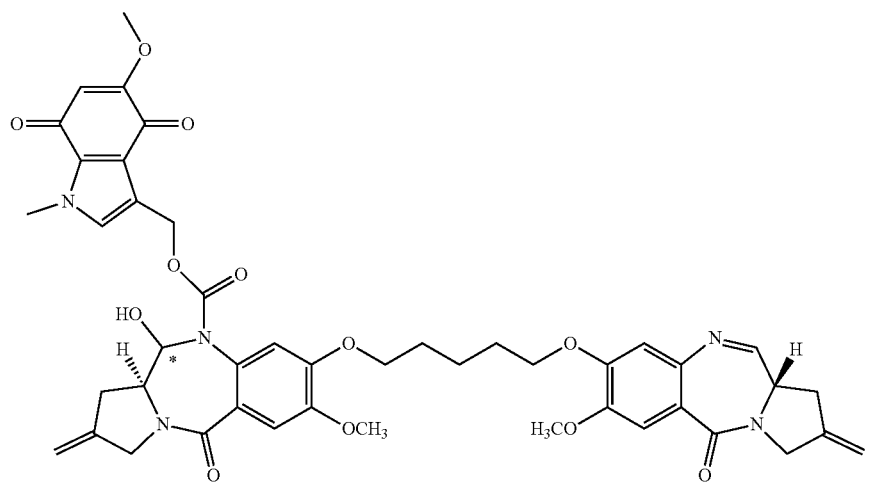 [SMILES: C=C1C[C@H]2C=Nc3cc(OCCCCCOc4cc5c(cc4OC)C(=O)N4CC(=C)C[C@H]4C(O)N5C(=O)OCc4cn(C)c5c4C(=O)C(OC)=CC5=O)c(OC)cc3C(=O)N2C1] |

| Reference Tag | Compound Structure |
|---|---|
| PBD dimer ADC diaphorase prodrug 1A wherein a 7C2 LC K149C antibody is conjugated to the maleimide moiety (Examples 10 and 25.) and PBD dimer ADC diaphorase prodrug 1B wherein a Ly6E LC K149C antibody is conjugated to the maleimide moiety (Example 8) | 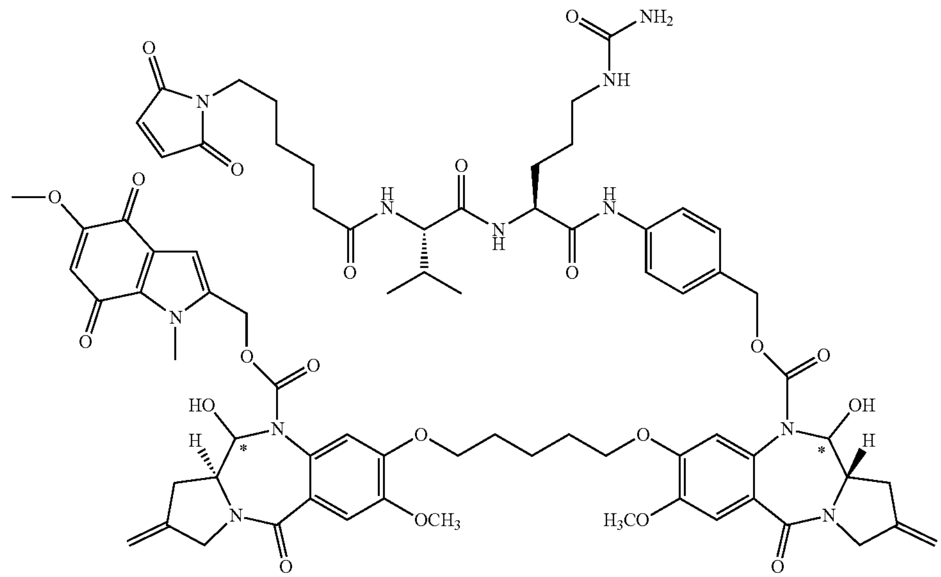 |

Example 1

General Method for ADC Preparation

Cysteine engineered antibodies, such as those listed in Tables A to D, were made reactive for conjugation with linker-drug intermediates in some aspects of the present disclosure by treatment with a reducing agent such as DTT (Cleland's reagent, dithiothreitol) or TCEP (tris(2-carboxyethyl)phosphine hydrochloride; see Getz et al (1999) Anal. Biochem. Vol 273:73-80 (incorporated herein by reference); Soltec Ventures, Beverly, Mass.) followed by re-formation of the inter-chain disulfide bonds (re-oxidation) with a mild oxidant such as dehydroascorbic acid. Full length, cysteine engineered monoclonal antibodies (THIOMAB™) expressed in CHO cells (see Gomez et al. (2010) Biotechnology and Bioeng. 105(4):748-760 (incorporated herein by reference); and Gomez et al (2010) Biotechnol. Prog. 26:1438-1445 (incorporated herein by reference)) were reduced, for example, with about a 50 fold excess of DTT overnight in 50 mM Tris, pH 8.0 with 2 mM EDTA at room temperature, which removes cysteine and GSH adducts as well as reduces interchain disulfide bonds in the antibody. Removal of the adducts was monitored by reverse-phase liquid chromatography/mass spectrometric Analysis ("LC/MS") using a PLRP-S column. The reduced THIOMAB™ was diluted and acidified by addition to at least four volumes of 10 mM sodium succinate, pH 5 buffer. Alternatively, the antibody was diluted and acidified by adding to at least four volumes of 10 mM succinate, pH 5 and titration with 10% acetic acid until pH was approximately five. The pH-lowered and diluted THIOMAB™ was subsequently loaded onto a HiTrap S cation exchange column, washed with several column volumes of 10 mM sodium acetate, pH 5 and eluted with 50 mM Tris, pH 8.0, 150 mM sodium chloride.

Disulfide bonds were reestablished between cysteine residues present in the parent Mab by carrying out reoxidation. The eluted reduced THIOMAB™ described above was treated with 15× dehydroascorbic acid (DHAA) for about 3 hours or, alternatively, with 200 nM to 2 mM aqueous copper sulfate (CuSO4) at room temperature overnight. Other oxidants, i.e. oxidizing agents, and oxidizing conditions, which are known in the art may be used. Ambient air oxidation may also be effective. This mild, partial reoxidation step formed intrachain disulfides efficiently with high fidelity. Reoxidation was monitored by reverse-phase LC/MS using a PLRP-S column. The reoxidized THIOMAB™ was diluted with succinate buffer as described above to reach pH approximately 5 and purification on an S column was carried out as described above with the exception that elution was performed with a gradient of 10 mM succinate, pH 5, 300 mM sodium chloride (buffer B) in 10 mM succinate, pH 5 (buffer A). EDTA was added to the eluted THIOMAB™ to a final concentration of 2 mM and concentrated, if necessary, to reach a final concentration of more than 5 mg/mL.

The resulting THIOMAB™, suitable for conjugation, was stored at −20° C. in aliquots. LC/MS Analysis was performed on a 6200 series TOF or QTOF Agilent LC/MS. Samples were chromatographed on a PRLP-S®, 1000 A, microbore column (50 mm×2.1 mm, Polymer Laboratories, Shropshire, UK) heated to 80° C. A linear gradient from 30-40% B (solvent A: 0.05% TFA in water, solvent B: 0.04% TFA in acetonitrile) was used and the eluent was directly ionized using the electrospray source. Data were collected and deconvoluted by the MassHunter software. Prior to LC/MS analysis, antibodies or drug conjugates (50 micrograms) were treated with PeptideN-Glucosidase F ("PNGase F") (2 units/ml; PROzyme, San Leandro, Calif.) for 2 hours at 37° C. to remove N-linked carbohydrates. Alternatively, antibodies or drug conjugates were partially digested with LysC (0.25 ug per 50 ug antibody or conjugate) for 15 minutes at 37 C to give a Fab and Fc fragment for analysis by LC/MS. Peaks in the deconvoluted LC/MS spectra were assigned and quantitated. Drug-to-antibody ratios (DAR) were calculated by calculating the ratio of intensities of the peak or peaks corresponding to drug-conjugated antibody relative to all peaks observed.

The THIOMAB™ for conjugation, in 10 mM succinate, pH 5, 150 mM NaCl, 2 mM EDTA, was adjusted to pH 7.5-8.5 with 1M Tris. An excess, from about 3 to 20 molar equivalents of a linker-drug intermediate of the present disclosure with a thiol-reactive pyridyl disulfide group was dissolved in DMF or DMA and added to the reduced, reoxidized, and pH-adjusted antibody. The reaction was incubated at room temperature or 37° C. and monitored until completion (1 to about 24 hours), as determined by LC/MS analysis of the reaction mixture. When the reaction is complete, the conjugate may be purified by one or any combination of several methods to remove remaining unreacted linker-drug intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used. The THIOMAB™ drug conjugates were formulated into 20 mM His/acetate, pH 5, with 240 mM sucrose using either gel filtration or dialysis. The purified conjugate is concentrated by centrifugal ultrafiltration and filtered through a 0.2-μm filter under sterile conditions and frozen for storage. The antibody-drug conjugates were characterized by BCA assay to determine protein concentration, analytical SEC (size-exclusion chromatography) for aggregation analysis and LC/MS after treatment with Lysine C endopeptidase (LysC) to calculate DAR.

Size exclusion chromatography was performed on conjugates using a Shodex KW802.5 column in 0.2M potassium phosphate pH 6.2 with 0.25 mM potassium chloride and 15% IPA at a flow rate of 0.75 ml/min. The aggregation state of the conjugate was determined by integration of eluted peak area absorbance at 280 nm.

LC/MS analysis may be performed on conjugates using an Agilent QTOF 6520 ESI instrument. As an example, the antibody-drug conjugate was treated with 1:500 w/w Endoproteinase Lys C (Promega) in Tris, pH 7.5, for 30 min at 37° C. The resulting cleavage fragments were loaded onto a 1000 Å (Angstrom), 8 μm (micron) PLRP-S (highly cross-linked polystyrene) column heated to 80° C. and eluted with a gradient of 30% B to 40% B in 5 minutes. Mobile phase A was H$_2$O with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

Example 2

Herceptin A118C Antibody-Probe Conjugates

Various probe compounds comprising a linker and a thiol leaving group were conjugated with Herceptin A118C. In each conjugation, 5 mg/mL antibody in a solvent system was contacted with a probe-linker-leaving group compound at an equivalent ratio of probe compound to antibody of 10:1 wherein the probe-linker is conjugated to the antibody via a disulfide bond. The solvent system comprised 75 mM Tris, pH 8.5 and 10 v/v % DMF. The conjugation reaction was run at room temperature for 24 hours. The reaction product mixture was analyzed by LC/MS to determine a drug to antibody ratio (DAR), an area percent of leaving group byproduct as compared to antibody-probe conjugate, an area percent of unconjugated dimer as compared to antibody-probe conjugate, and an area percent of unconjugated monomer as compared to antibody-probe conjugate.

The probe was of the formula below where the wavy line indicates the point of attachment to the linker:

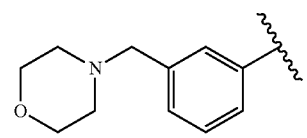 [SMILES: *c1cccc(CN2CCOCC2)c1]

Probe-linker-leaving group compounds evaluated included:

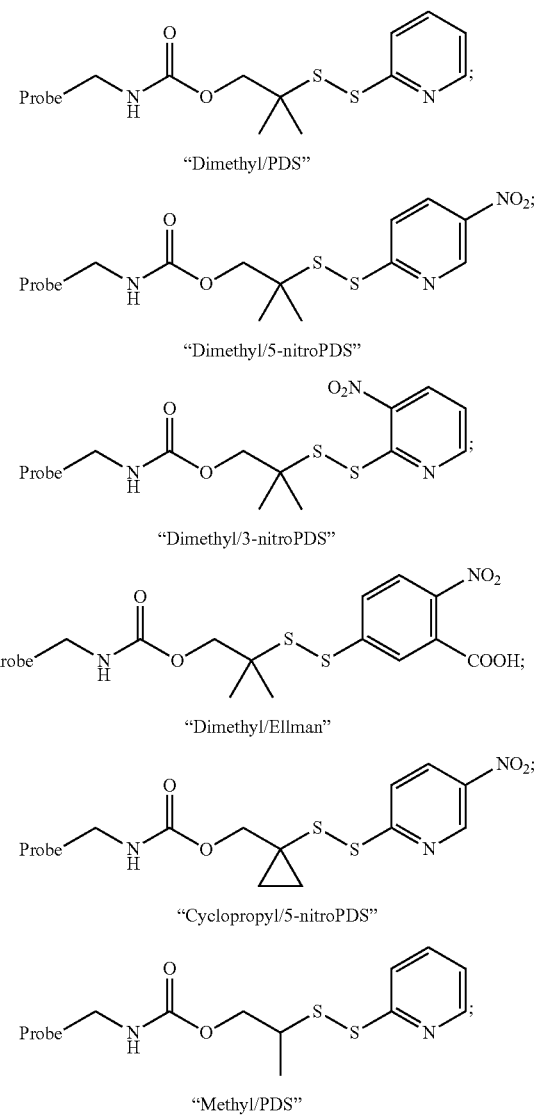

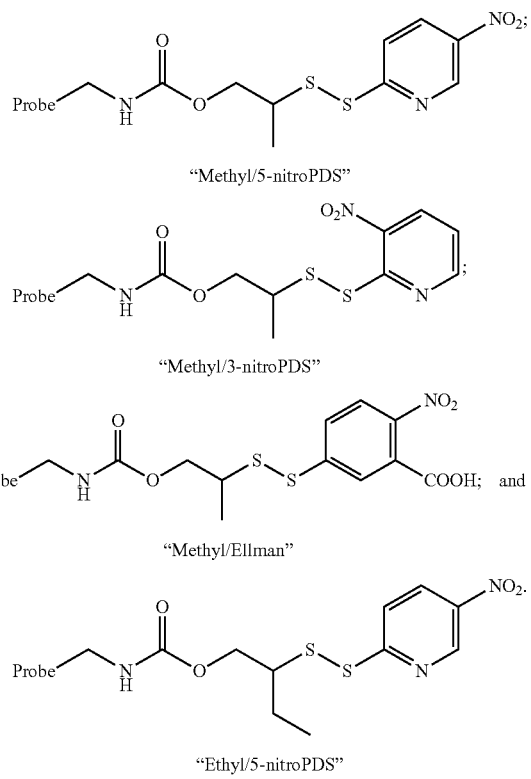

"Methyl/5-nitroPDS"

"Methyl/3-nitroPDS"

"Methyl/Ellman"

"Ethyl/5-nitroPDS"

The results are reported in Table 1 below where "DAR" refers to drug-antibody ratio, "% LG" refers to percent leaving group byproduct, "% Unconj. Dimer" refers to percentage of unconjugated antibody dimer and "% Unconj. Monomer" refers to percentage of unconjugated antibody dimer.

TABLE 1

| Linker-Leaving Group | DAR | % LG | % Unconj. Dimer | % Unconj. Monomer |
|---|---|---|---|---|
| Dimethyl/PDS | 0.6 | 64 | 3 | 6 |
| Dimethyl/5-nitroPDS | 0.7 | 35 | 22 | 1 |
| Dimethyl/3-nitroPDS | 0.2 | 69 | 18 | 2 |
| Dimethyl/Ellman | 0.2 | 89 | 2 | 1 |
| Cyclopropyl/5-nitroPDS | 2 | 1 | 0 | 0 |
| Ethyl/5-nitroPDS | 2 | 1 | 0 | 0 |
| Methyl/PDS | 1.1 | 39 | 0 | 3 |
| Methyl/5-nitroPDS | 1.4 | 27 | 1 | 1 |
| Methyl/3-nitroPDS | 2 | 2 | 0 | 0 |
| Methyl/Ellman | 1.7 | 17 | 1 | 0 |

Example 3

Herceptin K149C Antibody-Probe Conjugates

The probe compounds of Example 2 were evaluated for conjugation to Herceptin K149C via a disulfide bond under the reaction conditions of Example 2. The reaction product mixture was analyzed by LC/MS to determine a drug to antibody ratio (DAR) and an area percent of leaving group byproduct as compared to antibody-probe conjugate. The results are reported in Table 2 below.

TABLE 2

| Linker-Leaving Group | DAR | % LG |
|---|---|---|
| Dimethyl/PDS | 0.3 | 84 |
| Dimethyl/5-nitroPDS | 0.6 | 68 |
| Dimethyl/3-nitroPDS | 0.2 | 92 |
| Dimethyl/Ellman | 0.2 | 91 |
| Cyclopropyl/5-nitroPDS | 2 | 0.4 |
| Ethyl/5-nitroPDS | 2 | 0.3 |
| Methyl/PDS | 0.7 | 62 |
| Methyl/5-nitroPDS | 1.6 | 20 |
| Methyl/3-nitroPDS | 1.8 | 9 |
| Methyl/Ellman | 1.8 | 9 |

Example 4

Herceptin A118C ADC

Various drug compounds comprising a linker and a 5-nitroPDS thiol leaving group were conjugated via a disulfide bond with Herceptin2 4D5 HC A118C antibody. In each conjugation, 5 mg/mL antibody in a solvent system was contacted with a drug-linker-leaving group compound at an equivalent ratio of drug-linker-leaving group compound to antibody of 3:1. The solvent system comprised 75 mM Tris, pH 8.5. The conjugation reaction was run at room temperature for 3 hours. The reaction product mixture was analyzed by LC/MS to determine a drug to antibody ratio (DAR) and an area percent of leaving group byproduct as compared to antibody-probe conjugate.

The drug was of the formula below where the wavy line indicates the point of attachment to the linker:

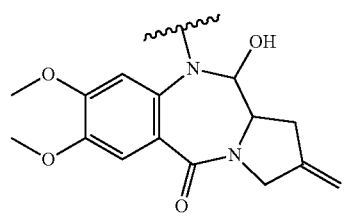

Drug-linker-leaving group compounds evaluated included where "D" denotes a drug:

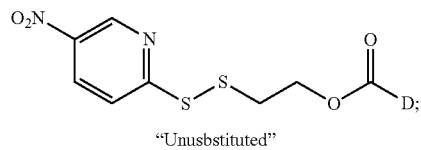

"Unusbstituted"

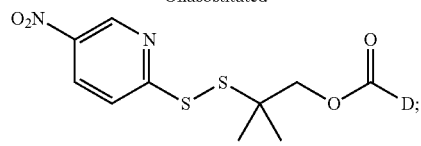

"Dimethyl"

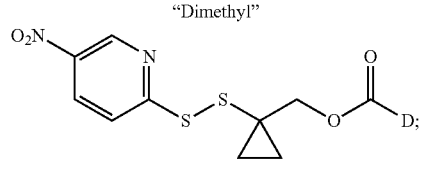

"Cyclopropyl"

-continued

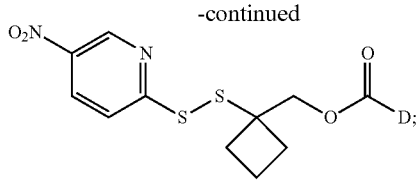

"Cyclobutyl"

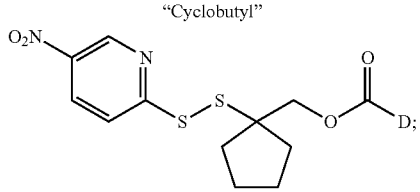

"Cyclopentyl"

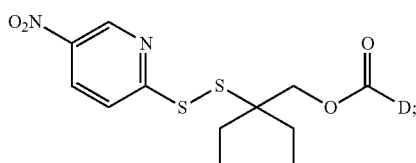

"Cyclohexyl"

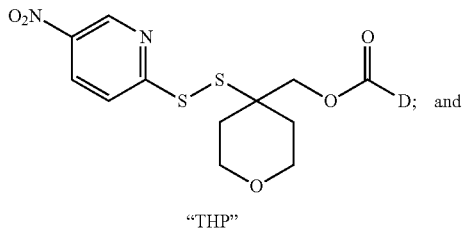

"THP"

-continued

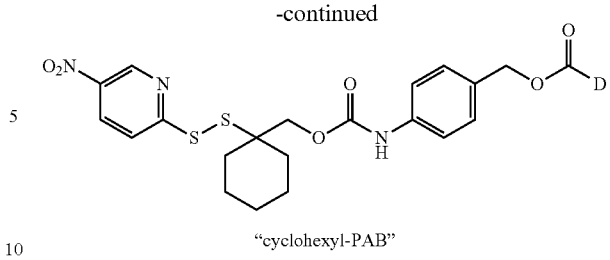

"cyclohexyl-PAB"

The results are reported in Table 3 below.

TABLE 3

| Linker-Leaving Group | DAR | % LG |
|---|---|---|
| Unsubstituted | 1.9 | 2.8 |
| Cyclopropyl | 1.9 | 4.8 |
| Cyclobutyl | 1.9 | 5 |
| Cyclopentyl | 0.8 | 48 |
| Dimethyl | 0.4 | 71 |
| Cyclohexyl | 0.3 | 54 |
| THP | 0 | 96 |
| Cyclohexyl-PAB | 0 | 10 with visible precipitate |

Example 5 xCD22 K149C ADC

A linker-drug compound comprising a methylsulfonate leaving group (MTS) (Linker 1) was conjugated via a disulfide bond with xCD22 K149C antibody in a first evaluation. In the second evaluation, a linker-drug compound comprising a MTS leaving group (Linker 2) was conjugated with antibody in a second evaluation. In each conjugation, 5 mg/mL antibody in a solvent system was contacted with a drug-linker-leaving group compound at an equivalent ratio of probe compound to antibody of 3:1. The solvent system comprised 75 mM Tris, pH 8.5. The conjugation reactions were run at room temperature for 3 hours. Linkers 1 and 2 are illustrated below:

Linker 1

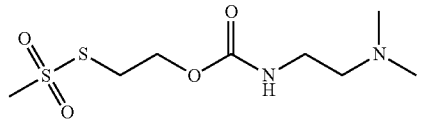

Linker 2

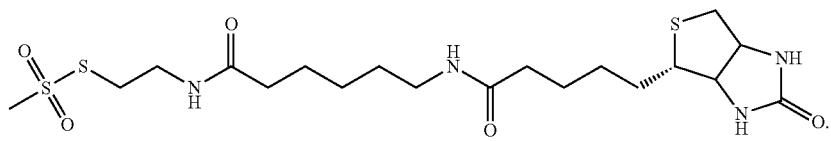

The reaction product mixture was analyzed by LC/MS to determine a drug to antibody ratio (DAR) and an area percent of leaving group byproduct as compared to antibody-probe conjugate. For Linker 1, the drug to antibody ratio was 2.0, the area percent of the antibody-drug conjugate was about 91%, the area percent of unconjugated antibody was less than 0.1%, and the area percent of MTS byproducts was about 0.5%. For Linker 2, the drug to antibody ratio was 1.5, the area percent of the antibody-drug conjugate was about 91%, the area percent of unconjugated antibody was less than 0.1%, and the area percent of MTS byproducts was about 0.5%.

Example 6

Toxicity of PBD Monomer Disulfide Prodrugs Against KPL-4 and WSU-DLCL2 Cell Lines The toxicity of PBD monomer disulfide prodrugs and diaphorase prodrugs were evaluated against KPL-4, WSU-DLCL2, HCT-116, HCC1395 and Jurkat cell cultures. KPL-4 (a breast cancer cell line) expresses Her2 and exhibits high GSH levels of from about 12 to about 24 mM. KPL-4 cells further have a high expression of DTD on the order of about 839 nRPKM (where nRPKM refers to normalized reads per Kb of transcript length per million mapped read). WSU-DLCL2 (a non-Hodgkin's lymphoma cell line) exhibits lo GSH levels of about 1.4 mM and low DTD expression of about 1.4 nRPKM.

Potency of the disulfide and DT-diaphorase prodrugs was measured by a cell proliferation assay employing the following protocol (CELLTITER GLO™ Luminescent Cell Viability Assay, Promega Corp.). First, an aliquot of 40 ul of cell culture containing about 8000 cells of WSU-DLCL2 cells (low NQO1 gene and GSH level), 4000 cells of KPL-4 (high NQO1 gene and GSH level), HCT-116 cells, HCC1395 cells or Jurkat cells in RPMI-1640 culture medium (supplemented with 10% fetal bovine serum, 2 mM glutamine, 50 uM cystine, and 0.015 g/L L-methionine) was deposited in each well of a 384-well flat clear bottom white polystyrene tissue culture-treated microplates (Corning, N.Y.). Second, control wells were prepared containing medium with and without cells. Third, compounds with and without disulfide or DT-diaphorase prodrugs (n=3) were added to the experimental wells using ECHO acoustic liquid handling technology (Labcyte Inc, Sunnyvale, Calif.) to create a 10-point dose-response curve in triplicate with 1:3× serial dilution. Fourth, cells were cultured in a humidified incubator set at 37° C. and maintaining an atmosphere of 5% $CO_2$. Fifth, the plates were equilibrated to room temperature for approximately 30 minutes. Sixth, a volume of CELLTITER GLO™ Reagent equal to the volume of cell culture medium present in each well was added. Seventh, the contents were mixed for 10 minutes on an orbital shaker in the dark to induce cell lysis. Eighth, the plate was incubated at room temperature for 30 minutes to stabilize the luminescence signal. Ninth, luminescence was recorded and reported in graphs as % activity where RLU (relative luminescence units) was normalized to controls (no compound control minus no cell control). Tenth, data was plotted as individual points for each replicate (n=3) for each antibody as the mean of luminescence for each set of replicates, with standard deviation error bars.

The $IC_{50}$ potency results are presented in Table 4 below in nM wherein the data in parenthesis represent $IC_{50}$ results for repeat evaluations:

TABLE 4

| PBD agent | KPL-4 | WSU-DLCL2 | HCT-116 | HCC1395 | Jurkat |
|---|---|---|---|---|---|
| PBD monomer control 1 | 330.1 (240.63) | 105.5 (108.7) | — | — | — |
| PBD monomer control 2 | >10,000 | >10,000 | — | — | — |
| PBD monomer disulfide prodrug 1 | 323.8 | 274 | — | — | — |
| PBD monomer disulfide prodrug 2 | 497.3 | 1015.7 | — | — | — |
| PBD monomer disulfide prodrug 3 | 359.7 | 530.6 | — | — | — |
| PBD monomer disulfide prodrug 4 | >10,000 | >10,000 | — | — | — |
| PBD monomer disulfide prodrug 5 | 1057.6 | 1349.7 | — | — | — |
| PBD monomer disulfide prodrug 6 | 805.7 | 2806.5 | — | — | — |
| PBD monomer diaphorase prodrug 2 | 343.8 (354.9) | 574.7 (287.5) | 223 | — | — |
| PBD monomer diaphorase prodrug 3 | 350.8 | 443.1 | — | — | — |
| PBD dimer diaphorase prodrug 1 | 69.2 (12.9) (45.6) | 17.1 (1.77) (3.67) | 21.3 | 14.2 | 2.05 |
| PBD dimer diaphorase prodrug 2 | 10.1 | 0.8 | — | 9.84 | 1.25 |
| PBD dimer diaphorase prodrug 3 | 1.87 | 0.24 | 1.23 | — | — |

Results against KPL-4 for PBD monomer control 1 and PBD monomer disulfide prodrugs 1 to 4 are depicted in FIG. 1 and results against WSU-DLCL2 for PBD monomer control 1 and PBD monomer disulfide prodrugs 1 to 4 are depicted in FIG. 2 where each figure is a plot of Activity [%] versus the log of prodrug concentration in moles per liter. Activity [%] is reported in negative values that refer to the reduction in cell viability. For instance, an Activity [%] of −50 refers to a 50% reduction in cell viability. Excluding Prodrug 4, for KPL-4, for prodrugs 1 to 3, the ratio of the parent compound to the prodrug having the greatest $IC_{50}$ (prodrug 2) was about 1.5. Excluding Prodrug 4, for WSU-DLDL2, for prodrugs 1 to 3, the ratio of the parent compound to the prodrug having the greatest $IC_{50}$ (prodrug 2) was about 9.6. Differential disulfide prodrug activation was observed in both the high GSH cell line (KPL-4) and the low GSH cell line (WSU-DLCL2). Less differentiation was observed for the KPL-4 cell line as compared to the WSU-DLCL2 cell line.

In addition to the potency evaluation, the release of PBD dimer diaphorase prodrug 1 was evaluated. The release was measured to be 12% after 90 minutes incubation according to the following method. First, a master mix reaction was prepared containing 0.5 uM of the PBD prodrug, 50 uM PBD, 200 mM NADPH was quenched and diluted with 40 uL of 0.1% formic acid in 96-well polypropylene plate. Second, the reaction mix was incubated at room temperature for 5, 30, 90 min. Third, standards in DMSO were prepared in 0.1% formic acid using ECHO acoustic liquid handling technology (Labcyte Inc, Sunnyvale, Calif.) to create a 10-point dose-response curve in triplicate with 1:2.5× serial dilution in 96-well polypropylene plate. Fourth, 10 uL of sample and standard was injected to an AB SCIEX QTRAP® 6500 mass spectrometer coupled with Waters liquid chromatography. The LC gradient used was Phenomenex Kinetex C18, 1.7 µm, 100 Å, 100×2.1 mm column, with mobile phase A (0.1% formic acid in water) and B (0.1% formic acid in acetonitrile) was 0-0.5 min 5% B, 1-1.10 min 70-95% B, 2.49-2.5 min 95% B, 2.5-3.0 min 95-5% B at a flow rate of 0.8 mL/min (column temperature of 30° C.). The retention time was 1.06 min. The multiple reaction monitor (MRM) transition in MS was (585/257.0) and (585/504.2). The compound-dependent MS parameters for MRM (585/257.0) are 51, 20, 206, and 10 for CE, CXP, DP, and EP, respectively and for MRM (585/504.2) are 27, 12, 206, and 10 for CE, CXP, DP, and EP, respectively. Finally, data was analyzed using MultiQuant analysis software and standards were calculated using GraphPad Prism 6 linear regression fit.

Example 7

Toxicity of PBD Monomer Disulfide Prodrugs Against SK-BR-3 Cell Line

The toxicity of PBD monomer disulfide prodrugs 1 to 4, PBD dimer disulfide prodrugs 1 and 4, PBD monomer control 1 and PBD dimer control 1 were evaluated against SK-BR-3 cell cultures. The SK-BR-3 cell line is a breast adenocarcinoma that overexpresses HER2 and exhibits GSH levels of from about 3 to about 10 mM. The HER2-positive breast cancer cell line, SK-BR-3, was obtained internally at Genentech after having been verified by sequence analysis. The cells were grown at 37 Celsius in DMEM+10% FBS supplemented with 2 mM L-glutamine for the duration of this assay. On the first day of the experiment, designated "Day −1", SK-BR-3 cells were harvested from tissue culture flasks, counted, and then seeded into 96-well plates at a concentration of 7,500 cells per well. The next day, designated "Day 0", cell culture media was removed from the cells and replaced with 100 uL of fresh media containing a serial dilution (1:3) of the compounds in Table 5 below. The plates were then returned to the 37 Celsius incubator and allowed to incubate for 3 days. On "Day 3" of the assay, the plates were removed from the incubator and allowed to equilibrate to room temperature before adding 100 uL of room-temperature CellTiter-Glo reagent (Promega). The plates were then agitated at 300 rpm for 10 minutes. The luminescence signal generated from this reaction was recorded on an Envision plate reader (Perkin-Elmer). The data were arranged in Excel (Microsoft) and graphed in Kaleidagraph (Synergy Software).

The $IC_{50}$ potency results are presented in Table 5 below:

TABLE 5

| PBD agent | SK-BR-3 $IC_{50}$ (nM) |
| --- | --- |
| PBD Monomer Control 1 | 124 |
| PBD Monomer Disulfide Prodrug 1 | 331 |
| PBD Monomer Disulfide Prodrug 3 | 616 |
| PBD Monomer Disulfide Prodrug 2 | 1757 |
| PBD Monomer Disulifde Prodrug 4 | >10,000 |
| PBD Dimer Control 1 | 0.144 |
| PBD Dimer Disulfide Prodrug 1 | 2.39 |
| PBD Dimer Disulfide Prodrug 4 | 3.09 |

The results for SK-BR-3 are depicted in FIGS. 3 and 10 where the figures are plots of Cell viability (% of control) versus PBD compound concentration on an nM basis. Based on the results, it is believed that bulkier disulfide prodrug moieties have reduced potency. Further, based on experimental results to date, it is believed that potency correlates with disulfide stability.

Example 8

Whole Blood Stability of PBD Monomer and Dimer Prodrugs

The whole blood stability of various PBD monomer and PBD dimer prodrugs of the present invention was evaluated.

Whole blood stability samples were prepared as follows. Stability samples were generated in Mouse (CB17 SCID), Rat (Sprague-Dawley), Cynomologus Monkey and Human Whole blood Plasma as well as Buffer (0 and 24 hour). Blood was collected by Bioreclamation then shipped cold overnight and samples were created immediately on arrival of whole blood. To create stability samples, initial dilutions of the source material were made in Buffer (1× PBS, 0.5% BSA, 15 PPM Proclin) so that all molecules were 1 mg/mL in concentration. Then a 1:10× dilution (36 uL of 1 mg/mL initial dilution+324 uL blood or buffer) was performed to generate the stability samples with a final concentration of 100 ug/mL. Once mixed, 150 µL of the Whole Blood/Buffer stability samples was aliquoted into two separate sets of tubes for the two different time points. The 0 hour time points were then placed in a −80° C. freezer, while the 24 hour time points were placed on a shaker in a 37° C. incubator. When the 24 hour samples reached the given time point they were also placed in the −80° C. freezer.

The whole blood stability samples were evaluated by affinity-capture LC-MS assay. First, Streptavidin-coated magnetic beads (Life Technologies Corporation, Grand Island, N.Y.) were washed 2× with HBS-EP buffer (GE Healthcare, Sunnyvale, Calif.), then mixed with biotinylated CD22 anti-idiotypic antibody using the KingFisher Flex (Thermo Fisher Scientific, Waltham, Mass.) and incubated for 2 hrs at room temperature with gentle agitation. After the 2 hrs, the SA-bead/Biotin-xId Ab complex was washed 2× with HBS-EP buffer, mixed with the diluted whole blood stability samples and then incubated for 2 hrs at room temperature with gentle agitation. After the 2 hrs, the SA-bead/Biotin-xId Ab/sample complex was washed 2× with HBS-EP buffer, mixed with the deglycosylation enzyme PNGase F (New England BioLabs, Ipswich, Mass.) and then incubated for overnight at 37° C. with gentle agitation. After the overnight incubation, the deglycosylated SA-bead/Biotin-xId Ab/sample complex was washed 2× with HBS-EP buffer, followed by 2× washes of water (Optima H$_2$O, Fisher Scientific, Pittsburgh, Pa.) and finally 1× wash with 10% acetonitrile. The beads were then placed in 30% acetonitrile/0.1% formic acid for elution where they incubated for 30 mins at room temperature with gentle agitation before the beads were collected. The eluted samples were injected and loaded onto a Thermo Scientific PepSwift RP monolithic column (500 μm×5 cm) maintained at 65 oC. The sample was separated on the column using a Waters Acquity UPLC system at a flow rate of 20 μL/min with the following gradient: 20% B (95% acetonitrile+0.1% formic acid) at 0-2 min; 35% B at 2.5 min; 65% B at 5 min; 95% B at 5.5 min; 5% B at 6 min. The column was directly coupled for online detection with a Waters Synapt G2-S Q-ToF mass spectrometry operated in positive ESI with an acquisition mass range from 500 to 5000 Th (m/z).

The in vitro whole blood stability of PBD monomer disulfide prodrugs 2 to 6, 8, 10 and 13, and PBD monomer control 1 were evaluated in humans and rats at 4- and 24-hour intervals. The results are presented in FIG. 4 as percent of the parent compound remaining relative to time zero.

The in vitro whole blood stability of PBD dimer ADC boronic acid prodrug 1, PBD dimer ADC diaphorase prodrug 1B, and PBD dimer ADC disulfide prodrugs 1, 2A, 2B and 3 to 5 were evaluated in mouse, rat, cyno and human and the results are presented in Table 6 below where "DAR" refers to drug to antibody ratio, "Delta % DAR2" refers to delta DAR2 at 24 hours relative to the buffer at 0 hours, and "Prodrug loss" refers to prodrug loss at 24 hours relative to the buffer at 0 hours.

TABLE 6

| Prodrug | Matrix | % DAR2 0 hr | % DAR2 24 hr | Delta % DAR2 | Prodrug loss |
|---|---|---|---|---|---|
| PBD dimer ADC disulfide prodrug 1 | Buffer | 100 | 100 | 0 | 0.23 |
| | Mouse | 100 | 100 | 0 | 3.00 |
| | Rat | 100 | 100 | 0 | 5.60 |
| | Cyno | 100 | 100 | 0 | 4.23 |
| | Human | 89 | 89 | 11 | 5.07 |
| PBD dimer ADC disulfide prodrug 2A | Buffer | 100 | 100 | 0 | 0 |
| | Mouse | 94.89 | 95.18 | 4.82 | 61.97 |
| | Rat | — | 100 | 0 | 72.09 |
| | Cyno | 93.94 | 100 | 0 | 91.01 |
| | Human | 94.33 | 100 | 0 | 55.15 |
| PBD dimer ADC disulfide prodrug 2B | Buffer | 100 | 100 | 0 | 0 |
| | Mouse | 100 | 100 | 0 | 61.42 |
| | Rat | 100 | 100 | 0 | 78.41 |
| | Cyno | 100 | 100 | 0 | 88.20 |
| | Human | 86 | 90 | 10 | 45.89 |
| PBD dimer ADC disulfide prodrug 3 | Buffer | 100 | 100 | 0 | 0 |
| | Mouse | 100 | 100 | 0 | 83.22 |
| | Rat | 100 | 100 | 0 | 87.21 |
| | Cyno | 100 | 100 | 0 | 92.20 |
| | Human | 84 | 80 | 20 | 79.74 |
| PBD dimer ADC disulfide prodrug 4 | Buffer | 100 | 100 | 0 | 0 |
| | Mouse | 100 | 100 | 0 | 32.47 |
| | Rat | 100 | 100 | 0 | 21.42 |
| | Cyno | 100 | 100 | 0 | 36.25 |
| | Human | 89 | 85 | 15 | 25.30 |
| PBD dimer ADC disulfide prodrug 5 | Buffer | 100 | 100 | 0 | 0.15 |
| | Mouse | 100 | 100 | 0 | 57.66 |
| | Rat | 100 | 100 | 0 | 81.35 |
| | Cyno | 100 | 100 | 0 | 97.36 |
| | Human | 100 | 100 | 0 | 67.90 |
| PBD dimer ADC boronic acid prodrug 1 | Buffer | 100 | 100 | 0 | 0 |
| | Mouse | 100 | 100 | 0 | 0 |
| | Rat | 100 | 100 | 0 | 0 |
| | Cyno | 100 | 100 | 0 | 0 |
| | Human | 100 | 100 | 0 | 0 |
| PBD dimer ADC diaphorase prodrug 1B | Buffer | 100 | 100 | 0 | 0.71 |
| | Mouse | 100 | 100 | 0 | 11.75 |
| | Rat | 100 | 100 | 0 | 11.32 |
| | Cyno | 100 | 100 | 0 | 4.67 |
| | Human | 100 | 100 | 0 | 2.30 |

Example 9

Toxicity of PBD Monomer Disulfide Prodrugs and PBD Dimer Disulfide Prodrugs Against Various Cell Lines The toxicity of various PBD monomer disulfide prodrugs and PBD dimer disulfide prodrugs was evaluated on UACC-257, Igrov-1 and A2058 cell lines. Cells were seeded in 384-well plate and treated with drug 24 hours later. After 4 days of drug incubation, the cell viability was determined using Promega CellTiter-Glo luminescent reagent, which measures ATP level (an indirect measure of cell number). The luminescent intensity was measured on PerkinElmer Envision reader. The relative cell viability was calculated by normalizing to non-drug treatment control and was graphed using KleidaGraph software package. IC$_{50}$ value was determined as the concentration to obtain 50% of the maximum cell killing.

The IC$_{50}$ results are presented in Table 7A below:

TABLE 7A

| PBD Agent | UACC-257 | Igrov-1 | A2058 |
| --- | --- | --- | --- |
| PBD monomer control 1 | 181.4 | 68.5 | 56.9 |
| PBD monomer control 2 | >20,000 | >20,000 | >20,000 |
| PBD monomer disulfide prodrug 1 | 275.7 | 122.8 | 82.9 |
| PBD monomer disulfide prodrug 2 | 1858.8 | 1871.8 | 635.2 |
| PBD monomer disulfide prodrug 3 | 356.0 | 253.9 | 75.2 |
| PBD monomer disulfide prodrug 4 | 19164.1 | 12640.1 | 8109.9 |
| PBD monomer disulfide prodrug 5 | 892.1 | 765.1 | 395.3 |
| PBD monomer disulfide prodrug 6 | 497.4 | 3262.3 | 566.6 |
| PBD monomer disulfide prodrug 7 | >30,000 | >30,000 | 10956 |
| PBD monomer disulfide prodrug 8 | 194.1 | 171.8 | 47.2 |
| PBD monomer disulfide prodrug 9 | 2109.1 | 1046.9 | 291.8 |
| PBD monomer disulfide prodrug 10 | 4732.3 | 4807.6 | 1827.9 |
| PBD monomer disulfide prodrug 11 | 331.1 | 206.7 | 108.3 |
| PBD monomer disulfide prodrug 12 | 155.8 | 83.6 | 31.1 |
| PBD monomer disulfide prodrug 13 | >10,000 | >10,000 | >10,000 |
| PBD monomer disulfide prodrug 15 | 1500.2 | 928.2 | 304.2 |
| PBD monomer disulfide prodrug 16 | 19460.1 | 18509.1 | 5593.4 |
| PBD monomer disulfide prodrug 19 | 147.3 | 77.4 | 37.7 |
| PBD monomer disulfide prodrug 22 | 80.6 | 39.8 | 23.7 |
| PBD monomer disulfide prodrug 23 | 866.2 | 687.2 | 206.3 |
| PBD monomer disulfide prodrug 24 | 2694.2 | 1479.9 | 596.1 |
| PBD monomer disulfide prodrug 25 | 241.6 | 129.4 | 47.7 |
| PBD monomer disulfide prodrug 26 | 328.3 | 245.8 | 84.5 |
| PBD monomer disulfide prodrug 27 | 939.1 | 957.9 | 261.2 |
| PBD monomer disulfide prodrug 28 | 2102.2 | 2304.1 | 920.1 |
| PBD monomer disulfide prodrug 29 | 142.1 | 57.8 | 29.1 |
| PBD monomer disulfide prodrug 30 | 307.6 | 234.8 | 107.6 |
| PBD dimer control 1 (in GSH cell panel) | 0.95 | 0.061 | — |
| PBD dimer disulfide prodrug 1 | 2.2 | 0.21 | — |
| PBD dimer disulfide prodrug 4 | 7.8 | 2.5 | — |

Note that an IC$_{50}$ ratio may be calculated for each prodrug as compared to the respective control. For instance, The IC$_{50}$ ratio of PBD dimer disulfide prodrug 1 is 2.3 and 3.4 for cell lines UACC-257 and IGROV-1, respectively, calculated as follows: (PBD dimer disulfide prodrug 1 UACC-257 IC$_{50}$ of 2.2)/(PBD dimer control 1 UACC-257 IC$_{50}$ of 0.95)=Ratio of 2.3); and (PBD dimer disulfide prodrug 1 IGROV-1 IC$_{50}$ of 0.21)/(PBD dimer control 1 IGROV-1 IC$_{50}$ of 0.061)= Ratio of 3.4).

PBD dimer control 1 and PBD dimer control 2 were further evaluated in standard cell panels against a number of cell lines. The IC50 results are reported in Table 7B below.

TABLE 7B

| Cell line | PBD dimer control 1 | PBD dimer control 2 |
| --- | --- | --- |
| MES-SA | 0.028 | 10.0 |
| MES-SA/Dx5 | 0.56 | >100 |
| BJAB | 0.015 | 4.9 |
| BJAB/Pgp | — | 53.7 |
| KPL-4 | 0.053 | 67.4 |
| HCC1569 X2 | 0.097 | — |
| T-47D | 0.032 | — |
| HCC1937 | 0.15 | — |
| NCI-H1781 | 0.011 | — |
| SW 900 | 0.078 | — |
| MDA-MB-231 | — | 73.2 |
| HCT 116 | — | 15.0 |
| A2058 | — | 5.3 |
| DLD-1 | — | >100 |
| HL-60 | — | 2.4 |

Figure 5:
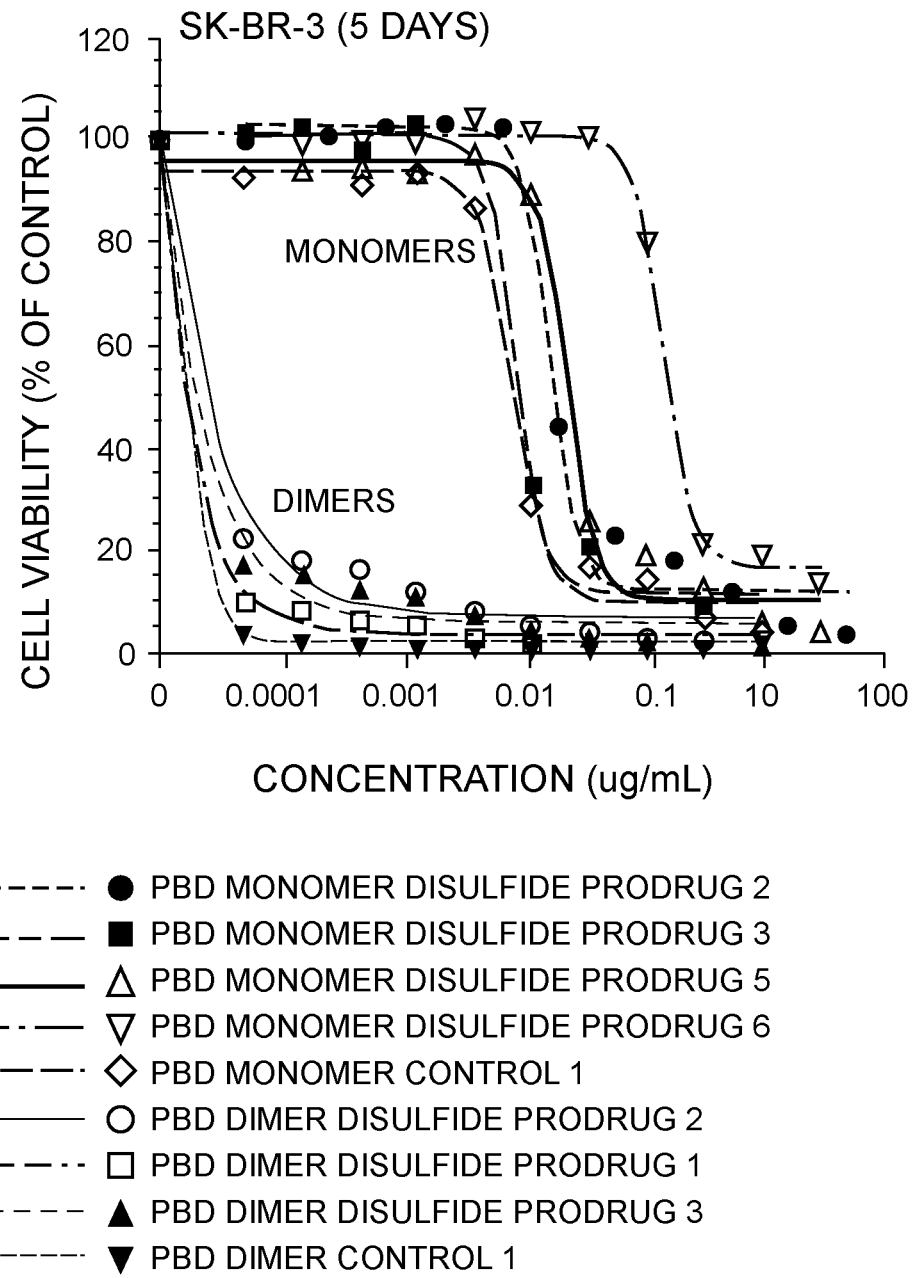
FIG. 5 depicts a plot of SK-BR-3 cell viability (% of control) versus PBD monomer disulfide prodrug concentration in micromoles and PBD dimer disulfide prodrug concentration in µg/mL.

The PBD monomer disulfide prodrugs 2, 3, 5, 6, PBD dimer disulfide prodrug 1 to 3, PBD monomer control 1 and PBD dimer control 1 results for SK-BR-3 are depicted in FIG. 5 and the results for KPL-4 are depicted in FIG. 6 where each figure is a plot of Cell viability (% of control) versus PBD compound concentration in µg/mL. Differential disulfide prodrug activation was observed in both the high GSH cell line (KPL-4) and the low GSH cell line (WSU-DLCL2). Less differentiation was observed for the KPL-4 cell line as compared to the WSU-DLCL2 cell line.

The results for the PBD dimer control 1 against UACC-257 and IGROV-1 cell lines is depicted in FIG. 7. The results for PBD dimer disulfide prodrug compound 1 against UACC-257 and IGROV-1 cell lines are depicted in FIG. 8. The results for PBD dimer disulfide prodrug compound 4 against UACC-257 and IGROV-1 cell lines is depicted in FIG. 9.

Example 10

Toxicity of PBD Dimer Disulfide Prodrug-Antibody Conjugates Against SK-BR-3 and KPL-4 Cell Lines The toxicity of various PBD dimer ADC disulfide prodrugs, PBD dimer ADC diaphorase prodrugs, and non-prodrug PBD dimer ADC controls were evaluated against KPL-4 and SK-BR-3 cell cultures. Cells were plated in black-walled 96-well plates (4000 per well for SK-BR-3; 1200 cells per well for KPL-4) and allowed to adhere overnight at 37° C. in a humidified atmosphere of 5% CO$_2$. Medium was then removed and replaced by fresh culture medium containing different concentrations of ADCs. After 5 days, Cell Titer-Glo reagent was added to the wells for 10 min at room temperature and the luminescent signal was measured using PerkinElmer EnVision.

The IC$_{50}$ results are presented in Table 8 below:

TABLE 8

| PBD agent | SK-BR-3 IC$_{50}$ (ng/mL) | KPL-4 IC$_{50}$ (ng/mL) |
| --- | --- | --- |
| PBD dimer ADC disulfide prodrug 3 | 7.0 | 5.7 |
| PBD dimer ADC disulfide prodrug 2B | 8.9 | 31.7 |
| PBD dimer ADC disulfide prodrug 2A | 8.4 (14) | 5.0 (10) |
| PBD dimer ADC disulfide prodrug 4 | 19.3 | 247 |
| PBD dimer ADC disulfide prodrug 1A | 16.1 | 33,000 |
| PBD dimer ADC disulfide prodrug 1B | 11.1 (18.5) | 8.8 (17.6) |
| Non-prodrug PBD dimer ADC control 1 | 0.6 | 0.5 |
| Non-prodrug PBD dimer ADC control 2 | 349 | 333 |
| Non-prodrug PBD dimer ADC control 3 | 4.1 | 1.3 |
| Non-prodrug PBD dimer ADC control 4 | 1.4 | >100,000 |
| PBD dimer ADC diaphorase prodrug 1A | 8.0 | 5.4 |
| PBD dimer ADC diaphorase prodrug 1B | >1,000 | <1,000 |

Figure 11:
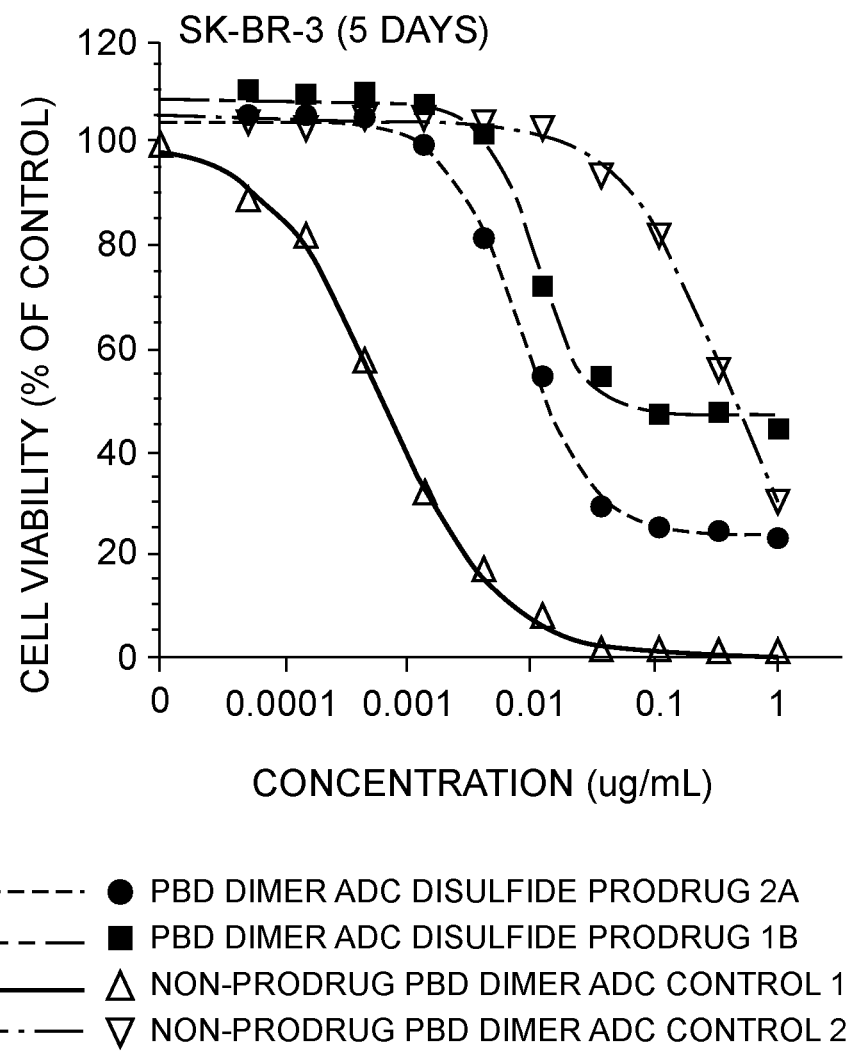
FIG. 11 depicts a plot of SK-BR-3 cell viability (% of control) versus the concentration of (i) a 7C2 HC A140C peptide-linked disulfide cyclopentyl prodrug ADC PBD dimer, (ii) a 7C2 LC K149C peptide-linked disulfide thiophenol prodrug ADC PBD dimer, (iii) a 7C2 HC A140C ADC PBD dimer not having a prodrug moiety, and (iv) a CD22 HC A140C ADC PBD dimer not having a prodrug moiety.

The PBD dimer ADC disulfide prodrug 2A, PBD dimer ADC disulfide prodrug 1B, non-prodrug PBD dimer ADC control 1 and non-prodrug PBD dimer ADC control 2 results for SK-BR-3 are depicted in FIG. 11 and the results for KPL-4 are depicted in FIG. 12 where each figure is a plot of Cell viability (% of control) after 5 days versus PBD compound concentration in µg/mL. Differential disulfide prodrug activation was observed with HER2 conjugates in HER2 cell lines.

Example 11

Toxicity of PBD Dimer Disulfide Prodrug-Antibody Conjugates Against SK-BR-3 and KPL-4 Cell Lines The toxicity of PBD dimer ADC disulfide prodrugs 1, 2B, 3 and 4 and non-prodrug PBD dimer ADC controls 1 and 2 were evaluated against SK-BR-3 and KPL-4 cell lines for cell viability after 5 days. Cells were plated in black-walled 96-well plates (4000 per well for SK-BR-3; 1200 cells per well for KPL-4) and allowed to adhere overnight at 37° C. in a humidified atmosphere of 5% $CO_2$. Medium was then removed and replaced by fresh culture medium containing different concentrations of ADCs. After 5 days, Cell Titer-Glo reagent was added to the wells for 10 min at room temperature and the luminescent signal was measured using PerkinElmer EnVision.

Figure 13:
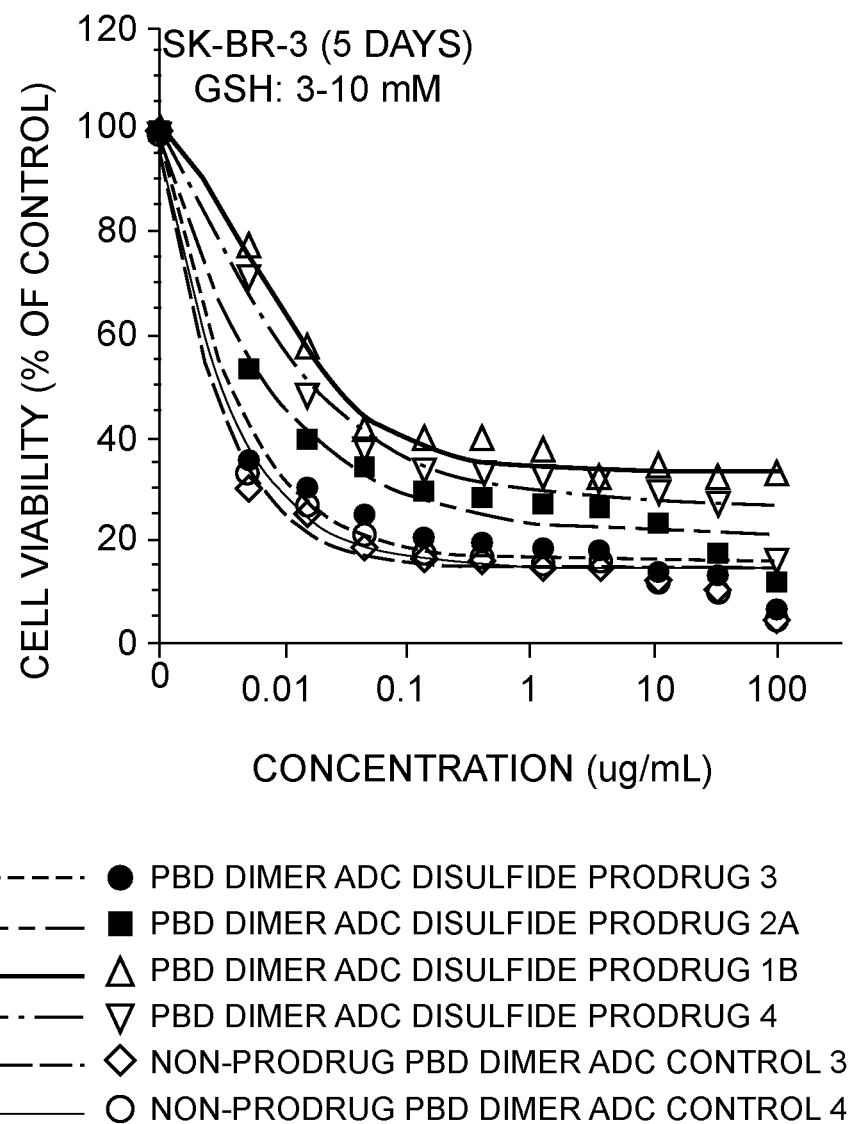
FIG. 13 depicts a plot of SK-BR-3 cell viability (% of control) versus the concentration of (i) 7C2 LC K149C peptide linked disulfide cyclobutyl prodrug ADC PBD dimer, (ii) 7C2 LC K149C peptide linked disulfide cyclopentyl prodrug ADC PBD dimer, (iii) 7C2 LC K149C peptide linked disulfide thio-phenol prodrug ADC PBD dimer, (iv) 7C2 LC K149C peptide linked disulfide isopropyl prodrug ADC PBD dimer, (v) 4D5 HC A118C ADC PBD dimer not having a prodrug moiety, and (vi) 4D5 LC V205C ADC PBD dimer not having a prodrug moiety.
Figure 14:
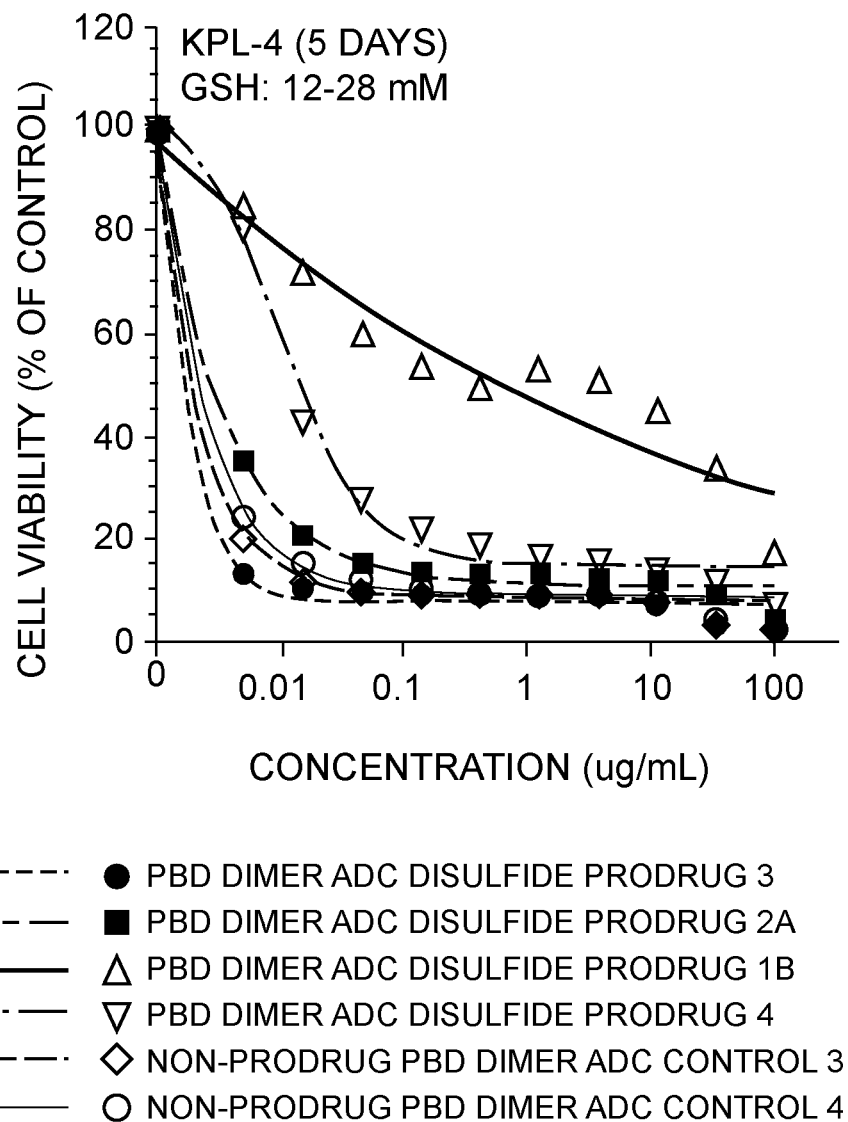
FIG. 14 depicts a plot of KPL-4 cell viability (% of control) versus the concentration of (i) 7C2 LC K149C peptide linked disulfide cyclobutyl prodrug ADC PBD dimer, (ii) 7C2 LC K149C peptide linked disulfide cyclopentyl prodrug ADC PBD dimer, (iii) 7C2 LC K149C peptide linked disulfide thio-phenol prodrug ADC PBD dimer, (iv) 7C2 LC K149C peptide linked disulfide isopropyl prodrug ADC PBD dimer, (v) 4D5 HC A118C ADC PBD dimer not having a prodrug moiety, and (vi) 4D5 LC V205C ADC PBD dimer not having a prodrug moiety.

The results are reported in FIGS. 13 and 14.

Example 12

Whole Blood Stability of PBD Dimer-Antibody Conjugate Disulfide Prodrugs

The stability of PBD dimer ADC disulfide prodrugs 1 and 2B were evaluated in a buffer ("Buffer"), in cynomolgus monkey whole blood ("CynoWB"), in human whole blood ("HumanWB), in mouse whole blood ("MouseWB"), and in rat whole blood ("RatWB"). The experimental protocol is described in Example 8. The results are reported in Table 9 below where percent loss refers to the total loss of prodrug as compared the prodrug concentration at time zero. Loss of prodrug includes loss of the imine form (i.e., a hydroxyl moiety at C11 adjacent to the N10 prodrug substitution point).

TABLE 9

| | PBD dimer ADC disulfide prodrug 1 | PBD dimer ADC disulfide prodrug 2B |
|---|---|---|
| Buffer | 5% loss | 5% loss |
| CynoWB | 10% loss | 90% loss |
| HumanWB | 10% loss | 40% loss |
| MouseWB | 8% loss | 63% loss |
| RatWB | 10% loss | 80% loss |

Example 13

Toxicity of a ROS-Activated PBD Dimer-Antibody Conjugate Aryl Boronic Acid Prodrugs The toxicity of various PBD monomer and dimer boronic acid prodrug compounds were evaluated for cell toxicity. In the in vitro tumor cell killing assay, the cells were added to each well of 96-well microtiter plates at 8,000 cells per well and were incubated overnight at 37° C. in a humidified atmosphere of 5% $CO_2$. The cells were exposed to various concentration of the indicated prodrug, positive control and negative control compounds. Where silvestrol was evaluated, a 1:3 serial dilution was used. After incubation for 3 days, Cell titer-Glo reagent (Promega, Madison Wis.) was added to the wells at 100 μL per well followed by a 10-minute incubation at room temperature, and the luminescent signal was measured using a Packard/Perkin-Elmer TopCount.

The toxicity of PBD dimer ADC boronic acid prodrug 1A and 1B were evaluated against WSU-DLCL and BJAB tumor cell lines for cell viability. PBD dimer ADC boronic acid control 1A was used as a negative control and PBD dimer ADC boronic acid control 2 was used as a positive control. The results are reported in FIGS. 15A, 15B and 16 as normalized percent of viable cells after 3 days as compared to the number of cells at time zero versus dosage in μg/mL. PBD dimer ADC boronic acid prodrug 1A provided an $EC_{50}$ of 1.701 nM and the non-prodrug PBD dimer ADC control 2 provided an $EC_{50}$ of 0.0236 nM. PBD dimer ADC boronic acid prodrug 1A provided an $EC_{50}$ of 0.0509 nM, PBD dimer ADC boronic acid prodrug 1B provided an $EC_{50}$ of 15.86 nM, and PBD dimer ADC boronic acid control 2 provided an $EC_{50}$ of 0.0274.

Figure 15A:
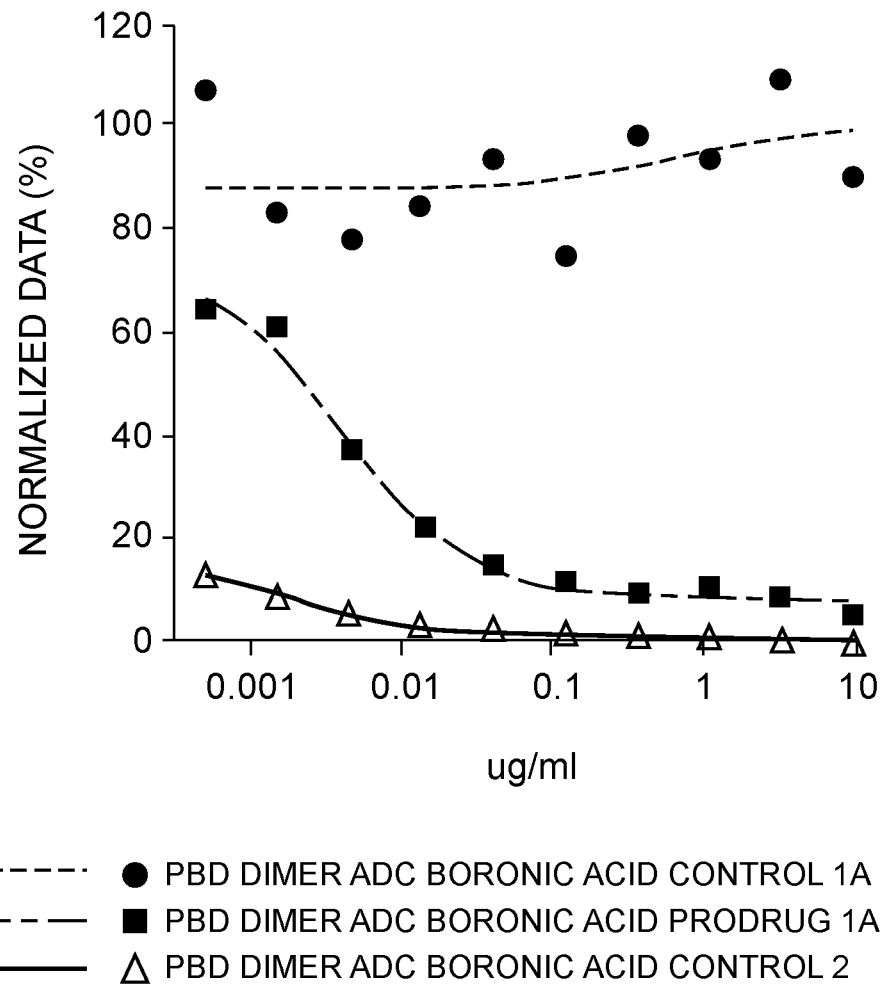
FIG. 15A depicts a plot of WSU-DLCL normalized percent of viable cells after 3 days as compared to the number of cells at time zero versus the concentration of (i) a CD22 antibody ADC PBD dimer having a benzyl formate ($C_6H_5$—$CH_2$—O—C(O)—) moiety at the N10 position of one PBD monomer (negative control), (ii) a CD22 antibody ADC PBD dimer aryl boronic acid prodrug (($OH)_2B$—$C_6H_4$—$CH_2$—O—C(O)—), and (iii) a CD22 antibody ADC PBD dimer not having a prodrug moiety (positive control).
Figure 15B:
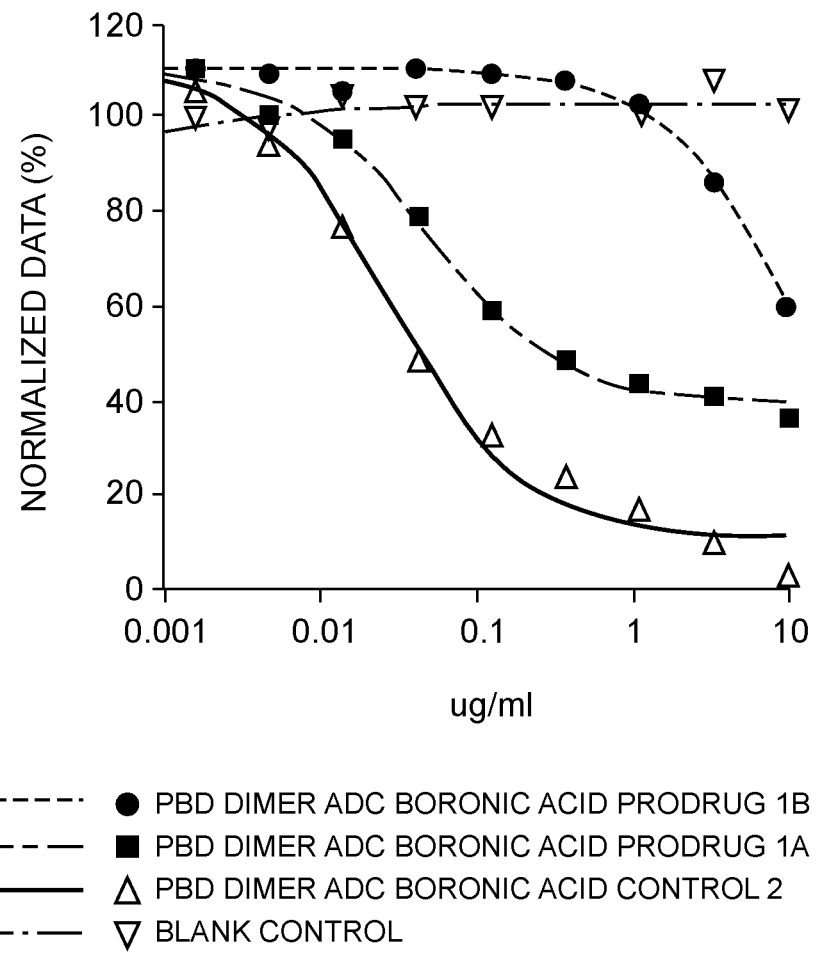
FIG. 15B depicts a plot of WSU-DLCL cell kill versus drug concentration in µg/mL three days after exposure to: (i) a CD22 antibody ADC PBD dimer having a boronic acid prodrug (PBD dimer ADC boronic acid prodrug 1A); (ii) a Ly6E antibody ADC PBD dimer having a boronic acid prodrug (PBD dimer ADC boronic acid prodrug 1B); (iii) a CD22 antibody ADC PBD dimer not having a prodrug moiety (PBD dimer ADC boronic acid control 2) (positive control) and (iv) a blank control.
Figure 15C:
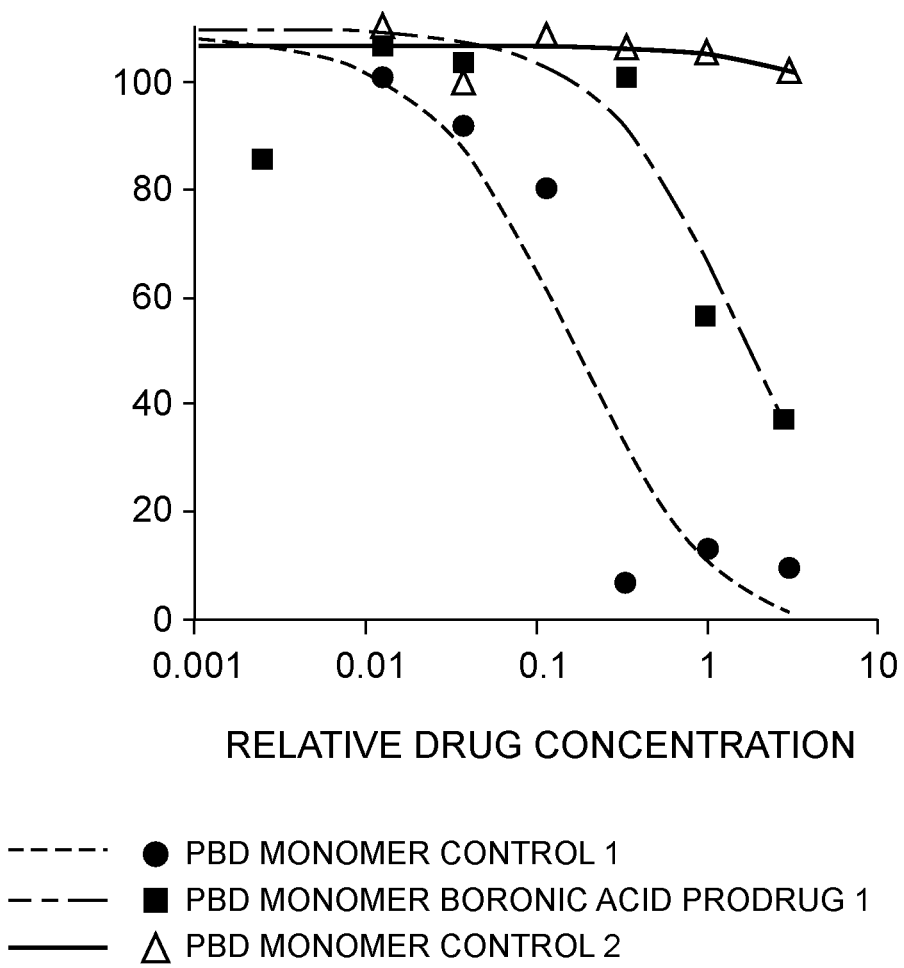
FIG. 15C depicts a plot of MDA-MB-453 cell kill versus drug concentration in µM three days after exposure to: (i) a PBD monomer control; (ii) a PBD monomer control having a benzyl formate moiety at the N10 PBD position; and (iii) a PBD monomer boronic acid prodrug.
Figure 15D:
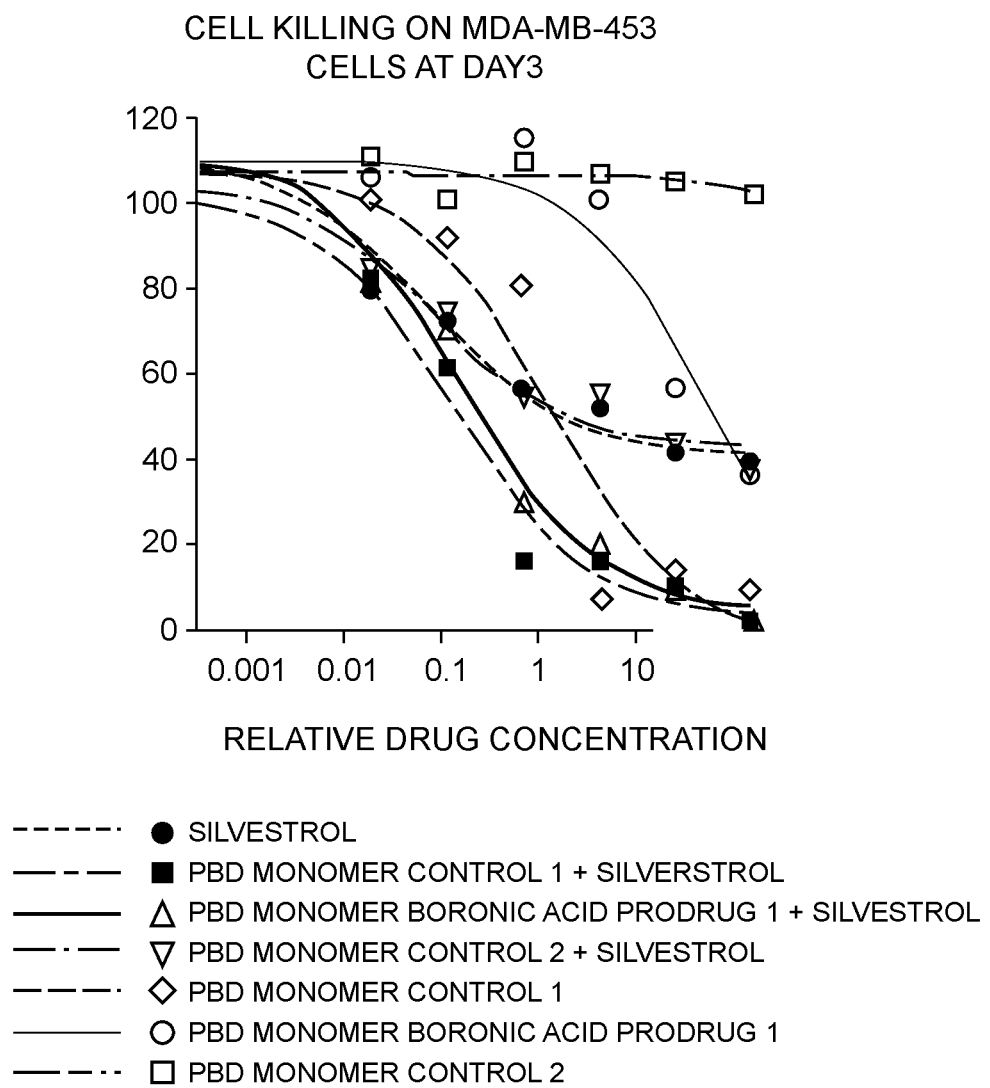
FIG. 15D depicts a plot of MDA-MB-453 cell kill versus drug concentration in µM three days after exposure to: (i) silvestrol, (ii) a PBD monomer control; (iii) a PBD monomer control having a benzyl formate moiety at the N10 PBD position; (iv) a PBD monomer boronic acid prodrug; (v) the PBD monomer control and silvestrol; (vi) the PBD monomer control having a benzyl formate moiety at the N10 PBD position and silvestrol; and (vii) the PBD monomer boronic acid prodrug and silvestrol.7

The toxicity of PBD monomer boronic acid prodrug 1 was evaluated against MDA-MB-453 tumor cell line for cell viability. PBD monomer control 1 was used as a positive control and PBD monomer control 2 was used as a negative control. The toxicity study was repeated wherein the PBD prodrug and controls were administered in combination with silvestrol. FIG. 15C depicts a plot of MDA-MB-453 cell kill versus drug concentration in μM three days after exposure to: (i) a PBD monomer control; (ii) a PBD monomer control having a benzyl formate moiety at the N10 PBD position; and (iii) a PBD monomer boronic acid prodrug. FIG. 15D depicts a plot of MDA-MB-453 cell kill versus drug concentration in μM three days after exposure to: (i) silvestrol, (ii) a PBD monomer control; (iii) a PBD monomer control having a benzyl formate moiety at the N10 PBD position; (iv) a PBD monomer boronic acid prodrug; (v) the PBD monomer control and silvestrol; (vi) the PBD monomer control having a benzyl formate moiety at the N10 PBD position and silvestrol; and (vii) the PBD monomer boronic acid prodrug and silvestrol. PBD monomer control 1 provided an $EC_{50}$ of 0.1635 nM, PBD monomer boronic acid prodrug 1 provided an $EC_{50}$ of 1.846 nM, and PBD monomer prodrug 2 provided an $EC_{50}$ of 267,356 nM.

The results indicate that the ROS aryl boronic acid prodrug provided for increased cell kill relative to the negative control.

Example 14

Efficacy of Anti-CD22 and Anti-Her2 Antibody Drug Conjugates

The efficacy of the anti-CD22 antibody-drug conjugates (ADCs) was investigated in a mouse xenograft model of BJAB-luc human Burkitt's lymphoma. The BJAB-luc cell line was obtained from Genentech cell line repository. This cell line was authenticated by short tandem repeat (STR) profiling using the Promega PowerPlex 16 System and compared with external STR profiles of cell lines to determine cell line ancestry. The BJAB-luc cell line expresses CD22 as determined by FACS and IHC. To establish the xenograft model, female C.B-17 SCID mice (Charles River Laboratories) were each inoculated subcutaneously in the flank area with the BJAB-luc cells (20 million cells suspended in 0.2 mL Hank's Balanced Salt Solution; Invitrogen).

The efficacy of the anti-Her2 antibody-drug conjugates (ADCs) was investigated in a mouse xenograft model of KPL4 human breast cancer. The KPL4 cell line was obtained from Dr. J. Kurebayashi lab (Japan) and this cell line expresses HER2 as determined by FACS and IHC. To establish the xenograft model, female C.B-17 SCID-beige mice (Charles River Laboratories) were each inoculated in the thoracic mammary fat pad area with the KPL4 cells (3 million cells suspended in 0.2 mL of 1:1 mixture of Hank's Balanced Salt Solution; Invitrogen and Matrigel; BD Biosciences). The KPL4 xenograft is a cachexia-inducing model where animals lost about 5% of their initial body weight in response to the tumor itself. Administration of anti-Her2 ADC attenuated this tumor associated weight loss, and was well tolerated in the animals.

Figure 24:
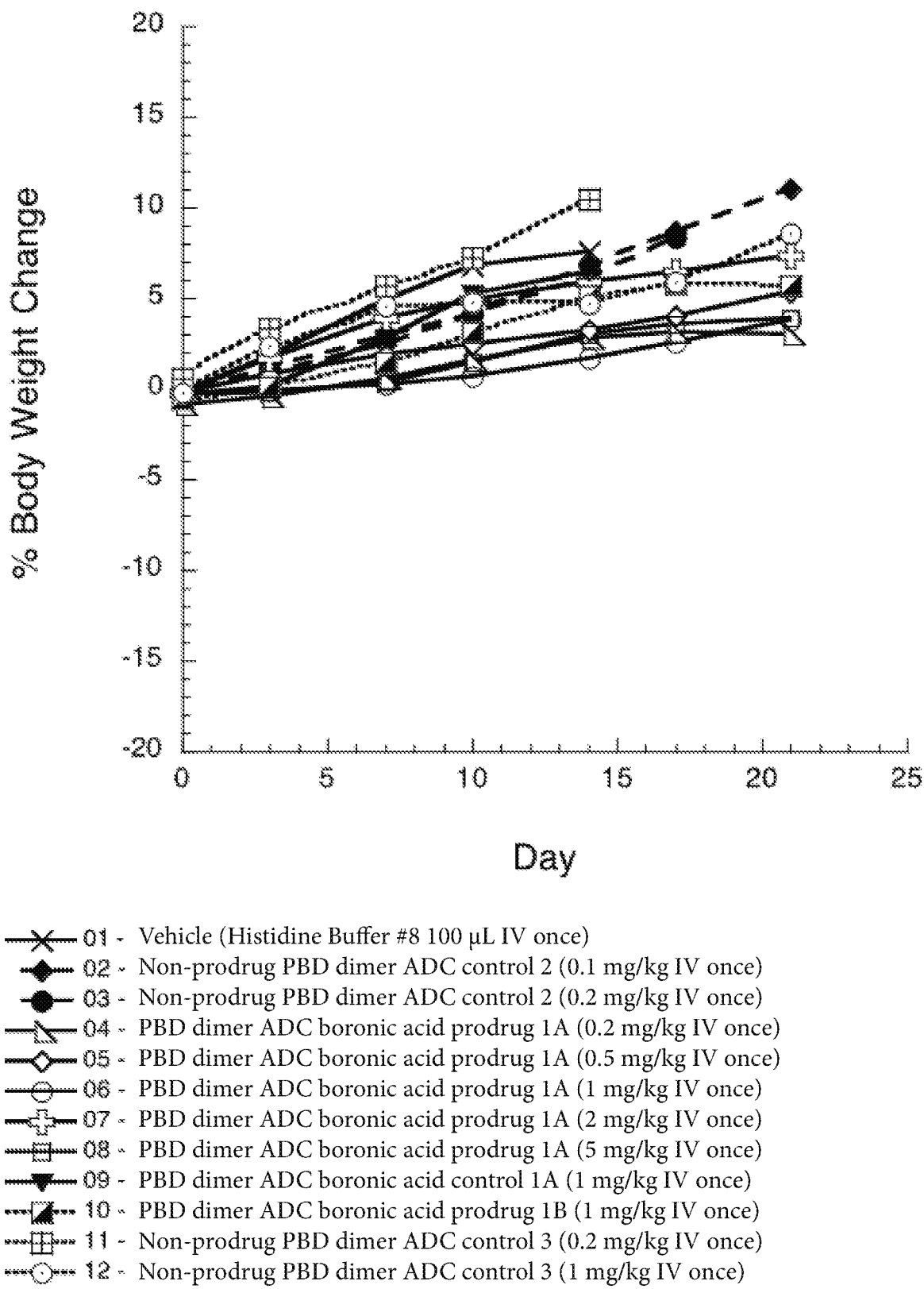
FIG. 24 depicts a plot of % body weight change versus days after treatment for SCID mice with BJAB-luc human Burkitt's lymphoma with: (i) histidine buffer vehicle; (ii) non-prodrug anti-CD22 HC-A118C PBD dimer ADC; (iii) anti-CD22 LC-K149C PDB dimer boronic acid prodrug ADC; (iv) anti-Ly6E LC-K149C PDB dimer boronic acid prodrug ADC; (v) non-prodrug anti-CD22 LC-K149C PDB dimer ADC; and (vi) non-prodrug anti-Her2 HC-A118C PBD dimer ADC.

When tumors reached an average tumor volume of 100-300 mm³, the animals were randomized into groups of 5-10 mice each and received a single intravenous injection of the ADCs (referred to as Day 0). In a first evaluation as depicted in FIGS. 23 and 24, mice were treated with the vehicle (histidine buffer #8, 100 μL IV once), non-prodrug PBD dimer ADC control 2 (0.1 mg/kg and 0.2 mg/kg IV once), PBD dimer ADC boronic acid prodrug 1A (0.2, 0.5, 1, 2, and 5 mg/kg IV once), PBD dimer ADC boronic acid control 1A (1 mg/kg IV once), PBD dimer ADC boronic acid prodrug 1B (1 mg/kg IV once) and non-prodrug PBD dimer ADC control 3 (0.2 and 1 mg/kg IV once). In a second evaluation depicted in FIGS. 25 and 26, mice were treated with the vehicle (histidine buffer #8, 100 μL IV once), non-prodrug PBD dimer ADC control 1 (0.3, 1 and 3 mg/kg IV once) and PBD dimer ADC disulfide prodrug 1B (1, 3, 6 and 10 mg/kg IV once). Tumors and body weights of mice were measured 1-2 times a week throughout the study. Mice were promptly euthanized when body weight loss was >20% of their starting weight. All animals were euthanized before tumors reached 3000 mm³ or showed signs of impending ulceration. Tumor volume was measured in two dimensions (length and width) using calipers and the tumor volume was calculated using the formula: Tumor size (mm3)=0.5×(length×width×width).

The results are presented in FIGS. 23 to 26.

FIG. 23 shows efficacy of anti-CD22 ADCs in C.B-17 SCID mice with BJAB-luc human Burkitt's lymphoma. Non prodrug PBD dimer ADC control 2 at the highest dose evaluated (0.2 mg/kg) only resulted in modest tumor growth delay. In contrast, PBD dimer ADC boronic acid prodrug 1A was very effective and drove tumor regression at the dose as low as 0.2 mg/kg. The PBD dimer ADC boronic acid control 1 did not show any effect on the tumor growth. The PBD dimer ADC boronic acid prodrug 1A and non-prodrug PBD dimer ADC control 3 conjugates had some anti-tumor activity; however, the activity of anti-CD22 conjugates at matched dose level was more superior.

FIG. 24 shows effect of the anti-CD22 ADCs (1) non prodrug PBD dimer ADC control 2, (2) PBD dimer ADC boronic acid prodrug 1A and (3) PBD dimer ADC boronic acid control 1 on the body weights of C.B-17 SCID mice with BJAB-luc human Burkitt's lymphoma. Administration of anti-CD22 ADCs was well tolerated in animals with no body weight loss observed.

Figure 25:
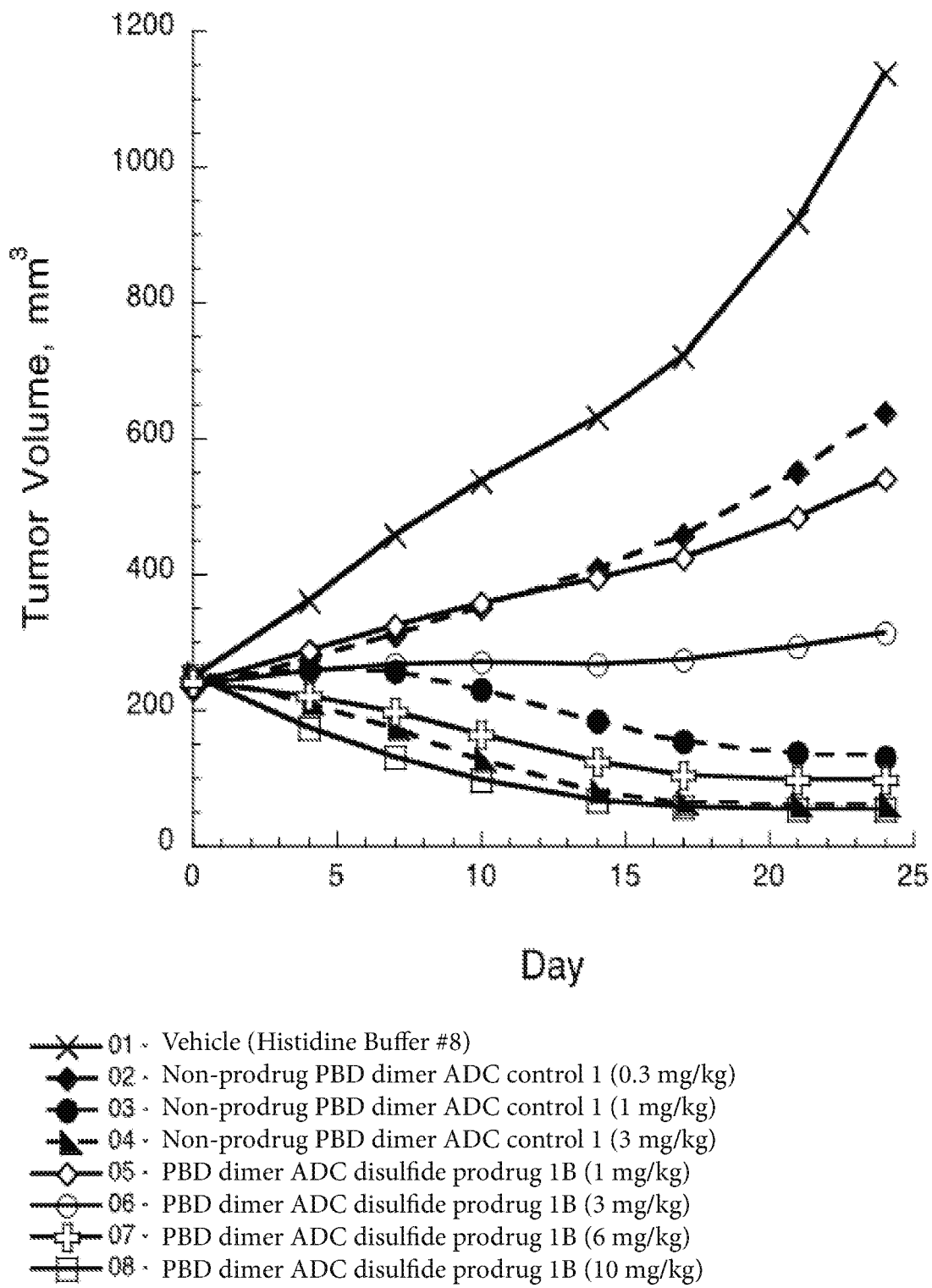
FIG. 25 depicts a plot of tumor volume (mm³) versus days after treatment for SCID-beige mice with KPL-4 human breast tumors with: (i) vehicle; (ii) non-prodrug anti-Her2 HC-A140C PBD dimer ADC; and (iii) anti-Her2 HC-A140C PBD thio-phenol prodrug ADC.

FIG. 25 shows efficacy of anti-Her2 ADCs in C.B-17 SCID-beige mice with KPL-4 human breast tumors. Non-prodrug PBD dimer ADC control 1 demonstrated dose-dependent inhibition of tumor growth with tumor regression at 1 mg/kg or above. Similarly, PBD dimer ADC disulfide prodrug 1 also showed dose-dependent efficacy with tumor regression at 6 mg/kg or above.

Figure 26:
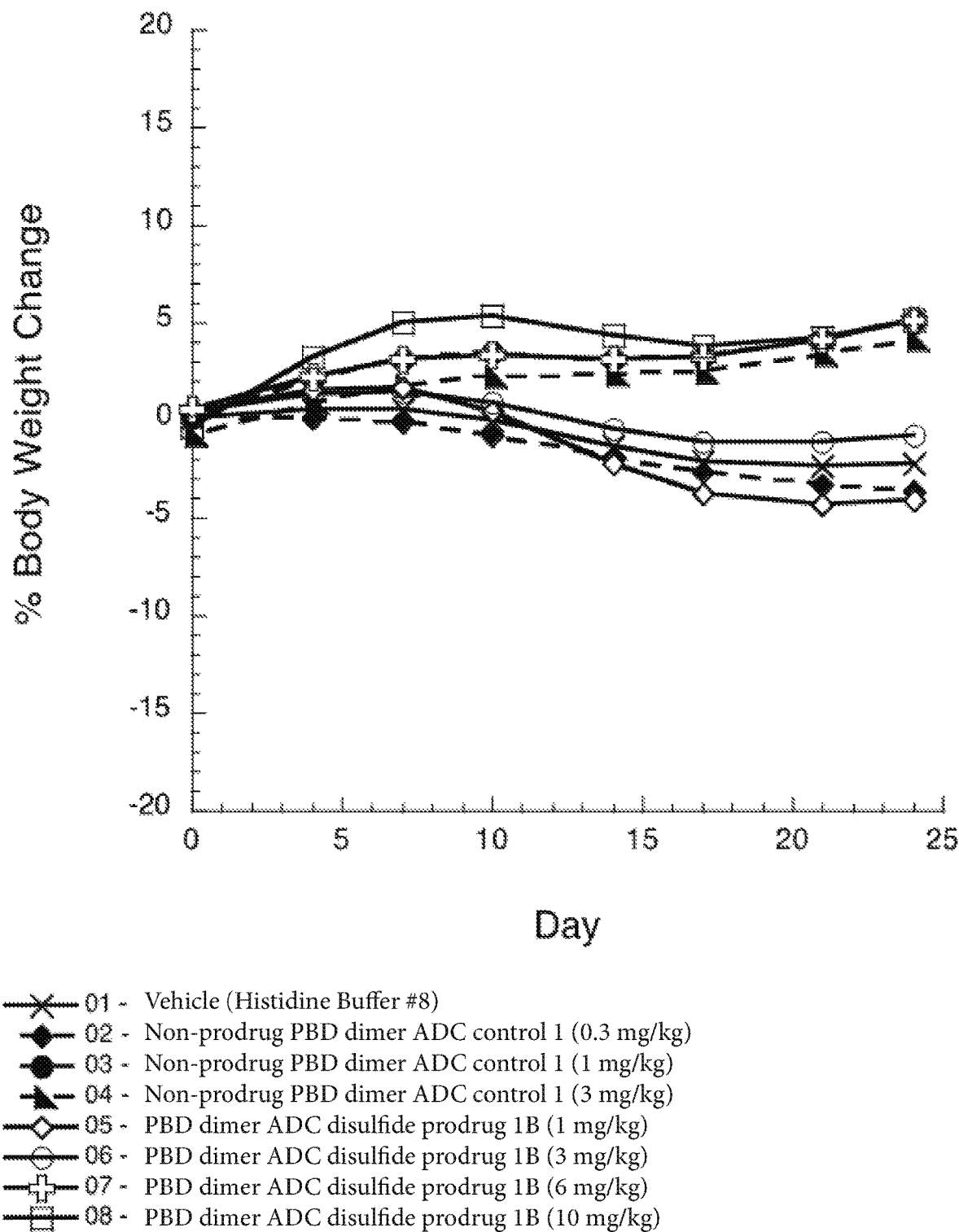
FIG. 26 depicts a plot of % body weight change versus days after treatment for SCID-beige mice with KPL-4 human breast tumors with: (i) vehicle; (ii) non-prodrug anti-Her2 HC-A140C PBD dimer ADC; and (iii) anti-Her2 HC-A140C PBD thio-phenol prodrug ADC.

FIG. 26 shows effect of non-prodrug PBD dimer ADC control 1 and PBD dimer ADC disulfide prodrug 1 (anti-Her2 ADCs) on the body weights of C.B-17 SCID-beige with KPL4 human breast tumors. The KPL4 xenograft is a cachexia-inducing model, where animals lose about 5% of their initial body weight in response to the tumor itself. Administration of anti-Her2 ADC attenuated this tumor associated weight loss, and was well tolerated in animals.

Example 15

Toxicity of a DTD-Activated PBD Monomer and Dimer Quinone Prodrugs

The toxicity of PBD dimer diaphorase prodrug 1, PBD monomer diaphorase prodrug 2, PBD dimer control 1 and PBD monomer control 1 were evaluated against KPL-4 and WSU cell lines for cell viability. The KPL-4 cell line is was a high DTD cell line characterized by NQO1 nRPKM of 839 and the WSU cell line was a low DTD cell line characterized by a NQO1 nRPKM of 1.36. The $IC_{50}$ ratios are based on the prodrug $IC_{50}$ value relative to the PBD dimer control.

The results are reported below in Table 10 and in FIGS. 17 to 20.

TABLE 10

| Compound | $IC_{50}$ Potency (nM) | Ratio |
|---|---|---|
| KPL-4 Cell line | | |
| PBD dimer diaphorase prodrug 1 | 35.48 | 17 |
| PBD dimer control 1 | 2.09 | |
| PBD monomer diaphorase prodrug 2 | 343.76 | 1 |
| PBD monomer control 1 | 330.11 | |
| WSU Cell line | | |
| PBD dimer diaphorase prodrug 1 | 8.56 | 43 |
| PBD dimer control 1 | 0.2 | |
| PBD monomer diaphorase prodrug 2 | 574.65 | 5 |
| PBD monomer control 1 | 105.53 | |

Example 16

Toxicity of a DTD-Activated PBD Monomer and Dimer Quinone Prodrugs

Figure 21:
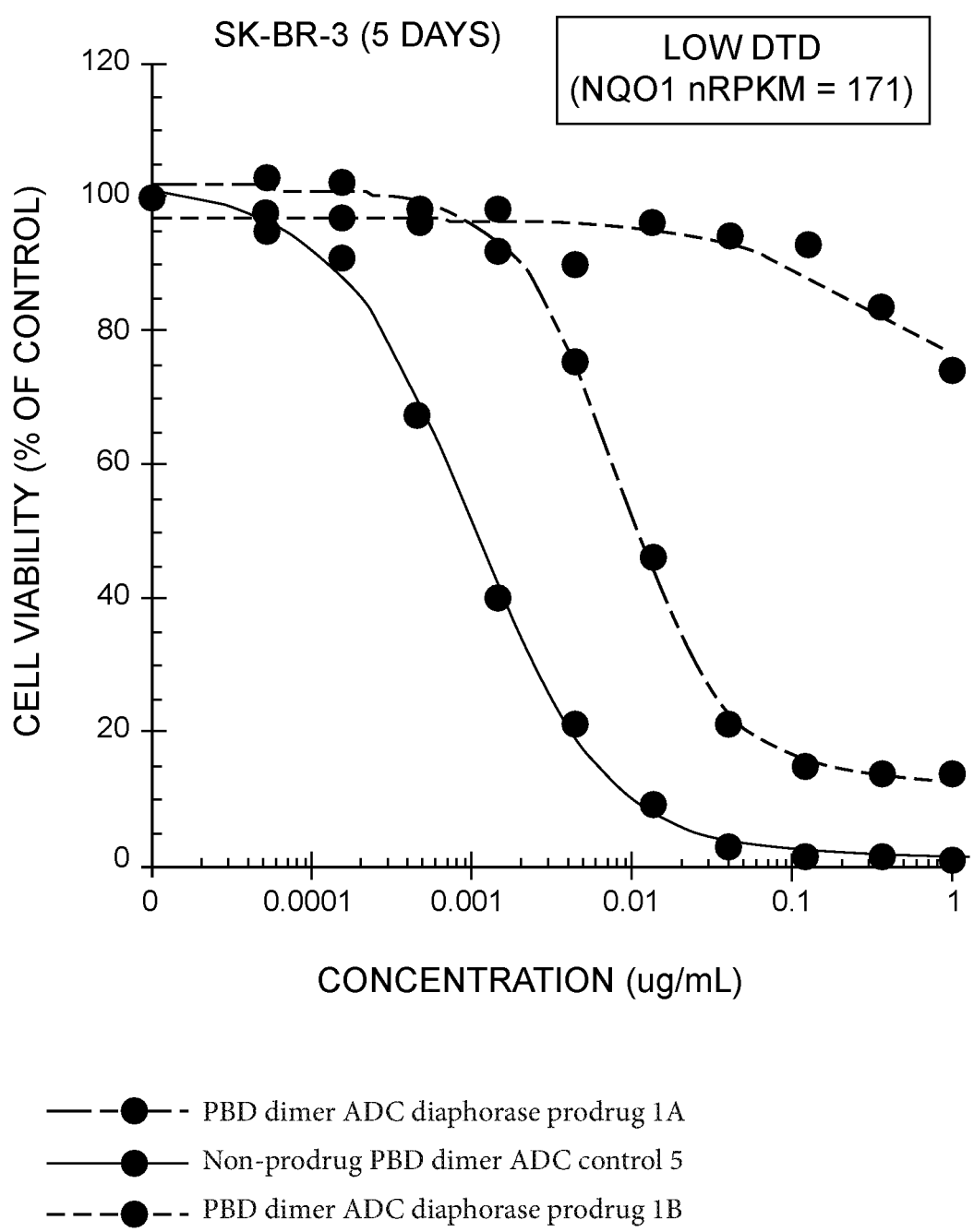
FIG. 21 depicts a plot of SK-BR-3 cell viability (% of control) versus the concentration in µg/mL of (i) 7C2 LC K149C VC-PBD DT diaphorase quinone prodrug ADC PBD dimer, (ii) Ly6E LC K149C VC-PBD DT diaphorase quinone prodrug ADC PBD dimer, and (iii) 4D5 HC A118C ADC PBD dimer not having a prodrug moiety.
Figure 22:
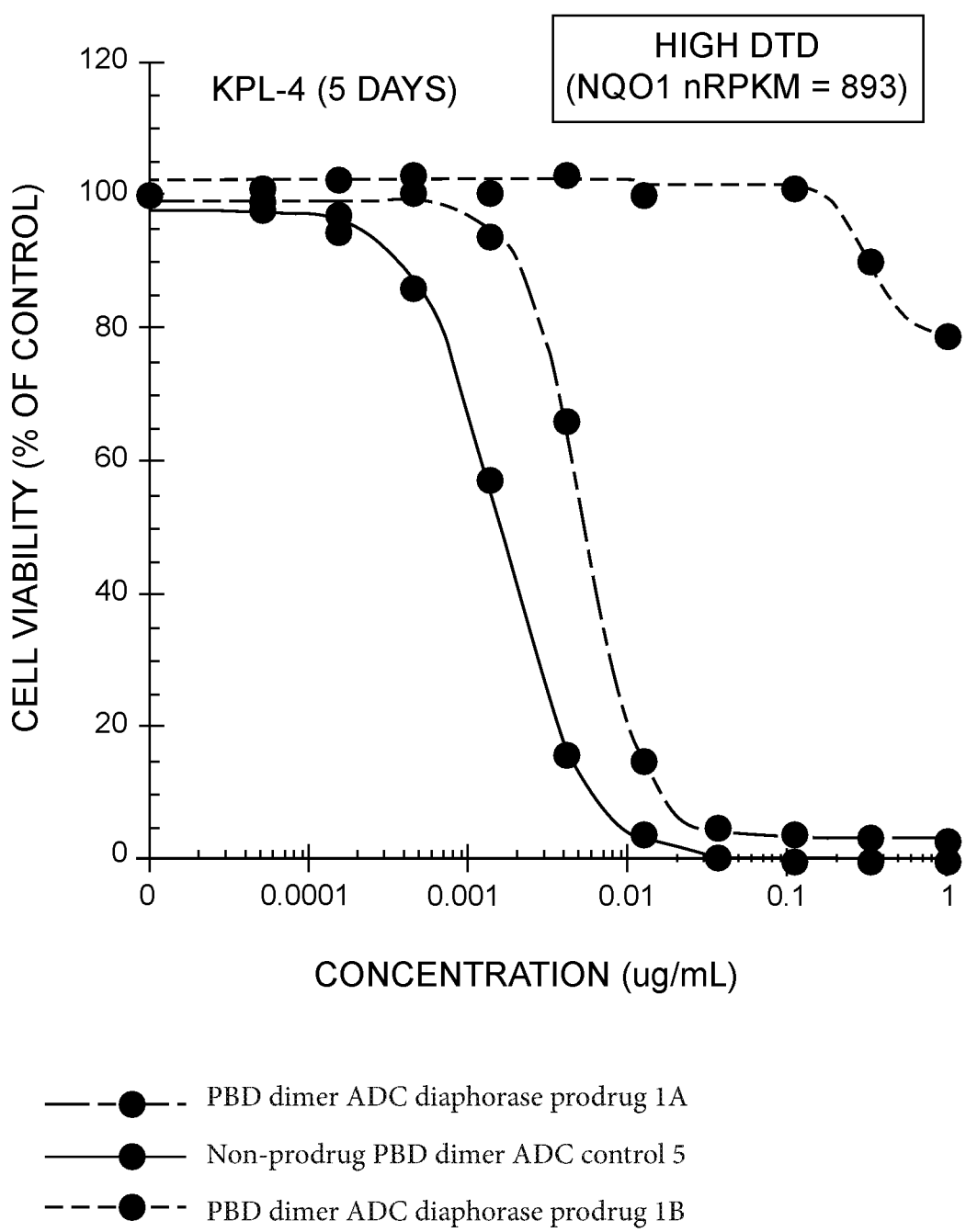
FIG. 22 depicts a plot of KPL-4 cell viability (% of control) versus the concentration in µg/mL of (i) 7C2 LC K149C VC-PBD DT diaphorase quinone prodrug ADC PBD dimer, (ii) Ly6E LC K149C VC-PBD DT diaphorase quinone prodrug ADC PBD dimer, and (iii) 4D5 HC A118C ADC PBD dimer not having a prodrug moiety.

The toxicity of PBD dimer ADC diaphorase prodrugs 1A and 1B and non-prodrug PBD dimer ADC control 5 were evaluated against KPL-4 and SK-BR-3 cell lines for cell viability. The KPL-4 cell line is was a high DTD cell line characterized by NQO1 nRPKM of 839 and the SK-BRO3 cell line was a low DTD cell line characterized by a NQO1 nRPKM of 171. The results are reported below in FIGS. 21 and 22.

Example 17

Disulfide Cleavage and DNA Oligo Binding of PBD Analogs

The cleavage of various prodrug disulfide compounds of the present disclosure after 24 hour exposure to cysteine and glutathione (GSH) was evaluated and the DNA binding of the PBD analogs were evaluated.

For disulfide cleavage determination, the compounds were incubated at 15 μM with 0.2 mM cysteine or 4 mM GSH in 100 mM Tris buffer pH 7.0 containing 5% methanol at 37° C. Aliquots were taken at specified time points and the samples were analyzed by LC/MS on Sciex TripleTOF 5600 on a Hypersil Gold C18 column (100×2.1, 1.9 Thermo Scientific). The column was eluted by a gradient of buffer A (0.1% formic acid in 10 mM ammonium acetate) to buffer B (0.1% formic acid in 10 mM ammonium acetate in 90% acetonitrile), 5% B 0-0.5 min, 5-25% B 0.5-8 min, 25-75% B 8-13 min, and 75-95% B 13-13.5 min, 95% B 13.5-14.5 min, 95-5% B 14.5-15 min at 0.4 mL/min. All products were separated and characterized by LC/MS/MS in a positive ESI ion mode. All analytes had the protonated molecular MH+ as the major species with little source fragmentation. Full scan accurate mass peak areas were used to estimate relative abundance of each component.

For DNA binding determination, the compounds were incubated at 100 μM with 100 μM double strand DNA Oligos 1 and 2 for 1 hour in 10 mM Bis-Tris, pH 7.1 at 37° C. The single strand DNA Oligos (5'-TATAGAATCTATA-3' and 3'-ATATCTTAGATAT-5') were synthesized at Genentech. The samples were analyzed by LC/MS/UV (210-450 nm) on Sciex TripleTOF 5600 on a Hypersil Gold C18 column (100×2.1, 1.9 Thermo Scientific). The column was eluted at 0.4 mL/min by a gradient of buffer A (50 mM hexafluoro-isopropanol and 15 mM diisopropylethylamine) to buffer B (50% A and 50% of 1:1 methanol:acetonitrile), 5% 0-0.5 min, 5-25% B 0.5-25 min, 25-95% B 25-40 min, and to 95% B 40-42 min. The % remaining was an average of the starting DNA oligos remaining in incubations (n=2). The products were characterized by LC/MS in a negative ESI ion mode.

The results are reported in Table 11 below.

acetonitrile), 5% B 0-0.5 min, 5-25% B 0.5-8 min, 25-75% B 8-13 min, and 75-95% B 13-13.5 min, 95% B 13.5-14.5 min, 95-5% B 14.5-15 min at 0.4 mL/min. All products were separated and characterized by LC/MS/MS in a positive ESI ion mode. Full scan accurate mass peak areas were used to estimate relative abundance of each component.

An in vitro DT diaphorase activated drug release assay was used to measure NADPH depletion. DT diaphorase activated release of Norfloxacin and Payload (PBD) was measured by the in vitro depletion of NADPH. The assay method was modified from the absorbance measurement of NADPH at A340 (Osman et. al, Chemico-Biological Interactions 147 (2004) 99-108) due to the interference of compounds. The depletion of NADPH was measured by monitoring the decrease of fluorescence intensity of

TABLE 11

| PBD Agent | % Remaining at 24 h by Cys | % Remaining at 24 h by GSH | % DNA oligo remaining |
|---|---|---|---|
| PBD monomer control 1 | NA | NA | 35% |
| PBD monomer control 2 | 100 | 100 | — |
| PBD monomer disulfide prodrug 1 | 17.9 | 0.5 | — |
| PBD monomer disulfide prodrug 2 | 77.6 | 0.4 (0) | — |
| PBD monomer disulfide prodrug 3 | 73.5 | 2.90 | — |
| PBD monomer disulfide prodrug 4 | 99.9 | 99.9 | — |
| PBD monomer disulfide prodrug 5 | 90.9 | 65.9 | — |
| PBD monomer disulfide prodrug 6 | 85.4 | 2.1 | — |
| PBD monomer disulfide prodrug 7 | 96.1 | 89.7 | — |
| PBD monomer disulfide prodrug 8 | 86.7 | 0.5 | — |
| PBD monomer disulfide prodrug 9 | 81.1 | 1 | — |
| PBD monomer disulfide prodrug 10 | 99.4 | 88.5 | — |
| PBD monomer disulfide prodrug 11 | 14.4 | 0 | — |
| PBD monomer disulfide prodrug 12 | 72.7 | 9.5 | — |
| PBD monomer disulfide prodrug 13 | 99.9 | 98.8 | — |
| PBD monomer disulfide prodrug 14 | 68.1 | 3 | — |
| PBD monomer disulfide prodrug 15 | 99.2 (90.8) | 85.2 (32.5) | — |
| PBD monomer disulfide prodrug 16 | 98.6 | 73.2 | — |
| PBD monomer disulfide prodrug 17 | 34.9 | 0 | — |
| PBD monomer disulfide prodrug 18 | 75.3 | 18.7 | — |
| PBD monomer disulfide prodrug 19 | 4.4 | 0 | — |
| PBD monomer disulfide prodrug 20 | 0 (34% at 4 h) | 0 | — |
| PBD monomer disulfide prodrug 21 | 74.7 | 0 | — |
| PBD monomer disulfide prodrug 22 | 1.4 | 0 | — |
| PBD monomer disulfide prodrug 23 | 41.6 | 0 | — |
| PBD monomer disulfide prodrug 24 | 0.1 | 0 | — |
| PBD monomer disulfide prodrug 25 | 0 | 0 | — |
| PBD monomer disulfide prodrug 26 | 29.1 | 0 | — |
| PBD monomer disulfide prodrug 27 | NA | 0 | — |
| PBD monomer disulfide prodrug 28 | 62.2 | 0 | — |
| PBD monomer disulfide prodrug 29 | 0 | 0 | — |
| PBD monomer disulfide prodrug 30 | 47.1 | 0 | — |
| PBD dimer disulfide prodrug 1 | — | — | >99.5 |
| PBD dimer control 1 | — | — | <1 |
| PBD dimer control 2 | — | — | 100% |

Example 18

GSH Adduct Formation and Stability of Quinones

The stability of quinones and PBD monomer and dimer diaphorase prodrugs within the scope of the present disclosure upon exposure to GSH and related GSH adduct formation were evaluated.

For degradation analysis, the compounds were incubated at 25 µM with 15 mM GSH in 200 mM Tris buffer pH 7.0 containing 5% methanol at 37° C. for 3 hours. The control incubations were conducted without GSH. The samples were analyzed by LC/MS on Sciex TripleTOF 5600 on a Hypersil Gold C18 column (100×2.1, 1.9 µM, Thermo Scientific). The column was eluted by a gradient of buffer A (0.1% formic acid in 10 mM ammonium acetate) to buffer B (0.1% formic acid in 10 mM ammonium acetate in 90%

NADPH at 480 nm after being excited at 340 nM. The materials and reagents were as follows: (1) Bovine Serum Albumin (BSA): Sigma cat #A7030-50G (>98% (agarose gel electrophoresis), lyophilized powder, essentially fatty acid free, essentially globulin free; (2) Assay buffer: 50 mM Tris-HCl/0.007% BSA buffer (pH 7.4); (3) DT Diaphorase preparation: Dissolve lyophilized human DT Diaphorase (Sigma Cat #D1315, Lot #SLBJ9723V, MW=32, 253 U/mg, 1.6 mg protein/vial, One unit will reduce 1 micromole of Cytochrome C per min in the presence of Menadione substrate at 37° C.) in 8.1 ml H2O as 50 U/0.2 mg/ml (6.25 uM protein), Store aliquots at –20° C. Prior to assay, 2.5 fold dilute the stock in assay buffer as 5× working solution (20 U/mL, 2.5 uM, 0.08 ug/mL); (4) β-Nicotinamide adenine dinucleotide phosphate (NADPH, reduced disodium salt hydrate, Sigma, cat #N6505-5G, >=94% (HPLC): prepare 48 mM NADPH stock in assay buffer and store at –20 C.

Prior to assay, dilute the stock to 1 mM as the 5× working solution; (5) DT Diaphorase specific Inhibitor: prepare 40 mM stock of Dicumarol (Sigma, Cat #M1390-5G, MW=336.29) in 0.13 N NaOH, stored at 4° C. Dilute the stock to 250 uM as the 5× working solution; (6) Compounds: dilute the Norfloxacin and PBD conjugated compounds in assay buffer to 250 uM as the 5× working solution; and (7) 384 well black plate with clear bottom. For the assay procedure: (1) The reaction mix containing 0.5 uM DT-D, 50 uM compound, 200 mM NADPH was set up in a 384 well plate at 50 ul/well. For the control with DT Diaphorase inhibitor, Dicumarol was added in the reaction mix at final 50 uM for each compound. Reaction mix containing NADPH and compound only was also added as the baseline controls. The DT Diaphorase was added in the last step; and (2) The reaction mixes were incubated at room temperature for 5, 30, 90 min. The fluorescence intensity (RFU) of DNAPH was recorded on M1000 plate reader (Tecan) with excitation at 340 nM and emission at 480 nM. For data analysis, data was analyzed and plotted using Prism Graph-Pad 6. The depletion of NADPH was calculated by the formula below at reaction time point at 90 min wherein: % NADPH depletion=[$RFU_{without\ inhibitor}-(RFU_{with\ inhibitor}/RFU_{without\ inhibitor})$]*100.

The results are reported in Table 12 below where: "% Rem." refers to percent remaining after 3 hours; "Degr" refers to degradation; "Pay. Rel." refers to payload release (MRM Qunat) (% recovery at 90-min relative to 0 hours) based on 2 μM of starting material; and "NADPH Dep." Refers to NADPH depletion at 90 minutes.

TABLE 12

| Quinone | % Rem. | GSH Adduct | Degr | Pay. Rel. | NADPH Dep. |
|---|---|---|---|---|---|
| 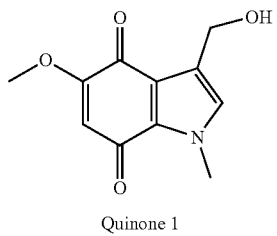 [SMILES: COC1=CC(=O)c2c(c(CO)cn2C)C1=O] Quinone 1 | 90 | yes | — | — | 95.99 |
| 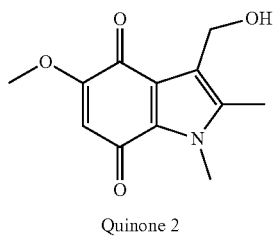 Quinone 2 | 87 | yes | — | — | 74.83 |
| 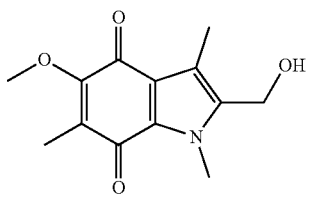 Quinone 3 | 92.5 | yes | — | — | None |
| 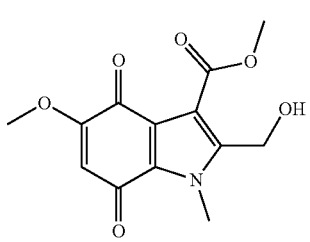 Quinone 4 | 100 | — | — | — | None |

TABLE 12-continued

| Quinone | % Rem. | GSH Adduct | Degr | Pay. Rel. | NADPH Dep. |
|---|---|---|---|---|---|
| Quinone 5 | 0 | — | yes | — | 96.92 |
| Quinone 6 | 63 | — | yes | 1% | 94/0 |
| Quinone 7 | 37.6 | — | yes | 2% | 53.23 |
| Quinone 8 | 82.1 | — | yes | — | 91.5 |
| Quinone 9 | — | — | — | 2% | 85.2 |

TABLE 12-continued
| Quinone | % Rem. | GSH Adduct | Degr | Pay. Rel. | NADPH Dep. |
|---|---|---|---|---|---|
| Quinone 10 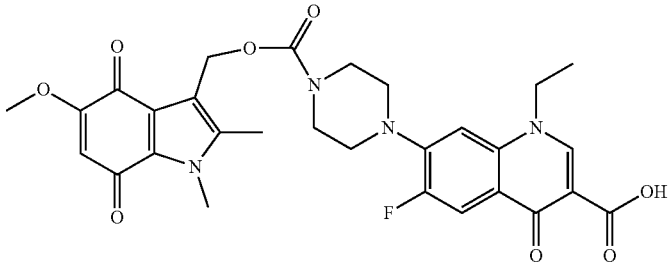 | 50 | — | yes | — | 2.01 |
| Quinone 11 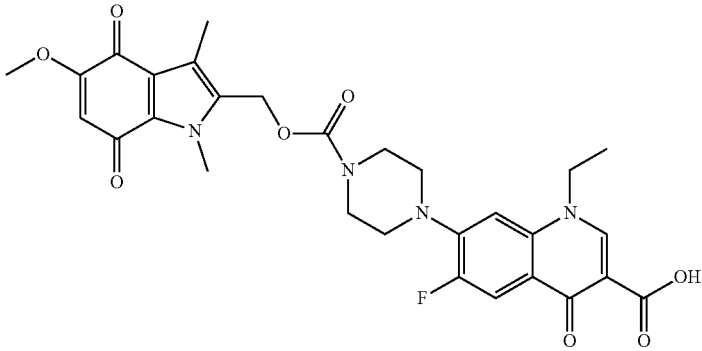 | 55.5 | — | yes | — | 26.1 |
| Quinone 12 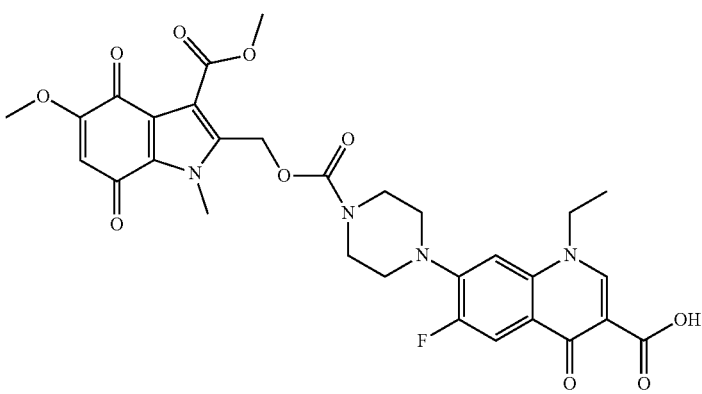 | 100 | — | — | — | 17.4 |
| PBD monomer diaphorase prodrug 1 | — | — | — | — | >90% at 30 min |
| PBD monomer diaphorase prodrug 2 | — | — | — | — | >90% in <5 min |
| PBD monomer diaphorase prodrug 3 | — | — | — | — | >90% at 90 min |
Example 19
Preparation of PBD Monomer Disulfide Prodrugs
Example 19 General Scheme 1
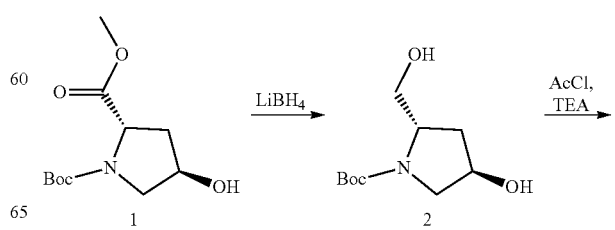
The overall reaction scheme for general scheme 1 was as follows:

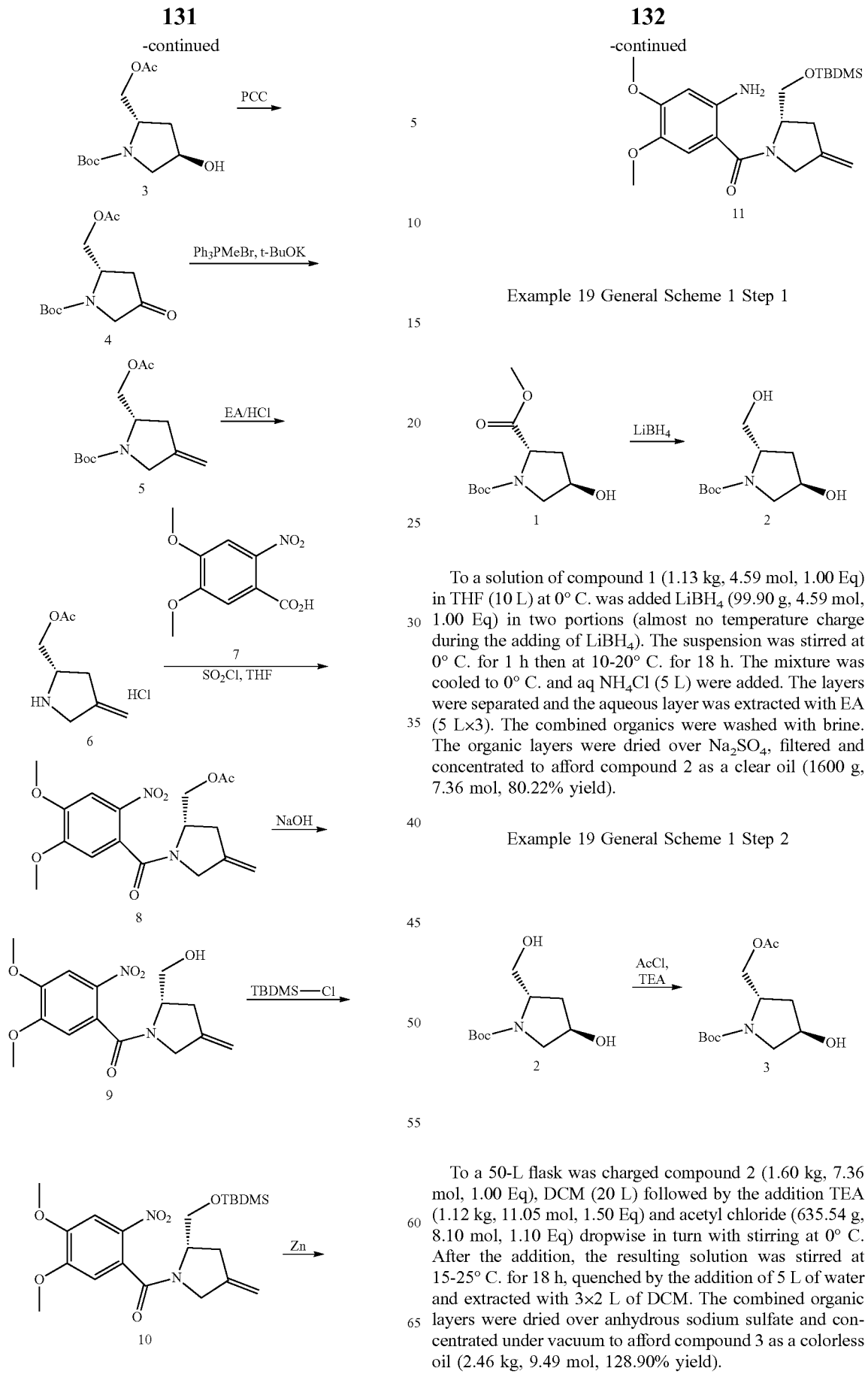

Example 19 General Scheme 1 Step 1

To a solution of compound 1 (1.13 kg, 4.59 mol, 1.00 Eq) in THF (10 L) at 0° C. was added LiBH$_4$ (99.90 g, 4.59 mol, 1.00 Eq) in two portions (almost no temperature charge during the adding of LiBH$_4$). The suspension was stirred at 0° C. for 1 h then at 10-20° C. for 18 h. The mixture was cooled to 0° C. and aq NH$_4$Cl (5 L) were added. The layers were separated and the aqueous layer was extracted with EA (5 L×3). The combined organics were washed with brine. The organic layers were dried over Na$_2$SO$_4$, filtered and concentrated to afford compound 2 as a clear oil (1600 g, 7.36 mol, 80.22% yield).

Example 19 General Scheme 1 Step 2

To a 50-L flask was charged compound 2 (1.60 kg, 7.36 mol, 1.00 Eq), DCM (20 L) followed by the addition TEA (1.12 kg, 11.05 mol, 1.50 Eq) and acetyl chloride (635.54 g, 8.10 mol, 1.10 Eq) dropwise in turn with stirring at 0° C. After the addition, the resulting solution was stirred at 15-25° C. for 18 h, quenched by the addition of 5 L of water and extracted with 3×2 L of DCM. The combined organic layers were dried over anhydrous sodium sulfate and concentrated under vacuum to afford compound 3 as a colorless oil (2.46 kg, 9.49 mol, 128.90% yield).

Example 19 General Scheme 1 Step 3

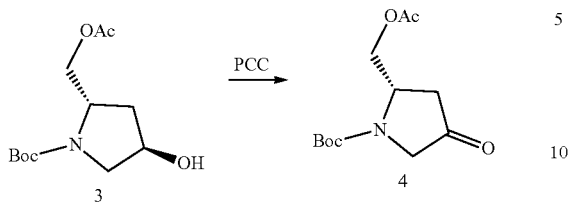

To a 20L 3-necked round-bottom flask was charged compound 3 (1.23 kg, 4.75 mol, 1.00 Eq) in DCM (12 L) followed by the addition of PCC (1.54 kg, 7.13 mol) in several batches at 15° C. The resulting solution was stirred at 15-25° C. for 18 h. The solids were filtered off and the filtrate was concentrated under vacuum. The residue was purified on a silica gel column eluting with ethyl acetate: petroleum ether (1:5) to afford compound 4 as a light yellow liquid (1.13 kg, 4.38 mol, 46.15% yield).

Example 19 General Scheme 1 Step 4

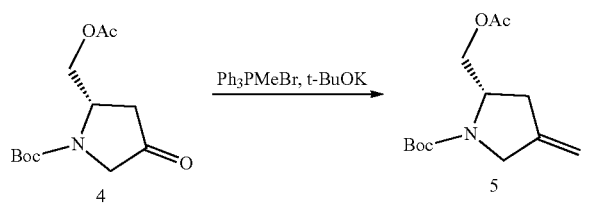

To a 10-L 3-necked round-bottom flask was charged methyl(triphenyl)phosphonium bromide (958.03 g, 2.68 mol), THF (2.5 L), followed by the addition of t-BuOH (300.94 g, 2.68 mol) in portions at 0° C. over 2 h. To this was added a solution compound 4 (460.00 g, 1.79 mol) in THF (2.5 L) dropwise with stirring at 0° C. The resulting solution was stirred at −5~0° C. for 20 min, quenched by the addition of 500 mL of water and extracted with 3×500 mL of ethyl acetate. The combined organic layers were dried over anhydrous sodium sulfate and concentrated under vacuum. The residue was purified on a silica gel column eluting with ethyl acetate: petroleum ether (1:20) to afford compound 5 as a light yellow liquid (275.00 g, 1.08 mol, 30.09%).

Example 19 General Scheme 1 Step 5

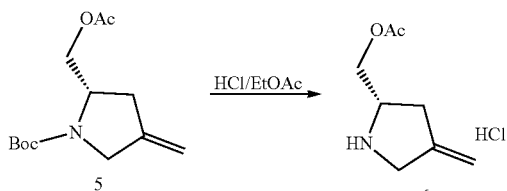

A mixture of compound 5 (330.00 g, 1.29 mol) in HCl (gas)/EtOAc (3 L, 4 M/L) was stirred at 0° C. 20 mins. Then the mixture was stirred at 10-30° C. for 1 h. The mixture was concentrated in vacuum to afford compound 6 as yellow solid (250.00 g, 1.30 mol, 101.12%), which is used in next step without purification.

Example 19 General Scheme 1 Step 6

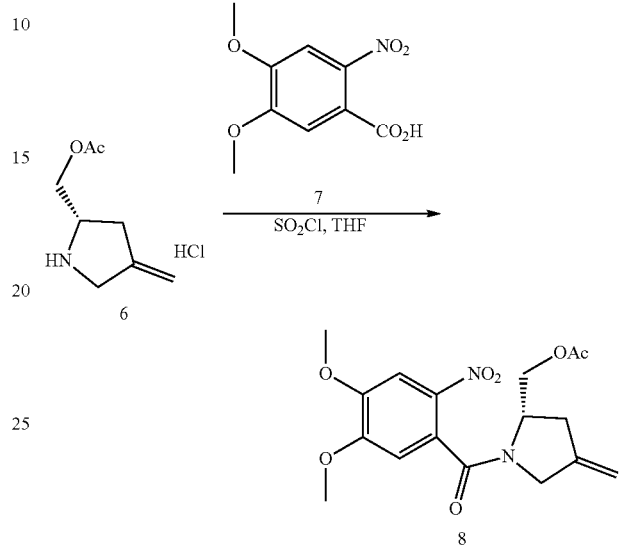

Into a 3000-mL 3-necked round-bottom flask purged and maintained with an inert atmosphere of nitrogen was charged a solution of compound 7 (354.42 g, 1.56 mol, 1.30 Eq) in THF (1.5 L), followed by the addition of $SOCl_2$ (1.71 kg, 14.33 mol, 11.94 Eq) dropwise with stirring. The resulting solution was stirred at 20-30° C. for 4 h and then concentrated under vacuum. Into another 3000-mL 3-necked round-bottom flask purged and maintained with an inert atmosphere of nitrogen was charged a solution of compound 6 (230.00 g, 1.20 mol, 1.00 Eq) in DCM (2.5 L). To this was added $Et_3N$ (485.75 g, 4.80 mol, 4.00 Eq) dropwise with stirring at −40° C., followed by the solution in the first flask at −40° C. The temperature was allowed to warm to 0° C. naturally, quenched by the addition of 3000 mL of water/ice and extracted with 3×1000 mL of dichloromethane. The combined organic layers were dried over anhydrous sodium sulfate and concentrated under vacuum. The residue was purified on a silica gel column eluting with EtOAc:PE (1:3) to afford compound 8 as a light brown oil (210.00 g), which is used in next step without purification.

Example 19 General Scheme 1 Step 7

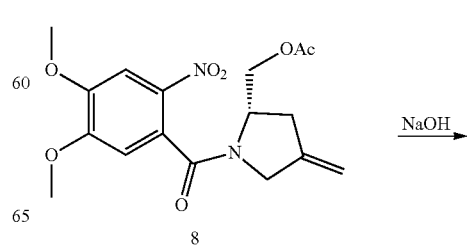

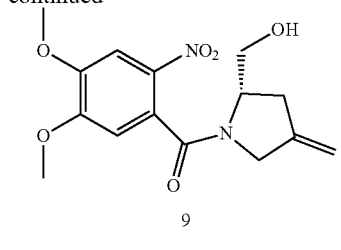

To a mixture of compound 8 (90.00 g, 247.02 mmol, 1.00 Eq) in THF (400 mL), MeOH (100 mL), H2O (400 mL), was added NaOH (29.64 g, 741.05 mmol, 3.00 Eq) in one portion at 0° C. The mixture was stirred at 20-30° C. for 18 h. The aqueous phase was extracted with EtOAc (300 mL×3). The combined organic phase was washed with saturated brine (100 mL), dried with anhydrous Na$_2$SO$_4$, filtered and concentrated in vacuum to afford compound 9 as yellow solid (90.26 g, crude), which was used for the next step without further purification.

Example 19 General Scheme 1 Step 8

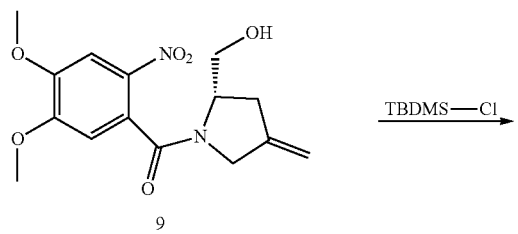

In a 2000 mL three-necked round bottom flask equipped with a temperature probe, magnetic stirrers and a nitrogen inlet, TBDMSCl (126.62 g, 840.12 mmol), imidazole (57.20 g, 840.12 mmol, 3.00 Eq) in DMF (1 L) were added. Then a solution of compound 9 (90.26 g, 280.04 mmol, 1.00 Eq) in DMF (1 L) was added to the mixture at 0° C. The resulting reaction mixture was stirred for 2 h at 25-30° C. The reaction mixture was poured into ice-water (1 L) and then extracted with DCM (200 mL×3). The combined organic phases were washed brine (100 mL), dried over Na$_2$SO$_4$ and concentrated in vacuum to give the residue, to give compound 10 as a yellow oil (126.00 g), which was used for the next step without further purification.

Example 19 General Scheme 1 Step 9

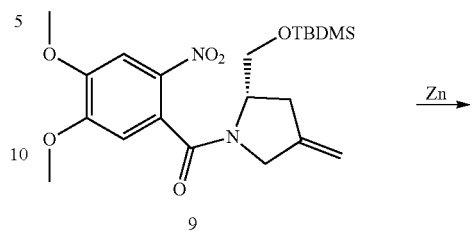

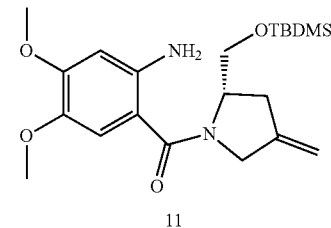

To a mixture of compound 10 (126.00 g, 288.61 mmol, 1.00 Eq) in AcOH (1 L), was added Zn (188.72 g, 2.89 mol) in portions by maintaining the temperature below 30° C. The mixture was stirred at 20-30° C. for 30 min. The residue was poured into EtOAc (500 mL) and filtered. The filtrate was concentrated in vacuum. The residue was purified by silica gel chromatography (PE/EtOAc=10/1, 1/1) to afford 11 as yellow oil (58.00 g, 142.64 mmol, 49% yield). 1H NMR (400 MHz, CHLOROFORM-d) d ppm 6.71 (s, 1H) 6.22 (s, 1H) 4.85-4.97 (m, 2H) 4.52 (br. s., 1H) 4.14-4.23 (m, 1H) 3.99-4.13 (m, 1H) 3.82 (s, 3H) 3.77 (s, 3H) 3.59 (d, J=5.73 Hz, 1H) 2.63-2.72 (m, 2H) 2.01-2.04 (m, 1H) 1.23 (t, J=7.06 Hz, 1H) 0.85 (s, 9 H) −0.06-0.06 (m, 5H).

Example 19 General Scheme 2 as Follows is a General Scheme for Preparing PBD Disulfide Prodrugs of the Present Disclosure

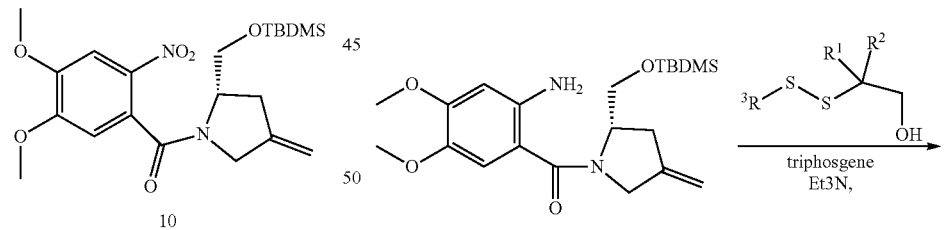

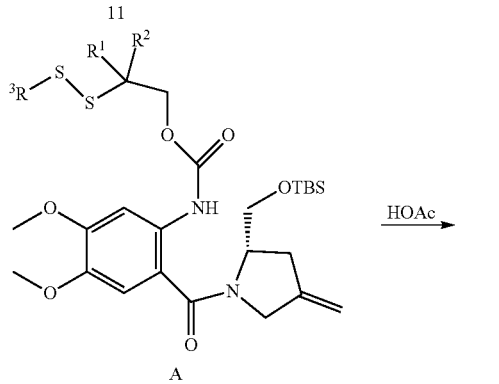

137

-continued

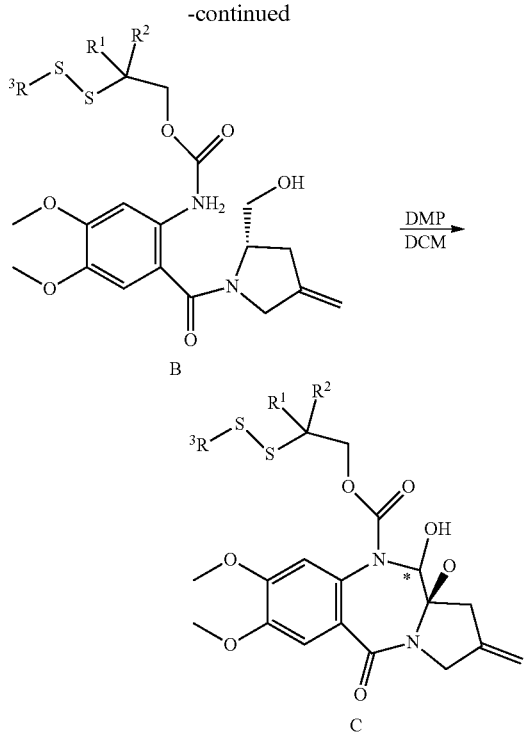

The asterisk in structure C, and elsewhere depicted in Example 19, represents a chiral center. In some aspects, $R^1$ recited in the above scheme corresponds to $R^{61}$ as described herein, $R^2$ recited in the above scheme corresponds to $R^{62}$ as described herein, and $R^3$ recited in the above scheme corresponds to $R^{50}$ as described herein.

Example 19A

Preparation of PBD Monomer Disulfide Prodrug 10

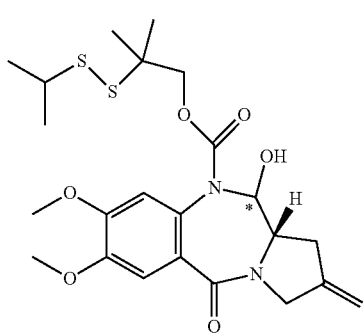 [SMILES: C=C1C[C@H]2C(O)N(C(=O)OCC(C)(C)SSC(C)C)c3cc(OC)c(OC)cc3C(=O)N2C1]

Example 19A General Procedure IA—Formation of Carbomate Method A (2-amino-4,5-dimethoxy-phenyl)-[(2S)-2-[[tert-butyl(dimethyl)silyl]oxymethyl]-4-methylene-pyrrolidin-1-yl]methanone (222 mg, 0.5460 mmol) was dissolved in 3 mL of DCM, then Et₃N was added via a pipette followed by triphosgene. After total of 20 min, 2-(tert-butyldisulfanyl)-2-methyl-propan-1-ol (B, 1.05 equiv., 0.5733 mmol, 100 mass %) in 2 mL of DCM (including 0.5 mL of rinsing) was

138 added followed by 10 uL of dibutyltin diacetate (20 μL, 0.07487 mmol). After about 1.5 hr, another 35 uL (28 mg) of disulfide alcohol and 8 uL of dibutyltin diacetate (2:57 pm) were added and the reaction was stirred overnight. The reaction was diluted with EtOAc, then washed with 1N HCl solution. The organics were washed with saturated sodium bicarbonate. The organic layer was dried over sodium sulfate and then concentrated. The residue was purified by flash chromatography (25 g silica gel, 20%-30%-50% EtOPc/Hept) to give the desired carbomate as a colorless oil (227 mg, 67% yield).

Example 19A General Procedure II—Removal of TBS Group by HOAc

[2-(tert-butyldisulfanyl)-2-methyl-propyl] N-[2-[(2S)-2-[[tert-butyl(dimethyl)silyl]oxymethyl]-4-methylene-pyrrolidine-1-carbonyl]-4,5-dimethoxy-phenyl]carbamate (200 mg, 0.319 mmol) was dissolved in 3 mL of THF, then water (0.8 mL) and acetic acid (3.4 mL) were added at room temperature. After the reaction was done, sodium carbonate was added to neutralize acetic acid. The mixture was extracted with EtOAc three times. The combined EtOAc extract was dried over sodium sulfate, concentrated to provide the crude alcohol (233 mg), which was used in the next step without purification.

Example 19A General Procedure III—DMP Oxidation & Cyclization

To 2-(isopropyldisulfanyl)-2-methyl-propyl] N-[2-[(2S)-2-(hydroxymethyl)-4-methylene-pyrrolidine-1-carbonyl]-4,5-dimethoxy-phenyl]carbamate (99.2 mg, 0.199 mmol, 100 mass %) in DCM (3.5 mL, was added Dess-Martin periodinane (86.1 mg, 0.203 mmol, 1.02 equiv.,) at rt. The reaction mixture diluted with DCM, then washed with mixed saturated. NaHCO₃ (about 3 mL) and 1 M sodium sulfite (about 3 mL), dried over sodium sulfate, concentrated to give about 120 mg crude (oil), which was purified by reverse-phase HPLC to give the desired carbomate (28.9 mg) along with recovered alcohol starting material (10.3 mg). LCMS: (5-95, AB, 5 min), RT=2.69 min, m/z=497 [M+1]+; 1H NMR (400 MHz, DMSO-d6) δ 7.08 (s, 1H), 6.82 (s, 1H), 6.64 (d, J=6.0 Hz, 1H), 5.49-5.33 (m, 1H), 5.13 (d, J=7.3 Hz, 2H), 4.21-4.05 (m, 2H), 4.04-3.91 (m, 1H), 3.81 (s, 4H), 3.79-z3.72 (m, 1H), 3.46 (t, J=9.3 Hz, 1H), 3.31 (s, 3H), 2.99-2.76 (m, 2H), 2.63-2.51 (m, 1H), 1.38-0.94 (m, 12H).

Example 19B

Preparation of PBD Monomer Disulfide Prodrug 4

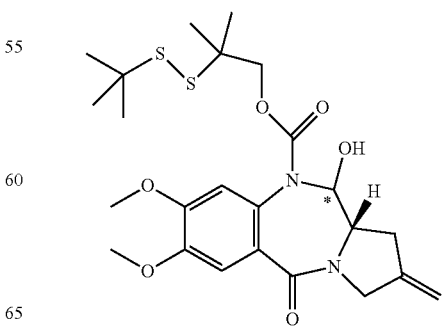

The title compound was synthesized in the same manner as example 19A except that General procedure IB below was used for the disulfide formation.

Example 19B General Procedure Ib—Formation of Carbomate Method B (2-amino-4,5-dimethoxy-phenyl)-[(2S)-2-[[tert-butyl(dimethyl)silyl]oxymethyl]-4-methylene-pyrrolidin-1-yl]methanone (121 mg, 0.2976 mmol) and N,N-diisopropylamine (3 equiv., 0.8928 mmol) was mixed in 3 mL of THF, then (4-nitrophenyl) carbonochloridate (75 mg, 0.3720 mmol) was added at room temperature. The mixture was heated to 75° C. After about 1 h 50 min, 2-(isopropyldisulfanyl)-2-methyl-propan-1-ol (71 mg, 0.3938 mmol) in 1.5 mL of THF was added. The mixture was stirred at 75° C. overnight, cooled down to room temperature, diluted in EtOAc, washed with 1N HCl and then sat. sodium bicarb. The solution was concentrated and the resulting residue was purified by silica gel chromatography (20% then 30% then 50% EtOAc/Hept) to give the disulfide (34 mg, 19% yield).

LCMS: (5-95, AB, 5 min), RT=2.78 min, m/z=511 [M+1]+; 1H NMR (400 MHz, DMSO-d6) δ 7.08 (s, 1H), 6.81 (s, 1H), 6.63 (d, J=5.9 Hz, 1H), 5.49-5.34 (m, 1H), 5.13 (d, J=6.1 Hz, 2H), 4.19-3.91 (m, 3H), 3.81 (s, 3H), 3.78-3.67 (m, 1H), 3.46 (t, J=9.2 Hz, 1H), 3.32 (s, 35H), 2.96-2.82 (m, 1H), 2.61-2.53 (m, 1H), 1.18 (s, 9H), 1.04 (d, J=3.7 Hz, 6H).

Example 19C

Preparation of PBD Monomer Disulfide Prodrug 15

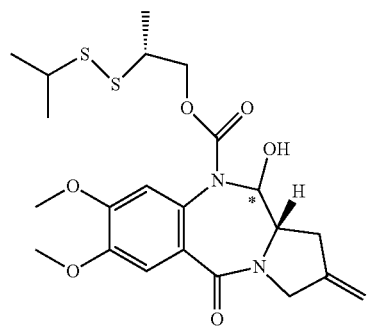 [SMILES: C=C1C[C@H]2C(O)N(C(=O)OC[C@@H](C)SSC(C)C)c3cc(OC)c(OC)cc3C(=O)N2C1]

PBD monomer disulfide prodrug 15 was prepared according to the following reaction scheme 3:

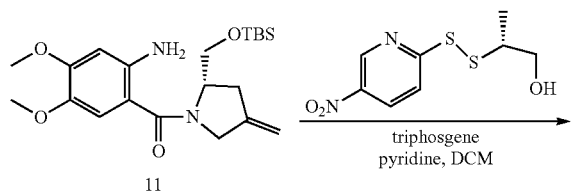

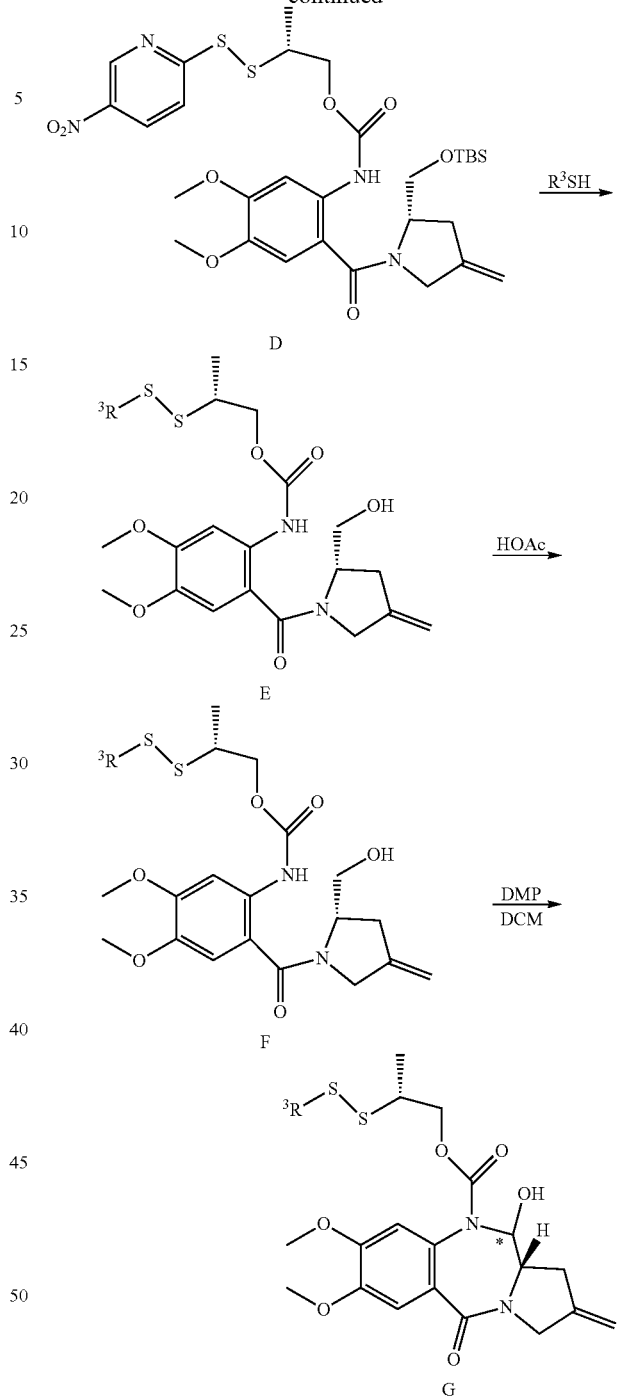

Triphosgene (116 mg, 0.39 mmol) was dissolved in 2 mL of DCM, then a solution of (2R)-2-[(5-nitro-2-pyridyl)disulfanyl]propan-1-ol (277 mg, 1.125 mmol) and pyridine (0.14 mL, 1.761 mmol) in 2 mL of DCM was added. After 30 min, this solution was added to a solution of (2-amino-4,5-dimethoxy-phenyl)-[(2S)-2-[[tert-butyl(dimethyl)silyl]oxymethyl]-4-methylene-pyrrolidin-1-yl]methanone (410 mg, 0.978 mmol, 97 mass %) and in 3 mL of DCM (plus 0.5 mL of rinsing). After the reaction was done, the mixture was diluted with EtOAc, washed with 1N aq. HCl and then saturated sodium bicarbonate. The organics were dried over sodium sulfate concentrated. The residue was purified by silica gel column chromatography (25 g silica gel, 30% then 40% then 50% EtOAc/Hept) to give [(2R)-2-[(5-nitro-2-pyridyl)disulfanyl]propyl] N-[2-[(2S)-2-[[tert-butyl(dimethyl)silyl]oxymethyl]-4-methylene-pyrrolidine-1-carbonyl]-4,5-dimethoxy-phenyl]carbamate (480 mg, 72% yield).

To [(2R)-2-[(5-nitro-2-pyridyl)disulfanyl]propyl] N-[2-[(2S)-2-[[tert-butyl(dimethyl)silyl]oxymethyl]-4-methylene-pyrrolidine-1-carbonyl]-4,5-dimethoxy-phenyl]carbamate (45 mg, 0.066 mmol, 100 mass %) in DMF (0.5 mL) was added propane-2-thiol (40 mg, 0.53 mmol) via a syringe without any solvent. The mixture was heated to 59° C. in a sealed vial. After the reaction was done, the mixture was concentrated under reduced pressure, azotroped with toluene once. The resulting residue was purified by silica gel chromatography (40 g silica gel, 20%-35%-50% EtOAc/Hept) to give [(2R)-2-(isopropyldisulfanyl)propyl] N-[2-[(2S)-2-[[tert-butyl(dimethyl)silyl]oxymethyl]-4-methylene-pyrrolidine-1-carbonyl]-4,5-dimethoxy-phenyl]carbamate as a yellow oil (134 mg, 89% yield).

PBD monomer disulfide prodrug 15 was then prepared according to general procedures II and III of example 19A.

LCMS: (5-95, AB, 5 min), RT=2.58 min, m/z=483 [M+1]+; 1H NMR (400 MHz, DMSO-d6) δ 7.07 (s, 1H), 6.82 (s, 1H), 6.63 (d, J=6.1 Hz, 1H), 5.38 (dd, J=9.7, 6.1 Hz, 1H), 5.20-5.07 (m, 2H), 4.20 (dd, J=11.1, 6.1 Hz, 1H), 4.15-4.05 (m, 1H), 3.97 (d, J=15.4 Hz, 2H), 3.80 (s, 6H), 3.45 (t, J=9.3 Hz, 1H), 3.10-2.82 (m, 3H), 2.58-2.53 (m, 1H), 1.18 (t, J=6.2 Hz, 7H), 1.04 (d, J=6.9 Hz, 3H).

Example 19D

Preparation of PBD Monomer Disulfide Prodrug 13

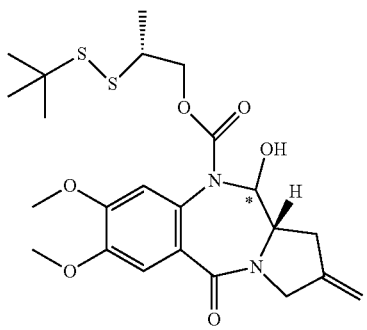 [SMILES: C=C1C[C@H]2C(O)N(C(=O)OC[C@@H](C)SSC(C)(C)C)c3cc(OC)c(OC)cc3C(=O)N2C1]

PBD monomer disulfide prodrug 13 was prepared according to the method of Example 19C. LCMS: (5-95, AB, 5 min), RT=2.70 min, m/z=497 [M+1]+; 1H NMR (400 MHz, DMSO-d6) δ 7.07 (s, 1H), 6.81 (s, 1H), 6.65 (d, J=5.9 Hz, 1H), 5.38 (dd, J=9.7, 5.9 Hz, 1H), 5.19-5.04 (m, 2H), 4.20 (dd, J=11.2, 5.9 Hz, 1H), 4.10 (d, J=15.8 Hz, 1H), 4.04-3.91 (m, 2H), 3.80 (s, 6H), 3.45 (t, J=9.3 Hz, 1H), 3.04-2.82 (m, 2H), 2.58-2.53 (m, 1H), 1.23 (s, 9H), 1.03 (d, J=6.9 Hz, 3H).

Example 19E

Preparation of PBD Monomer Disulfide Prodrug 2

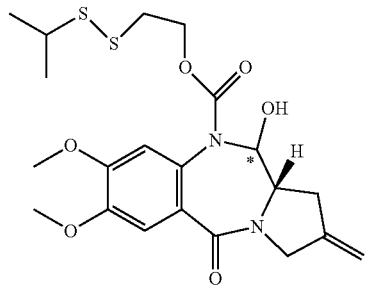 [SMILES: C=C1C[C@H]2C(O)N(C(=O)OCCSSC(C)C)c3cc(OC)c(OC)cc3C(=O)N2C1]

PBD monomer disulfide prodrug 2 was prepared according to the following reaction scheme:

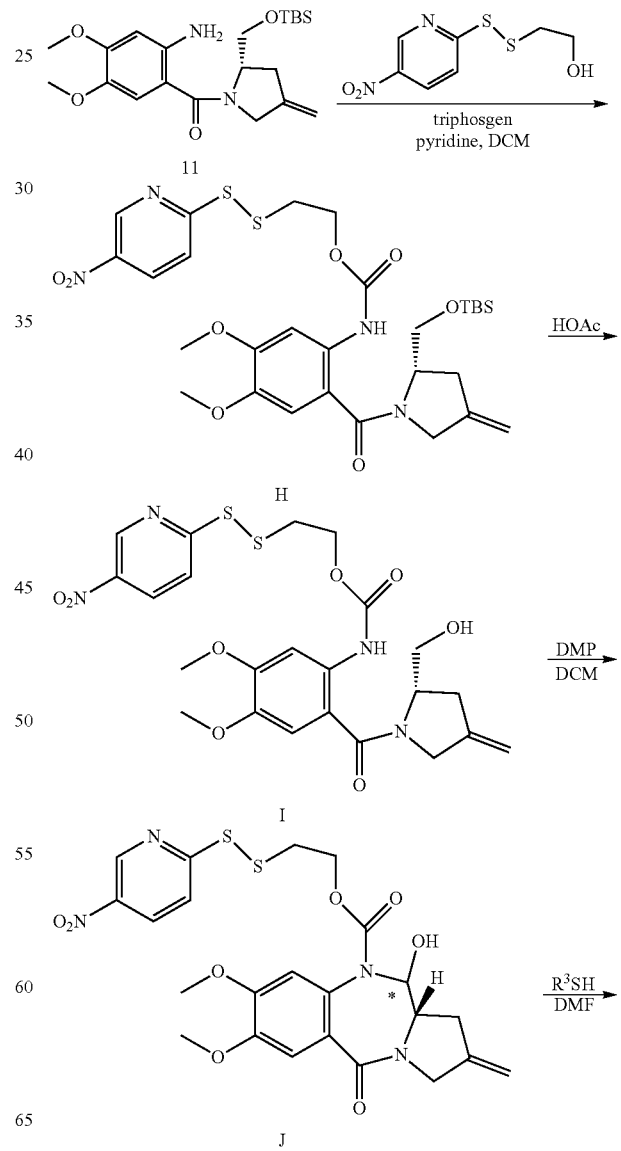

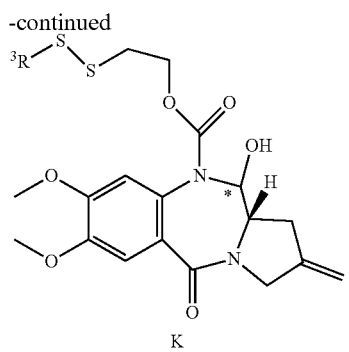

In some aspects, $R^3$ corresponds to $R^{50}$ as described elsewhere herein.

Triphosgene (268 mg, 0.9046 mmol, 100 mass %) was dissolved in 3 mL of DCM in a flask, then a solution of 2-[(5-nitro-2-pyridyl)disulfanyl]ethanol (604 mg, 2.601 mmol) in 6 mL of DCM was added followed by neat pyridine (1.8 equiv., 4.071 mmol, 100 mass %). After 30 min, this solution was added to a solution of (2-amino-4,5-dimethoxy-phenyl)-[(2S)-2-[[tert-butyl(dimethyl)silyl]oxymethyl]-4-methylene-pyrrolidin-1-yl]methanone (948 mg, 2.262 mmol) and in 5 mL of DCM (plus 0.8 mL of rinsing). After about 20 min, the mixture was diluted with EtOAc, washed with 1N HCl and then saturated sodium bicarbonate. The organics were dried over sodium sulfate concentrated and columned (40 g silica gel, 25% then 45% EtOAc/Hept) to give the carbamate as a yellow fluffy solid (1.07 g, 71% yield).

2-[(5-nitro-2-pyridyl)disulfanyl]ethyl N-[2-[(2S)-2-[[tert-butyl(dimethyl)silyl]oxymethyl]-4-methylene-pyrrolidine-1-carbonyl]-4,5-dimethoxy-phenyl]carbamate (1.067 g, 1.61 mmol) was dissolved in THF, then water (1.5 mL) was added followed by acetic acid (8 mL) was added at rt. The mixture was heated to 55° C. and stirred overnight. After the mixture was cooled to room temperature, sodium carbonate was added to neutralize acetic acid. The mixture was extracted with EtOAc three times. The combined EtOAc extract was dried over sodium sulfate, concentrated to provide the crude alcohol (1.26 g), which was used in the next step without purification.

To the above alcohol (884 mg, 1.61 mmol) in DCM (16 mL) was added Dess-Martin periodinane (715 mg, 1.685 mmol) at room temperature. After about 70 min, another 105 mg of D-M periodinane was added. After 2.5 hrs, another 76 mg of D-M periodinane was added. As soon as the all the starting material had consumed, the mixture was diluted with DCM, then washed with mixed saturated NaHCO₃ (about 6 mL) and 1 M sodium sulfite (about 6 mL), dried over sodium sulfate, concentrated under reduced pressure. The resulting residue was purified by silica gel column chromatography (40 g silica gel, 50% then 80% then 100% EtOAc/Hept) to give 2-[(5-nitro-2-pyridyl)disulfanyl]ethyl (6S,6aR)-6,6a-dihydroxy-2,3-dimethoxy-8-methylene-11-oxo-7,9-dihydro-6H-pyrrolo[2,1-c][1,4]benzodiazepine-5-carboxylate as a yellow solid (765 mg, 84% yield).

To 2-[(5-nitro-2-pyridyl)disulfanyl]ethyl (6aS)-6-hydroxy-2,3-dimethoxy-8-methylene-11-oxo-6,6a,7,9-tetrahydropyrrolo[2,1-c][1,4]benzodiazepine-5-carboxylate (63 mg, 0.115 mmol) in 0.2 mL of DMSO was added propane-2-thiol (0.5 mL,) via a syringe, then heated to 59° C. After the reaction was done, the mixture was cooled to room temperature, co-evaporated with EtOAc in a rotavap twice to remove as much of the thiol as possible. The resulting residue was purified by reverse-phase HPLC to give 2-sulfanylethyl (6aS)-6-hydroxy-2,3-dimethoxy-8-methylene-11-oxo-6,6a,7,9-tetrahydropyrrolo[2,1-c][1,4]benzodiazepine-5-carboxylate (38.6 mg).

LCMS: (5-95, AB, 5 min), RT=2.42 min, m/z=469 [M+1]+; 1H NMR (400 MHz, DMSO-d6) δ 7.06 (s, 1H), 6.80 (s, 1H), 6.62 (s, 1H), 5.37 (dd, J=9.6, 5.4 Hz, 1H), 5.13 (d, J=7.0 Hz, 2H), 4.37 (dt, J=12.2, 6.3 Hz, 1H), 4.14-3.93 (m, 4H), 3.80 (s, 6H), 3.45 (t, J=9.3 Hz, 1H), 3.01-2.83 (m, 3H), 1.23-1.16 (m, 6H).

Example 19F

Preparation of PBD Monomer Disulfide Prodrug 16

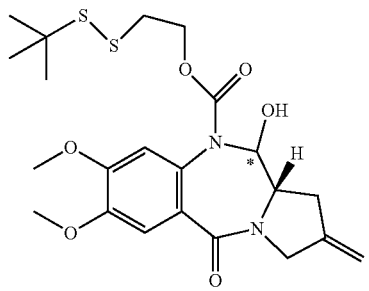 [SMILES: C=C1C[C@H]2C(O)N(C(=O)OCCSSC(C)(C)C)c3cc(OC)c(OC)cc3C(=O)N2C1]

PBD monomer disulfide prodrug 16 was prepared according to the method of example 19E. LCMS: (5-95, AB, 5 min), RT=2.56 min, m/z=483 [M+1]+; 1H NMR (400 MHz, DMSO-d6) δ 7.06 (s, 1H), 6.79 (s, 1H), 6.62 (s, 1H), 5.37 (dd, J=9.7, 5.9 Hz, 1H), 5.16-5.09 (m, 2H), 4.35 (dt, J=12.2, 6.3 Hz, 1H), 4.10 (d, J=16.0 Hz, 1H), 3.98 (d, J=16.0 Hz, 2H), 3.80 (s, 6H), 3.44 (t, J=9.3 Hz, 1H), 2.88 (t, J=12.6 Hz, 3H), 2.54 (s, 1H), 1.25 (s, 9H), 0.08 (s, 1H).

Example 19G

Preparation of PBD Monomer Disulfide Prodrug 29

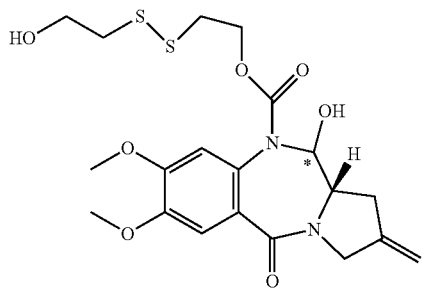 [SMILES: C=C1C[C@H]2C(O)N(C(=O)OCCSSCCO)c3cc(OC)c(OC)cc3C(=O)N2C1]

PBD monomer disulfide prodrug 29 was prepared according to the method of example 19E. LCMS: (5-95, AB, 5 min), RT=1.72 min, m/z=471 [M+1]+; 1H NMR (400 MHz, DMSO-d6) δ 7.06 (s, 1H), 6.79 (d, J=4.9 Hz, 1H), 6.62 (s, 1H), 5.37 (dd, J=9.7, 5.8 Hz, 1H), 5.13 (d, J=7.0 Hz, 2H), 4.88-4.80 (m, 1H), 4.45-4.34 (m, 1H), 4.14-4.05 (m, 1H), 4.02-3.93 (m, 1H), 3.80 (s, 6H), 3.79-3.78 (m, 1H), 3.60 (dq, J=14.2, 6.5 Hz, 2H), 3.49-3.40 (m, 1H), 2.94-2.69 (m, 4H), 2.54 (s, 1H).

Example 19H

Preparation of PBD Monomer Disulfide Prodrug 28

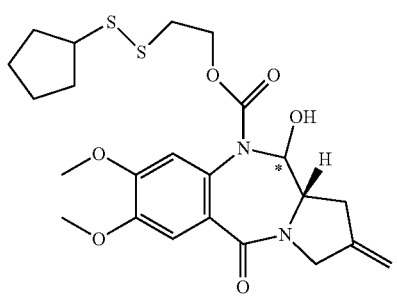 [SMILES: C=C1C[C@H]2C(O)N(C(=O)OCCSSC3CCCC3)c3cc(OC)c(OC)cc3C(=O)N2C1]

PBD monomer disulfide prodrug 28 was prepared according to the method of example 19D. LCMS: (5-95, AB, 5 min), RT=2.68 min, m/z=495 [M+1]+; 1H NMR (400 MHz, DMSO-d6) δ 7.06 (s, 1H), 6.80 (s, 1H), 6.62 (s, 1H), 5.37 (dd, J=9.7, 5.8 Hz, 1H), 5.13 (d, J=6.8 Hz, 2H), 4.44-4.33 (m, 1H), 4.15-4.05 (m, 1H), 4.02-3.93 (m, 1H), 3.81 (s, 6H), 3.44 (t, J=9.1 Hz, 1H), 2.88 (d, J=7.8 Hz, 3H), 2.55 (dt, J=5.7, 2.5 Hz, 2H), 2.48-2.42 (m, 1H), 1.89 (d, J=8.4 Hz, 2H), 1.64 (s, 2H), 1.53 (s, 4H).

Example 19I

Preparation of PBD Monomer Disulfide Prodrug 27

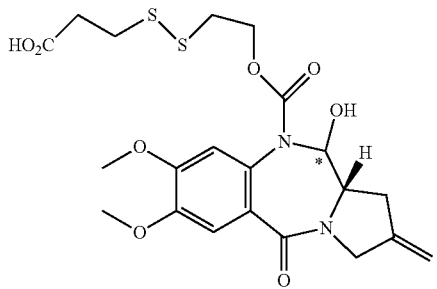 [SMILES: C=C1C[C@H]2C(O)N(C(=O)OCCSSCCC(=O)O)c3cc(OC)c(OC)cc3C(=O)N2C1]

PBD monomer disulfide prodrug 27 was prepared according to the method of example 19E. LCMS: (5-95, AB, 5 min), RT=1.83 min, m/z=499 [M+1]+; 1H NMR (400 MHz, DMSO-d6) δ 7.06 (s, 1H), 6.80 (s, 1H), 5.37 (d, J=9.7 Hz, 1H), 5.16-5.09 (m, 2H), 4.45-4.34 (m, 1H), 4.16-3.93 (m, 2H), 3.80 (s, 6H), 3.44 (t, J=9.2 Hz, 1H), 3.05-2.79 (m, 5H), 2.65-2.50 (m, 1H), 2.46 (s, 1H), 2.07 (s, 3H).

Example 19J

Preparation of PBD Monomer Disulfide Prodrug 7

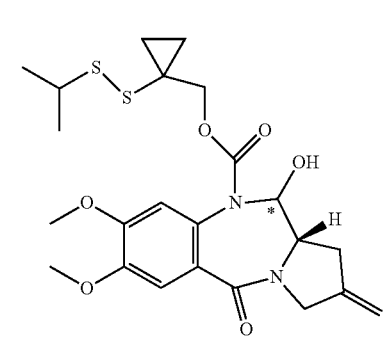 [SMILES: C=C1C[C@H]2C(O)N(C(=O)OCC3(SSC(C)C)CC3)c3cc(OC)c(OC)cc3C(=O)N2C1]

PBD monomer disulfide prodrug 7 was prepared according to the method of example 19E. LCMS: (5-95, AB, 5 min), RT=2.62 min, m/z=495 [M+1]+; 1H NMR (400 MHz, DMSO-d6) δ 7.07 (s, 1H), 6.82 (s, 1H), 6.66-6.60 (m, 1H), 5.41-5.36 (m, 1H), 5.16-5.09 (m, 2H), 4.30 (d, J=11.7 Hz, 1H), 4.15-4.06 (m, 1H), 4.02-3.88 (m, 2H), 3.81 (s, 6H), 3.45 (t, J=9.3 Hz, 1H), 2.91 (td, J=16.0, 8.6 Hz, 2H), 2.57-2.53 (m, 1H), 1.14 (dd, J=11.4, 6.6 Hz, 6H), 0.96-0.81 (m, 4H).

Example 19K

Preparation of PBD Monomer Disulfide Prodrug 1

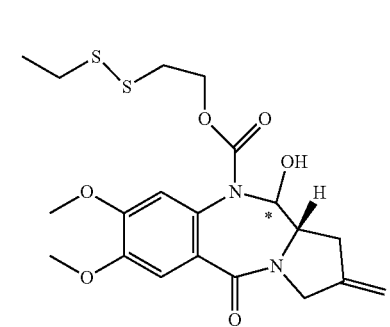 [SMILES: C=C1C[C@H]2C(O)N(C(=O)OCCSSCC)c3cc(OC)c(OC)cc3C(=O)N2C1]

PBD monomer disulfide prodrug 1 was prepared according to the method of example 19E. LCMS: (5-95, AB, 5 min), RT=2.20 min, m/z=455 [M+1]+; 1H NMR (400 MHz, DMSO-d6) δ 7.06 (s, 1H), 6.80 (s, 1H), 6.62 (s, 1H), 5.37 (dd, J=9.7, 5.1 Hz, 1H), 5.16-5.09 (m, 2H), 4.39 (dt, J=12.2, 6.3 Hz, 1H), 4.15-3.93 (m, 3H), 3.80 (s, 6H), 3.45 (t, J=9.3 Hz, 1H), 2.88 (dd, J=16.1, 9.0 Hz, 3H), 2.65 (q, J=12.6, 6.8 Hz, 2H), 2.54 (d, J=2.3 Hz, 1H), 1.23-1.14 (m, 3H).

Example 19L

Preparation of PBD Monomer Disulfide Prodrug 26

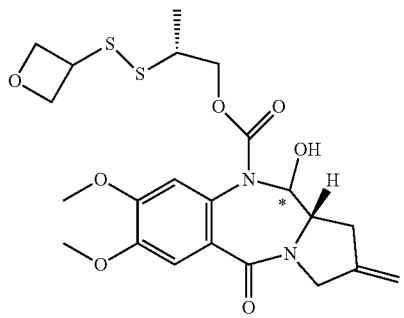 [SMILES: C=C1C[C@H]2C(O)N(C(=O)OC[C@@H](C)SSC3COC3)c3cc(OC)c(OC)cc3C(=O)N2C1]

PBD monomer disulfide prodrug 26 was prepared according to the method of example 19E. LCMS: (5-95, AB, 5 min), RT=2.08 min, m/z=497 [M+1]+; 1H NMR (400 MHz, DMSO-d6) δ 7.08 (s, 1H), 6.82 (s, 1H), 6.65 (s, 1H), 5.38 (d, J=9.7 Hz, 1H), 5.13 (d, J=6.6 Hz, 2H), 4.77 (s, 3H), 4.45-4.34 (m, 1H), 4.26-4.06 (m, 3H), 4.02-3.93 (m, 1H), 3.81 (s, 6H), 3.45 (t, J=9.3 Hz, 1H), 3.09 (s, 1H), 2.94-2.83 (m, 1H), 2.62-2.53 (m, 1H), 1.04 (d, J=6.9 Hz, 2H), −0.03--0.13 (m, 1H).

Example 19M

Preparation of PBD Monomer Disulfide Prodrug 25

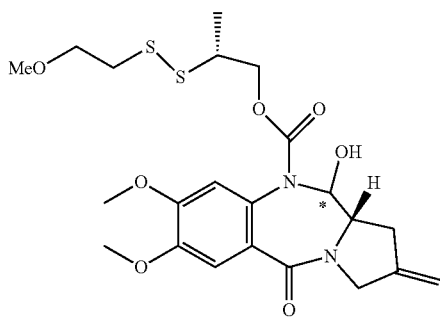 [SMILES: C=C1C[C@H]2C(O)N(C(=O)OC[C@@H](C)SSCCOC)c3cc(OC)c(OC)cc3C(=O)N2C1]

PBD monomer disulfide prodrug 25 was prepared according to the method of example 19E. LCMS: (5-95, AB, 5 min), RT=2.16 min, m/z=499 [M+1]+; 1H NMR (400 MHz, DMSO-d6) δ 7.07 (s, 1H), 6.82 (s, 1H), 6.63 (br s, 1H), 5.38 (d, J=9.7 Hz, 1H), 5.14 (s, 2H), 4.2-4.1 (m, 2H), 3.99 (s, 1H), 3.81 (s, 6H), 3.46 (s, 4H), 3.22 (s, 3H), 2.79 (s, 2H), 2.69-2.54 (m, 3H), 1.05 (s, 2H).

Example 19N

Preparation of PBD Monomer Disulfide Prodrug 24

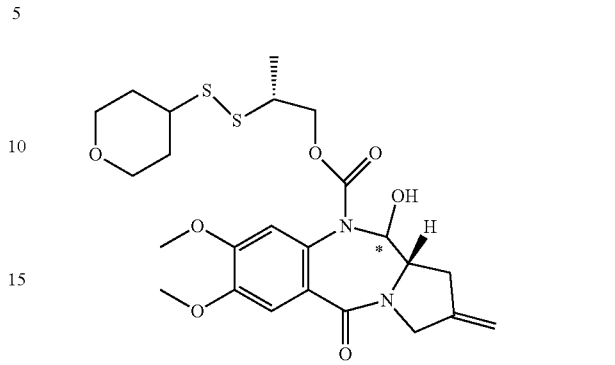

PBD monomer disulfide prodrug 24 was prepared according to the method of example 19E.

The thiol was synthesized according to the following scheme:

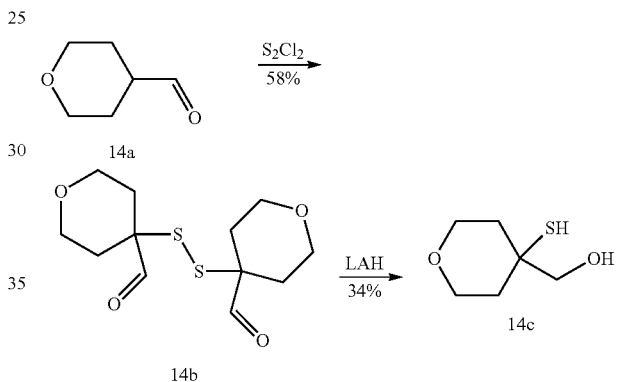

To a solution of tetrahydro-2H-pyran-4-carbaldehyde 14a (5 g, 43.8 mmol) in MTBE (50 mL) was added S₂Cl₂ (2.96 g, 21.9 mmol). The reaction mixture was stirred at 55° C. for 16 hours under nitrogen, and then the reaction mixture was cooled to ambient temperature, removed solvent under vacuum and purified by silica gel column chromatography (silica:200-300 mesh, PE/EtOAc=5/1) to give disulfide 14b (5 g, 58%) as a yellow oil. 1H NMR (300 MHz, CDCl3) δ 9.05 (s, 1H), 3.92-3.42 (m, 8H), 2.22-1.58 (m, 8H).

To a solution of 4,4'-disulfanediylbis(tetrahydro-2H-pyran-4-carbaldehyde) 7 (5 g, 12.82 mmol) in THF (50 mL) was added LiAlH₄ (0.97 g, 25.64 mmol) in portions. After addition, the reaction mixture was stirred at ambient temperature for 2 hours, and then the reaction mixture was acidified with HCl (3 N) to PH=6, extracted with ethylacetate (30 mL×3), dried over Na₂SO₄, removed solvent and purified with silica gel column chromatography (silica:200-300 mesh, PE/EA=10/1) to give thiol 14c (2.02 g, 34%) as yellow oil. 1H NMR (300 MHz, CDCl3) δ 3.86-.383 (m, 4H), 3.53 (s, 2H), 2.25 (s, 1H), 1.86-1.43 (m, 5H). GCMS (m/z) ES=148.

LCMS: (5-95, AB, 5 min), RT=2.24 min, m/z=525 [M+1]+; 1H NMR (400 MHz, DMSO-d6) δ 7.07 (s, 1H), 6.82 (s, 1H), 6.61 (s, 1H), 5.37 (d, J=9.6 Hz, 1H), 5.13 (d, J=7.0 Hz, 2H), 4.23 (dd, J=11.1, 6.0 Hz, 1H), 4.10 (d, J=15.7 Hz, 1H), 4.02-3.83 (m, 4H), 3.81 (s, 6H), 3.45 (t, J=9.3 Hz, 1H), 3.02 (dt, J=11.1, 4.1 Hz, 1H), 2.94-2.83 (m, 2H), 2.59-2.52 (m, 2H), 1.95-1.76 (m, 2H), 1.55-1.37 (m, 2H), 1.27-1.21 (m, 1H), 1.05 (d, J=6.9 Hz, 3H).

Example 19O

Preparation of PBD Monomer Disulfide Prodrug

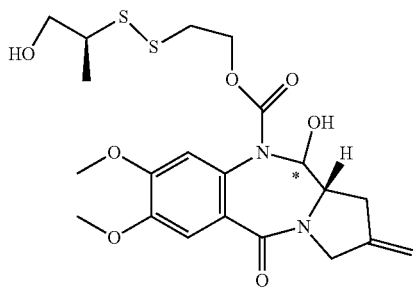 [SMILES: C=C1C[C@H]2C(O)N(C(=O)OCCSS[C@@H](C)CO)c3cc(OC)c(OC)cc3C(=O)N2C1]

The above PBD monomer disulfide prodrug was prepared according to the method of example 19E. LCMS: (5-95, AB, 5 min), RT=1.86 min, m/z=485 [M+1]+; 1H NMR (400 MHz, DMSO-d6) δ 7.06 (s, 1H), 6.79 (s, 1H), 6.62 (s, 1H), 5.37 (dd, J=9.7, 6.0 Hz, 1H), 5.13 (d, J=7.0 Hz, 2H), 4.88 (t, J=5.7 Hz, 1H), 4.38 (d, J=7.5 Hz, 1H), 4.16-3.95 (m, 2H), 3.80 (s, 6H), 3.46 (d, J=11.3 Hz, 2H), 3.38-3.34 (m, 1H), 2.86 (s, 4H), 2.58-2.53 (m, 1H), 1.19 (dd, J=12.6, 6.6 Hz, 3H).

Example 19P

Preparation of PBD Monomer Disulfide Prodrug 12

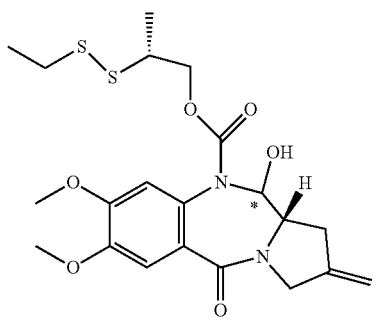 [SMILES: C=C1C[C@H]2C(O)N(C(=O)OC[C@@H](C)SSCC)c3cc(OC)c(OC)cc3C(=O)N2C1]

PBD monomer disulfide prodrug 12 was prepared according to the method of example 19E. LCMS: (5-95, AB, 5 min), RT=2.40 min, m/z=469 [M+1]+; 1H NMR (400 MHz, DMSO-d6) δ 7.07 (s, 1H), 6.82 (s, 1H), 6.63 (s, 1H), 5.38 (dd, J=9.7, 5.9 Hz, 1H), 5.13 (d, J=6.7 Hz, 2H), 4.21 (dd, J=11.1, 6.2 Hz, 1H), 4.10 (d, J=16.0 Hz, 1H), 3.97 (d, J=16.1 Hz, 2H), 3.81 (d, J=2.3 Hz, 6H), 3.45 (t, J=9.3 Hz, 1H), 3.05 (s, 1H), 2.94-2.83 (m, 1H), 2.70-2.53 (m, 3H), 2.45 (p, J=1.9 Hz, 1H), 1.16 (t, J=7.2 Hz, 3H), 1.08-1.02 (m, 2H).

Example 19Q

Preparation of PBD Monomer Disulfide Prodrug 3

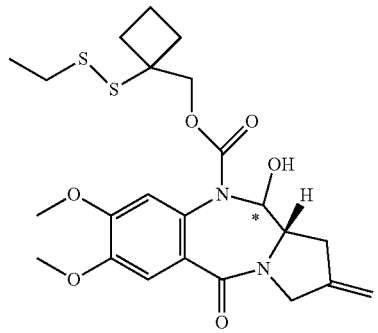 [SMILES: C=C1C[C@H]2C(O)N(C(=O)OCC3(SSCC)CCC3)c3cc(OC)c(OC)cc3C(=O)N2C1]

PBD monomer disulfide prodrug 3 was prepared according to the method of example 19E.

The para-nitropyridine disulfide was synthesized according to the following scheme:

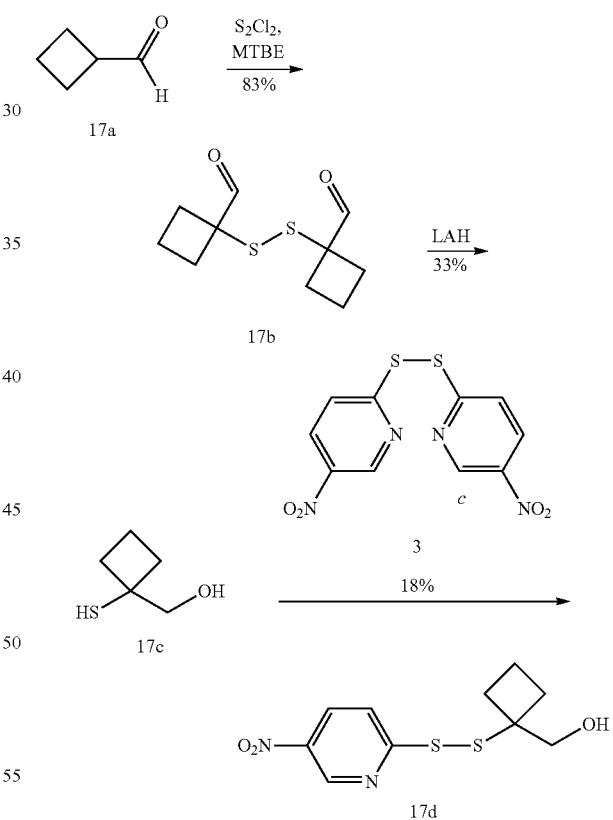

To a solution of cyclobutanecarbaldehyde 17a (9.8 g, 120 mmol) in MTBE (80 mL) was added S₂Cl₂ (8.1 g, 60 mmol). The reaction mixture was stirred at 55° C. for 16 hours under nitrogen. The reaction mixture was cooled to ambient temperature, remove solvent under vacuum and purified with silica gel column chromatography (silica:200-300 mesh, PE/EtOAc=20/1) to give 1,1'-disulfanediyldicyclobutanecarbaldehyde (11.2 g, 83%) as brown oil. 1H NMR (300 MHz, CDCl3) δ9.28 (s, 2H), 3.06-1.20 (m, 12H).

To a solution of 1,1'-disulfanediyldicyclobutanecarbaldehyde 5 (11.2 g, 49 mmol) in THF (200 mL) was added LiAlH$_4$ (3.7 g, 97 mmol) in portions. After addition, the reaction mixture was stirred at ambient temperature for 2 hours. The reaction mixture was acidified with HCl (3 N) to pH=6, extracted with ethylacetate(200 mL×3), dried over Na$_2$SO$_4$, remove solvent and purified with silica gel column chromatography (silica:200-300 mesh, PE/EtOAc=10/1) to give thiol 17c (3.8 g, 33%) as yellow oil. 1H NMR (300 MHz, CDCl3) δ 3.64 (s, 2H), 2.35-2.09 (m, 5H), 2.05-1.87 (m, 2H), 1.81 (s, 1H).GCMS (ES) m/z=+118.

A mixture of 17c (4.88 g, 41.35 mmol) and 1,2-bis(5-nitropyridin-2-yl)disulfane (12.82 g, 41.35 mmol) in MeOH (100 mL) was stirred at ambient temperature for 16 hours under nitrogen. The solution was concentrated under vacuum and the residue was purified by silica gel column chromatography (silica:200-300 mesh, PE/EA=10/1) to give target compound 17d (2.01 g, 18%) as yellow solid. 1H NMR (400 MHz, DMSO) 69.30 (s, 1H), 8.34 (dd, J=8.8, 2.6 Hz, 1H), 7.60 (d, J=8.8 Hz, 1H), 3.57 (s, 2H), 3.41 (s, 1H), 2.27-2.14 (m, 5H), 2.08-1.93 (m, 1H); LCMS (ES) m/z=+273 (M+1).

LCMS: (5-95, AB, 5 min), RT=2.61 min, m/z=495 [M+1]+; 1H NMR (400 MHz, DMSO-d6) 6 7.08 (s, 1H), 6.82 (s, 1H), 6.64 (d, J=6.0 Hz, 1H), 5.45-5.36 (m, 1H), 5.13 (d, J=7.2 Hz, 2H), 4.30 (d, J=11.5 Hz, 1H), 4.10 (d, J=15.8 Hz, 1H), 3.97 (d, J=13.7 Hz, 2H), 3.80 (s, 6H), 3.46 (td, J=9.5, 1.8 Hz, 1H), 2.89 (dd, J=15.8, 9.2 Hz, 1H), 2.62-2.52 (m, 2H), 1.91 (s, 6H), 1.63 (s, 1H), 1.13 (t, J=7.5 Hz, 3H).

Example 19R

Preparation of PBD Monomer Disulfide Prodrug 5

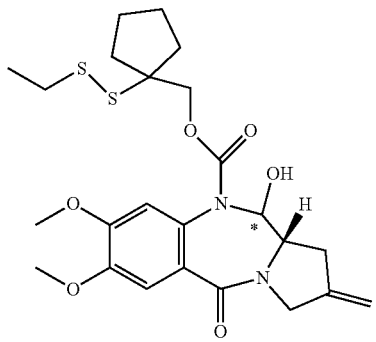 [SMILES: C=C1C[C@H]2C(O)N(C(=O)OCC3(SSCC)CCCC3)c3cc(OC)c(OC)cc3C(=O)N2C1]

PBD monomer disulfide prodrug 5 was prepared according to the method of example 19E.

The para-nitropyridine disulfide was synthesized according to the following scheme:

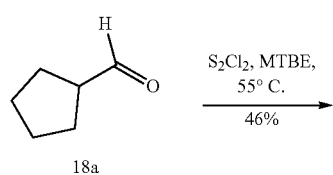

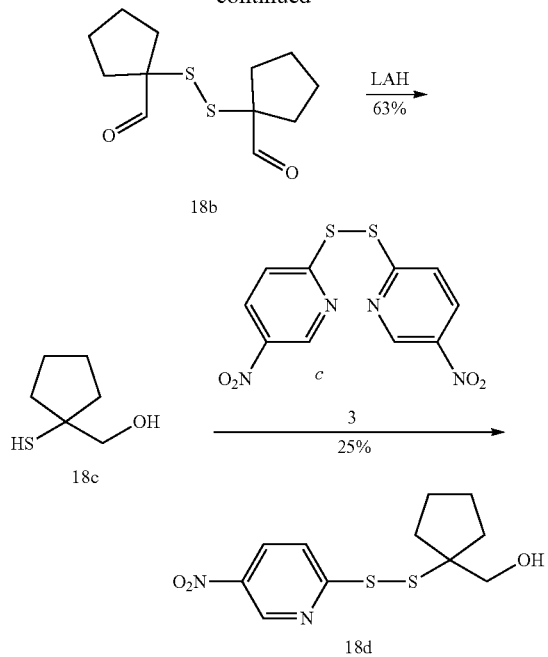

To a solution of cyclopentanecarbaldehyde 18a (9.0 g, 92 mmol) in MTBE (30 mL) was added S$_2$Cl$_2$ (7.4 g, 55 mmol). The reaction mixture was stirred at 55° C. for 16 hours under nitrogen. The reaction mixture was cooled to ambient temperature, removed solvent under vacuum and purified with silica gel column chromatography (silica:200-300 mesh, PE/EtOAc=80/1) to give 1,1'-disulfanediyldicyclopentanecarbaldehyde 18b (5.5 g, 46%) as brown oil. 1H NMR (300 MHz, CDCl3) δ 9.23 (s, 2H), 2.41-1.51 (m, 16H).

To a solution of 1,1'-disulfanediyldicyclopentanecarbaldehyde 18b (8.5 g, 32.9 mmol) in THF (60 mL) was added LiAlH$_4$ (2.5 g, 65.8 mmol) in portions. After addition, the reaction mixture was stirred at ambient temperature for 2 hours, and then the solution was acidified with HCl (3 N) to pH=6, extracted with ethylacetate (150 mL×2), dried over Na$_2$SO$_4$, removed solvent and purified by silica gel column chromatography (silica:200-300 mesh, PE/EtOAc=20/1) to give 18c (5.5 g, 63%) as yellow oil. 1H NMR (300 MHz, CDCl3) δ 3.51 (s, 2H), 2.04 (s, 1H), 1.85-1.67 (m, 7H), 1.64 (s, 1H). GCMS (ES) m/z=+132.

A mixture of 18c (3.5 g, 26.5 mmol) and 1,2-bis(5-nitropyridin-2-yl)disulfane 3 (12.3 g, 39.8 mmol) in MeOH (50 mL) was stirred at ambient temperature for 16 hours under nitrogen. After the reaction was completed, the solution was concentrated under vacuum. The residue was purified with silica gel column chromatography (silica:200-300 mesh, PE/EtOAc=10/1) to give target compound 18d (1.9 g, 25%) as a yellow solid. 1H NMR (400 MHz, DMSO): δ 9.24-9.20 (m, 1H), 8.58 (dd, J=8.9, 2.7 Hz, 1H), 8.17 (dd, J=8.9, 0.5 Hz, 1H), 5.18 (t, J=5.5 Hz, 1H), 3.40 (d, J=5.5 Hz, 2H), 1.63-1.82 (m, 8H); LCMS (ES) m/z=+287 (M+1).

LCMS: (5-95, AB, 5 min), RT=2.48 min, m/z=509 [M+1]+; 1H NMR (400 MHz, DMSO-d6) δ 7.08 (s, 1H), 6.82 (s, 1H), 6.73-6.60 (m, 1H), 5.40 (d, J=7.7 Hz, 1H), 5.13 (d, J=7.2 Hz, 2H), 4.22 (d, J=11.0 Hz, 1H), 4.10 (d, J=15.9 Hz, 1H), 4.01-3.84 (m, 2H), 3.81 (s, 6H), 3.46 (t, J=9.2 Hz, 1H), 2.88 (dd, J=15.9, 9.3 Hz, 1H), 2.55 (dd, J=4.1, 2.3 Hz, 2H), 1.81-1.39 (m, 10H), 1.12 (t, J=7.3 Hz, 3H).

Example 19S

Preparation of PBD Monomer Disulfide Prodrugs 11 and 30

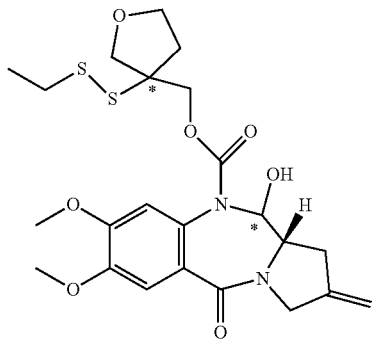 [SMILES: C=C1C[C@H]2C(O)N(C(=O)OCC3(SSCC)CCOC3)c3cc(OC)c(OC)cc3C(=O)N2C1]

PBD monomer disulfide prodrugs 11 and 30 correspond to the above structure and are are diastereomers having a different configuration at one or more of the chiral centers designated with the asterisk. The compounds were prepared according to the method of example 19E.

The para-nitropyridine disulfide was synthesized according to the following scheme using the procedure described in Example 19N.

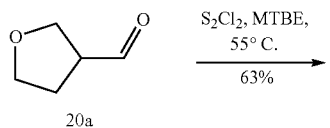

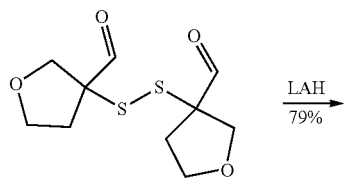

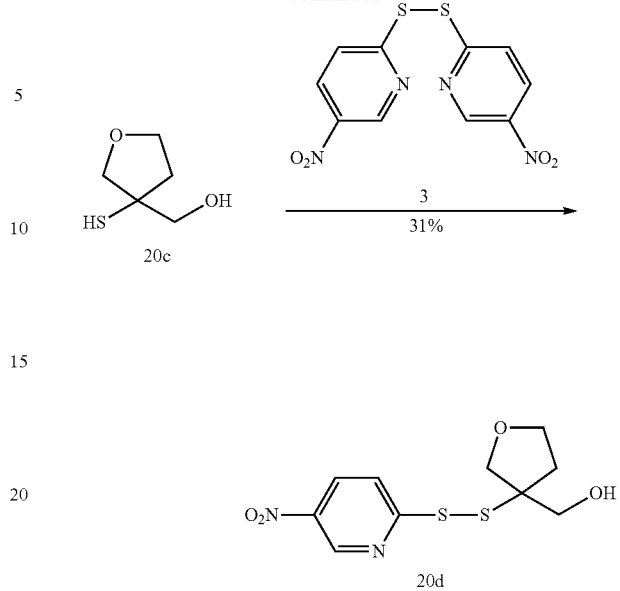

PBD monomer disulfide prodrug 11 LCMS: (5-95, AB, 5 min), RT=1.95 min, m/z=511 [M+1]+; 1H NMR (400 MHz, DMSO-d6) δ 7.08 (s, 1H), 6.83 (s, 1H), 6.64 (s, 1H), 5.39 (d, J=9.7 Hz, 1H), 5.13 (d, J=7.1 Hz, 2H), 4.34 (d, J=11.5 Hz, 1H), 4.10 (d, J=16.0 Hz, 1H), 3.98 (t, J=15.3 Hz, 2H), 3.81 (d, J=2.4 Hz, 6H), 3.78-3.72 (m, 1H), 3.63 (s, 1H), 3.54 (s, 2H), 3.46 (t, J=9.2 Hz, 1H), 2.89 (dd, J=15.7, 9.4 Hz, 1H), 2.62-2.50 (m, 3H), 1.83 (d, J=37.2 Hz, 2H), 1.12 (t, J=7.3 Hz, 3H).

PBD monomer disulfide prodrug 30 LCMS: (5-95, AB, 5 min), RT=1.99 min, m/z=511 [M+1]+; 1H NMR (400 MHz, DMSO-d6) δ 7.08 (s, 1H), 6.82 (s, 1H), 6.66 (s, 1H), 5.48-5.34 (m, 1H), 5.21-5.07 (m, 2H), 4.33 (d, J=11.5 Hz, 1H), 4.18-3.91 (m, 3H), 3.81 (s, 6H), 3.79-3.70 (m, 0H), 3.48 (d, J=17.5 Hz, 2H), 2.97-2.82 (m, 1H), 2.55 (dd, J=4.2, 2.2 Hz, 2H), 2.47-2.29 (m, 1H), 1.85 (d, J=13.2 Hz, 2H), 1.13 (t, J=7.4 Hz, 3H).

Example 20

Preparation of PBD Dimer Disulfide Prodrugs

Example 20A

Preparation of PBD Dimer Disulfide Prodrug 4

PBD dimer disulfide prodrug 4 was prepared according to the following reaction scheme:

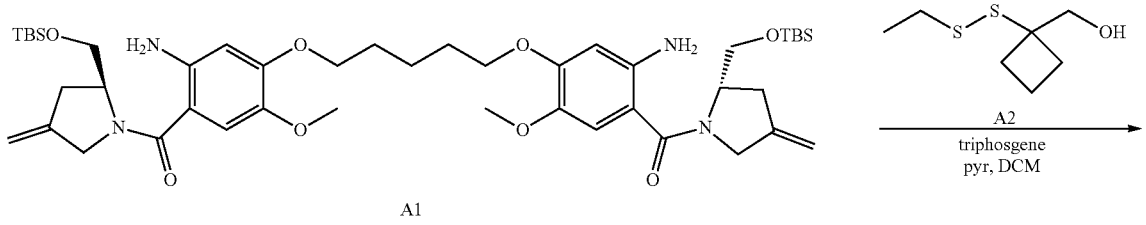

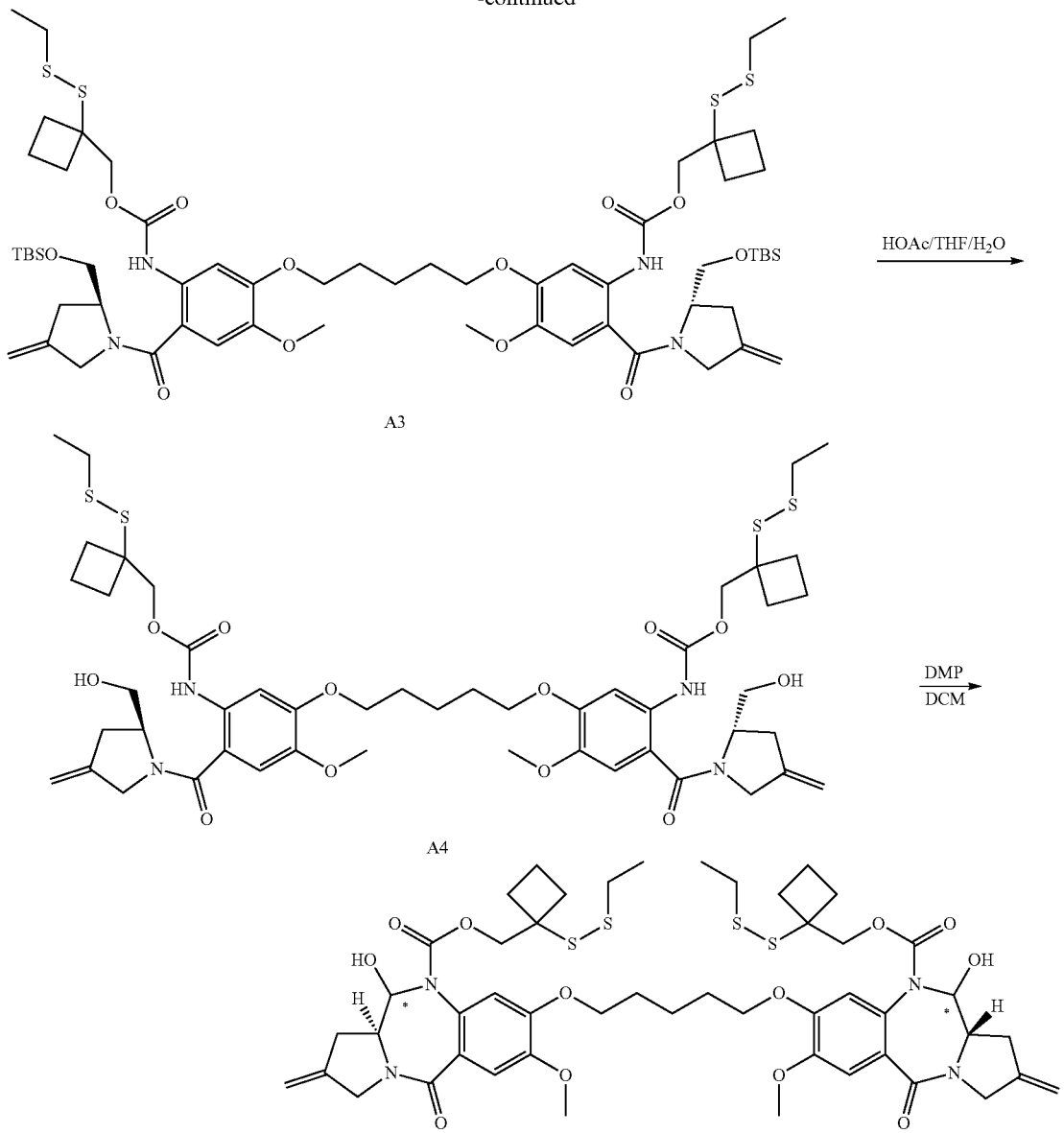

Each asterisk in the above structure, and elsewhere depicted in Example 20, represents a chiral center.

To a solution of triphosgene (83.2 mg, 0.280 mmol) in DCM (2.0 mL) was added a solution of compound A2 and pyridine in DCM (3.0 mL) at 0° C. The mixture was stirred at 20° C. for 30 min and was concentrated in vacuo. It was dissolved in DCM (5.0 mL) and added dropwise to a solution of pyridine (18.5 mg, 0.234 mmol) and compound A1 (124 mg, 0.516 mmol) at 20° C. After the reaction mixture was stirred at 20° C. for 2 h, it was concentrated in vacuo and purified by column chromatography (0-50% EtOAc in petroleum ether) to give compound A3 as a yellow solid (150 mg, 54%). LCMS (5-95, AB, 1.5 min): RT=1.419 min, m/z=1261.4 [M+1]+.

A solution of compound A3 (150 mg, 0.119 mmol) in THF (4.0 mL), $H_2O$ (4.0 mL) and HOAc (6.0 mL) was stirred at 10° C. for 8 h. The mixture was diluted with EtOAc (15 mL) and washed with $H_2O$ (10 mL), aqueous $NaHCO_3$ (10 mL), and brine (10 mL). The organic layer was dried over $Na_2SO_4$, filtered, concentrated and purified by prep-TLC (5% $CH_3OH$ in DCM) to give compound A4 (75 mg, 60.4%) as a colorless oil. LCMS (5-95, AB, 1.5 min): RT=0.941 min, m/z=1033.3 [M+1]+.

A mixture of compound A4 (44 mg, 0.04 mmol) and DMP (54 mg, 0.13 mmol) in DCM (15 mL) was stirred at 13° C. for 16 h. The reaction mixture was concentrated in vacuo and purified by prep-TLC (5.6% MeOH in DCM Rf=0.5), followed by prep-HPLC (10 mM, $NH_4HCO_3$-ACN) to give PBD dimer disulfide prodrug 4 (15 mg, 34%) as a white solid. LCMS (5-95, AB, 1.5 min): RT=0.941 min, m/z=1051.2 [M+23]+; 1H NMR (400 MHz, CDCl3) δ 7.19 (s, 2H), 6.73 (s, 2H), 5.59-5.57 (m, 2H), 5.12 (s, 4H), 4.43 (d, J=10.8 Hz, 2H), 4.26-4.15 (m, 1H), 4.11 (s, 1H), 4.02-3.98 (m, 3H), 3.96 (s, 4H), 3.88 (s, 6H), 3.80-3.65 (m, 2H), 3.62 (m, 2H), 2.90-2.80 (m, 2H), 2.72-2.60 (m, 6H), 2.18 (br, 2H), 2.02-1.92 (br, 13H),1.70-1.63 (m, 3H),1.22-1.19 (m, 6H).

Example 20B
Preparation of PBD Dimer Disulfide Prodrug 1
PBD dimer disulfide prodrug 1 was prepared according to the following reaction scheme:
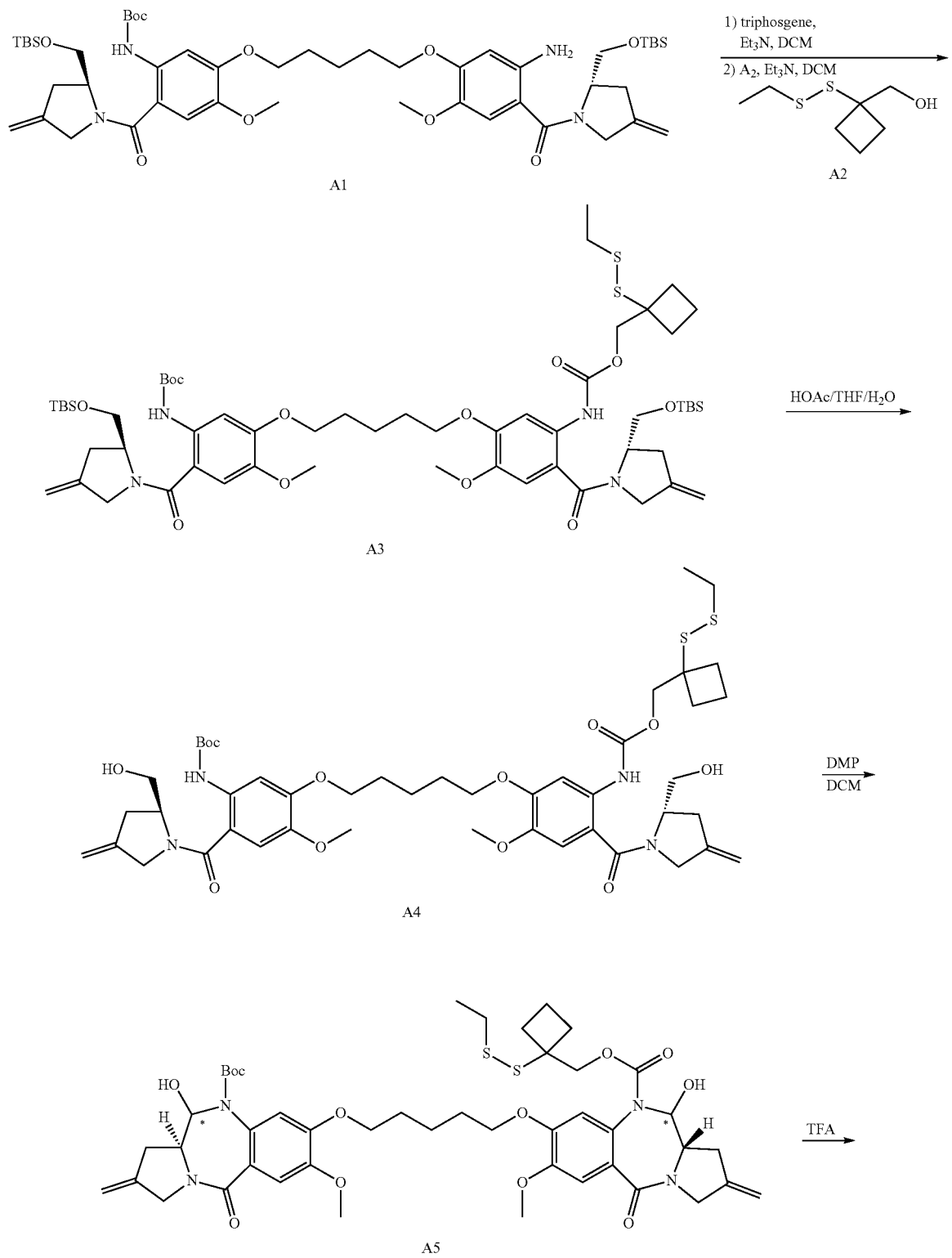

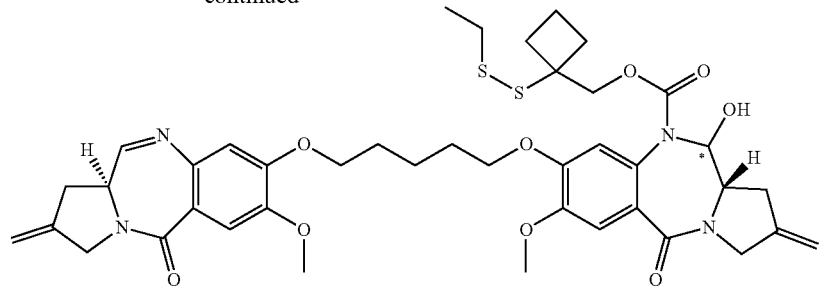

To a solution of triphosgene (42.02 mg, 0.140 mmol) in DCM (4.0 mL) added the solution of compound A1 (300.0 mg, 0.310 mmol) and triethylamine (63.68 mg, 0.630 mmol) in DCM (4 mL) dropwise. After the mixture stirred at 0° C. for 30 min, a solution of compound A2 (112.16 mg, 0.630 mmol) and triethylamine (127 mg, 1.26 mmol) in DCM (2.0 mL) was added and the mixture was stirred at 18° C. for 18 h. The mixture was partitioned between water (20.0 mL) and DCM (40.0 mL), and the organic layer was washed with water (20.0 mL), brine (20.0 mL), and concentrated. It was purified on column chromatography (EtOAc:petroleum ether 1:2) to afford compound A3 (240 mg, 65%) as a yellow oil. LCMS (5-95, AB, 1.5 min): RT=1.296 min, m/z=1157.4 [M+1]+.

To a solution of compound A3 (240.0 mg, 0.210 mmol) in THF (1.5 mL) was added a mixture of HOAc/H2O (4.0 mL, 3/1) dropwise. The mixture was stirred at 8° C. for 18 h. The pH was adjusted to 8 with a NaHCO₃ solution, and it was extracted with EtOAc (3×50 mL). The combined organic layer was dried over Na₂SO₄, filtered and concentrated. It was purified by column chromatography (DCM:MeOH=20:1) to give compound A4 (130 mg, 68%) as a yellow oil. LCMS (5-95, AB, 1.5 min): RT=0.868 min, m/z=929.3 [M+1]+.

To a solution of compound A4 (60.0 mg, 0.0600 mmol) in DCM (6.0 mL) added DMP (95.83 mg, 0.230 mmol), and the mixture stirred at 18° C. for 1.0 h. The mixture was filtered, washed with aqueous Na₂SO₃ (20.0 mL), brine (20.0 mL) and water (20.0 mL). The organic layer was dried over Na₂SO₄, concentrated, and purified by prep-TLC (7% MeOH in DCM) to give the compound A5 (30 mg, 49%) as a white solid. LCMS (5-95, AB, 1.5 min): RT=0.804 min, m/z=925.3 [M+1]+.

TFA (1.0 mL) was added dropwise to compound A5 (30.0 mg, 0.030 mmol) at 0° C. After it was stirred for 20 min, the mixture was added to a sat. NaHCO₃ solution (40.0 mL) dropwise at 0° C., and extracted with DCM (3×15 mL). The combined organic layer was dried over Na₂SO₄, concentrated, and purified by prep-TLC (18% MeOH in DCM, Rf=0.6) to afford PBD dimer disulfide prodrug 1 (5.8 mg, 22%) as a white solid. LCMS (5-95, AB, 1.5 min): RT=0.890 min, m/z=807.2 [M+1]+.

Example 20C

Preparation of PBD Dimer Disulfide Prodrug 2

PBD dimer disulfide prodrug 2 was prepared according to the following reaction scheme:

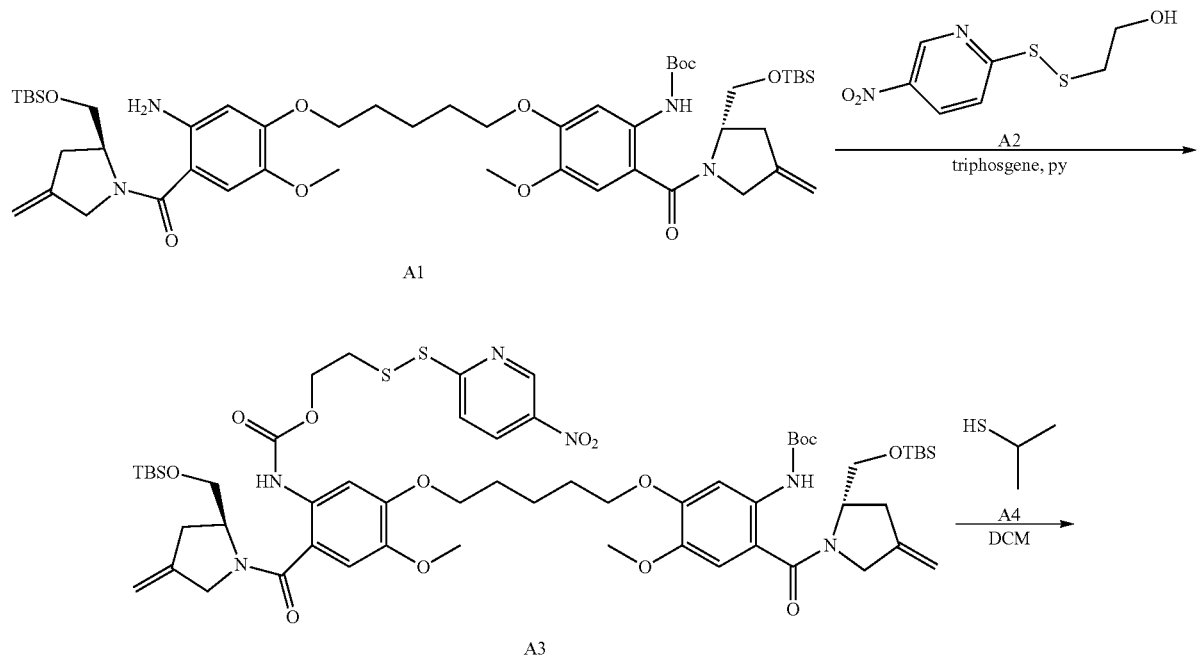

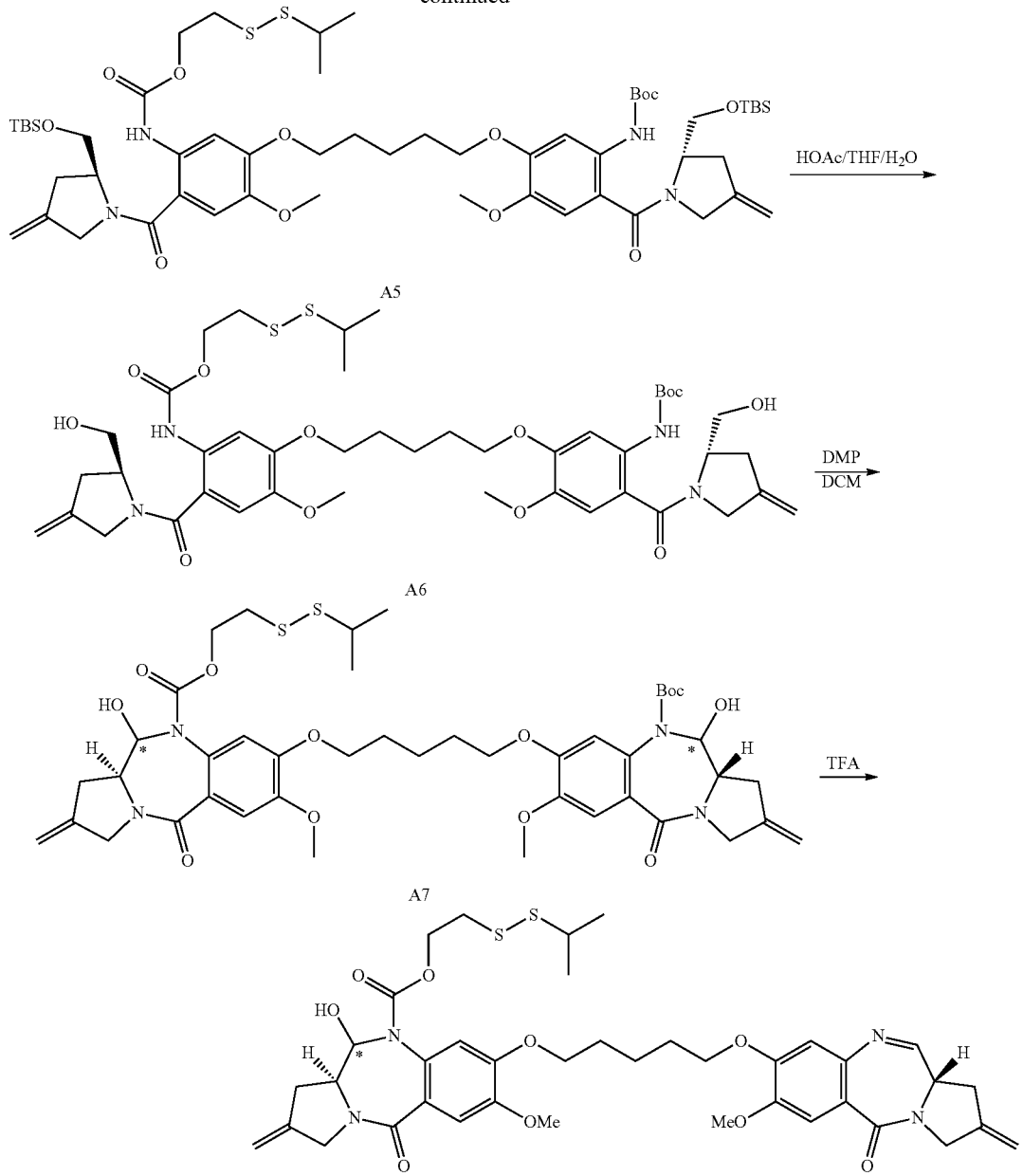

To a solution of triphosgene (89.43 mg, 0.300 mmol) and 4 Å molecular sieves (50 mg) in DCM (5.0 mL) was added a solution of compound A2 (165.0 mg, 0.710 mmol) and pyridine (168.58 mg, 2.13 mmol) in DCM (5.0 mL). The mixture was stirred at 0° C. for 30 min. The resulting mixture was added dropwise to a solution of compound A1 (745 mg, 0.780 mmol), pyridine (169 mg, 2.13 mmol) and 4 Å MS in DCM (5.0 mL). It was stirred at 0° C. for 30 min, and washed with water (5.0 mL). Organic phase was dried, concentrated and purified by flash column chromatography (5% MeOH in DCM) to give the product A3 (698 mg, 81%) as a yellow oil. LCMS (5-95, AB, 1.5 min): RT=1.187 min, m/z=606.5 [M/2+1]+.

To a solution of compound A3 (698.0 mg, 0.580 mmol) in DCM (10.0 mL) was added 2-propanethiol (439 mg, 5.76 mmol). After the mixture was stirred at 20° C. for 1 h, MnO$_2$ (100 mg) was added and stirred for 5 min, and filtered. The filtrate was concentrated and purified by prep-TLC (50% EtOAc in petroleum ether) to give compound A5 (620 mg, 95%) as a yellow solid. LCMS (5-95, AB, 1.5 min): RT=1.221 min, m/z=1131.4 [M+1]+.

To a solution of compound A5 (620.0 mg, 0.550 mmol) in THF (6.0 mL) and water (6.0 mL) was added HOAc (3.29 g, 54.8 mmol). The mixture was stirred at 40° C. for 16 h and concentrated. It was purified by column chromatography (10% MeOH in DCM) to afford compound A6 (208 mg, 42%) as yellow oil. LCMS (5-95, AB, 1.5 min): RT=0.854 min, m/z=903.3 [M+1]+.

To a solution of compound A6 (208.0 mg, 0.230 mmol) in DCM (8.0 mL) was added 4 Å molecular sieves, DMP (224.7 mg, 0.530 mmol). The mixture was stirred at 20° C. for 2 h and was quenched with saturated NaHCO$_3$ and Na$_2$S$_2$O$_3$ solution (2.0 mL/2.0 mL). After it was stirred for 5 min, DCM (5.0 mL) was added and separated. DCM phase was washed with water (2×5 mL). It was dried, concentrated and purified by prep-TLC (5% MeOH in DCM, Rf=0.2) to afford compound A7 (121 mg, 58%) as a light yellow foam. LCMS (5-95, AB, 1.5 min): RT=0.783 min, m/z=781.3 [M−100+1]+.

TFA (1.0 mL, 13.5 mmol) was added to compound A7 (121.0 mg, 0.130 mmol) at 0° C. After the mixture was stirred for 10 min, it was added to a cold saturated NaHCO$_3$ solution (20 mL) and extracted with DCM (3×10 mL). The combined organic layer was concentrated and purified by prep-TLC (10% MeOH in DCM, Rf=0.2) followed by prep-HPLC (ACN, acetonitrile: 42~62%, 0.225% FA) to afford PBD dimer disulfide prodrug 2 (7.2 mg, 7.0%). LCMS (5-95, AB, 1.5 min): RT=0.868 min, m/z=781.3 [M+1]+.

Example 20D

Preparation of PBD Dimer Disulfide Prodrug 3

PBD dimer disulfide prodrug 3 was prepared according to the following reaction scheme:

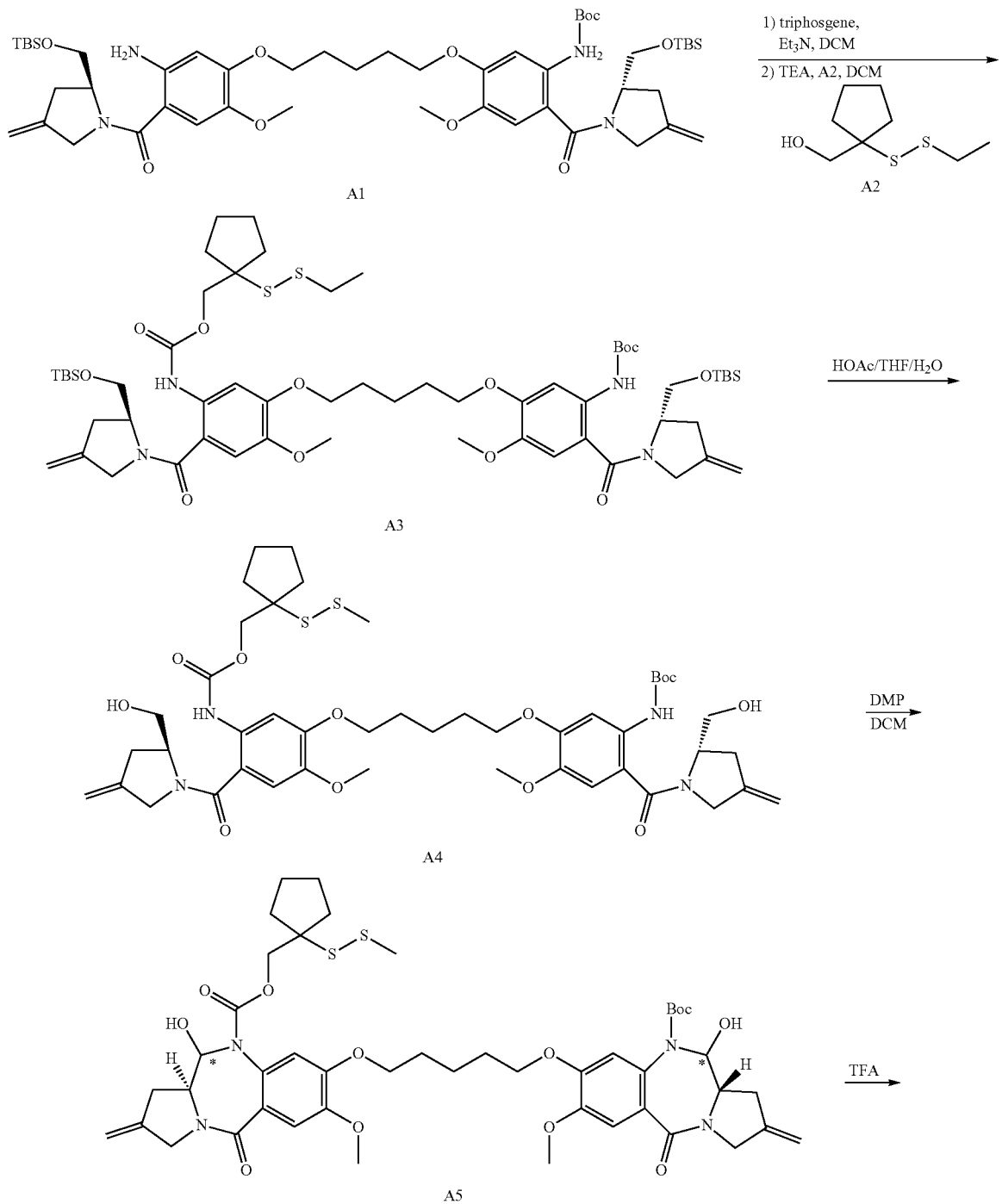

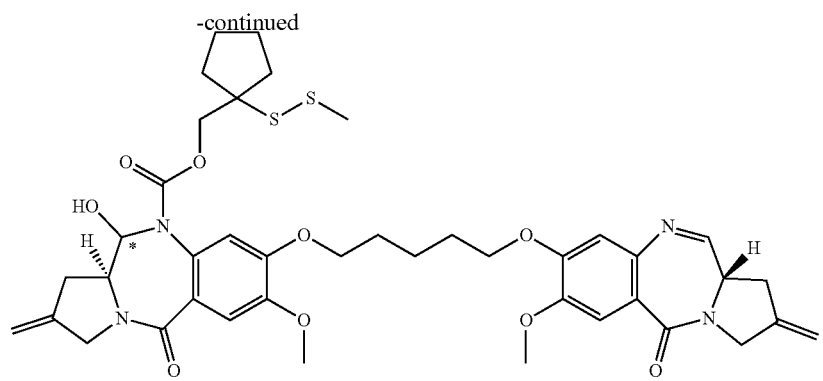
-continued

A solution of triphosgene (65.37 mg, 0.220 mmol) in DCM (2.0 mL) was added a mixture of compound A1 (420.0 mg, 0.440 mmol) and triethylamine (89.16 mg, 0.880 mmol) in DCM (3.0 mL) at 0° C. under $N_2$. After the mixture was stirred at 21° C. for 30 min, it was concentrated, and DCM (18 mL) was added. A solution of A2 (75.0 mg, 0.390 mmol) and triethylamine (78.91 mg, 0.780 mmol) in DCM (2.0 mL) was added at 0° C. under $N_2$. After the reaction mixture was stirred at 20° C. for 1 h, it was concentrated in vacuo and purified by column chromatography (0-50% EtOAC in petroleum ether) to give compound A3 (350 mg, 74%) as a yellow solid. LCMS (5-95, AB, 1.5 min): RT=1.379 min, m/z=1171.5 [M+1]+.

To a solution of compound A3 (415.2 mg, 0.350 mmol) in THF (30 mL) and water (15 mL) was added HOAc (2.02 mL, 35.2 mmol). The reaction solution was stirred at 20° C. for 12 h. It was concentrated in vacuo and diluted with EtOAc (200 mL), washed with $H_2O$ (2×100 mL), then aq. $NaHCO_3$ solution (2×60 mL). The EtOAc layer was dried over $Na_2SO_4$, filtered, and concentrated. It was purified by column chromatography (0-10% MeOH in DCM) to afford compound A4 (320 mg, 87.1%) as a yellow solid. LCMS (5-95, AB, 1.5 min): RT=1.080 min, m/z=943.5 [M+1]+.

To a solution of compound A4 (170.0 mg, 0.180 mmol) in DCM (20 mL) was added DMP (229.3 mg, 0.540 mmol). After the reaction mixture was stirred at 18° C. for 1 h, it was diluted with $H_2O$ (20 mL), and aq. $Na_2SO_3$ solution (20 mL), and aq. $NaHCO_3$ solution (20 mL) were added. The mixture was extracted with EtOAc (3×60 mL). The combined organic layers were dried over $Na_2SO_4$, filtered, concentrated, and purified by column chromatography (0-5% MeOH in DCM) to give compound A5 (150 mg, 75%) as a white solid. LCMS (5-95, AB, 1.5 min): RT=0.814 min, m/z=961.5 [M+23]+.

A solution of compound A5 (75.0 mg, 0.080 mmol) in TFA (9.5 mL) and water (0.50 mL) was stirred at 14° C. for 1 h. The reaction mixture was poured into cold saturated $NaHCO_3$ (100 mL) and extracted with DCM (2×100 mL). The combined organic layer was dried, concentrated, and purified by prep-TLC (4% MeOH in DCM Rf=0.5) followed by prep-HPLC (Waters Xbridge Prep OBD C18 150*30 5 u, Condition:0.225% FA-CAN) to give PBD dimer disulfide prodrug 3 (9.5 mg, 14%) as a white solid. LCMS (5-95, AB, 1.5 min): RT=0.956 min, m/z=821.3 [M+23]+.

Example 20E

Preparation of PBD Dimer Control 1

PBD dimer control 1 was prepared according to the following reaction scheme:

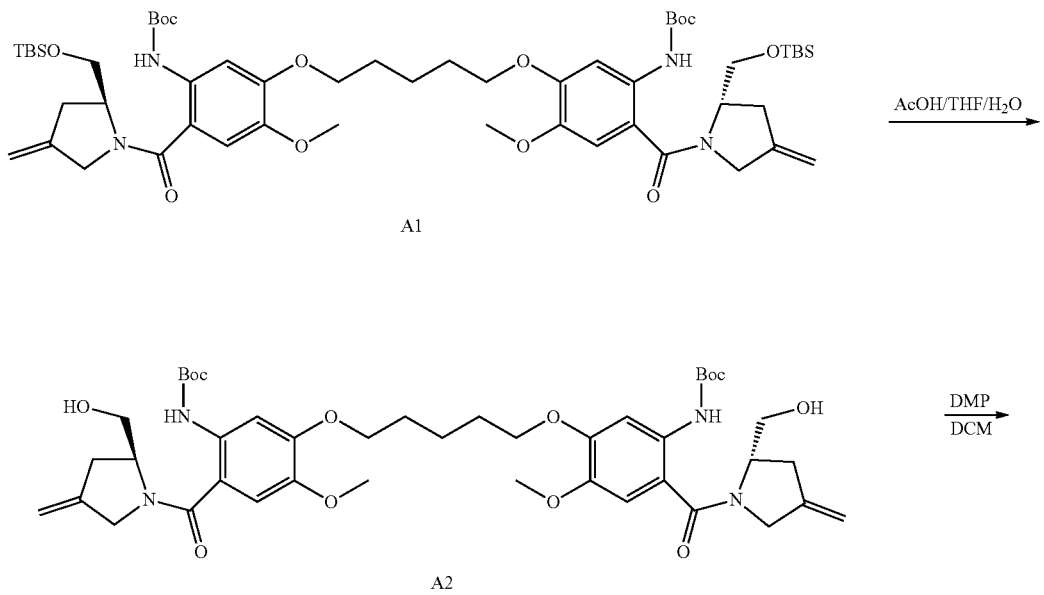

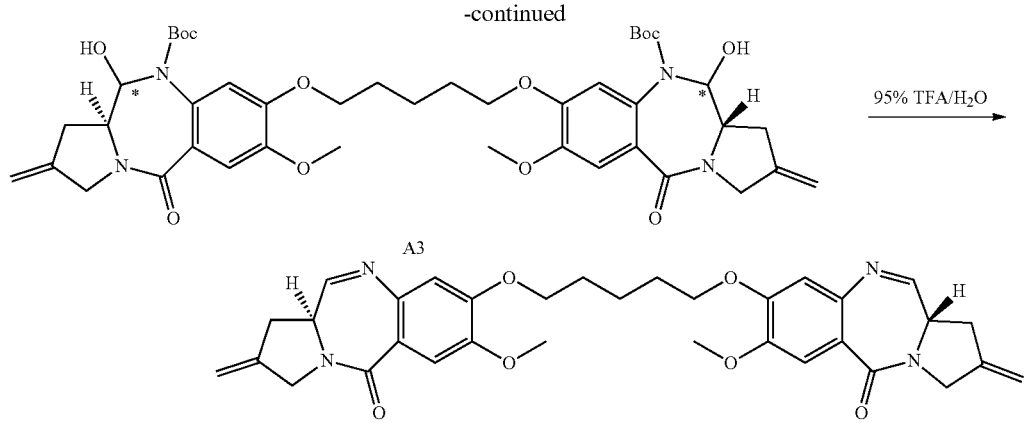

A solution of compound A1 (1.80 g, 1.71 mmol) in HOAc/THF/H₂O (9.0 mL/4.5 mL/3.0 mL) was stirred at rt for 48 h. The solution was diluted with EtOAc (150 mL), washed with H₂O (4×40 mL), aq. NaHCO₃ (4×40 mL), and H₂O (40 mL). The EtOAc layer was dried over Na₂SO₄, filtered, and concentrated to afford compound A2 (1.38 g, 91%) as an oil.

To a stirred solution of compound A2 (800 mg, 0.99 mmol) in DCM (20 mL) was added DMP (1.26 g, 2.97 mmol) at 0° C. The reaction mixture was stirred at rt for 3 h. It was diluted with EtOAc (100 mL), and quenched with aq. Na₂SO₃ solution (30 mL) at 0° C. The organic layer was washed with H₂O (3×30 mL), aq. NaHCO₃ solution (30 mL), and H₂O (30 mL). It was dried over Na₂SO₄, filtered, concentrated, and purified by prep-TLC (DCM/MeOH=15:1) to afford compound A3 (400 mg, 50.0%) as colorless solid. LCMS (ESI, 5-95AB/1.5 min): RT=0.767 min, [M+Na]+=843.4.

A solution of compound A3 (300 mg, 0.36 mmol) in 95% TFA/H₂O (4.0 mL) was stirred at 0° C. for 2 h. Then the solution was added dropwise into a saturated NaHCO₃ solution (120 mL) at 0° C. The mixture was extracted with DCM (3×20 mL). The combined organic layer was dried over Na₂SO₄, filtered, dried, concentrated and purified by prep-HPLC to afford PBD dimer control 1 (70 mg, 33%) as a white solid. LCMS (ESI, 5-95AB/1.5 min): RT=0.767 min, [M+Na]+=843.4 1H NMR (400 MHz, CDCl3) δ ppm 7.69 (d, J=4.80 Hz, 2H), 7.50 (s, 2H), 6.81 (s, 2H), 5.19 (d, J=10.80 Hz, 4H), 4.29 (s, 5H), 4.02-4.19 (m, 4H), 3.94 (s, 6H), 3.83-3.92 (m, 3H), 3.09-3.16 (m, 2H), 2.90-2.99 (m, 2H), 1.98-1.94 (m, 4H), 1.66-1.70 (m, 2H).

Example 20F

Preparation of PBD Dimer Control 2

PBD dimer control 2 was prepared according to the following reaction scheme:

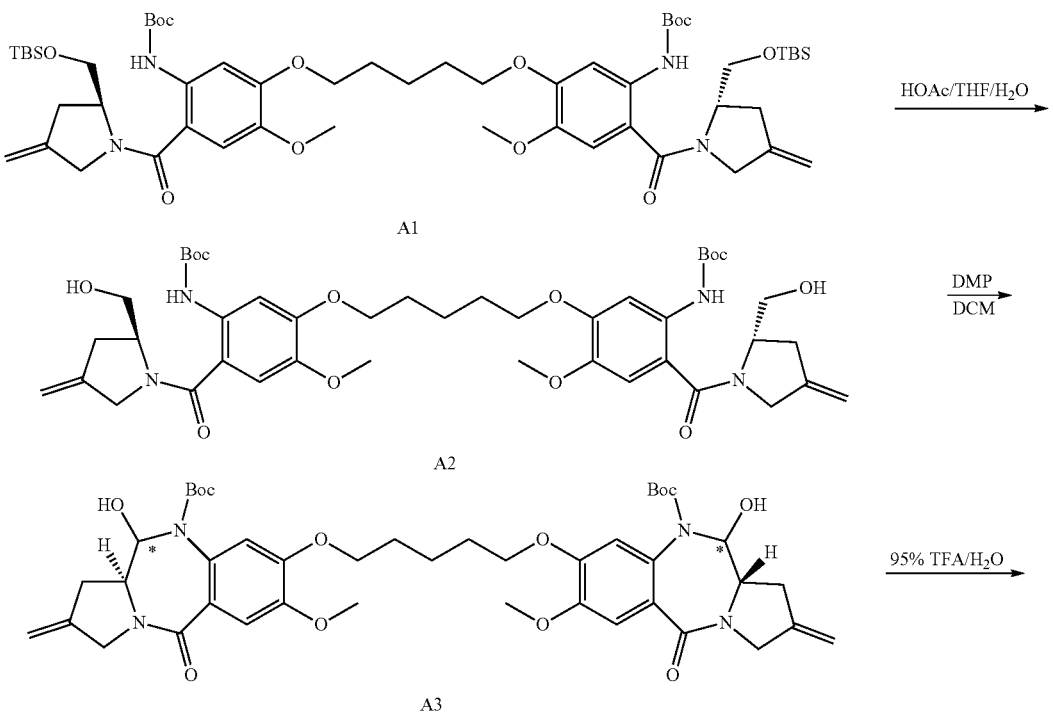

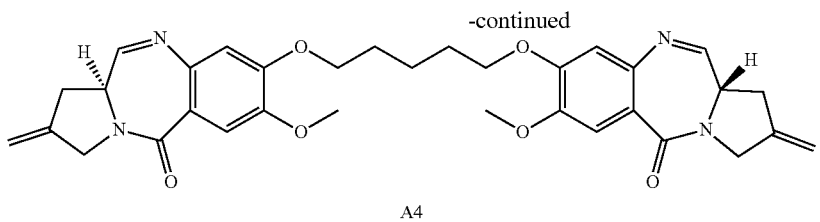

A4

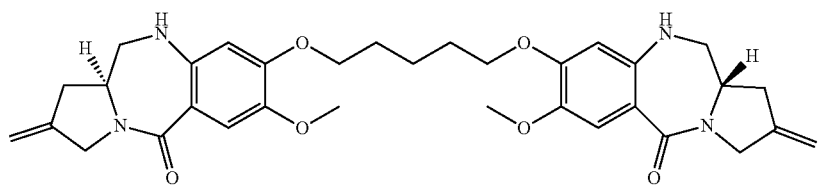

A solution of compound A1 (1.80 g, 1.71 mmol) in HOAc/THF/H₂O (9.0 mL/4.5 mL/3.0 mL) was stirred at rt for 48 h. It was diluted with EtOAc (150 mL), washed with H₂O (4×40 mL), aq. NaHCO₃ (2×40 mL), and H₂O (40 mL). The EtOAc layer was dried over Na₂SO₄, filtered, and concentrated to afford compound 2 (1.38 g, 91%) as an oil.

To a stirred solution of compound A2 (800 mg, 0.99 mmol) in DCM (20 mL) was added DMP (1.26 g, 2.97 mmol) at 0° C., and the reaction mixture was stirred at rt for 3 h. Then the mixture was diluted with EtOAc (100 mL), and quenched with aq. Na₂SO₃ solution (30 mL) at 0° C. The organic layer was washed with H₂O (3×30 mL), saturated NaHCO₃ solution (30 mL), and H₂O (30 mL), dried over Na₂SO₄, filtered, and concentrated. The residue was purified by prep-TLC (DCM/MeOH=15:1) to afford compound A3 (400 mg, 50.0%) as a colorless solid. LCMS (ESI, 5-95AB/1.5 min): RT=0.867 min, [M+Na]+=843.4. 1H NMR (400 MHz, CDCl3) δ 7.20 (s, 2H), 6.61 (s, 2H), 5.49 (d, J=9.2 Hz, 2H), 5.14 (d, J=4.8 Hz, 4H), 4.32-4.14 (m, 5H), 4.07-3.99 (m, 5H), 3.90 (s, 6H), 3.62 (t, J=9.2 Hz, 2H), 2.96-2.89 (m, 2H), 2.73-2.69 (m, 2H), 1.98-1.94 (m, 4H), 1.69-1.67 (m, 2H), 1.37 (s, 18H).

A solution of compound A3 (120 mg, 0.147 mmol) in 95% TFA/H₂O (2.0 mL) was stirred at 0° C. for 2 h. Then the solution was added dropwise to a saturated NaHCO₃ solution (120 mL) at 0° C. The mixture was extracted with DCM (3×20 mL). The combined organic layer was dried over Na₂SO₄, and concentrated to afford compound 4 (86 mg, 100%) as crude product. LCMS (ESI, 5-95AB/1.5 min): RT=0.764 min, [M+H]+=585.3.

To a solution of compound A4 (86 mg, 0.147 mmol) in anhydrous DCM/MeOH (5.0 mL/2.5 mL) was added NaBH₃CN (92 mg, 1.47 mmol). The reaction mixture was stirred at rt overnight. It was concentrated and the residue was diluted with saturated NaHCO₃ (20 mL), and extracted with DCM (3×20 mL). The combined DCM layer was dried over Na₂SO₄, filtered, and concentrated. The residue was purified by prep-HPLC (FA) to afford PBD dimer control 2 (15.6 mg, 18.1%) as white solid. LCMS (ESI, 5-95AB/1.5 min): RT=0.808 min, [M+H]+=589.3. 1H NMR (400 MHz, CDCl3) δ 7.58 (s, 2H), 6.05 (s, 2H), 5.06 (d, J=11.6 Hz, 4H), 4.42-4.27 (m, 6H), 3.98 (t, J=6.8 Hz, 6H), 3.84 (s, 6H), 3.55 (d, J=12.0 Hz, 2H), 3.35-3.30 (dd, J=12.4, 9.6 Hz, 2H), 2.93-2.87 (m, 2H), 2.46-2.42 (m, 2H), 1.94-1.89 (m, 4H), 1.62-1.60 (m, 2H).

Example 21

Preparation of PBD Dimer Disulfide Prodrugs Comprising a Linker for Conjugation to an Antibody Example 21A Preparation of PBD Dimer Disulfide Prodrug 4 Comprising a Linker PBD dimer disulfide prodrug 4 comprising a linker was prepared according to the following reaction scheme:

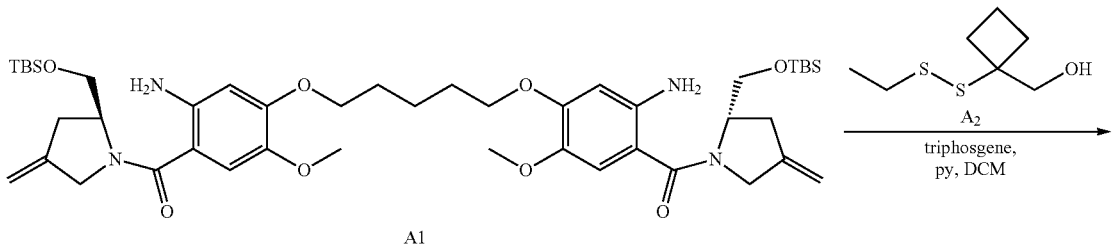

-continued
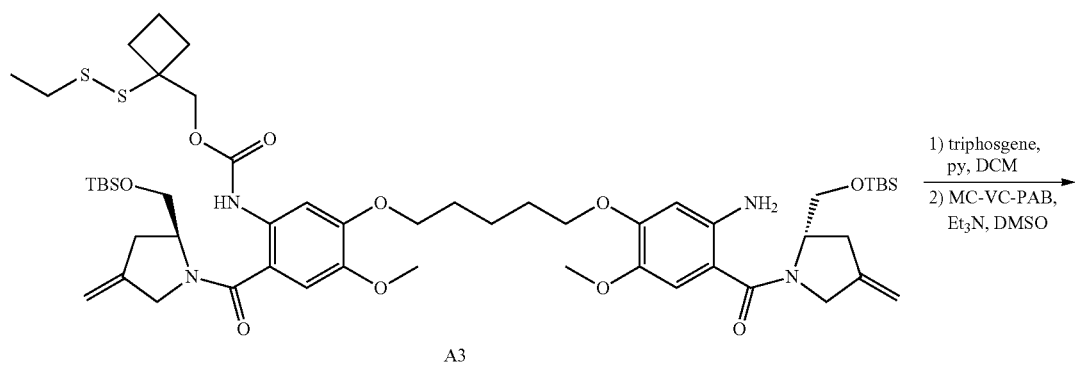
A3
1) triphosgene, py, DCM
2) MC-VC-PAB, Et₃N, DMSO
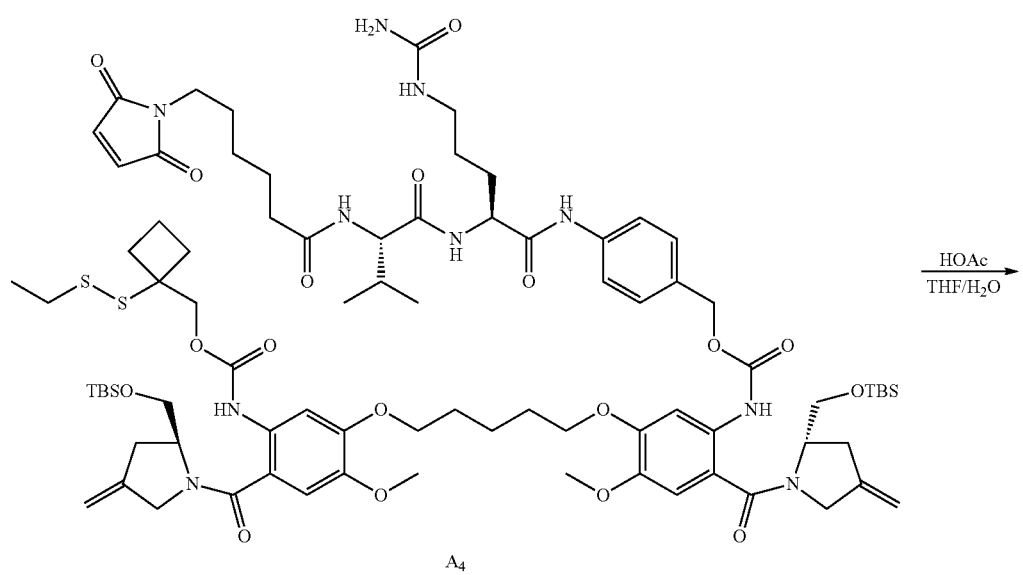
A4
HOAc
THF/H₂O
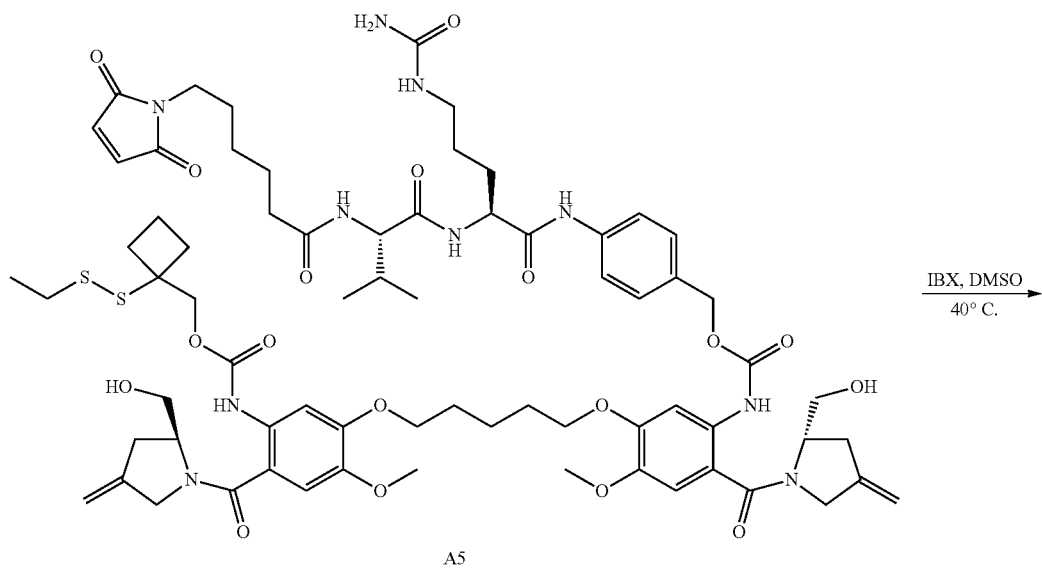
A5
IBX, DMSO
40° C.

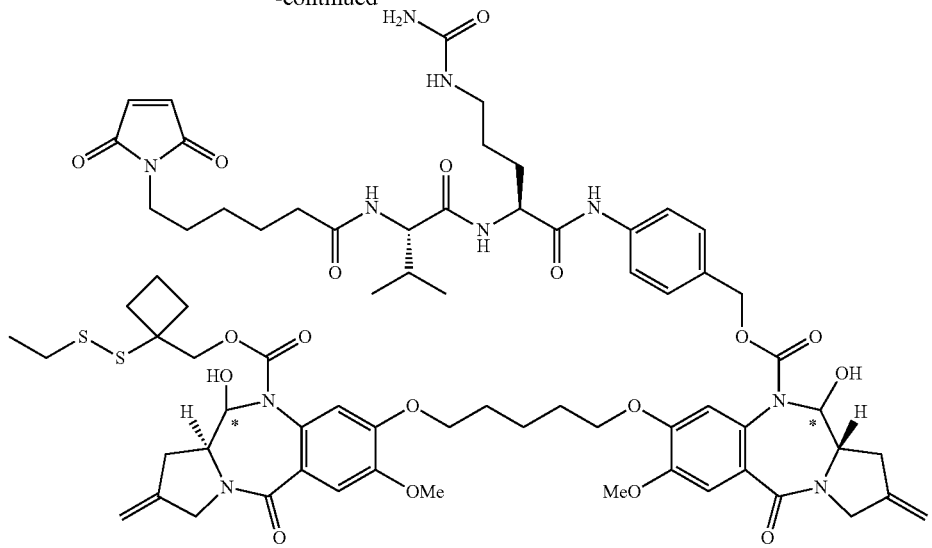

Synthesis of A2

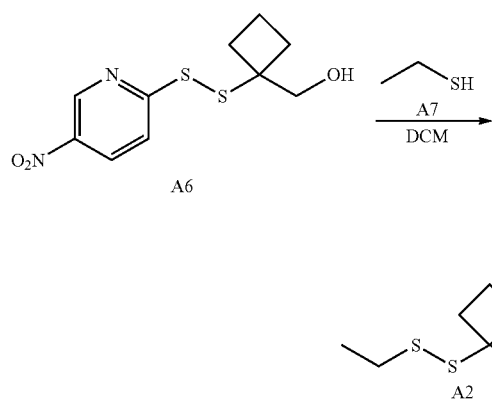

Each asterisk in the above structure, and elsewhere depicted in Example 21, represents a chiral center.

To the mixture of A6 (400.0 mg, 1.47 mmol) in DCM (10 mL) was added ethanethiol A7 (2.74 g, 44.1 mmol). The reaction mixture was stirred at 40° C. for 30 h. The mixture was treated with $MnO_2$ (0.20 g) for 5 min, and filtered. The filtrates were concentrated and the residue was purified by prep-TLC (100% DCM, Rf=0.5) to give compound A2 (110 mg, 42%) as a colorless oil. 1H NMR (400 MHz, CDCl3) δ 3.74 (s, 2H), 2.75-2.70 (m, 2H), 2.13-1.87 (m, 6H), 1.84 (s, 1H), 1.30 (t, J=7.6 Hz, 3H).

To a solution of triphosgene (82.4 mg, 0.28 mmol) in DCM (4.0 mL) was added a solution of A2 (110.0 mg, 0.620 mmol) and pyridine (146.4 mg, 1.85 mmol) in DCM (4.0 mL) dropwise. The mixture was stirred at 15° C. for 30 min and was concentrated. It was dissolved in DCM (5.0 mL) and added dropwise to a solution of A1 (1.05 g, 1.23 mmol) and pyridine (145.87 mg, 1.84 mmol) in DCM (15.0 mL) at 0° C. After the mixture was stirred at 15° C. for 2 h, it was concentrated and the residue was purified by column chromatography (0-50% EtOAc in petroleum ether) to afford A3 (310 mg, 45.8%) as a yellow oil. LCMS (5-95, AB, 1.5 min): RT=1.151 min, m/z=1057.4 [M+1]+.

To the solution of triphosgene (26.5 mg, 0.090 mmol) in DCM (5.0 mL) was added a solution of A3 (210 mg, 0.200 mmol) and triethylamine (60.28 mg, 0.60 mmol) in DCM (5.0 mL) at 0° C. The reaction mixture was stirred at 15° C. for 30 min. To the above mixture was added a solution of MC-VC-PAB (166.0 mg, 0.290 mmol) and triethylamine (59.0 mg, 0.58 mmol) in DMSO (3.0 mL) dropwise. The reaction mixture was stirred at 40° C. for 2 h. The mixture was diluted with DCM (30 mL) and washed with water (3×10 mL). The combined organic layer was dried, concentrated, and purified by column chromatography (0-10% MeOH in DCM) to afford A4 (160 mg, 48.4%) as a yellow oil. LCMS (5-95, AB, 1.5 min): RT=1.271 min, m/z=828.6 [M/2+1]+.

To the mixture of A4 (160.0 mg, 0.100 mmol) in THF (3.0 mL) and water (3.0 mL) was added acetic acid (4.5 mL). The reaction mixture was stirred at 15° C. for 15 h. The mixture was diluted with EtOAc (30 mL), washed with water (2×10 mL), saturated $NaHCO_3$ (2×10 mL) and brine (10 mL). The organic phase was dried over $Na_2SO_4$ and concentrated to give the crude A5 (120 mg, 82.7%) as yellow oil, which was used in the next step without further purification. LCMS (5-95, AB, 1.5 min): RT=0.801 min, m/z=714.6 [M/2+1]+.

To the mixture of A5 (60.0 mg, 0.040 mmol) in DMSO (3.0 mL) was added IBX (58.8 mg, 0.21 mmol). The reaction mixture was stirred at 40° C. for 16 h. The mixture was purified by prep-HPLC (ACN 40-70%/0.225% FA in water) to afford (15 mg, 25.1%) as a white solid. LCMS (5-95, AB, 1.5 min): RT=0.758 min, m/z=712.5 [M/2+1]+.

In some aspects of the disclosure, PBD dimer disulfide prodrug 4 comprising a linker may be conjugated to an antibody to form PBD dimer ADC disulfide prodrug 4.

Example 21B

Preparation of PBD Dimer Disulfide Prodrug 3 Comprising a Linker

PBD dimer disulfide prodrug 3 comprising a linker was prepared according to the following reaction scheme:

175 176
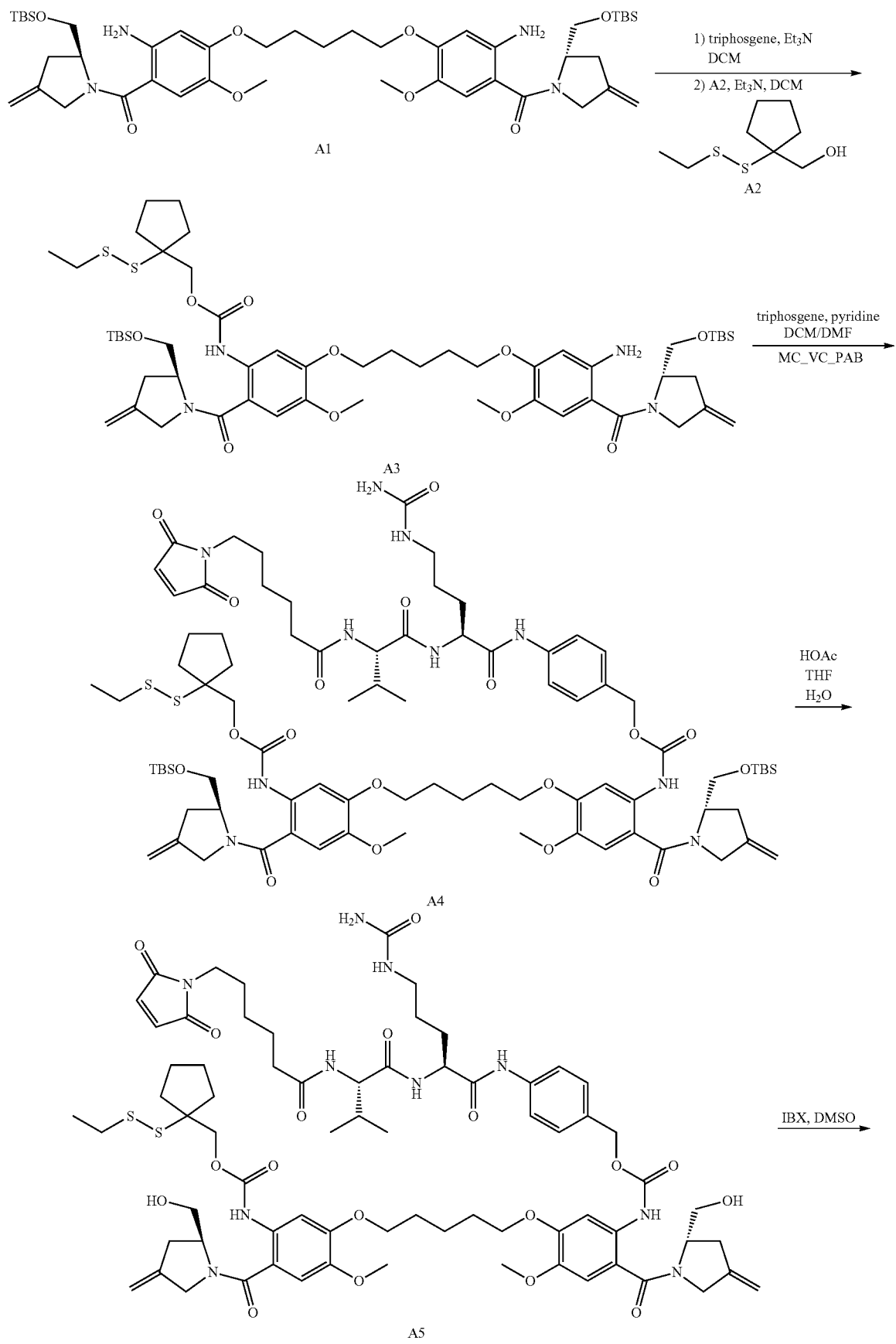

-continued

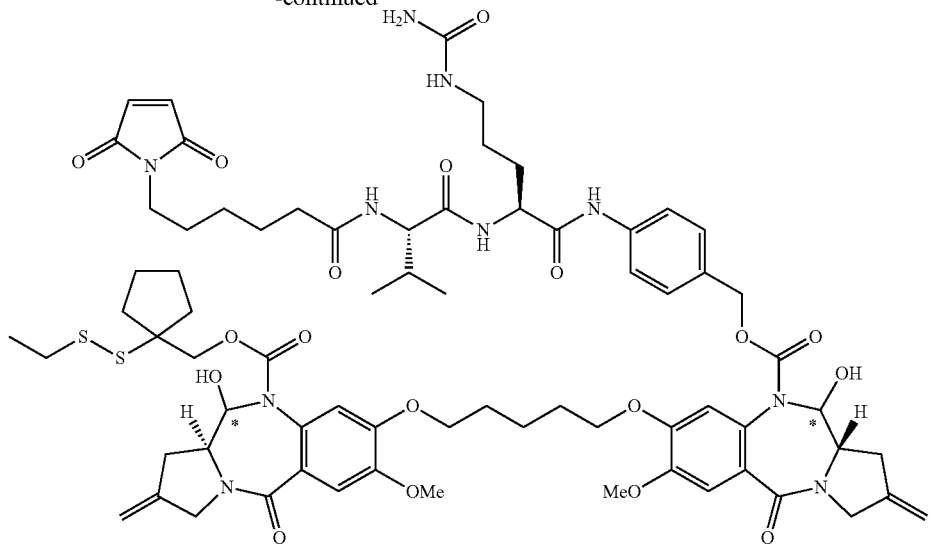

To a solution of triphosgene (486.9 mg, 1.64 mmol) in DCM (10 mL) was added a solution of compound A1 (1.40 g, 1.64 mmol) and triethylamine (664 mg, 6.56 mmol) in DCM (10 mL). The mixture was stirred at 8° C. for 10 min. The mixture was concentrated to give the crude product (1.48 g, 99.6%) as a yellow solid. To a solution of the above crude product (1.41 g, 1.56 mmol) in DCM (15 mL) was added a solution of compound A2 (150.0 mg, 0.780 mmol) and triethylamine (158 mg, 1.56 mmol) in DCM (6.0 mL). After the mixture was stirred at 8° C. for 1 h, it was concentrated and purified by flash column chromatography (50% EtOAc in petroleum ether) to give the product compound A3 (300 mg, 30%) as a yellow solid. LCMS (5-95, AB, 1.5 min): RT=1.193 min, m/z=1071.5 [M+1]+.

To a solution of triphosgene (41.6 mg, 0.140 mmol) in DCM (6.0 mL) was added a solution of compound A3 (300 mg, 0.280 mmol) and triethylamine (56.7 mg, 0.560 mmol) in DCM (5.0 mL). The mixture was stirred at 8° C. for 15 min. The mixture was concentrated to give the crude product (307 mg, 99.9%) as a yellow solid, which was used for next step directly. To a solution of the crude product (300.0 mg, 0.270 mmol) in DCM (10 mL) was added a solution of MC_VC_PAB (156 mg, 0.270 mmol) and triethylamine (27.7 mg, 0.270 mmol) in DMF (6.0 mL). After the mixture was stirred at 8° C. for 12 h, it was concentrated and purified by flash column chromatography (6% MeOH in DCM) to give the product compound A4 (140 mg, 31%) as a yellow solid. LCMS (5-95, AB, 1.5 min): RT=1.354 min, m/z=836.4 [M/2+1]+.

A mixture of compound A4 (140.0 mg, 0.080 mmol) in THF (2.0 mL), water (2.0 mL) and acetic acid (3.0 mL) was stirred at 8° C. for 12 h. The mixture was diluted with EtOAc (60 mL) and washed with water (3×50 mL), saturated NaHCO$_3$ (50 mL), brine (50 mL). The organic layer was dried and concentrated to give the crude product compound A5 (120 mg, 99%) as a yellow solid. LCMS (5-95, AB, 1.5 min): RT=0.983 min, m/z=722.0 [M/2+1]+.

To a solution of compound A5 (140.0 mg, 0.100 mmol) in DMSO (4.0 mL) was added IBX (108 mg, 0.390 mmol) at 18° C. The reaction mixture was stirred at 40° C. for 8 h. The mixture was purified by prep-HPLC (ACN 40-70%/0.225% FA in water) to give the product PBD dimer disulfide prodrug 2 comprising a linker (20 mg, 14%) as a white solid. LCMS (5-95, AB, 1.5 min): RT=0.760 min, m/z=719.7 [M/2+1]+.

In some aspects of the disclosure, PBD dimer disulfide prodrug 3 comprising a linker may be conjugated to an antibody to form PBD dimer ADC disulfide prodrug 2A or PBD dimer ADC disulfide prodrug 2B.

Example 21C

Preparation of PBD Dimer Disulfide Prodrug 2 Comprising a Linker

PBD dimer disulfide prodrug 2 comprising a linker was prepared according to the following reaction scheme:

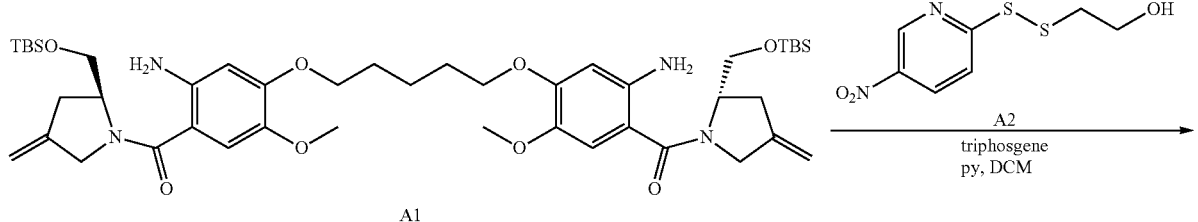

-continued
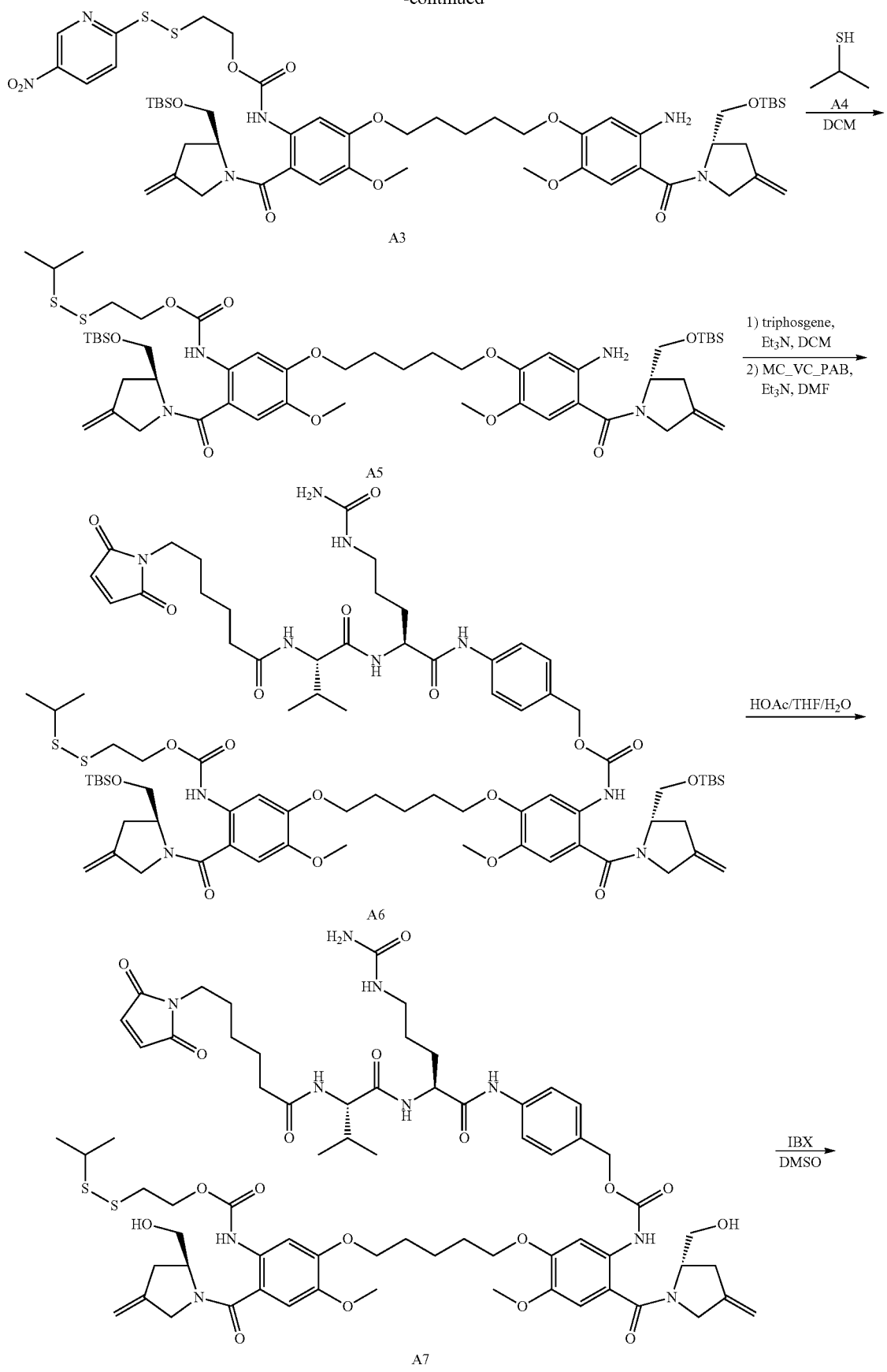

-continued

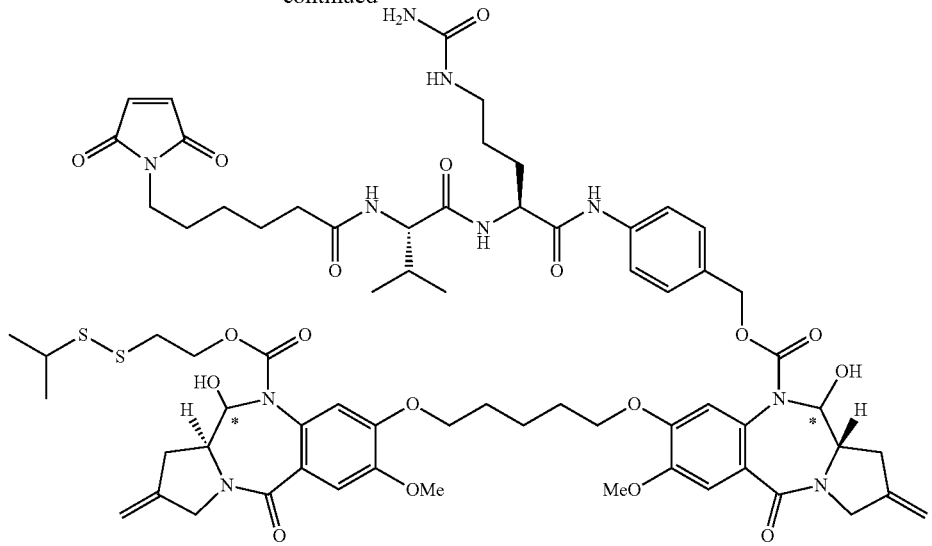

Synthesis of INTA2:

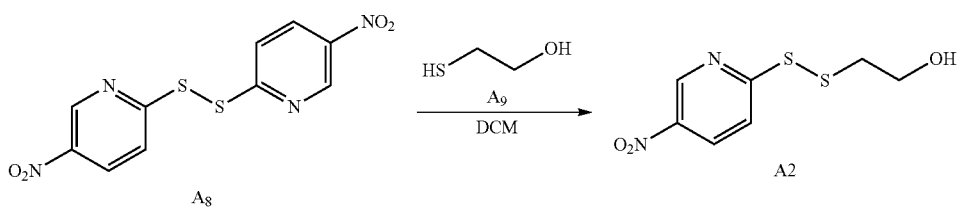

To a solution of compound A8 (3.18 g, 10.24 mmol) in DCM (25.0 mL) was added compound A9 (400 mg, 5.12 mmol). The mixture was stirred at 8° C. for 12 h. To the mixture was added $MnO_2$ (100 mg) and stirred for 10 min and filtered. The filtrate was concentrated and purified by flash column chromatography (100% DCM) to give compound 2 (620 mg, 2.67 mmol, 52.1%) as a yellow solid.

To a solution of triphosgene (191.6 mg, 0.65 mmol) in DCM (5.0 mL) was added a solution of compound A2 (300 mg, 1.29 mmol) and pyridine (306 mg, 3.87 mmol) in DCM (5.0 mL). The mixture was stirred at 8° C. for 10 min. The resulting mixture was added dropwise to a solution of compound A1 (1.43 g, 1.68 mmol) and pyridine (306 mg, 3.87 mmol) in DCM (15.0 mL). After the mixture was stirred at 8° C. for 30 min, it was concentrated and purified by flash column chromatography (50% EtOAc in petroleum ether) to give the product compound A3 (0.50 g, 0.427 mmol, 33.1%) as a yellow oil. LCMS (5-95, AB, 1.5 min): RT=1.077 min, m/z=1111.7 [M+1]+.

To a solution of compound A3 (300 mg, 0.270 mmol) in DCM (10 mL) was added compound A4 (205 mg, 2.7 mmol). The mixture was stirred at 8° C. for 10 min. To the mixture was added $MnO_2$ (100 mg), stirred for 10 min and filtered. The filtrate was concentrated and purified by flash column chromatography (50% EtOAc in petroleum ether) to give the product compound A5 (210 mg, 0.204 mmol, 75.4%) as a yellow solid.

To a solution of triphosgene (30.2 mg, 0.100 mmol) in DCM (5.0 mL) was added a solution of compound A5 (210 mg, 0.200 mmol) and triethylamine (61.7 mg, 0.610 mmol) in DCM (5.0 mL). The mixture was stirred at 8° C. for 30 min. Then the mixture was added dropwise to a solution of MC_VC_PAB (139.8 mg, 0.240 mmol) and triethylamine (61.7 mg, 0.610 mmol) in DMF (5.0 mL). The mixture was stirred at 8° C. for 12 h. The mixture was concentrated and purified by flash column chromatography (8% MeOH in DCM) to give the product compound A6 (140 mg, 0.085 mmol, 41.8%) as a yellow oil. LCMS (5-95, AB, 1.5 min): RT=1.248 min, m/z=816.1[M/2+1]+.

A mixture of compound A6 (140.0 mg, 0.090 mmol) in acetic acid (3.0 mL), THF (2.0 mL) and water (2.0 mL) was stirred at 8° C. for 8 h. The mixture was diluted with EtOAc (60 mL), washed with water (3×50 mL), saturated $NaHCO_3$ (50 mL), brine (50 mL) and concentrated to give the product compound A7 (120 mg, 0.0856 mmol, 99.7%) as a white solid. LCMS (5-95, AB, 1.5 min): RT=0.787 min, m/z=701.6[M/2+1]+.

To a solution of compound A7 (130.0 mg, 0.090 mmol) in DMSO (3.0 mL) was added IBX (129.9 mg, 0.460 mmol) at 9° C. The reaction mixture was stirred at 50° C. for 48 h. The mixture was purified by prep-HPLC (ACN 35-65%/0.225% FA in water) to give the product PBD dimer disulfide prodrug 4 comprising a linker (10 mg, 0.0071 mmol, 7.6%) as a white solid. LCMS (5-95, AB, 1.5 min): RT=0.728 min, m/z=1397.9[M+1]+.

In some aspects of the disclosure, PBD dimer disulfide prodrug 2 comprising a linker may be conjugated to an antibody to form PBD dimer ADC disulfide prodrug 4.

Example 21D

Preparation of a PBD dimer disulfide prodrug comprising a linker for conjugation to form PBD dimer diaphorase prodrug 1A and 1B, and having the structure:

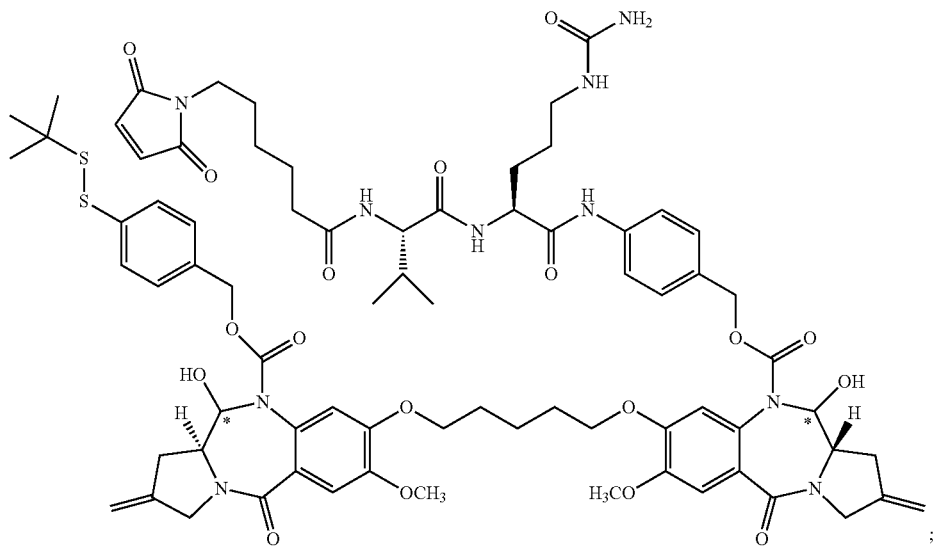 [SMILES: C=C1C[C@H]2C(O)N(C(=O)OCc3ccc(NC(=O)[C@H](CCCNC(N)=O)NC(=O)[C@@H](NC(=O)CCCCCN4C(=O)C=CC4=O)C(C)C)cc3)c3cc(OCCCCCOc4cc5c(cc4OC)C(=O)N4CC(=C)C[C@H]4C(O)N5C(=O)OCc4ccc(SSC(C)(C)C)cc4)c(OC)cc3C(=O)N2C1]

and the name: 4-(tert-butyldisulfaneyl)benzyl (11aS)-8-((5-(((11aS)-10-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-2-methylene-5-oxo-2,3,11,11a-tetrahydro-1H-benzo[e]pyrrolo[1,2-a][1,4]diazepine-10(5H)-carboxylate.

A PBD dimer disulfide prodrug comprising a linker was prepared according to the following reaction scheme:

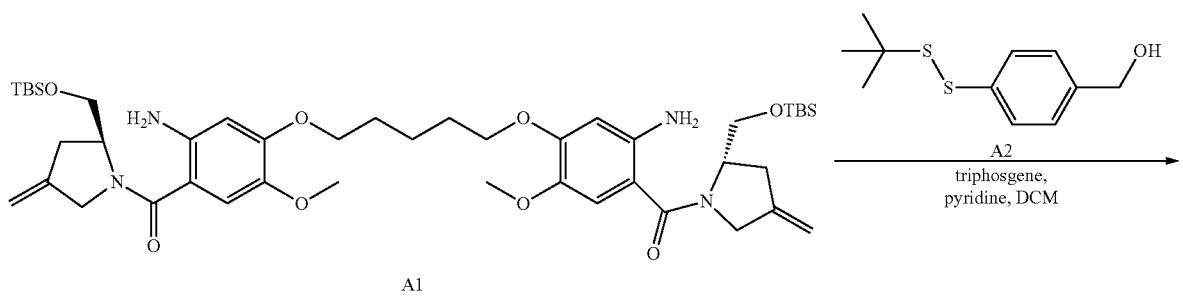

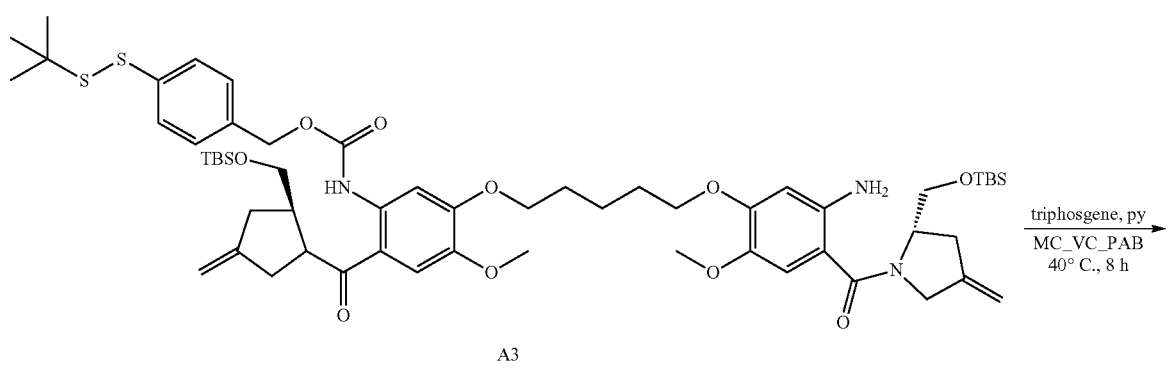

185 186
-continued
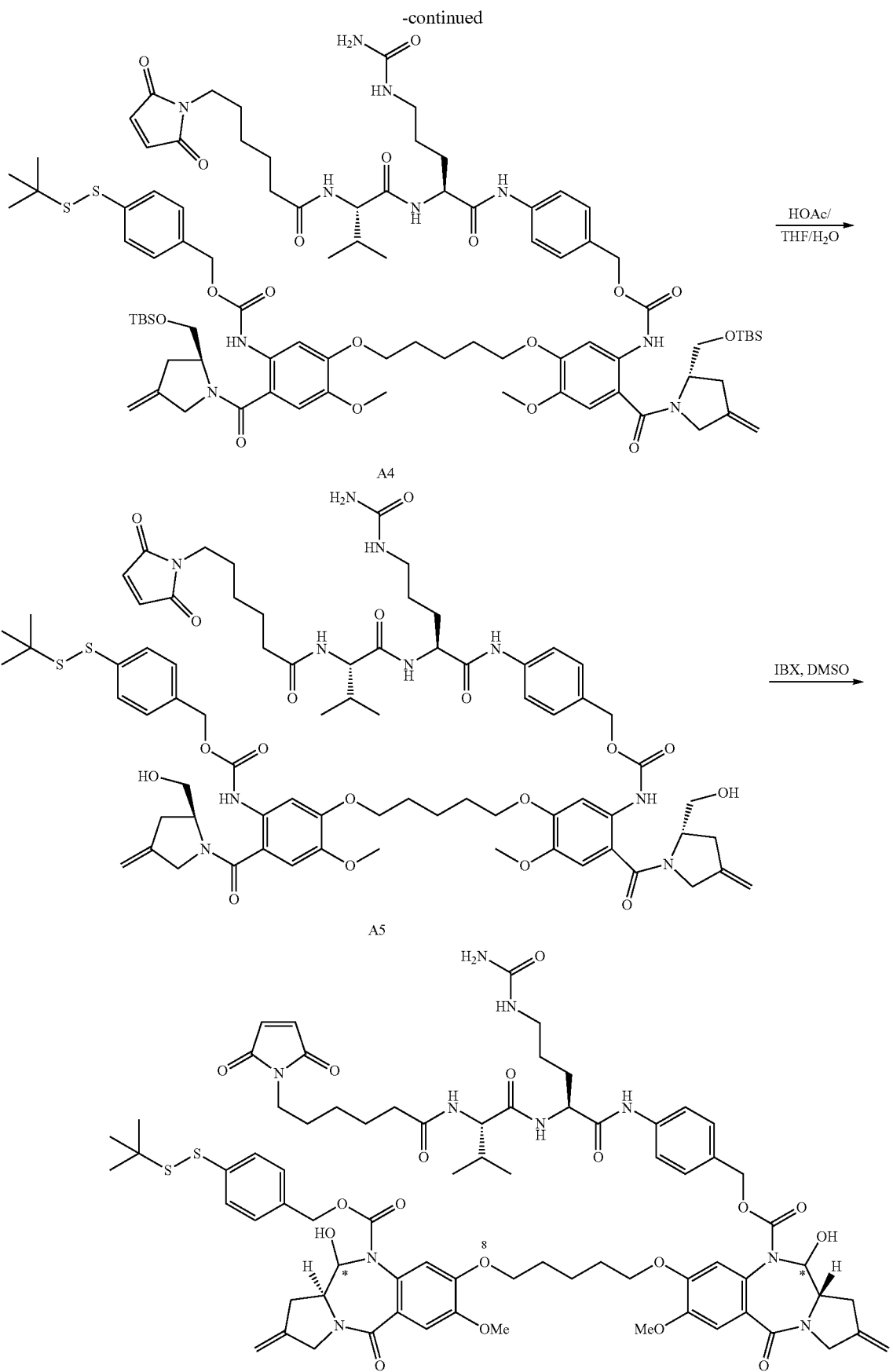

Synthesis of INTA2:

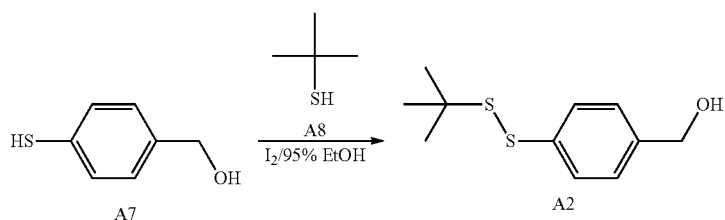

To a solution of A7 (250 mg, 1.78 mmol) in 95% EtOH (10 mL) was added A8 (2.01 mL, 17.85 mmol). The mixture was cooled to 0° C. and a solution of iodine (200 mg, 0.79 mmol) in 95% EtOH (10 mL) was added drop-wise until the color of the mixture changed from colorless to brown. After it was stirred for 2 h, saturated NaHCO$_3$ (2.0 mL) was added at 0° C. until the pH was greater than 7. The solution was concentrated in vacuo. EtOAc (20 mL) was added, and the organic layer was washed with 10% NaHCO$_3$ (3×15 mL) and brine. The organic layer was dried over Na$_2$SO$_4$, filtered and concentrated and purified by flash column chromatography (0-32% EtOAc in petroleum ether) to afford compound A2 (280 mg, 68.8%) as yellow oil. 1H NMR (400 MHz, CDCl3) δ 7.51 (d, J=8.4 Hz, 2H), 7.23 (d, J=8.4 Hz, 2H), 4.57 (s, 2H), 2.40 (br, 1H), 1.29 (s, 9H).

To a solution of triphosgene (26 mg, 0.090 mmol) in DCM (1.0 mL) was added a solution of compound A2 (50.0 mg, 0.220 mmol) and pyridine (18.0 mg, 0.230 mmol) in DCM (4.0 mL) at 0° C. under N$_2$. After the reaction mixture was stirred at 0° C. under N$_2$ for 5 min, it was added dropwise to a solution of pyridine (34.0 mg, 0.430 mmol) and A1 (277 mg, 0.320 mmol) at 0° C. under N$_2$. The reaction mixture was stirred at 20° C. under N$_2$ for 2 h. Solvent was removed and the residue was purified by prep-TLC (50% EtOAc in petroleum ether, Rf=0.4) to afford compound A3 (70 mg, 28.3%) as a yellow foam. LCMS (5-95, AB, 1.5 min): RT=1.328 min, m/z=1108.7 [M+1]+.

To a solution of triphosgene (46.0 mg, 0.160 mmol) in DCM (7.0 mL) was added a mixture of compound A3 (400.0 mg, 0.360 mmol) and triethylamine (37.0 mg, 0.370 mmol) in DCM (3.0 mL) at 0° C. under N$_2$. After the reaction mixture was stirred at 0° C. for 30 min, a solution of MC-VC-PAB (247.0 mg, 0.430 mmol) and triethylamine (73.0 mg, 0.720 mmol) in DMF (3.0 mL) was added at 20° C. under N$_2$. The reaction mixture was stirred at 40° C. under N$_2$ for 8 h. The mixture was concentrated and purified by column chromatography (0-6% MeOH in DCM) to afford compound A4 (190 mg, 30.7%) as a yellow solid. LCMS (5-95, AB, 1.5 min): RT=1.308 min, m/z=854.2 [M/2+1]+.

To a solution of compound A4 (415 mg, 0.240 mmol) in water (2.0 mL) and THF (2 mL) was added HOAc (6.47 mL, 113 mmol) at 15° C. After the reaction mixture was stirred at 15° C. for 7 h, it was diluted with EtOAc (30 mL) and washed with water (2×15 mL), saturated aq. NaHCO$_3$ (15 mL) and brine (15 mL). It was dried and concentrated to give the crude compound A5 (150 mg, 41.7%) as a yellow solid, which used directly for the next step without further purification. LCMS (5-95, AB, 1.5 min): RT=0.997 min, m/z=739.4 [M/2+1]+.

To a solution of compound A5 (50.0 mg, 0.030 mmol) in DMSO (3.0 mL) was added IBX (38.0 mg, 0.140 mmol) at 18° C. The reaction mixture was stirred at 37° C. for 8 h. The mixture was purified by prep-HPLC (ACN 40-70%/0.225% FA in water) to afford PBD dimer disulfide prodrug 1 comprising a linker (17.2 mg, 33.1%) as a white solid. LCMS (5-95, AB, 1.5 min): RT=0.806 min, m/z=737.1 [M/2+1]+.

In some aspects of the disclosure, the PBD dimer disulfide prodrug comprising a linker may be conjugated to an antibody to form PBD dimer ADC disulfide prodrug 1A or PBD dimer ADC disulfide prodrug 1B.

Example 21E

Preparation of PBD Dimer Disulfide Prodrug 5 Comprising a Linker

PBD dimer disulfide prodrug 5 comprising a linker was prepared according to the following reaction scheme:

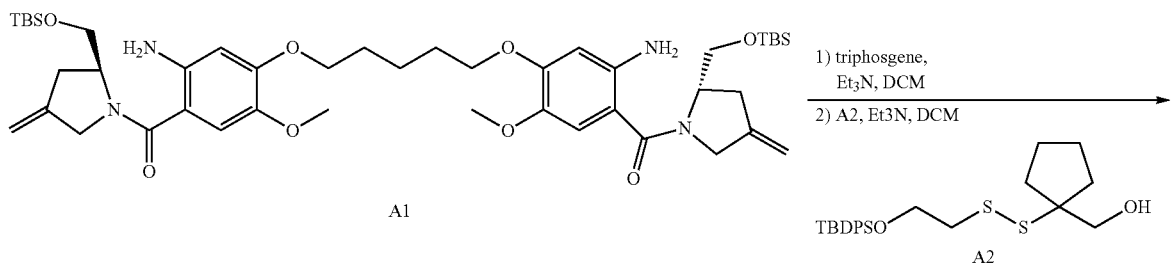

-continued
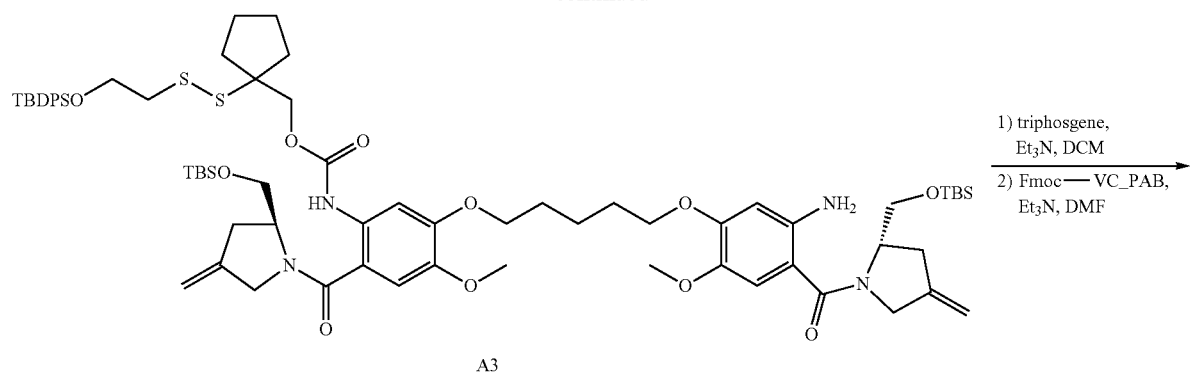
A3
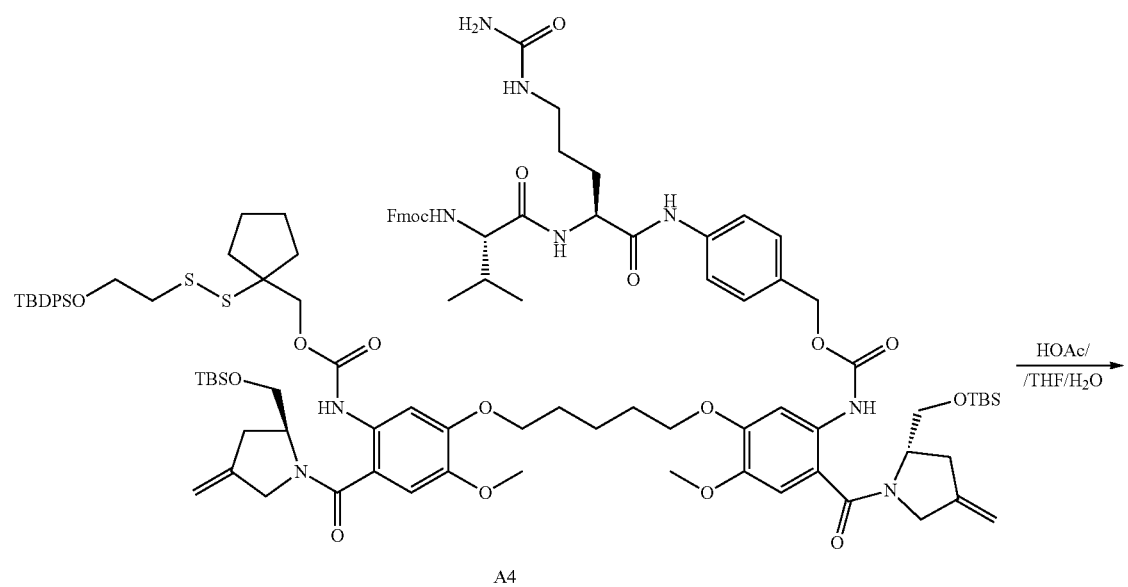
A4
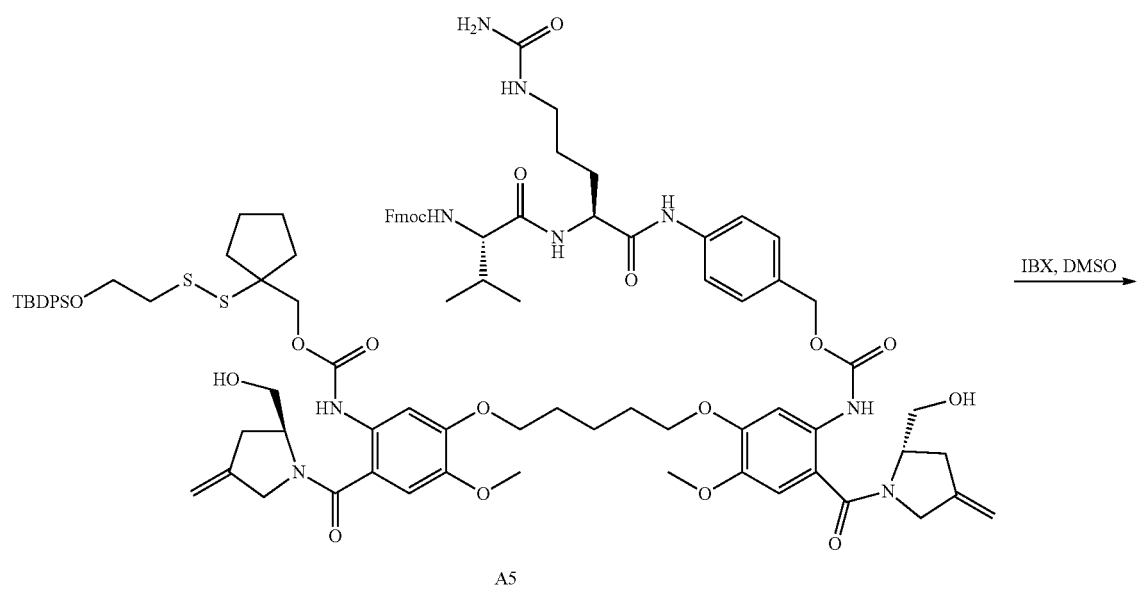
A5

191 192
-continued
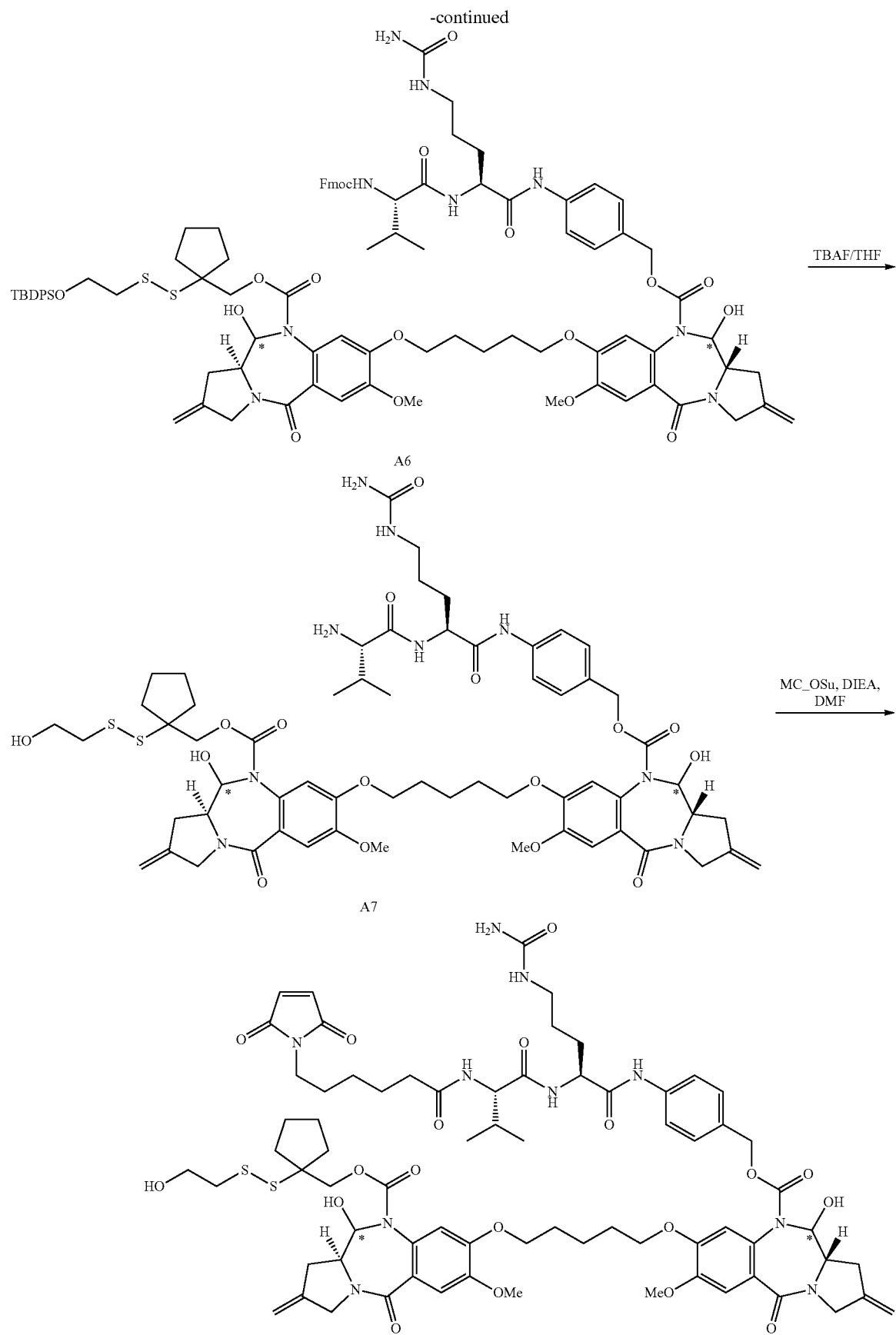

Synthesis of INTA2:

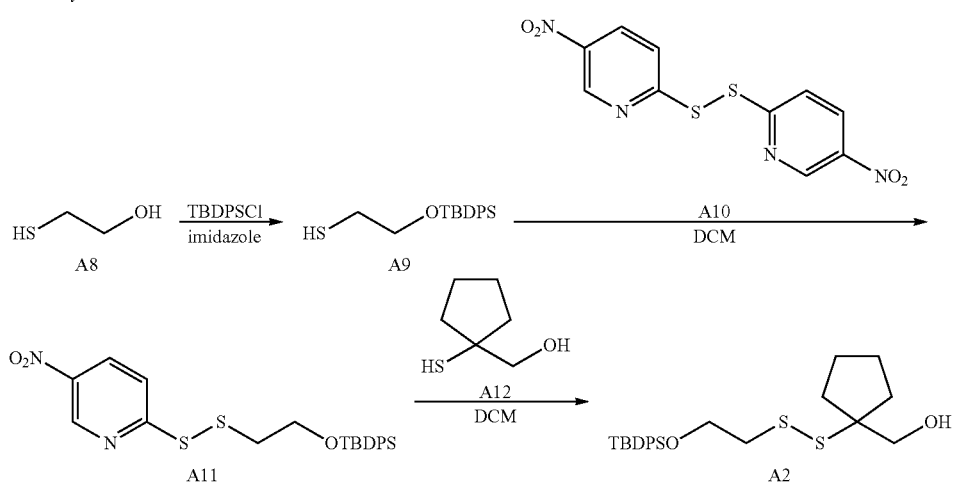

To a solution of TBDPSCl (8.62 g, 31.36 mmol) in DMF (40 mL) was added a solution of compound A8 (2.27 g, 29.05 mmol) in DMF (30 mL). After the solution was stirred for 10 min, imidazole (4.27 g, 62.7 mmol) in DMF (8.0 mL) was added and the reaction mixture was stirred at 20° C. for 24 h. The mixture was concentrated and taken up in DCM (30 mL), filtered, and washed with H2O (3×30 mL). The organic layer was dried with MgSO4, filtered, and the solvent was removed. The residue was purified by flash column chromatography (3% EtOAc in petroleum ether) to give compound A9 (7.0 g, 76%) as a colorless oil.

To a solution of compound A9 (1.00 g, 3.16 mmol) in DCM (10 mL) was added a solution of compound A10 (1.96 mg, 6.32 mmol) in DCM (10 mL) dropwise over 15 min. After the mixture was stirred for another 1 h at 26° C., manganese dioxide (1.00 g, 11.5 mmol) was added and stirred for 10 min, until the yellow solution became colorless. Manganese dioxide was filtered off, and the filtrate was concentrated. MeOH (5.0 mL) was added and the solid was filtered to remove compound A10. The residue was purified by column chromatography (0-2.5% EtOAc in petroleum ether) to afford compound A11 (0.90 g, 61%) as a yellow solid.

To a solution of compound A11 (250 mg, 1.89 mmol) in DCM (6.0 mL) was added a solution of compound A12 (0.50 g, 1.58 mmol) in DCM (4.0 mL) dropwise over 15 min. After addition, the mixture was stirred for another 1 h at 26° C. Manganese dioxide (1.0 g, 11.5 mmol) was added. The mixture was stirred for another 10 min, until yellow reaction solution became colorless. Manganese dioxide was filtered off, the filtrate was concentrated and MeOH (5.0 mL) was added. Solid was filtered off and the residual was purified by column chromatography (0-14% EtOAc in petroleum ether) to afford compound A2 (0.500 g, 71%) as a yellow oil.

To a solution of triphosgene (695 mg, 2.34 mmol) in DCM (5.0 mL) was added a solution of compound A1 (2.0 g, 2.34 mmol) and triethylamine (711.0 mg, 7.03 mmol) in DCM (10 mL) at 0° C. The mixture was stirred at 0° C. for 30 min. The reaction mixture was concentrated, and a solution of compound A2 (680 mg, 1.52 mmol) and triethylamine (308 mg, 3.04 mmol) in DCM (4.0 mL) was added. The mixture stirred at 25° C. for 2 h, concentrated, and purified by column chromatography (0-50% EtOAc in petroleum ether) to afford A3 (700 mg, 33%) as a yellow solid. LCMS (5-95, AB, 1.5 min): RT=1.401 min, m/z=1326.0 [M+1]+.

To a solution of triphosgene (54.0 mg, 0.180 mmol) in DCM (10 mL) was added a mixture of compound A3 (500 mg, 0.450 mmol) and triethylamine (50.0 mg, 0.490 mmol) in DCM (5.0 mL) at 0° C. under $N_2$. The reaction mixture was stirred at 0° C. for 30 min. To the reaction mixture was added a solution of Fmoc-VC PAB (260.0 mg, 0.450 mmol) and triethylamine (78.0 mg, 0.770 mmol) in DMF (3.0 mL). The mixture was stirred at 40° C. for 8 h, concentrated, and purified by column chromatography (0-8% MeOH in DCM) to give compound A4 (130 mg, 14%) as a yellow solid. LCMS (5-95, AB, 1.5 min): RT=1.474 min, m/z=978.1 [M/2+1]+.

To a solution of compound A4 (130.0 mg, 0.070 mmol) in water (2.0 mL) and THF (2.0 mL) was added HOAc (3.0 mL, 52.5 mmol) at 26° C. and stirred at 26° C. for 7 h. The reaction mixture was diluted with EtOAc (20 mL), washed with water (2×15 mL), saturated $NaHCO_3$ (10 mL) and brine (10 mL). It was dried and concentrated to give the crude compound A5 (130 mg, 83%) as a yellow solid, which used directly for the next step without further purification. LCMS (5-95, AB, 1.5 min): RT=1.065 min, m/z=863.2 [M/2+1]+.

To a solution of compound A5 (130.0 mg, 0.080 mmol) in DMSO (3.0 mL) was added and 2-iodoxybenzoic acid (84.4 mg, 0.300 mmol) at 25° C. After the mixture was stirred at 40° C. for 10 h, it was purified by prep-HPLC (ACN 85-100%, 0.225% FA in water) to afford product A6 (60 mg, 45%) as a white solid. LCMS (5-95, AB, 1.5 min): RT=1.178 min, m/z=861.4 [M/2+1]+.

To a solution of compound A6 (60.0 mg, 0.035 mmol) in THF (3.0 mL) was added TBAF (39.4 mg, 0.150 mmol) at 26° C. The reaction mixture was stirred at 26° C. for 2 h. The reaction mixture was diluted with DCM (20 mL), washed with water (3×15 mL), dried over $Na_2SO_4$, and concentrated to give the crude compound A7 (70 mg, crude) as a yellow oil.

To a stirred solution of Compound A7 (70.0 mg, 0.060 mmol) in DMF (2.0 mL) was added MC_OSu (51.4 mg, 0.170 mmol) at 26° C. The mixture was stirred at 26° C. for 2 h. The reaction mixture was purified by prep-HPLC (ACN 35-55%/0.225% FA in water) to afford (5.5 mg, 6.7%) as a white solid. LCMS (5-95, AB, 1.5 min): RT=0.852 min, m/z=1453.5 [M+1]+.

In some aspects of the disclosure, PBD dimer disulfide prodrug 5 comprising a linker may be conjugated to an antibody to form PBD dimer ADC disulfide prodrug 5.

Example 22

Preparation of PBD Dimer Boronic Acid Prodrugs Comprising a Linker for Conjugation to an Antibody Example 22A Preparation of PBD Dimer Boronic Acid Prodrug 1 Comprising a Linker PBD dimer boronic acid prodrug 1 comprising a linker was prepared according to the following reaction scheme:

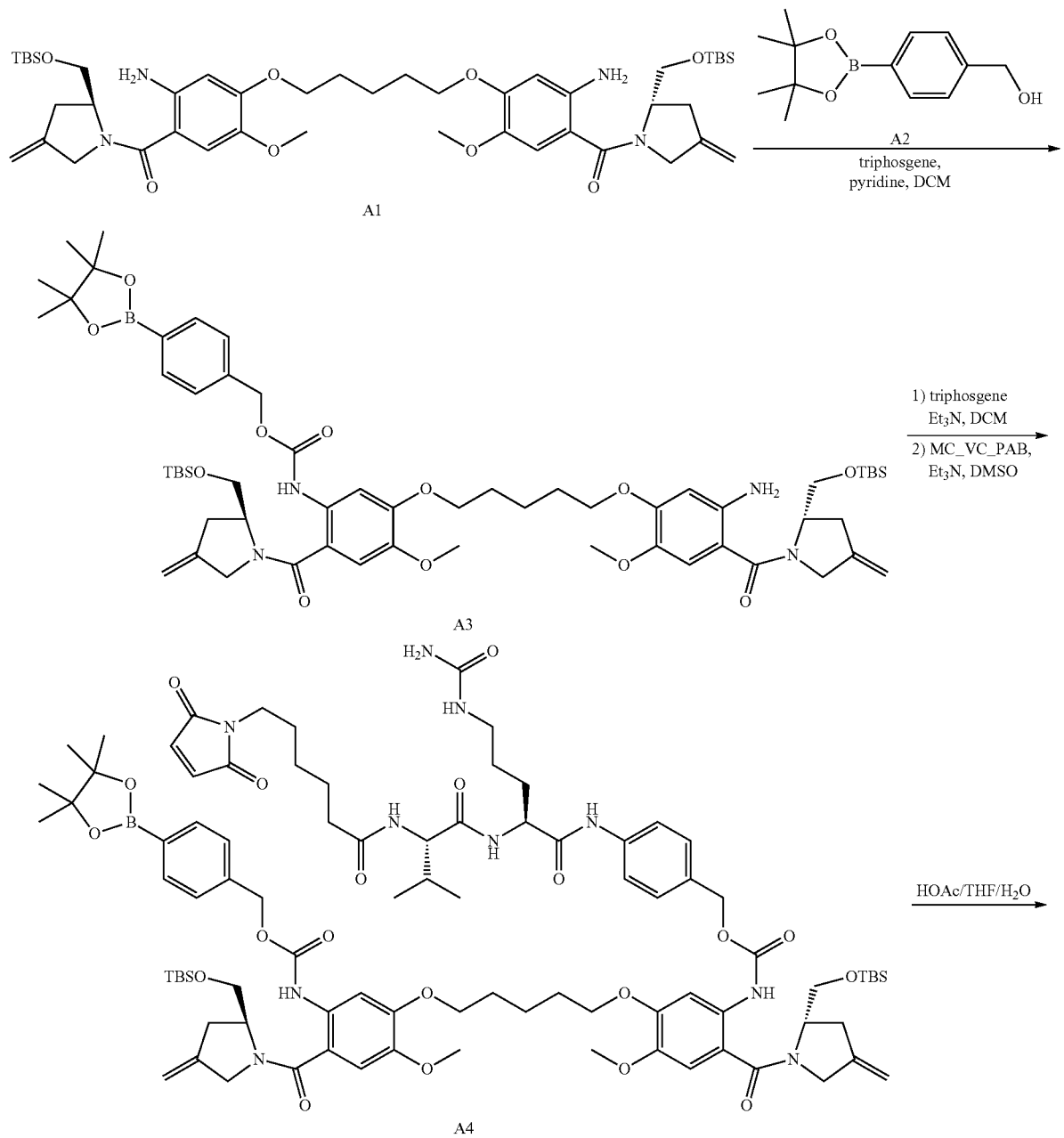

-continued

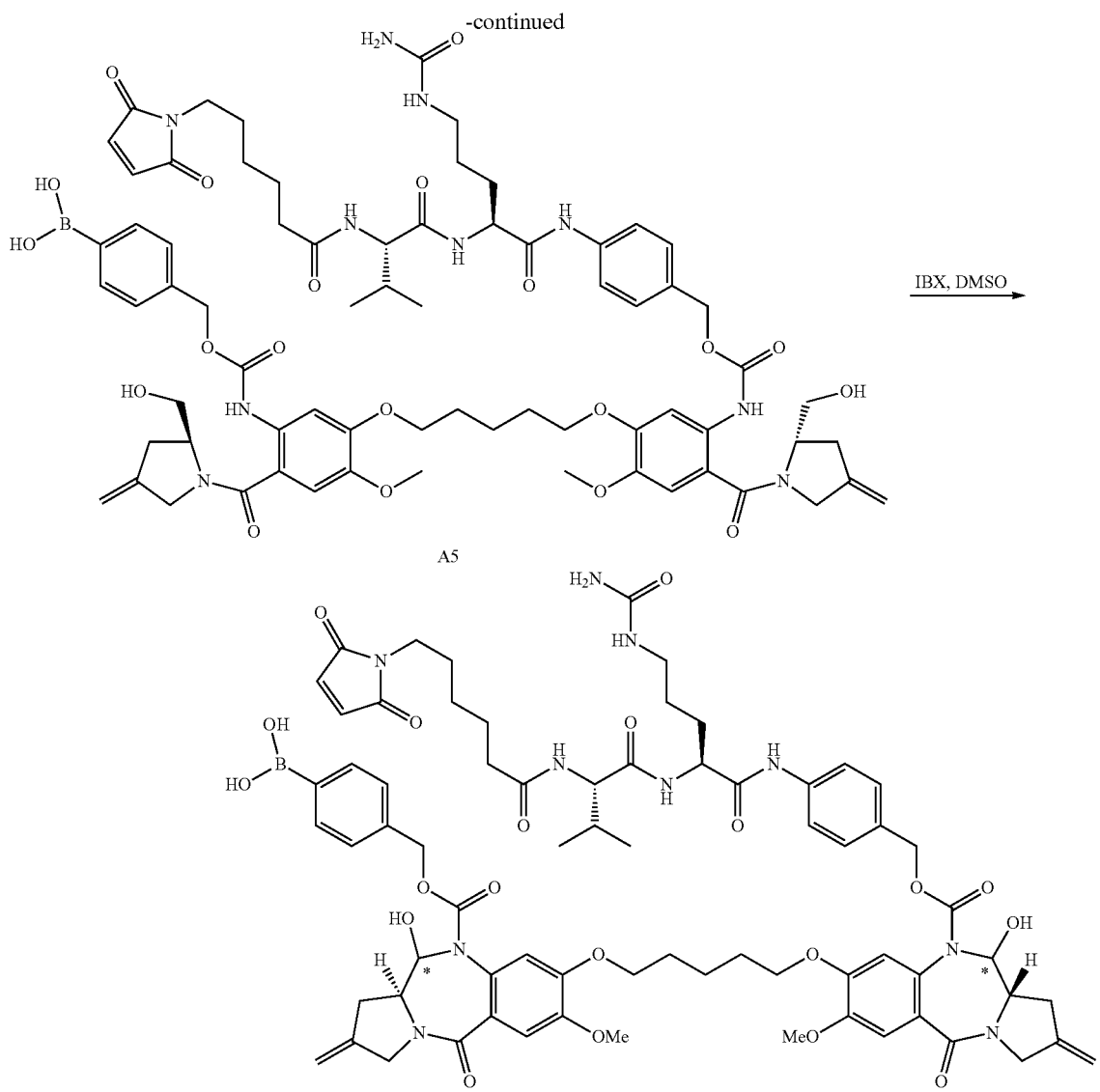

Each asterisk in the above structure, and elsewhere depicted in Example 22, represents a chiral center.

To a solution of triphosgene (228 mg, 0.77 mmol) in THF (15 mL) was added a solution A2 (450 mg, 1.92 mmol) and pyridine (304 mg, 3.84 mmol) in THF (5.0 mL) at 0° C. under $N_2$. The mixture was stirred at 0° C. for 20 min under $N_2$ and was added to a solution of A1 (2.04 g, 2.39 mmol) and triethylamine (389 mg, 3.84 mmol) in DCM (20 mL) at 0° C. under $N_2$. The reaction mixture was stirred at 10° C. for 2 h. The mixture was concentrated and purified by prep-TLC (30-60% EtOAc in petroleum ether) to give compound A3 (500 mg, 26%) as a yellow solid. LCMS (5-95, AB, 1.5 min): RT=1.268 min, m/z=1113.4 [M+1]+.

To a solution of triphosgene (53 mg, 0.18 mmol) in DCM (15 mL) was added a mixture of compound A3 (500 mg, 0.39 mmol) and triethylamine (45 mg, 0.44 mmol) in DCM (5.0 mL) at 0° C. under $N_2$. The reaction mixture was stirred at 0° C. for 30 min. To this reaction mixture was added a solution of MC_VC_PAB (308 mg, 0.54 mmol) and triethylamine (90 mg, 0.89 mmol) in DMSO (4.0 mL) at 10° C. under $N_2$. The reaction mixture was stirred at 40° C. under $N_2$ for 6 h. The mixture was diluted with DCM (30 mL), washed with water (2×15 mL) and the aqueous layer was extracted with EtOAc (2×20 mL). The combined organic layer was dried over $Na_2SO_4$, concentrated and purified by flash column (0-10% MeOH in DCM) to afford compound 8 (300 mg, 34% yield) as a yellow solid. LCMS (5-95, AB, 1.5 min): RT=1.253 min, m/z=857.1 [M/2+1]+.

To a solution of compound A4 (100.0 mg, 0.050 mmol) in water (2.0 mL) and THF (2.0 mL) was added HOAc (3.0 mL) at 10° C. The reaction mixture was stirred at 10° C. for 6 h. The reaction mixture was diluted with EtOAc (20 mL), washed with water (2×15 mL), saturated aq. $NaHCO_3$ (15 mL) and brine (15 mL). It was dried over $Na_2SO_4$ and concentrated to give the crude compound A5 (71 mg, 99.8% yield) as a yellow solid. LCMS (5-95, AB, 1.5 min): RT=0.829 min, m/z=857.1 [M/2-17]+.

To a solution of compound A5 (36 mg, 0.030 mmol) in DMSO (3.0 mL) was added 2-iodoxybenzoic acid (22 mg, 0.080 mmol) at 9° C. The reaction mixture was stirred at 40° C. for 6 h. The mixture was purified by prep-HPLC (ACN 27-47%/0.225% FA in water) to afford PBD dimer boronic acid prodrug 1 comprising a linker (2.0 mg, 5.5%) as a white solid. LCMS (5-95, AB, 1.5 min): RT=0.813 min, HRMS: m/z=1397.5906 [M+1]+.

In some aspects of the disclosure, PBD dimer boronic acid prodrug 1 comprising a linker may be conjugated to an antibody to form PBD dimer ADC boronic acid prodrug 1A or PBD dimer ADC boronic acid prodrug 1B.

Example 22B

Preparation of PBD Dimer Boronic Acid Control 1 Comprising a Linker PBD Dimer Boronic Acid Control 1 Comprising a Linker was Prepared According to the Following Reaction Scheme

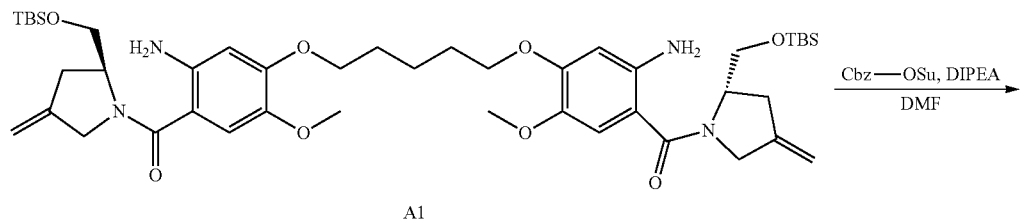

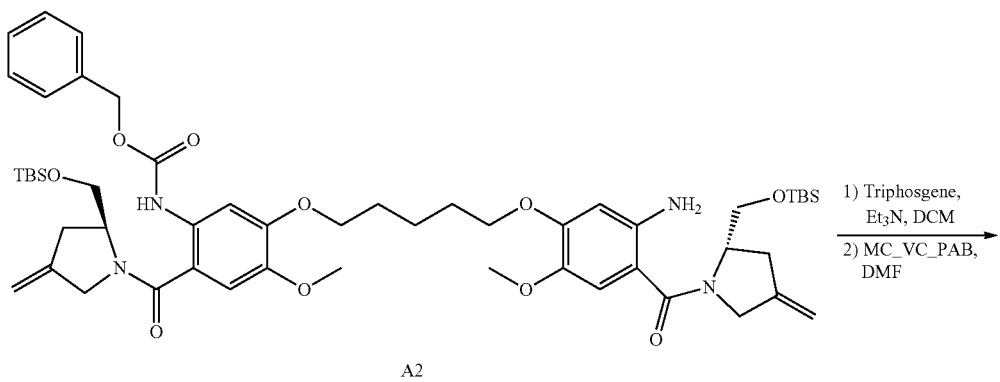

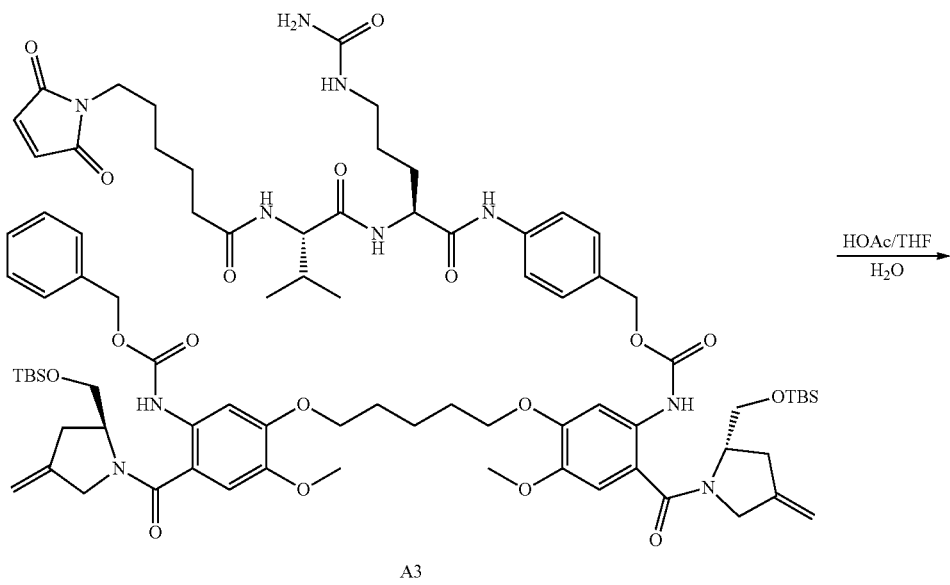

-continued

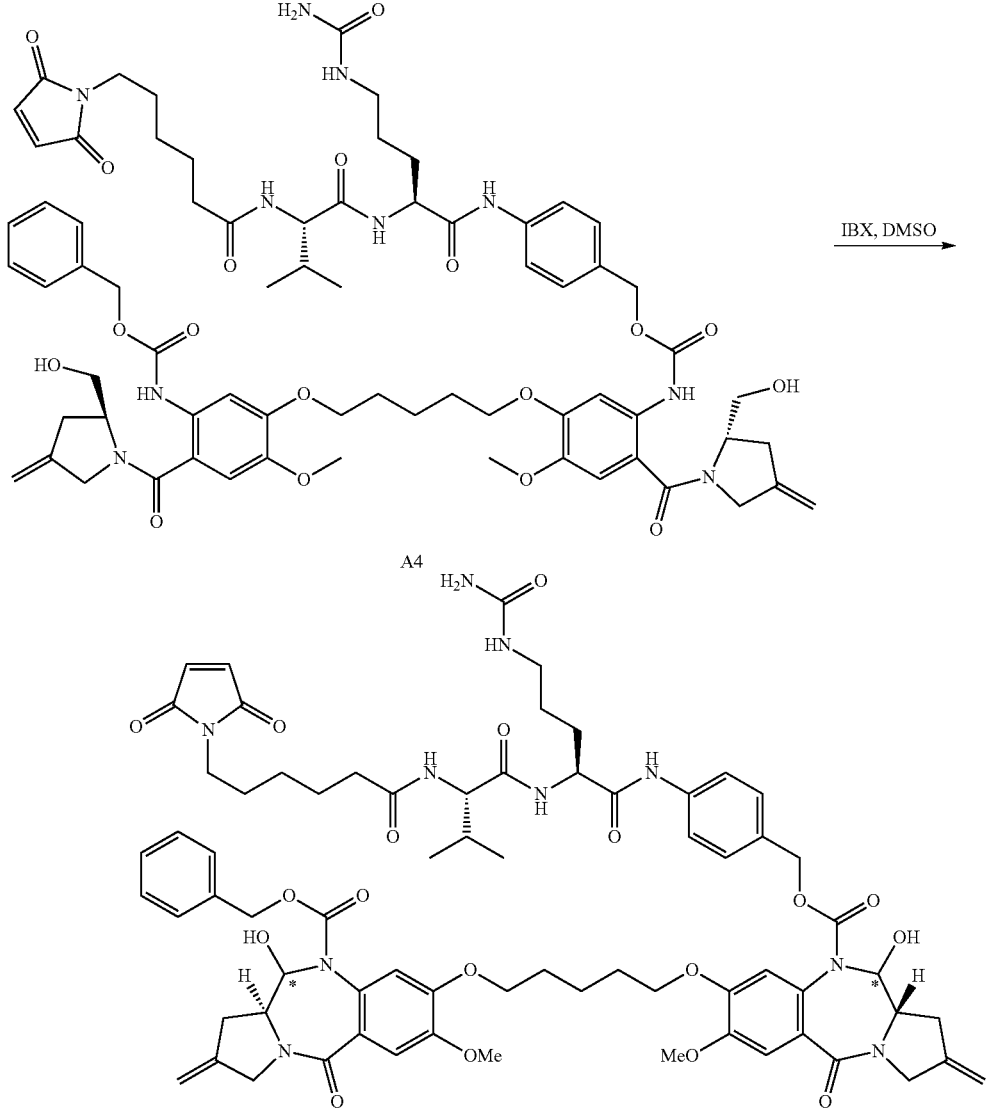

To compound A1 (500.0 mg, 0.590 mmol) in DMF (2.0 mL) was added Cbz-OSu (161 mg, 0.640 mmol). After the mixture was stirred at 50° C. for 4 h, another batch of Cbz-OSu (161 mg, 0.640 mmol) was added. The mixture was stirred at 50° C. for another 16 h, and purified by prep-TLC (5% MeOH in DCM, Rf=0.8), followed by prep-HPLC to afford compound A2 (220 mg, 35.2%) as an orange oil. LCMS (5-95, AB, 1.5 min): RT=1.097 min, m/z=987.5 [M+1]+.

To a mixture of triphosgene (26.45 mg, 0.090 mmol) and 4 Å MS (30 mg) in DCM (3.0 mL) was added a solution of compound A2 (220.0 mg, 0.220 mmol) and triethylamine (22.6 mg, 0.220 mmol) in DCM (2.0 mL) at 0° C. The mixture was stirred at 0° C. for 1 h, and concentrated. To the solution this isocyanate (225.0 mg, 0.220 mmol) in DCM (6.0 mL) was added a solution of MC_VC_PAB (34.59 mg, 0.060 mmol), Et$_3$N (23 mg, 0.22 mmol) and 4 Å MS (30 mg) in DMF (2.0 mL) at 0° C. After the mixture was stirred at 20° C. for 16 h, it was quenched with water. DCM (10 mL) was added, separated, and DCM phase was concentrated and purified by prep-TLC (15% MeOH in DCM, Rf=0.4) to afford compound A3 (70 mg, 19.8%) as light yellow oil. LCMS (5-95, AB, 1.5 min): RT=1.107 min, m/z=793.9 [M/2+1]+.

Compound A3 (70.0 mg, 0.040 mmol) in mixture of THF (3.0 mL) and water (2.0 mL) was added HOAc (1.0 mL, 17.49 mmol), and the mixture stirred at 40° C. for 8 h. The mixture was concentrated and purified by prep-TLC (13% MeOH in DCM, Rf=0.5), to afford compound A4 (40 mg, 67.8%) as a yellow oil. LCMS (5-95, AB, 1.5 min): RT=0.751 min, m/z=679.6 [M/2+1]+.

To a solution of compound A4 (30.0 mg, 0.020 mmol) in DMSO (3.0 mL) was added 2-iodoxybenzoic acid (30.9 mg, 0.110 mmol) at 18° C. After the reaction mixture was stirred at 40° C. for 16 h, it was purified by prep-TLC (10% MeOH in DCM, Rf=0.4) to afford PBD dimer boronic acid control 1 comprising a linker (13 mg, 43.5%) as a white solid. LCMS (5-95, AB, 1.5 min): RT=0.726 min, m/z=677.5 [M/2+1]+.

In some aspects of the disclosure, PBD dimer boronic acid control 1 comprising a linker may be conjugated to an

Example 23

Preparation of PBD Monomer and Dimer Diaphorase Prodrugs

Example 23A

Preparation of PBD Monomer Diaphorase Prodrug 2

PBD monomer diaphorase prodrug 2 was prepared according to the following reaction scheme:

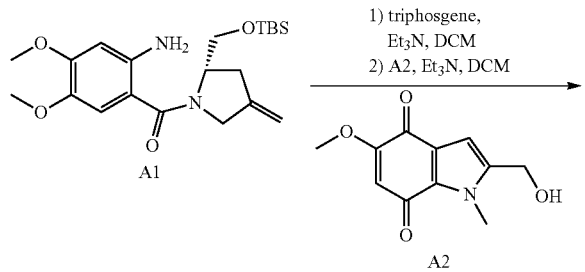

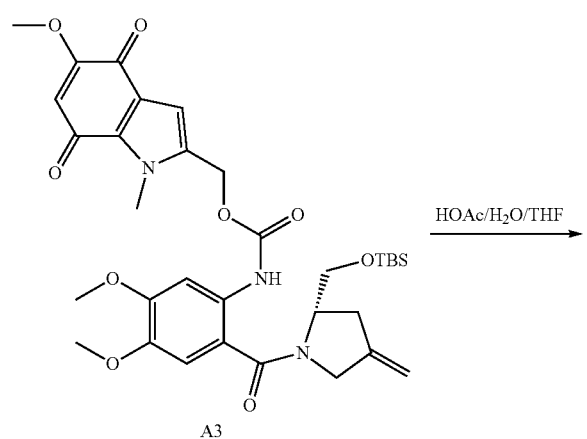

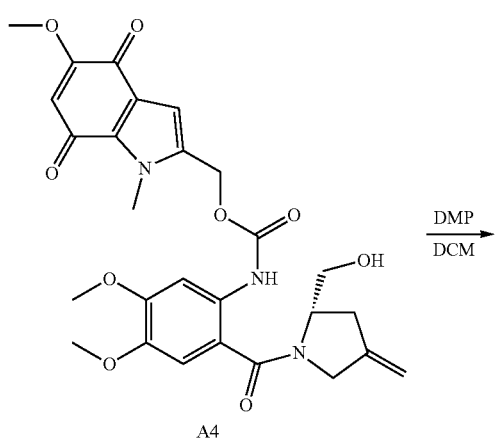

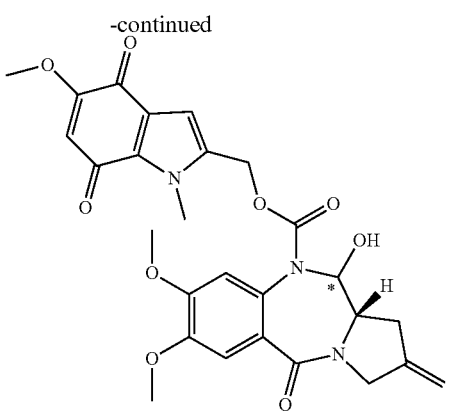

Each asterisk in the above structure, and elsewhere depicted in Example 23, represents a chiral center.

To a solution of triphosgene (58.39 mg, 0.200 mmol) in DCM (2.0 mL) at 0° C. was added solution of compound A1 in DCM (5.0 mL) under $N_2$ slowly, and the mixture stirred at 0° C. for 1 h. Compound A2 (100.0 mg, 0.450 mmol) and triethylamine (91.5 mg, 0.900 mmol) in DCM (2.0 mL) was added to above solution at 0° C. dropwise over 10 min. The mixture was stirred at 0° C. for 1 h. The mixture was quenched with water (5.0 mL), separated and concentrated. It was purified by prep-TLC (5% MeOH in DCM, Rf=0.7) to afford compound A3 (63 mg, 19%) as orange solid. LCMS (5-95, AB, 1.5 min): RT=1.007 min, m/z=654.3 [M+1]+.

To a solution of Compound A3 (63.0 mg, 0.100 mmol) THF (2.0 mL) and water (1.0 mL) was added acetic acid (2.0 mL, 2.1 mmol). The mixture was stirred at 15° C. for 16 h. The mixture was concentrated and purified by prep-TLC (5% MeOH in DCM, Rf=0.3) to afford A4 (40 mg, 77%) as orange solid. LCMS (5-95, AB, 1.5 min): RT=0.761 min, m/z=540.1 [M+1]+.

Compound A4 (26.0 mg, 0.050 mmol) in DCM (3.0 mL) was added DMP (40.0 mg, 0.090 mmol), the mixture was allowed to stir at 10° C. for 16 h. The mixture was quenched with mixture of saturated $Na_2SO_3$ and $NaHCO_3$ solution (3.0 mL/3.0 mL). Organic phase was separated, concentrated, and purified by prep-HPLC (Diamonsil 150*20 mm*5 um, 0.225% FA-ACN, ACN 23-53%) to afford PBD monomer diaphorase prodrug 2 (20 mg, 74%) as orange solid. LCMS (5-95, AB, 1.5 min): RT=0.747 min, m/z=538.1 [M+1]+.

1H NMR (400 MHz, CDCl3) δ 7.22 (s, 1H), 6.64 (s, 1H), 6.52 (s, 1H), 5.69 (s, 1H), 5.59-5.57 (d, J=9.6 Hz, 1H), 5.30-5.27 (d, J=13.6 Hz, 1H), 5.16-5.15 (m, 2H), 4.94-4.90 (d, J=13.6 Hz, 1H), 4.32-4.27 (d, J=16.4 Hz, 1H), 4.17-4.13 (d, J=16.4, 1H), 3.93 (s, 3H), 3.83 (s, 3H), 3.78-3.76 (m, 6H), 3.64-3.59 (m, 1H), 2.47 (m, 1H), 2.96-2.89 (m, 1H), 2.73-2.69 (m, 1H).

Example 23B

Preparation of PBD Dimer Diaphorase Prodrug 1

PBD dimer diaphorase prodrug 1 was prepared according to the following reaction scheme:

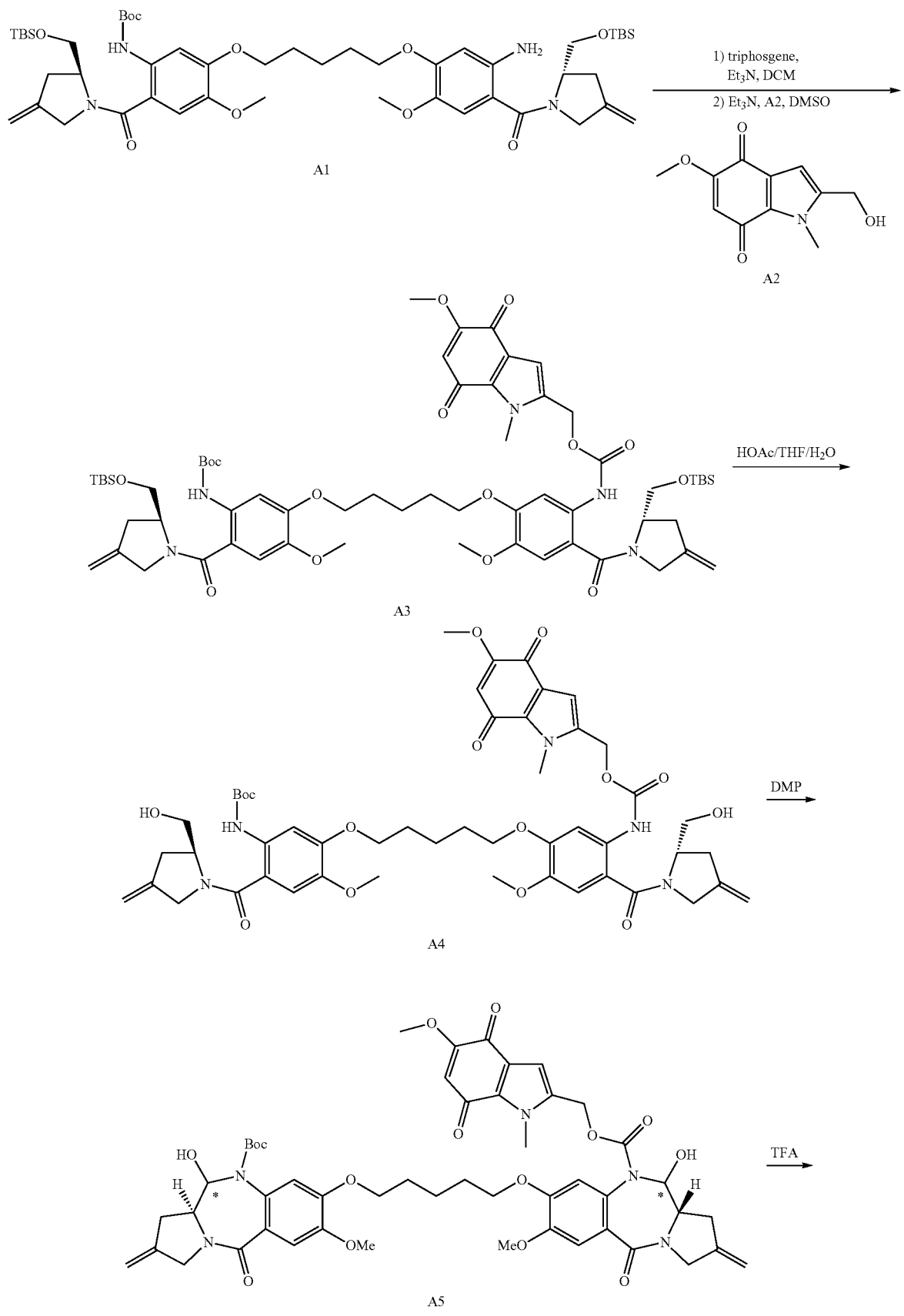

-continued

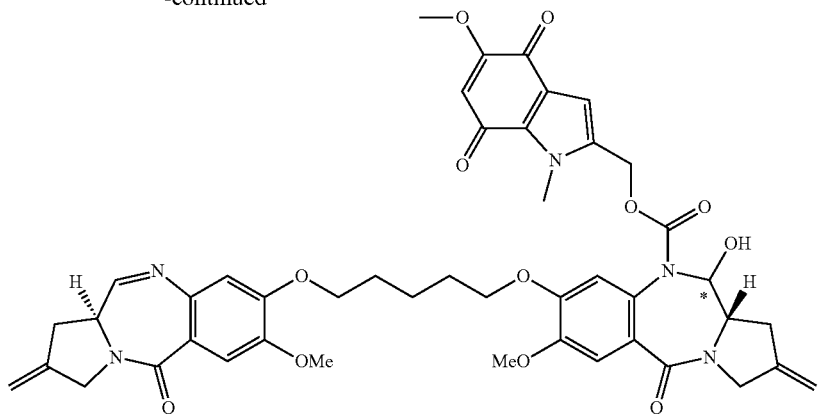

To a solution of triphosgene (56.03 mg, 0.190 mmol) in DCM (2.0 mL) was added a solution of compound A1 (400 mg, 0.420 mmol) and triethylamine in DCM (5.0 mL) dropwise at 0° C. After the mixture was stirred for 1 h at 19° C., a solution of compound A2 (92.8 mg, 0.420 mmol) and triethylamine (42.5 mg, 0.420 mmol) in DMSO (0.50 mL)/DCM (2.50 mL) was added. The mixture was stirred at 19° C. for 2.0 h. The mixture was diluted with DCM (20.0 mL), washed with water (2×10.0 mL), and separated. The aqueous layer was extracted with EtOAc (2×20 mL), and the combined organic layer was dried over $Na_2SO_4$, concentrated and purified by prep-TLC (20% MeOH in DCM, Rf=0.7) to afford compound A3 (150 mg, 30%). LCMS (5-95, AB, 1.5 min): RT=1.118 min, m/z=1201.7 [M+1]+.

To a solution of compound A3 (130.0 mg, 0.110 mmol) in THF (2.0 mL) was added acetic acid (3.0 mL) and water (1.0 mL). The mixture was stirred at 18° C. for 18 h. Saturated $NaHCO_3$ was added to adjust pH=8, and the mixture was extracted with DCM (2×50 mL). The organic layer was combined, washed with brine (30 mL) and water (30 mL), and dried over $Na_2SO_4$. It was concentrated and purified by prep-TLC (6.7% MeOH in DCM) to afford compound A4 (72 mg, 68%) as yellow solid. LCMS (5-95, AB, 1.5 min): RT=0.766 min, m/z=972.3 [M+1]+.

To a solution of compound 4 (50.0 mg, 0.050 mmol) in DCM (10 mL) was added DMP (76.36 mg, 0.180 mmol), and the mixture was stirred at 18° C. for 18 h. The mixture was filtered, and the filtrate was washed with saturated $Na_2CO_3$ (20.0 mL). The aqueous layer was extracted with DCM (2×20.0 mL), and the organic layer was combined, dried over $Na_2SO_4$ and concentrated. It was purified by prep-TLC (6.7% MeOH in DCM, Rf=0.5) to give compound A5 (40 mg, 74%) as yellow solid. LCMS (5-95, AB, 1.5 min): RT=0.731 min, m/z=990.2 [M+23]+.

TFA (1.0 mL) was added dropwise to compound A5 (40.0 mg, 0.040 mmol) at 0° C. The mixture was stirred at 0° C. for 30 min. Saturated $NaHCO_3$ was added to the mixture dropwise at 0° C. to adjust pH=7. It was extracted with DCM (3×20.0 mL), and the combined organic layer was washed with brine (20.0 mL), dried over $Na_2SO_4$ and concentrated. The residue was purified by prep-TLC (6.7% MeOH in DCM, Rf=0.6) to afford PBD dimer diaphorase prodrug 1 (4.9 mg, 14%) as yellow solid. LCMS (5-95, AB, 1.5 min): RT=0.807 min, m/z=850.2 [M+23]+.

Example 23C

Preparation of PBD Monomer Diaphorase Prodrug 3

PBD monomer diaphorase prodrug 3 was prepared according to the following reaction scheme:

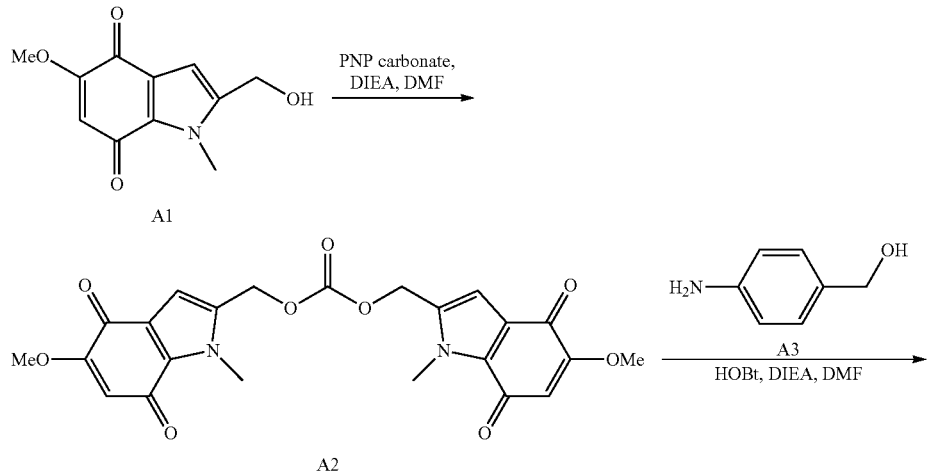

-continued
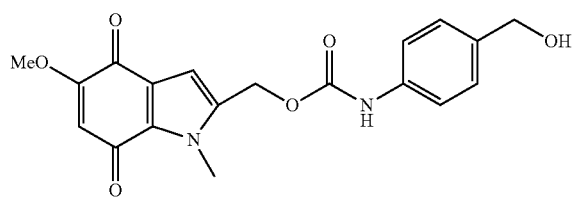
A4
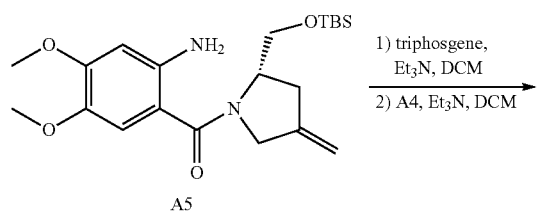
A5
1) triphosgene, Et₃N, DCM
2) A4, Et₃N, DCM
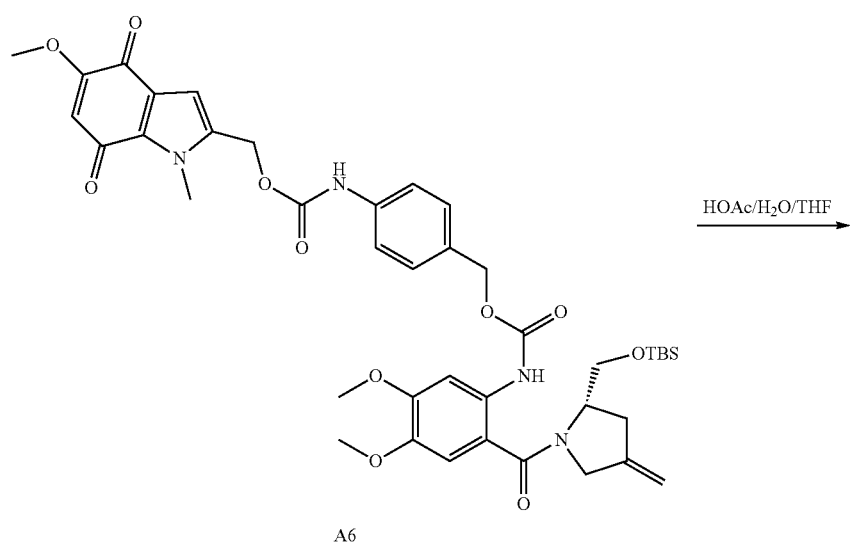
A6
HOAc/H₂O/THF
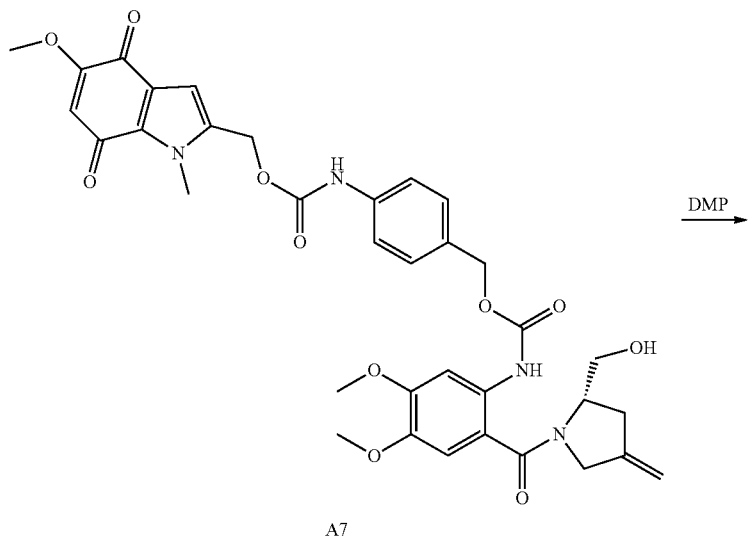
A7
DMP -continued

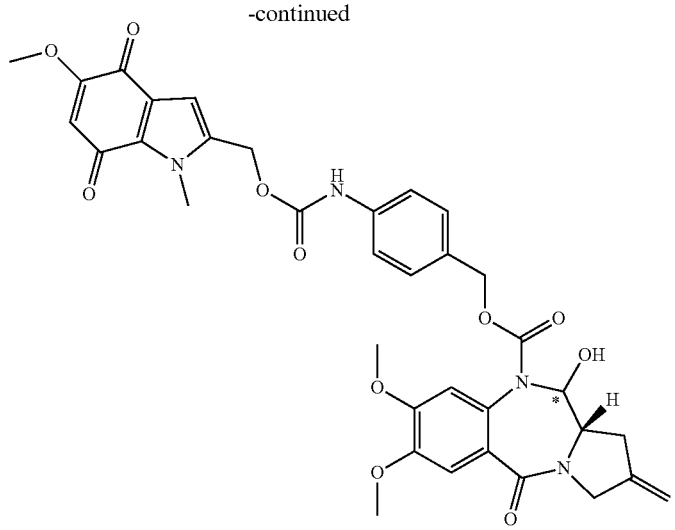

To a solution of compound A1 (280 mg, 1.27 mmol) in DMF (10 mL) was added DIEA (490 mg, 3.79 mmol) and bis (4-nitrophenyl) carbonate (770 mg, 2.53 mmol) at 16° C. The reaction mixture was stirred at 16° C. under $N_2$ for 2 h. The reaction solution was concentrated and washed with MTBE to afford compound A2 (500 mg, 78%) as an orange solid. LCMS (5-95, AB, 1.5 min): RT=0.726 min, m/z=491.0 [M+23]+.

To a solution of compound A2 (500 mg, 0.99 mmol), compound A3 (240 mg, 1.95 mmol) and HOBt (13 mg, 0.10 mmol) in DMF (8.0 mL) was added DIEA (340 mg, 2.63 mmol) at 16° C. The reaction mixture was stirred at 50° C. under $N_2$ for 2 h. The reaction was concentrated and the residue was washed by MeCN (3×8 mL) to give compound A4 (350 mg, 95%) as an orange solid. LCMS (5-95, AB, 1.5 min): RT=0.745 min, m/z=393.1 [M+23]+.

To a solution of triphosgene (58 mg, 0.20 mmol) in DCM (8.0 mL) was added a solution of compound A5 (200 mg, 0.49 mmol) and triethylamine (60.0 mg, 0.59 mmol) in DCM (1.5 mL) at 0° C. under $N_2$. The reaction mixture was stirred at 12° C. under $N_2$ for 30 min and a solution of compound A4 (91 mg, 0.25 mmol), TEA (75 mg, 0.74 mmol) and DMAP (6 mg, 0.05 mmol) in DCM (1.5 mL) and DMSO (1.0 mL) at 0° C. was added under $N_2$. After the reaction mixture was stirred at 12° C. under $N_2$ for 6 h, it was diluted with DCM (30 mL), washed with water (2×15 mL). The aqueous layer was extracted with EtOAc (2×20 mL), and the combined organic layer was dried over $Na_2SO_4$, concentrated, and purified by prep-HPLC (ACN 66-86%/0.225% FA in water) to afford compound A6 (60 mg, 12%) as an orange solid. LCMS (5-95, AB, 1.5 min): RT=1.051 min, m/z=803.2 [M+1]+.

To a solution of compound A6 (40 mg, 0.05 mmol) in water (1.0 mL) and THF (1.0 mL) was added HOAc (1.5 mL, 26 mmol) at 10° C. The reaction mixture was stirred at 10° C. for 6 h. The reaction mixture was diluted with EtOAc (20 mL) and washed with water (2×15 mL), saturated $NaHCO_3$ (15 mL) and brine (15 mL). It was dried over $Na_2SO_4$, concentrated, and purified by prep-TLC (6.25% MeOH in DCM) to afford compound A7 (35 mg, 97%) as an orange solid. LCMS (5-95, AB, 1.5 min): RT=0.819 min, m/z=689.1 [M+1]+.

To a solution of compound A7 (35 mg, 0.050 mmol) in DCM (4.0 mL) was added DMP (61 mg, 0.14 mmol) at 0° C. The reaction mixture was stirred at 10° C. for 10 h. The reaction was quenched with saturated $NaHCO_3/Na_2SO_3$ (4.0 mL/4.0 mL) and extracted with DCM (3×10 mL). The combined organic layer was washed with $NaHCO_3/Na_2SO_3$ (4.0 mL/4.0 mL), brine (7.0 mL). It was dried over $Na_2SO_4$, concentrated, and purified by prep-HPLC (ACN 30-60%/0.225% FA in water) to afford PBD monomer diaphorase prodrug 3 (15 mg, 45%) as an orange solid. LCMS (5-95, AB, 1.5 min): RT=0.806 min, m/z=687.2 [M+1]+; 1H NMR (400 MHz, CDCl3) δ 7.30-7.25 (m, 2H), 7.18-7.15 (M, 4H), 6.77 (s, 1H), 6.69 (S, 1H), 6.50 (s, 1H), 5.67 (s, 1H), 5.56 (d, J=9.2 Hz, 1H), 5.27 (d, J=12.4 Hz, 1H), 5.17-5.12 (m, 4H), 4.81 (d, J=12.4 Hz, 1H), 4.27 (d, J=16.0 Hz, 1H), 4.12 (d, J=16.0 Hz, 1H), 3.33 (s, 3H), 3.89 (s, 3H), 3.81 (s, 3H), 3.68-3.59 (m, 4H), 2.93-2.87 (m, 1H), 2.69 (d, J=15.6 Hz, 1H).

Example 23D

Preparation of PBD Dimer Diaphorase Prodrug 2

PBD dimer diaphorase prodrug 2 was prepared according to the following reaction scheme:

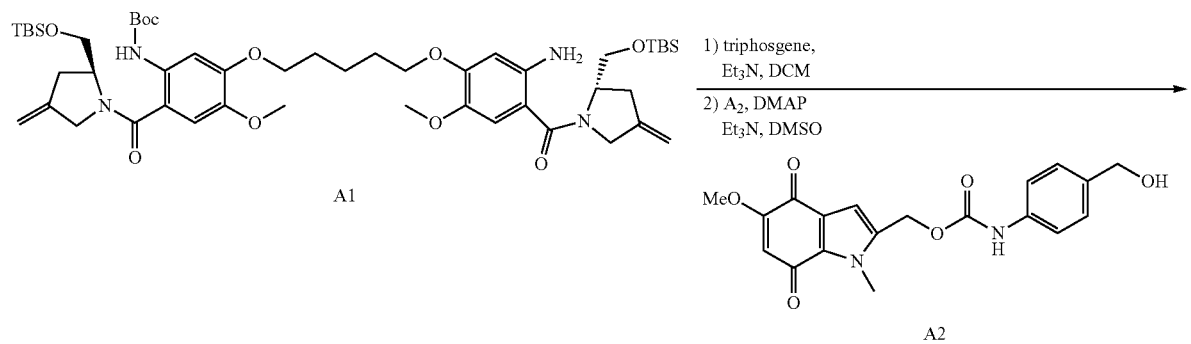
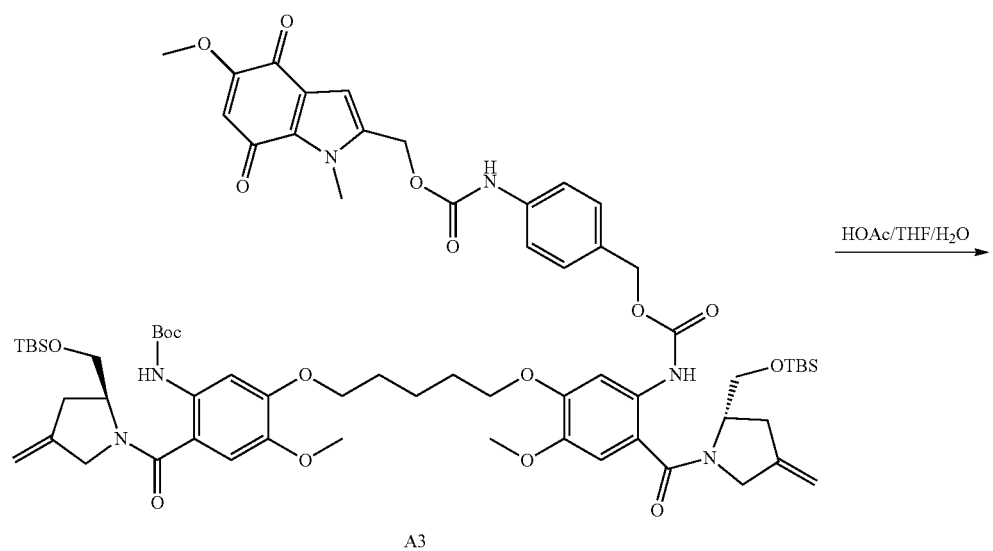
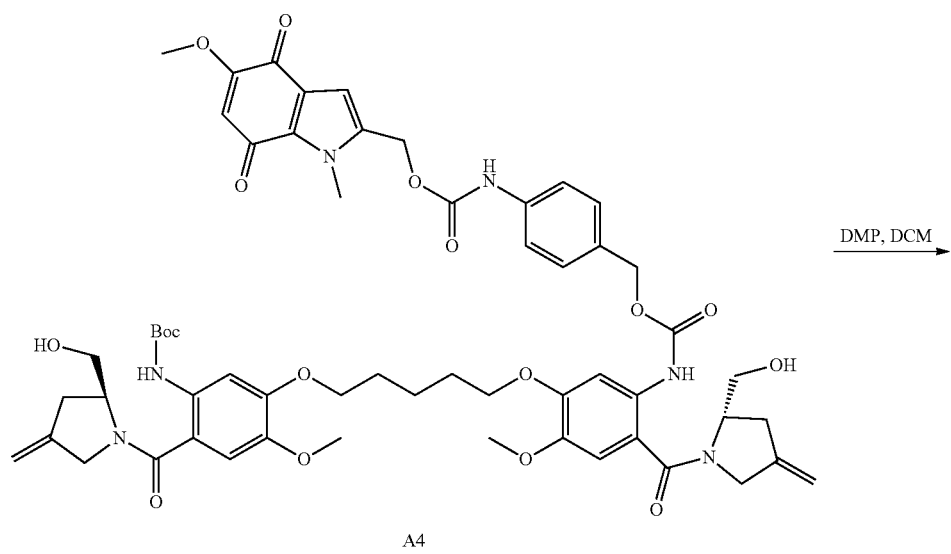

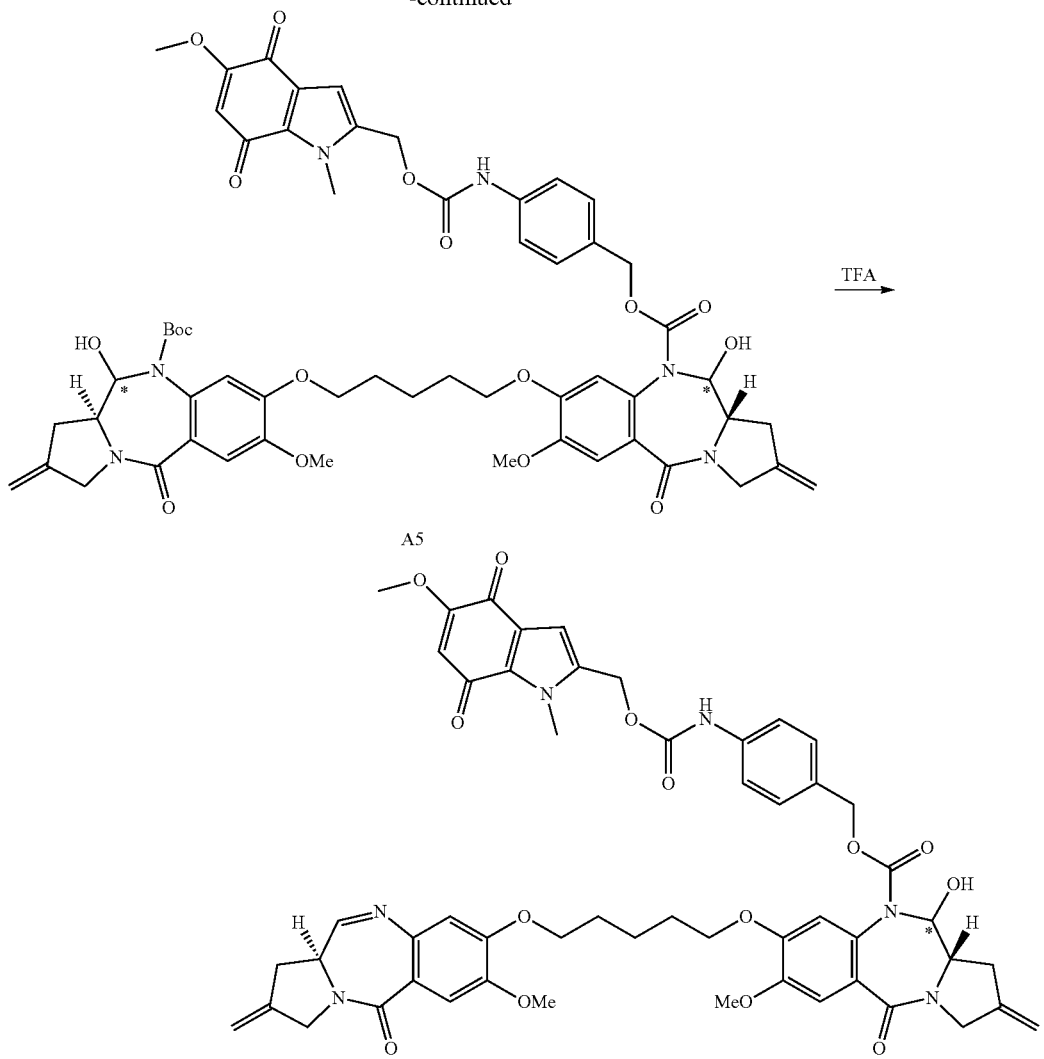

To a solution of triphosgene (62.0 mg, 0.210 mmol) in DCM (12 mL) was added a solution of compound A1 (500.0 mg, 0.520 mmol) and triethylamine (63.0 mg, 0.620 mmol) in DCM (2.0 mL) at 0° C. under $N_2$. The reaction mixture was stirred at 12° C. under $N_2$ for 30 min, and a solution of compound A2 (97.0 mg, 0.260 mmol), DMAP (6.0 mg, 0.050 mmol) and triethylamine (79.0 mg, 0.780 mmol) in DCM (1.5 mL) and DMSO (0.60 mL) was added at 0° C. under $N_2$. The reaction mixture was stirred at 12° C. under $N_2$ for 6 h. It was diluted with DCM (30 mL), washed with water (2×15 mL). The aqueous layer was extracted with EtOAc (2×20 mL), and the organic layer was dried over $Na_2SO_4$. It was purified by silica chromatography (3% MeOH in DCM) to afford compound A3 (200 mg, 49%) as an orange solid. LCMS (5-95, AB, 1.5 min): RT=1.294 min, m/z=1349.6 [M+1]+.

To a solution of compound A3 (206.9 mg, 0.130 mmol) in water (2.0 mL) and THF (2.0 mL) was added HOAc (3.0 mL, 52.46 mmol) at 9° C. The reaction mixture was stirred at 9° C. for 10 h. It was diluted with DCM (20 mL), and the mixture was washed with NaHCO$_3$ (2×15 mL), water (15 mL). It was dried over $Na_2SO_4$, concentrated, and purified by prep-TLC (6.25% MeOH in DCM) to afford compound A4 (100 mg, 66%) as a yellow solid. LCMS (5-95, AB, 1.5 min): RT=0.932 min, m/z=1121.6 [M+1]+.

To a solution of compound A4 (100.0 mg, 0.090 mmol) in DCM (10 mL) was added DMP (113.0 mg, 0.270 mmol) at 0° C. The reaction mixture was stirred at 9° C. for 10 h. The reaction was quenched with a saturate solution of NaHCO$_3$/Na$_2$SO$_3$ (5.0 mL/5.0 mL) and extracted with DCM (3×10 mL). The combined organic layer was washed with NaHCO$_3$/Na$_2$SO$_3$ (5 mL/5 mL), brine (10 mL), dried and concentrated. The residue was purified by prep-TLC (6.25% MeOH in DCM) to give compound A5 (45 mg, 46%) as an orange solid. LCMS (5-95, AB, 1.5 min): RT=0.884 min, m/z=1140.0 [M+23]+.

Cold TFA (95% in water, 2.0 mL) was added to compound A5 (35.0 mg, 0.030 mmol) at 0° C. The reaction mixture was stirred at 0° C. for 15 min. The reaction mixture was added dropwise to a saturate aq. NaHCO$_3$ (4.0 mL) at 0° C. and extracted with DCM (4×8.0 mL). The combined organic layer was washed with brine (15 mL), dried over Na$_2$SO$_4$, and concentrated. It was purified by prep-HPLC (ACN 36-66/0.225% FA in water) to afford PBD dimer diaphorase prodrug 2 (6.1 mg, 19%) as an orange solid. LCMS (5-95, AB, 1.5 min): RT=0.831 min, m/z=999.3 [M+1]+.

Example 23E
Preparation of PBD Dimer Diaphorase Prodrug 3
PBD dimer diaphorase prodrug 3 was prepared according to the following reaction scheme:
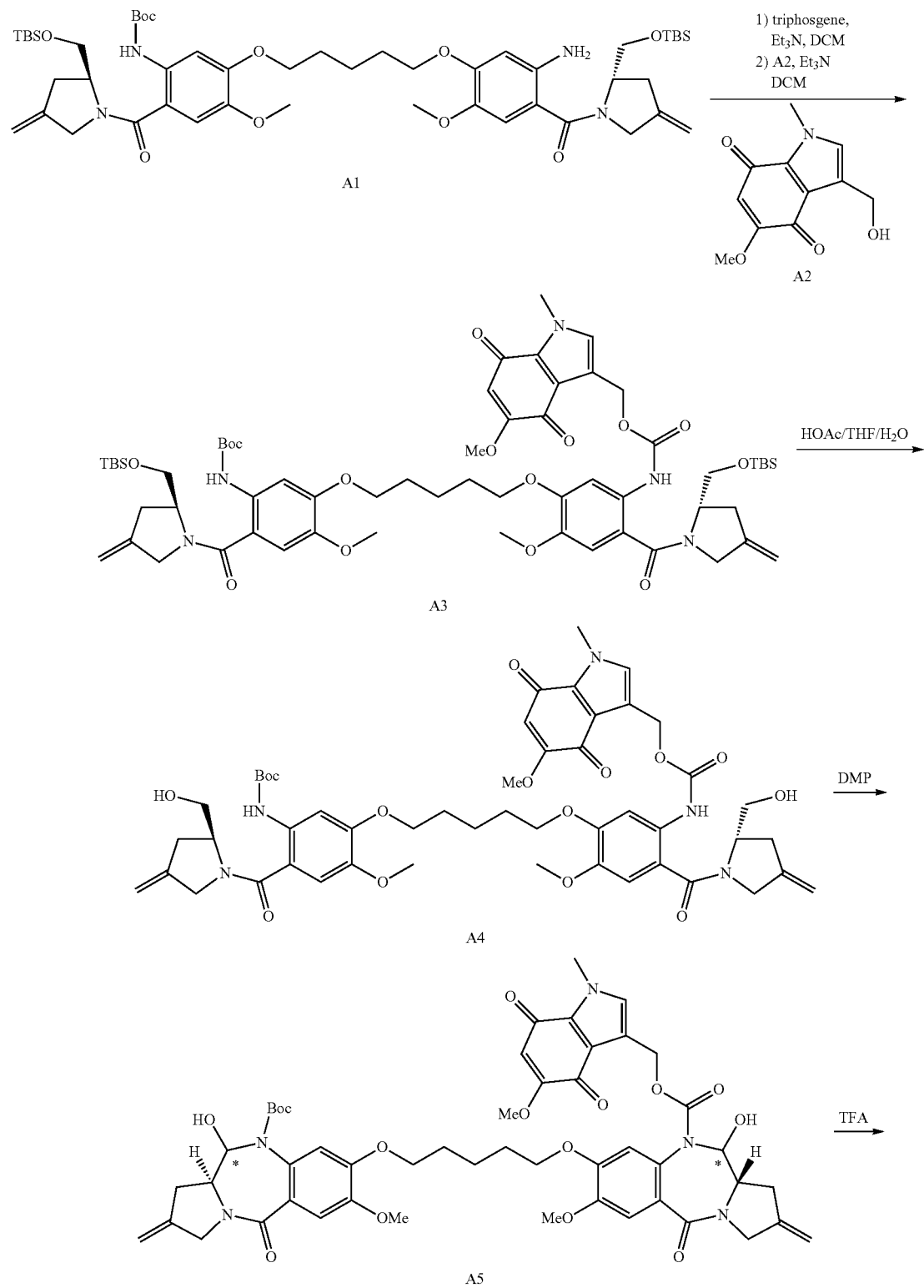

-continued

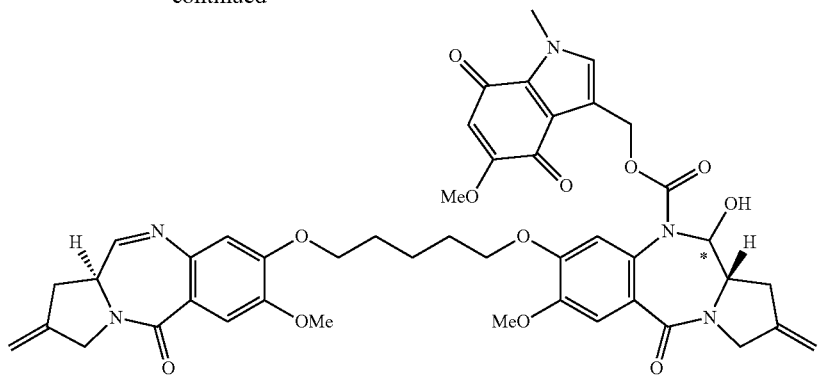

To a solution of triphosgene (28.0 mg, 0.090 mmol) in DCM (5.0 mL) was added a solution of compound A1 (200 mg, 0.210 mmol) and triethylamine (42.0 mg, 0.420 mmol) in DCM (3.0 mL) at 0° C. It was stirred at 26° C. for 20 min under N₂. The mixture was concentrated and redissolved in DCM (3.0 mL), and added to a stirred solution of triethylamine (38.0 mg, 0.380 mmol) and compound A2 (51.0 mg, 0.230 mmol) in DCM (3.0 mL) at 0° C. It was stirred at 26° C. for 2 h under N₂, and purified by column chromatography (0-40% EtOAc in petroleum ether) to afford compound A3 (240 mg, 90%) as a yellow solid. LCMS (5-95, AB, 1.5 min): RT=1.159 min, m/z=1200.5 [M+1]+.

A solution of compound A3 (240.0 mg, 0.200 mmol) in THF (4.0 mL) and water (4.0 mL) was added HOAc (6.0 mL, 153 mmol) at 25° C. The mixture was stirred for 10 h at 25° C., and EtOAc (100 mL) was added. It was washed with water (50 mL), saturated NaHCO₃ (50 mL), then brine (50 mL). The organic layer was dried and concentrated to give the crude product compound A4 (194 mg, 99.8%) as a yellow solid. LCMS (5-95, AB, 1.5 min): RT=0.767 min, m/z=972.4 [M+1]+.

To a solution of compound A4 (194.0 mg, 0.200 mmol) in DCM (15 mL) was added DMP (211.6 mg, 0.500 mmol). The mixture stirred at 26° C. for 1 h, and was quenched with saturated Na₂SO₃/NaHCO₃ (10 mL/10 mL). It was diluted with DCM (2×30 mL), and separated. DCM phase was washed with water (20 mL), dried over Na₂SO₄, concentrated and purified by prep-HPLC (ACN 43-63/0.225% FA in water) to afford compound A5 (70 mg, 36% yield) as a yellow solid. LCMS (5-95, AB, 1.5 min): RT=0.733 min, m/z=968.6 [M+1]+.

TFA (0.20 mL, 2.68 mmol) was added to compound A5 (40.0 mg, 0.040 mmol) at 0° C. The reaction mixture was stirred at 0° C. for 30 min, and was quenched with cool saturated NaHCO₃ (2.0 mL). DMSO (2.0 mL) was added, and the mixture was purified by prep-HPLC (ACN 36-66%/10 mM NH₄HCO₃ in water) to afford PBD dimer diaphorase prodrug 3 (9.9 mg, 28%) as a yellow solid. LCMS (5-95, AB, 1.5 min): RT=0.695 min, m/z=850.3 [M+1]+.

Example 24

Synthesis of Quinones

Example 24A

Synthesis of Quinone 1

Quinone 1 was prepared according to the following reaction scheme:

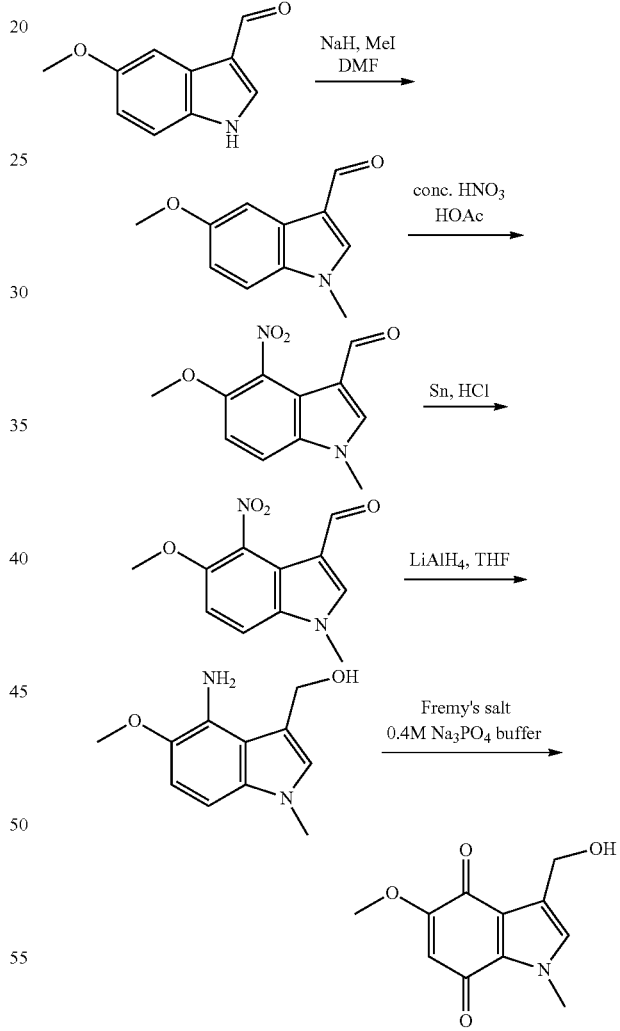

To a suspension of NaH (8.9 g, 0.223 mol) in DMF (300 mL) was cooled in an ice-bath. To this, a solution of the starting amine (30 g, 0.171 mol) in DMF (150 mL) was added dropwise. The reaction mixture was stirred at rt for 60 minutes. Then iodomethane (31.5 g, 0.223 mol) was added. The reaction mixture was stirred at rt for 1 hour. Then the mixture was poured onto 10% aqueous solution of NaHCO₃, extracted with EA. The combined organic phases were washed with 10% aqueous solution of NaHCO$_3$, brine and dried. The solution was concentrated to get crude product, which was triturated from EA/Hex to afford product as a light-yellow solid (29.5 g, 91.2%).

To a solution of the starting aldehyde (29.5 g, 156 mmol, 1 eq.) 5-methoxy-1-methyl-1H-indole-3-carbaldehyde in acetic acid (300 mL), cooled to 10° C. To this, a mixture of nitric acid (4.6 mL) in acetic acid (20 mL) was added. The reaction mixture was then stirred at rt for 16 h. A yellow suspension was obtained which was poured on to an ice-water mixture and the crystals obtained were filtered off and dried. Crude product was triturated from EA/Hex to afford product as a yellow solid (30.0 g, 82.1%).

To suspension of the starting material (10 g, 43 mmol) in ethanol (600 mL) was added tin powder (44.23 g, 0.37 mol). Followed by the addition of 3 N HCl (200 mL). The reaction was stirred at rt for 2 hours. The solution was diluted with saturated aqueous NaHCO$_3$. The mixture was filtered and washed with EA. The organic phase was separated, and aqueous was extracted with EA. The combined organic phase was washed with brine, dried and concentrated to get crude product, which was triturated from EA/Hex=1/20 to afford product as a gray solid (6.0 g, 68.3%).

The starting aldehyde (5.0 g, 24.5 mmol, 1 eq.) was dissolved in 100 mL THF. To a suspension of LiAlH$_4$ (1.86 g, 49 mmol, 2 eq.) in 200 mL THF and cooled to 0° C. The solution of aldehyde was added to the LiAlH$_4$ solution dropwise. The reaction was allowed to reach rt and stirred for 30 min at rt. It was quenched with water and then filtered through celite, dried with MgSO$_4$ and evaporated. The residue was used directly in the next reaction. The residue was solved in 300 mL of acetone. To 300 mL of a 0.3 M solution of NaH$_2$PO$_4$, 19.7 g (73.5 mmol, 3 eq.) of Fremy's salt was added. This mixture was added to the residue in acetone and stirred at rt for 0.5 h. The excess acetone was removed in vacuo. The resulting residue was extracted with dichloromethane and washed with water. The organic layer was dried (MgSO$_4$) and evaporated. Crude product was triturated from EA/Hex to get product as an orange solid (2.51 g, 46.1%, two steps).

1H NMR (400 MHz, CDCl3) δ 6.70 (s, 1H), 5.69 (s, 1H), 4.64 (d, J=6.9 Hz, 2H), 3.93 (s, 3H), 3.84 (s, 3H), 3.78 (t, J=7.0 Hz, 1H).

Example 24B

Synthesis of Quinone 2

Quinone 2 was prepared according to the following reaction scheme:

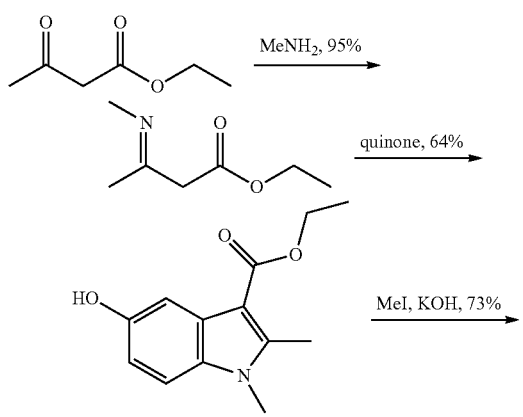

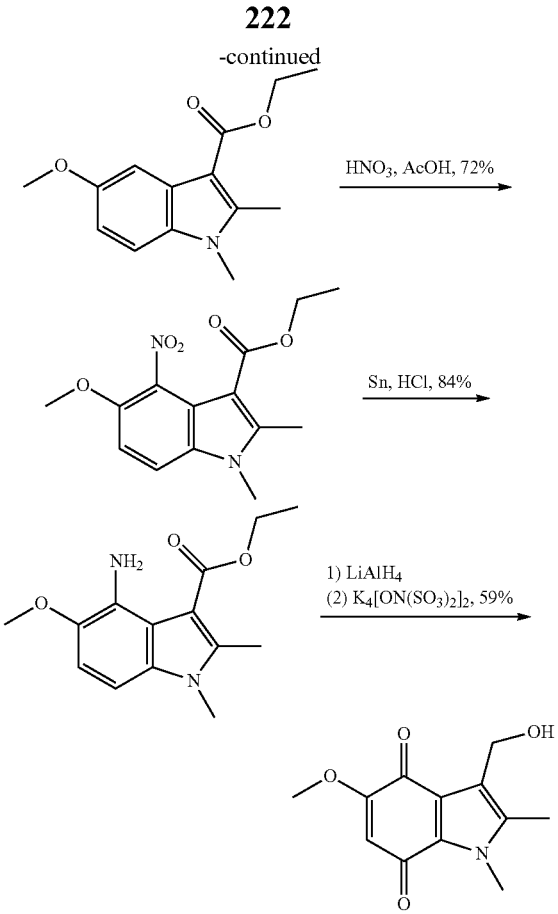

4.6 g Silicagel was added to ethyl 3-oxobutanoate (50 g, 0.38 mmol). To this, methylamine solution (aqueous; 40%, 35.7 g, 0.46 mol) was added and the mixture stirred overnight. The reaction mixture was extracted with DCM, dried with MgSO$_4$, filtered and evaporated to get product as colourless oil (50 g, 92%).

50 g (0.35 mol 1 eq.) of the imine and 37.7 g (0.35 mol 1 eq.) 1,4-benzoquinone is dissolved in 400 mL nitromethane. The mixture is left for 24 hrs (no stirring). Crystals of product precipitate. They were filtered, washed with nitromethane and recrystallized from EtOAc. Yellow solid, yield: 25 g, 30.6%.

To a solution of the alcohol (25 g, 0.11 mol) and KOH (25.5 g, 0.46 mol) in DMSO (200 mL) was stirred at rt for 30 minutes. Then iodomethane (62 g, 0.44 mol) was added. The mixture was diluted with EA (700 mL), washed with 1 N HCl, brine and dried. The solution was concentrated to get crude product, which was purified by silica gel column to afford product as a gray solid (20 g, 75.5%).

To a solution of 20 g (81 mmol, 1 eq.) ethyl 5-methoxy-1,2-dimethyl-1H-indole-3-carboxylate in acetic acid (200 mL), cooled to 0° C. was added a mixture of nitric acid (4.6 mL) and acetic acid (20 mL). The mixture was then stirred at rt for 2 h. A yellow suspension was obtained which was poured on to an ice-water mixture and the crystals obtained were filtered off and dried. Crude product was purified by flash chromatography to afford product as a yellow solid (14.0 g, 59.3%).

To suspension of the starting ester (8.0 g, 27 mmol) in ethanol (600 mL) was added tin powder (14.6 g, 0.123 mol). Followed by the addition of 3 N HCl (200 mL). The reaction was stirred at rt for 2 hours. The solvents were removed, and the residue was diluted with water, neutralized with saturated NaHCO$_3$. The mixture was filtered and washed with EA. The organic phase was separated, and aqueous was extracted with EA. The combined organic phase was washed with brine, dried and concentrated to get crude product, which was triturated from EA/Hex=1/20 to afford product as a gray solid (5.0 g, 70.6%).

5.0 g (19.06 mmol, 1 eq.) of the starting material was dissolved in 50 mL THF. 2.9 g (76.25 mmol, 4 eq.) LiAlH$_4$ was solved in 250 mL THF and cooled to 0° C. The solution of starting material was added to the LiAlH$_4$ solution dropwise. The reaction was allowed to reach RT and stirred for 30 min at rt. It was quenched with water, NaOH and silica gel. It was filtered through celite, dried with MgSO$_4$ and evaporated. The residue was used directly in the next reaction. The residue was solved in 330 mL of acetone. To 330 mL of a 0.3 M solution of NaH$_2$PO$_4$ 15.32 g (57.18 mmol, 3 eq.) of Fremy's salt was added. This mixture was added to the hydroxymethyl indole in acetone and stirred at rt for 1 h. The excess acetone was removed in vacuo. The resulting residue was extracted with dichloromethane and washed with water. The organic layer was dried (MgSO$_4$) and evaporated. Crude product was purified by flash chromatography to get product as a red solid (2.51 g, 56%).

1H NMR (400 MHz, CDCl3) δ 5.63 (s, 1H), 4.61 (s, 2H), 3.88 (s, 3H), 3.82 (s, 3H), 2.23 (s, 3H).

Example 24C

Synthesis of Quinone 3

Quinone 3 was prepared according to the following reaction scheme:

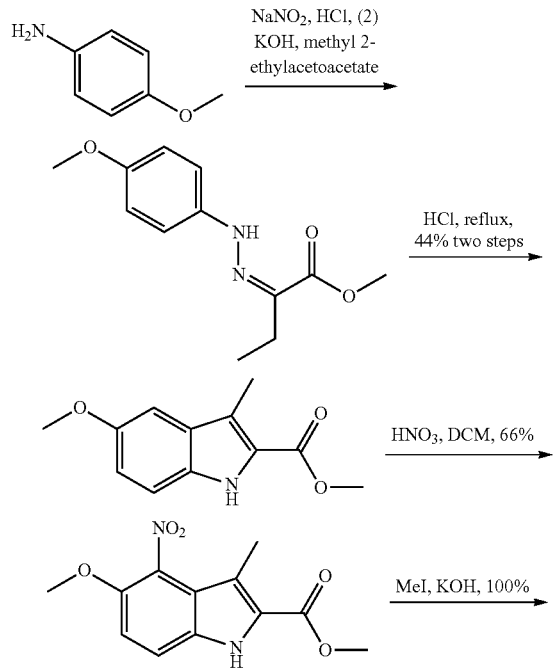

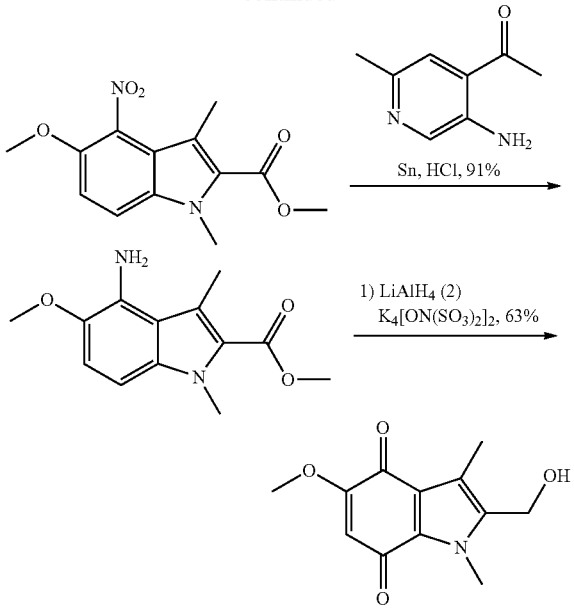

4-methoxyaniline (32 g, 259.2 mmol) was solved in HCl (37%,64 mL) and water (112 mL). A solution of NaNO$_2$ (19.5 g,283.2 mmol) in water (32 mL) was added drop wise at −5° C. After addition, the mixture was stirred at 0° C. for 15 min and brought to pH 3-4 by addition of CH$_3$COONa (16.8 g,204.8 mmol). Ethyl-2-ethylacetoacetate (44.8 g,283.2 mmol) was solved in ethanol (200 mL) at 0° C. To this solution a solution of KOH (15.6 g, 283.2 mmol) in water (24 mL) was added. The resulting solution was treated with 320 g of ice. The diazonium salt of 4-methoxyaniline was immediately added. The mixture was then adjusted to pH 5-6 and stirred at 0° C. for 4 h. The solution was stored at 4° C. overnight and extracted with EA (4×200 mL). The combined extracts were washed with brine and dried by NaSO$_4$. Most of solvent was evaporated and the residue was directly used in next reaction (180 mL).

(Z)-ethyl 2-(2-(4-methoxyphenyl)hydrazono)butanoate (180 mL) was added dropwise to a solution of 3M HCl/EtOH (180 mL) at 80° C. After addition, the mixture was held at 80° C. for 3 h. The solvent was evaporated, and the residue was treated with water (60 mL) and DCM(300 mL). the aqueous layers were then extracted with DCM (3×100 mL). The combined organic layers were washed with brine (150 mL), dried over Na$_2$SO$_4$ and evaporated to dryness to give crude compound, which was triturated from Hex to afford product as a yellow solid (32.0 g, 53.2%).

Ethyl 5-methoxy-3-methyl-1H-indole-2-carboxylate (20.0 g,85.7 mmol) was dissolved in DCM (200 mL) and the mixture was cooled to −20° C., HNO$_3$ (70%, 9 mL) was added and the mixture was stirred for 20 min. It was neutralized with NaHO$_3$ and extracted with DCM (3×100 mL), dried with NaSO$_4$ and concentrated to dryness. Crude product was purified by flash chromatography to afford product as a yellow solid (15.5 g, 59.3%).

MeI (30 mL) was added to ethyl 5-methoxy-3-methyl-4-nitro-1H-indole-2-carboxylate (14.5 g, 52.1 mmol) in acetone (500 mL) containing KOH (10 g.178 mmol). After addition, the mixture was stirred at room temperature for 1 h. The solvent was decanted from the excess KOH, and the mixture was neutralized with HCl. Then the mixture was extracted with DCM (3×100 mL). The combined organic layers were washed with brine (150 mL), dried over Na$_2$SO$_4$ and evaporated to dryness to give crude compound, which was triturated from Hex and DCM to afford product as a yellow solid (14.0 g, 53.2%).

Tin powder (9.14 g, 77 mol) was added to a suspension of ethyl 5-methoxy-1,3-dimethyl-4-nitro-1H-indole-2-carboxylate (5.0 g,17.1 mmol) in ethanol (500 mL). 3 N HCl (130 mL) was then added. The reaction was stirred at rt for 2 hours. The solvent was removed, and the residue was diluted with water and neutralized with saturated NaHCO$_3$. The mixture was filtered and washed with DCM. The organic phase was separated, and the aqueous phase was extracted with DCM. The combined organic phase was washed with brine, dried and concentrated to get crude product, which was triturated from EA/Hex=1/20 to afford product as a gray solid (4.0 g, 80%).

Ethyl 4-amino-5-methoxy-1,3-dimethyl-1H-indole-2-carboxylate (1.5 g,5.72 mmol) was dissolved in 90 mL THF. 0.88 g (22.68 mmol, 4 eq.) LiAlH$_4$ was dissolved in 180 mL THF and cooled to 0° C. The solution of ethyl 4-amino-5-methoxy-1,3-dimethyl-1H-indole-2-carboxylate was added to the LiAlH$_4$ solution dropwise. The reaction was allowed to reach rt and stirred for 30 min at rt. It was then quenched with water, NaOH and silica gel. It was then filtered through celite, dried with MgSO$_4$ and evaporated. The residue was dissolved in 170 mL of acetone and was used directly in the next reaction. To 180 mL of a 0.3 M solution of NaH$_2$PO$_4$, Fremy's salt (4.6 g, 17.16 mmol, 3 eq.) was added. This mixture was added to the hydroxymethyl indole in acetone and stirred at rt for 1 h. The excess acetone was removed in vacuo. The resulting residue was extracted with dichloromethane and washed with water. The organic layer was dried (MgSO$_4$) and evaporated. The crude product was purified by flash chromatography to get product as an orange solid (1.0 g, 56%).

1H NMR (400 MHz, CDCl3) δ 5.63 (s, 1H), 4.65 (s, 2H), 4.02 (s, 3H), 3.81 (s, 3H), 2.34 (s, 3H).

Example 24D

Synthesis of Quinone 4

Quinone 4 was prepared according to the following reaction scheme:

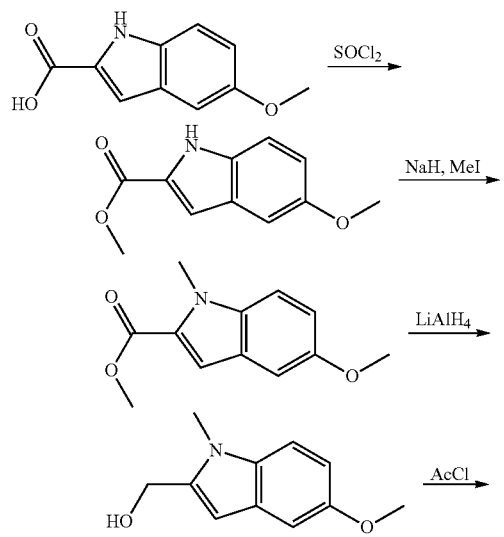

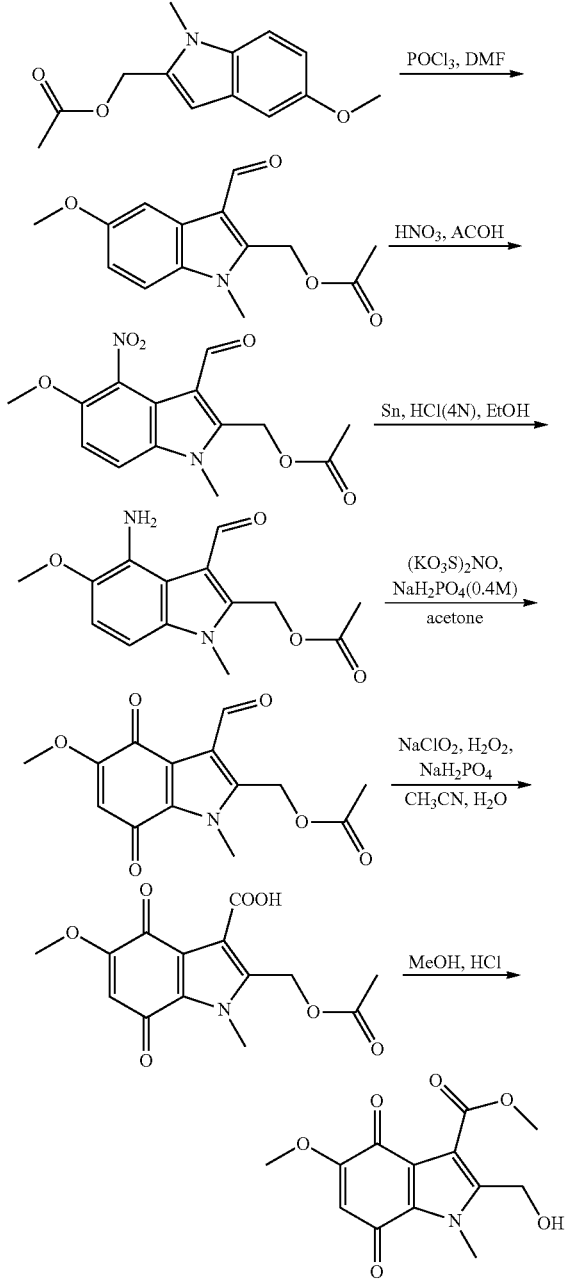

Into a 250-mL round-bottom flask was placed a solution of 5-methoxy-1H-indole-2-carboxylic acid (10 g, 52.31 mmol, 1.00 equiv) in methanol (100 mL), followed by the addition of thionyl chloride (12.5 g, 105.07 mmol, 2.00 equiv) dropwise with stirring. The resulting solution was heated to reflux for 4 h, cooled to room temperature and concentrated under vacuum to afford 11 g (crude) of methyl 5-methoxy-1H-indole-2-carboxylate as a gray solid.

Into a 5-L 4-necked round-bottom flask, purged and maintained with an inert atmosphere of nitrogen, was placed N,N-dimethylformamide (2 L), followed by the addition of sodium hydride (37.6 g, 1.10 mol, 1.50 equiv, 70%) in several batches with stirring. To this was added methyl 5-methoxy-1H-indole-2-carboxylate (150 g, 730.96 mmol, 1.00 equiv) dropwise with stirring at less than 10° C. The mixture was stirred for 0.5 h. To the mixture was added MeI (125 g, 0.88 mol, 1.20 equiv) dropwise with stirring. The resulting solution was stirred overnight at room temperature and diluted with 5 L of water. The solids were collected by filtration, washed with 3×1 L of water and dried to afford 163 g (crude) of methyl 5-methoxy-1-methyl-1H-indole-2-carboxylate as a yellow solid.

Into a 5000-mL 4-necked round-bottom flask purged and maintained with an inert atmosphere of nitrogen was placed a solution of LiAlH$_4$ (111 g, 2.92 mol, 4.00 equiv) in tetrahydrofuran (1500 mL), followed by the addition of a solution of methyl 5-methoxy-1-methyl-1H-indole-2-carboxylate (160 g, 729.81 mmol, 1.00 equiv) in tetrahydrofuran (1000 mL) dropwise with stirring at 0° C. over 30 min. The mixture was stirred at 0° C. for 1 h and at room temperature for 3 h. The mixture was then quenched by the addition of 111 g of water, 333 mL of aqueous NaOH (15%) and 111 g of water at 0° C. The solids were filtered out. The filtrate was dried over anhydrous sodium sulfate and concentrated under vacuum to afford 100 g (72%) of (5-methoxy-1-methyl-1H-indol-2-yl)methanol as a yellow solid.

Into a 3000-mL 4-necked round-bottom flask purged and maintained with an inert atmosphere of nitrogen was placed a solution of (5-methoxy-1-methyl-1H-indol-2-yl)methanol (100 g, 522.94 mmol, 1.00 equiv) in dichloromethane (2000 mL), followed by the addition of triethylamine (61.6 g, 608.76 mmol, 1.50 equiv) dropwise with stirring at rt. The mixture was stirred for 30 min. To this was added acetyl chloride (79 g, 1.01 mol, 1.50 equiv) dropwise with stirring at room temperature. The resulting solution was stirred at room temperature for 3 h and concentrated under vacuum. The residue was purified on a silica gel column eluting with ethyl acetate: petroleum ether (1:10-1:5) to afford 75 g (61%) of (5-methoxy-1-methyl-1H-indol-2-yl)methyl acetate as a yellow solid.

Into a 250-mL 3-necked round-bottom flask purged and maintained with an inert atmosphere of nitrogen was placed N,N-dimethylformamide (20 g, 273.64 mmol, 6.00 equiv), followed by the addition of POCl$_3$ (9.85 g, 0.0642 mol, 1.50 equiv) dropwise with stirring at 0° C. The mixture was stirred at room temperature for 30 min. To this was added (5-methoxy-1-methyl-1H-indol-2-yl)methyl acetate (10 g, 42.87 mmol, 1.00 equiv) in portions with stirring at less than 0° C. The resulting solution was stirred at room temperature for 2 h and quenched by the addition of 100 mL of water/ice. The pH value of the solution was adjusted to 7-8 with aqueous sodium hydroxide (2 N). The resulting solution was extracted with 3×200 mL of ethyl acetate. The organic layers were combined, dried over anhydrous sodium sulfate and concentrated under vacuum. The residue was purified on a silica gel column eluting with ethyl acetate: petroleum ether (1:3) to afford 9 g (80%) of (3-formyl-5-methoxy-1-methyl-1H-indol-2-yl)methyl acetate as a yellow solid.

Into a 250-mL 3-necked round-bottom flask purged and maintained with an inert atmosphere of nitrogen was placed (3-formyl-5-methoxy-1-methyl-1H-indol-2-yl)methyl acetate (9 g, 3.60 mmol, 1.00 equiv), AcOH (100 mL), followed by the addition of a solution of HNO$_3$ (20 mL) in AcOH (50 mL) dropwise with stirring at less than 5° C. The resulting solution was stirred at room temperature for 30 min, diluted with 1000 mL of water and stirred for 30 min. The solids were collected by filtration, washed with 3×100 mL of water and dried to afford 8.6 g (crude) of (3-formyl-5-methoxy-1-methyl-4-nitro-1H-indol-2-yl)methyl acetate as a light red solid.

Into a 1000-mL 3-necked round-bottom flask purged and maintained with an inert atmosphere of nitrogen was placed (3-formyl-5-methoxy-1-methyl-4-nitro-1H-indol-2-yl)methyl acetate (8 g, 26.12 mmol, 1.00 equiv), ethanol (400 mL), followed by the addition of Sn (34.1 g, 11.00 equiv) in portions with stirring at 0° C. To this was added hydrogen chloride (4 N) (400 mL) dropwise with stirring. The resulting solution was stirred at 0° C. for 2 h, concentrated under vacuum and diluted with 500 mL of water. The pH value of the solution was adjusted to 7-8 with saturated aqueous sodium bicarbonate. The solids were filtered out and washed with 3×50 mL of EA. The filtrate was extracted with 4×200 mL of ethyl acetate. The organic layers were combined, dried over anhydrous sodium sulfate and concentrated under vacuum. The residue was purified on a silica gel column eluting with ethyl acetate: petroleum ether (1:2) to afford 6.5 g (90%) of (4-amino-3-formyl-5-methoxy-1-methyl-1H-indol-2-yl)methyl acetate as a yellow solid.

Into a 2000-mL 3-necked round-bottom flask purged and maintained with an inert atmosphere of nitrogen was placed (4-amino-3-formyl-5-methoxy-1-methyl-1H-indol-2-yl)methyl acetate (6 g, 21.72 mmol, 1.00 equiv), acetone (600 mL), followed by the addition of a solution of (KO$_3$S)$_2$NO (17.48 g, 65.2 mol, 3.00 equiv) in NaH$_2$PO$_4$ (0.4 M) (1200 mL) dropwise with stirring at less than 10° C. The resulting solution was stirred at room temperature for 2 h and concentrated under vacuum. The residue was extracted with 3×300 mL of dichloromethane. The organic layers were combined, washed with 3×300 mL of water, dried over anhydrous sodium sulfate and concentrated under vacuum. The residue was purified on a silica gel column eluting with ethyl acetate: petroleum ether (1:2) to afford 3.5 g (55%) of (3-formyl-5-methoxy-1-methyl-4,7-dioxo-4,7-dihydro-1H-indol-2-yl)methyl acetate as a yellow solid.

Into a 500-mL 3-necked round-bottom flask was placed (3-formyl-5-methoxy-1-methyl-4,7-dioxo-4,7-dihydro-1H-indol-2-yl)methyl acetate (3.5 g, 12.02 mmol, 1.00 equiv), CH$_3$CN (200 mL), NaH$_2$PO$_4$ (0.6 g, 4 mmol, 0.30 equiv), H$_2$O$_2$ (2 g, 59 mmol, 5.00 equiv), NaClO$_2$ (2.5 g, 28 mmol, 2.41 equiv), and H$_2$O (50 mL). The resulting solution was stirred at room temperature for 2 h and quenched by the addition of 500 mL of water. The pH value of the solution was adjusted to 2 with HCl (2 mol/L). The resulting solution was extracted with 4×300 mL of ethyl acetate. The organic layers were combined, washed with 2×200 mL of brine, dried over anhydrous sodium sulfate and concentrated under vacuum to afford 3.5 g (95%) of 2-[(acetyloxy)methyl]-5-methoxy-1-methyl-4,7-dioxo-4,7-dihydro-1H-indole-3-carboxylic acid as a red solid.

Into a 250-mL 3-necked round-bottom flask purged and maintained with an inert atmosphere of nitrogen was placed 2-[(acetyloxy)methyl]-5-methoxy-1-methyl-4,7-dioxo-4,7-dihydro-1H-indole-3-carboxylic acid (3.8 g, 12.37 mmol, 1.00 equiv), methanol (100 mL), and hydrogen chloride (20 mL). The resulting solution was stirred at 60° C. for 4 h, concentrated under vacuum, quenched by the addition of 500 mL of water and extracted with 4×200 mL of ethyl acetate. The organic layers were combined, dried over anhydrous sodium sulfate and concentrated under vacuum. The residue was purified on a silica gel column eluting with ethyl acetate: petroleum ether (1:3). The crude product was purified by Prep-HPLC to afford 0.3 g (9%) of methyl 2-(hydroxymethyl)-5-methoxy-1-methyl-4,7-dioxo-4,7-dihydro-1H-indole-3-carboxylate as a yellow solid.

LC-MS (ES, m/z): 280 [M+H]+. 1H-NMR-300 MHz, CDCl3, ppm): δ 5.73 (s, 1H), 4.77 (s, 2H), 4.09 (s, 3H), 3.95 (s, 3H), 3.85 (s, 3H).

Example 24E

Synthesis of Quinone 5

Quinone 5 was prepared according to the following reaction scheme:

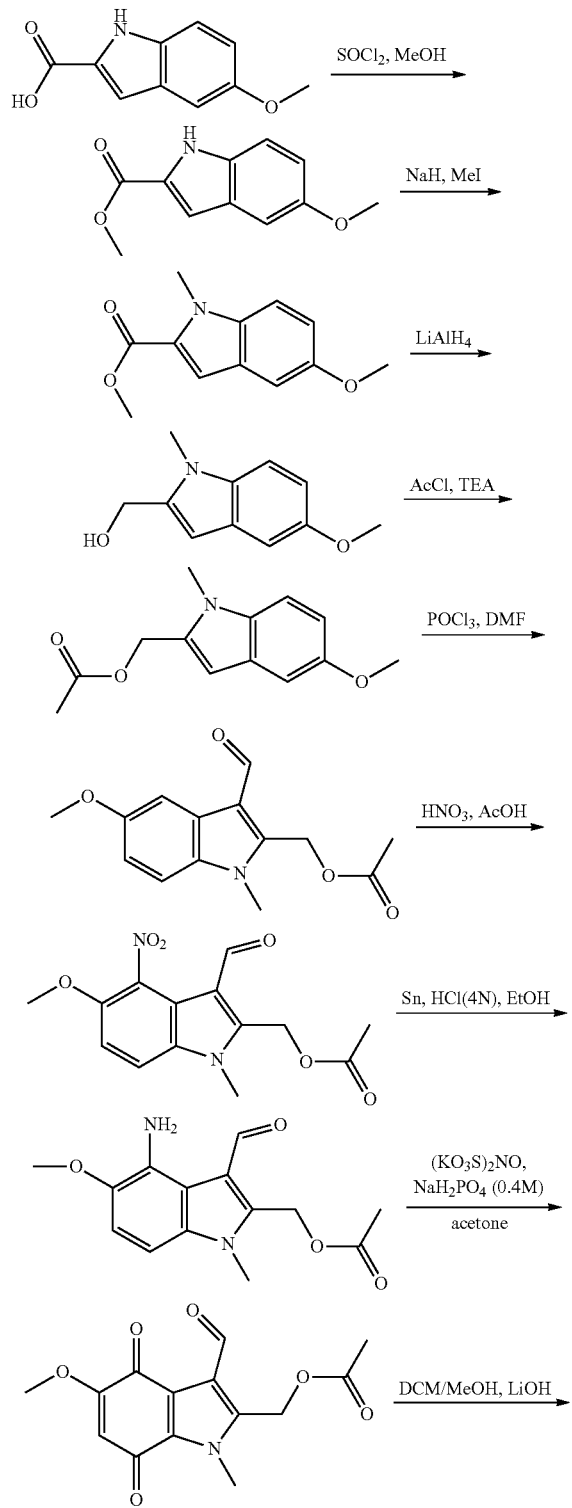

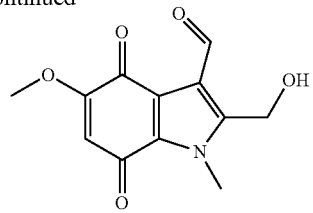

Into a 250-mL round-bottom flask was placed a solution of 5-methoxy-1H-indole-2-carboxylic acid (10 g, 52.31 mmol, 1.00 equiv) in methanol (100 mL), followed by the addition of thionyl chloride (12.5 g, 105.07 mmol, 2.00 equiv) dropwise with stirring. The resulting solution was heated to reflux for 4 h, cooled to room temperature and concentrated under vacuum to afford 11 g (crude) of methyl 5-methoxy-1H-indole-2-carboxylate as a gray solid.

Into a 5-L 4-necked round-bottom flask purged and maintained with an inert atmosphere of nitrogen was placed N,N-dimethylformamide (2 L), followed by the addition of sodium hydride (37.6 g, 1.10 mol, 1.50 equiv, 70%) in several batches with stirring. To this was added methyl 5-methoxy-1H-indole-2-carboxylate (150 g, 730.96 mmol, 1.00 equiv) dropwise with stirring at less than 10° C. The mixture was stirred for 0.5 h. To the mixture was added MeI (125 g, 0.88 mol, 1.20 equiv) dropwise with stirring. The resulting solution was stirred overnight at room temperature and diluted with 5 L of water. The solids were collected by filtration, washed with 3×1 L of water and dried to afford 163 g (crude) of methyl 5-methoxy-1-methyl-1H-indole-2-carboxylate as a yellow solid.

Into a 5000-mL 4-necked round-bottom flask purged and maintained with an inert atmosphere of nitrogen was placed a solution of LiAlH$_4$ (111 g, 2.92 mol, 4.00 equiv) in tetrahydrofuran (1500 mL), followed by the addition of a solution of methyl 5-methoxy-1-methyl-1H-indole-2-carboxylate (160 g, 729.81 mmol, 1.00 equiv) in tetrahydrofuran (1000 mL) dropwise with stirring at 0° C. over 30 min. The mixture was stirred at 0° C. for 1 h and at room temperature for 3 h. The mixture was then quenched by the addition of 111 g of water, 333 mL of aqueous NaOH (15%) and 111 g of water at 0° C. The solids were filtered out. The filtrate was dried over anhydrous sodium sulfate and concentrated under vacuum to afford 100 g (72%) of (5-methoxy-1-methyl-1H-indol-2-yl)methanol as a yellow solid.

Into a 3000-mL 4-necked round-bottom flask purged and maintained with an inert atmosphere of nitrogen was placed a solution of (5-methoxy-1-methyl-1H-indol-2-yl)methanol (100 g, 522.94 mmol, 1.00 equiv) in dichloromethane (2000 mL), followed by the addition of triethylamine (61.6 g, 608.76 mmol, 1.50 equiv) dropwise with stirring at room temperature. The mixture was stirred for 30 min. To this was added acetyl chloride (79 g, 1.01 mol, 1.50 equiv) dropwise with stirring at room temperature. The resulting solution was stirred at room temperature for 3 h and concentrated under vacuum. The residue was purified on a silica gel column eluting with ethyl acetate: petroleum ether (1:10-1:5) to afford 75 g (61%) of (5-methoxy-1-methyl-1H-indol-2-yl)methyl acetate as a yellow solid.

Into a 250-mL 3-necked round-bottom flask purged and maintained with an inert atmosphere of nitrogen was placed N,N-dimethylformamide (20 g, 273.64 mmol, 6.00 equiv), followed by the addition of POCl$_3$ (9.85 g, 0.0642 mol, 1.50 equiv) dropwise with stirring at 0° C. The mixture was stirred at room temperature for 30 min. To this was added (5-methoxy-1-methyl-1H-indol-2-yl)methyl acetate (10 g, 42.87 mmol, 1.00 equiv) in portions with stirring at less than 0° C. The resulting solution was stirred at room temperature for 2 h and quenched by the addition of 100 mL of water/ice. The pH value of the solution was adjusted to 7-8 with aqueous sodium hydroxide (2 N). The resulting solution was extracted with 3×200 mL of ethyl acetate. The organic layers were combined, dried over anhydrous sodium sulfate and concentrated under vacuum. The residue was purified on a silica gel column eluting with ethyl acetate: petroleum ether (1:3) to afford 9 g (80%) of (3-formyl-5-methoxy-1-methyl-1H-indol-2-yl)methyl acetate as a yellow solid.

Into a 250-mL 3-necked round-bottom flask purged and maintained with an inert atmosphere of nitrogen was placed (3-formyl-5-methoxy-1-methyl-1H-indol-2-yl)methyl acetate (9 g, 3.60 mmol, 1.00 equiv), AcOH (100 mL), followed by the addition of a solution of $HNO_3$ (20 mL) in AcOH (50 mL) dropwise with stirring at less than 5° C. The resulting solution was stirred at room temperature for 30 min, diluted with 1000 mL of water and stirred for 30 min. The solids were collected by filtration, washed with 3×100 mL of water and dried to afford 8.6 g (crude) of (3-formyl-5-methoxy-1-methyl-4-nitro-1H-indol-2-yl)methyl acetate as a light red solid.

Into a 1000-mL 3-necked round-bottom flask purged and maintained with an inert atmosphere of nitrogen was placed (3-formyl-5-methoxy-1-methyl-4-nitro-1H-indol-2-yl) methyl acetate (8 g, 26.12 mmol, 1.00 equiv), ethanol (400 mL), followed by the addition of Sn (34.1 g, 11.00 equiv) in portions with stirring at 0° C. To this was added hydrogen chloride (4 N) (400 mL) dropwise with stirring. The resulting solution was stirred at 0° C. for 2 h, concentrated under vacuum and diluted with 500 mL of water. The pH value of the solution was adjusted to 7-8 with saturated aqueous sodium bicarbonate. The solids were filtered out and washed with 3×50 mL of EA. The filtrate was extracted with 4×200 mL of ethyl acetate. The organic layers were combined, dried over anhydrous sodium sulfate and concentrated under vacuum. The residue was purified on a silica gel column eluting with ethyl acetate: petroleum ether (1:2) to afford 6.5 g (90%) of (4-amino-3-formyl-5-methoxy-1-methyl-1H-indol-2-yl)methyl acetate as a yellow solid.

Into a 2000-mL 3-necked round-bottom flask purged and maintained with an inert atmosphere of nitrogen was placed (4-amino-3-formyl-5-methoxy-1-methyl-1H-indol-2-yl) methyl acetate (6 g, 21.72 mmol, 1.00 equiv), acetone (600 mL), followed by the addition of a solution of $(KO_3S)_2NO$ (17.48 g, 65.2 mol, 3.00 equiv) in $NaH_2PO_4$ (0.4 M) (1200 mL) dropwise with stirring at less than 10° C. The resulting solution was stirred at room temperature for 2 h and concentrated under vacuum. The residue was extracted with 3×300 mL of dichloromethane. The organic layers were combined, washed with 3×300 mL of water, dried over anhydrous sodium sulfate and concentrated under vacuum. The residue was purified on a silica gel column eluting with ethyl acetate: petroleum ether (1:2) to afford 3.5 g (55%) of (3-formyl-5-methoxy-1-methyl-4,7-dioxo-4,7-dihydro-1H-indol-2-yl)methyl acetate as a yellow solid.

Into a 250-mL 3-necked round-bottom flask was placed (3-formyl-5-methoxy-1-methyl-4,7-dioxo-4,7-dihydro-1H-indol-2-yl)methyl acetate (3.5 g, 12.02 mmol, 1.00 equiv), dichloromethane (47 mL), followed by the addition of a solution of LiOH (380 mg, 15.87 mmol, 1.30 equiv) in methanol (40 mL) dropwise with stirring. The resulting solution was stirred at room temperature for 30 min, diluted with 80 mL of DCM and washed with 3×100 mL of water. The organic phase was dried over anhydrous sodium sulfate and concentrated under vacuum. The residue was purified on a silica gel column eluting with ethyl acetate: petroleum ether (1:2) to afford 1.1 g (37%) of 2-(hydroxymethyl)-5-methoxy-1-methyl-4,7-dioxo-4,7-dihydro-1H-indole-3-carbaldehyde as a yellow solid.

LC-MS (ES, m/z): 250 [M+H]+. 1H-NMR (CDCl3, 300 MHz, ppm): ☐ 10.55 (s, 1H), 5.79 (s, 1H), 4.83 (s, 2H), 4.09 (s, 3H), 3.89 (s, 3H).

Example 24F

Synthesis of Quinone 6

Quinone 6 was prepared according to the following reaction scheme:

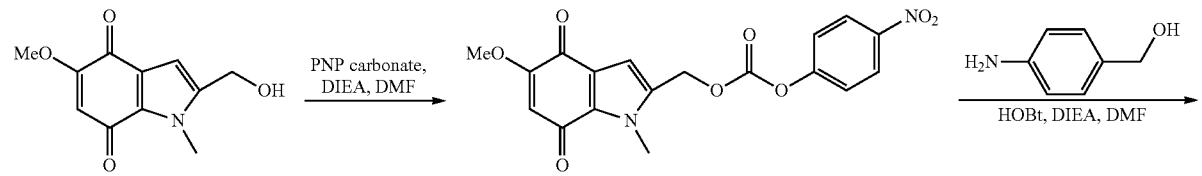

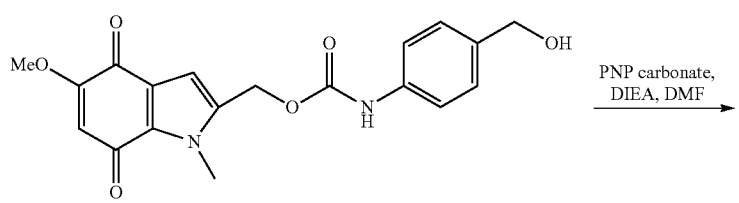

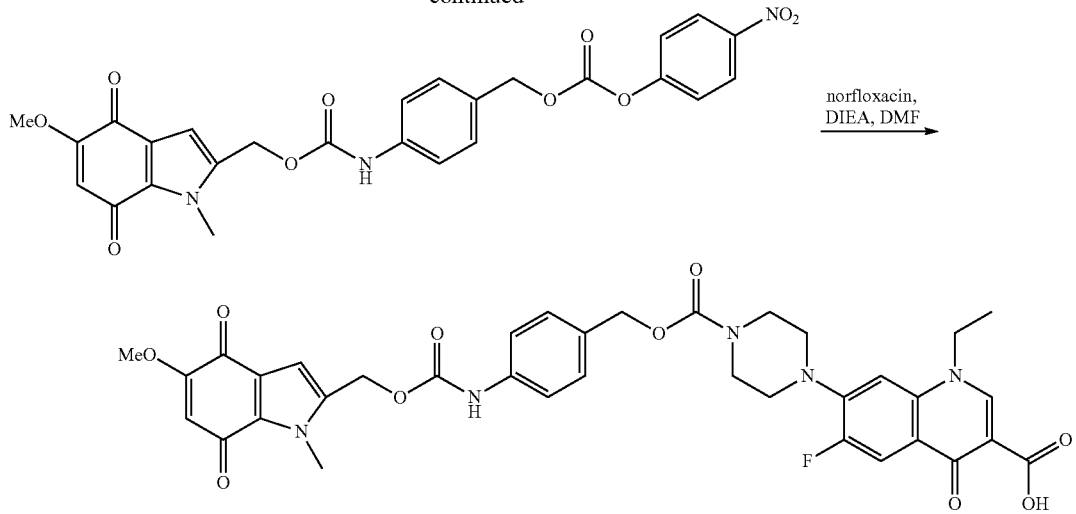

To a stirred solution of compound 1 (30 mg, 0.135 mmol) in dry DMF (2.0 mL) was added bis(4-nitrophenyl) carbonate (82.5 mg, 0.271 mmol) and DIEA (87.5 mg, 0.678 mmol) at 0° C., then the mixture was stirred at 25° C. for 2 h under $N_2$. The mixture was used for next step without further purification.

To a mixture of above was added compound 3 (100.2 mg, 0.814 mmol), DIEA (87.6 mg, 0.678 mmol), DMF (2.0 mL) and catalytic amount of HOBt (5.0 mg) at 0° C. Then the mixture was stirred at 25° C. for 15 h under $N_2$. It was diluted with water (15 mL), and extracted it with EtOAc (30 mL×4). The combined organic phase was washed it with brine (30 mL), dried over $Na_2SO_4$, and concentrated to give the desired product (26 mg, 52%) as a red solid. LCMS: (5-95 AB, 1.5 min), 0.714 min, MS=392.8 [M+23].

To a solution of compound 4 (26 mg, 0.070 mmol) in dry DMF (1.0 mL) was added bis(4-nitrophenyl) carbonate (42.7 mg, 0.140 mmol) and DIEA (45.4 mg, 0.351 mmol) at 0° C. Then the mixture was stirred at 25° C. for 15 h under $N_2$. The mixture was used for next step without further purification.

To the solution of compound 5 (37.59 mg, 0.070 mmol) in dry DMF (1.0 mL) was added norfloxacin (44.83 mg, 0.140 mmol) and DIEA (45.36 mg, 0.351 mmol) at 0° C. The mixture was stirred at 25° C. for 2 h under $N_2$. It was filtered and the filtrate was purified by prep-HPLC (FA) to give the product (30 mg, 59.7%) as a yellow solid. LCMS: (5-95, AB, 1.5 min), RT=0.862 min, MS=715.9[M+1]+; 1H NMR (400 MHz, DMSO-d6) δ 9.86 (s, 1H), 8.95 (s, 1H), 8.28 (s, 1H), 7.95-7.93 (d, J=8.0 Hz, 1H), 7.46-7.44 (d, J=8.0 Hz, 2H), 7.33-7.31 (d, J=8.0, 2H), 7.19 (s, 1H), 6.68 (s, 1H), 5.85 (s, 1H), 5.22 (s, 2H), 5.04 (s, 2H), 4.57 (s, 2H), 3.96 (s, 3H), 3.77 (s, 3H), 3.60 (s, 8H), 1.40 (s, 3H).

Example 24G

Synthesis of Quinone 7

Quinone 7 was prepared according to the following reaction scheme:

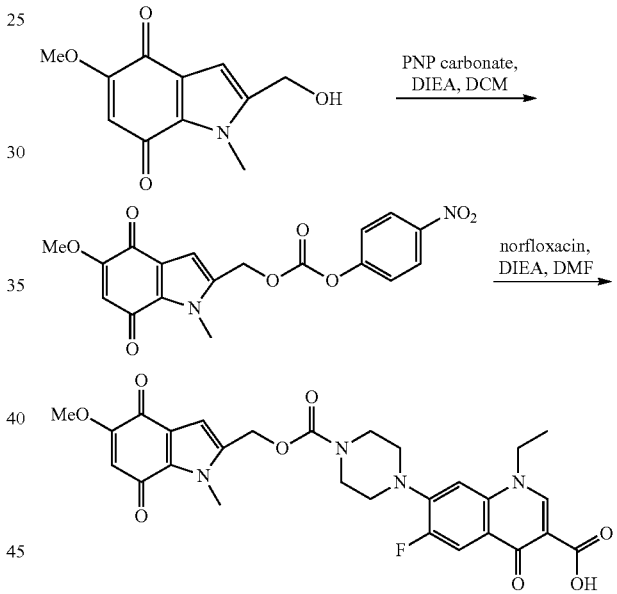

To a solution of compound 1 (100 mg, 0.45 mmol) in dry DMF (10 mL) was added bis(4-nitrophenyl) carbonate (280 mg, 0.9 mmol) and DIEA (175 mg, 1.36 mmol) at 30° C. The mixture was stirred at 30° C. for 16 h under $N_2$. It was used in the next step without further purification.

To a solution of compound 2, norfloxacin (288 mg, 0.9 mmol) in dry DMF (10.0 mL) was added DIEA (116 mg, 0.90 mmol) at 30° C. After the mixture was stirred at 30° C. for 2 h, it was filtered and the filter cake was washed with DCM/MeOH (10/1) and then concentrated to give the desired product as a yellow solid (150 mg, 59%).

LCMS: (5-95, AB, 1.5 min), RT=0.824 min, MS=566.9 [M+1]; 1H NMR (400 MHz, DMSO-d6) δ 8.89 (s, 1H), 7.94 (d, J=13.2 Hz, 1H), 7.20 (d, J=7.2 Hz, 1H), 6.63 (s, 1H), 5.83 (s, 1H), 5.22 (s, 2H), 4.57 (d, J=6.8 Hz, 2H), 3.97 (s, 2H), 3.80 (s, 2H), 3.63 (s, 3H), 3.37 (s, 3H), 3.21 (s, 4H), 1.46 (d, J=7.2 Hz, 3H).

235

Example 24H

Synthesis of Quinone 8

Quinone 8 was prepared according to the following reaction scheme:

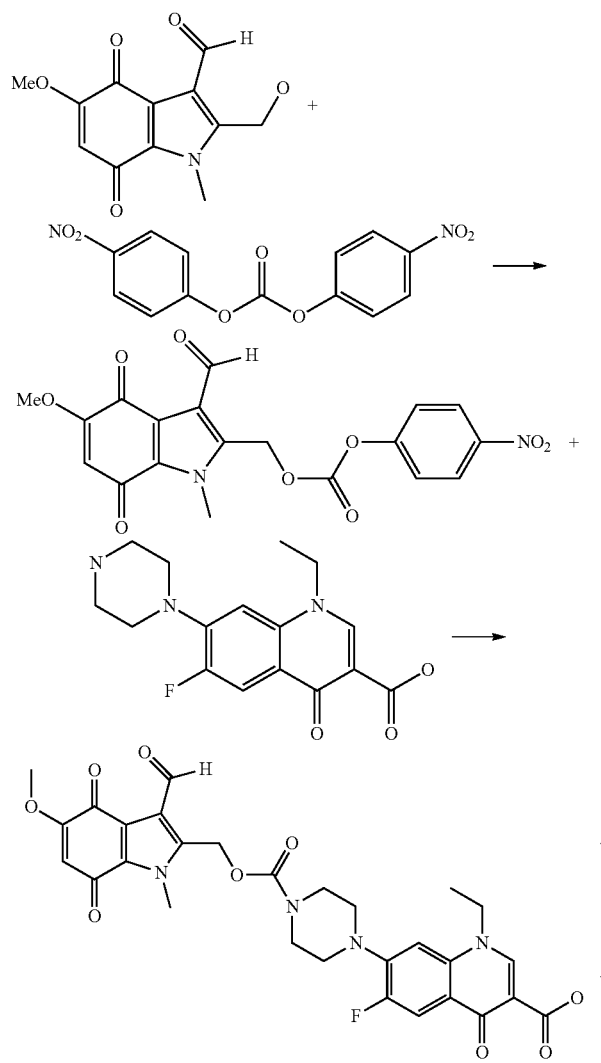

The alcohol (100 mg, 0.4 mmol) was dissolved in DMF (2 mL). p-nitrophenylcarbonate (610 mg, 2.0 mmol, 5 eq.) was added, followed by DIPEA (0.35 mL, 2.0 mmol, 5 eq.) and the reaction was stirred for 3 h at rt. The reaction was concentrated and carried on crude.

Norfloxacin (130 mg, 0.4 mmol, 1 eq.) was added to a vial, followed by the starting carbonate (200 mg, 0.4 mmol), followed by DMF (3 mL). HOBt (10 mg, 0.08 mmol, 0.2 eq.), then pyridine (0.3 mL, 4 mmol, 10 eq.) added and the reaction was stirred at rt for 19 h. The reaction was purified by HPLC to give 136 mg of the product (57% over two steps).

1H NMR (400 MHz, DMSO-d6) δ 10.40 (s, 1H), 8.96 (s, 1H), 7.94 (d, J=13.2 Hz, 1H), 7.20 (d, J=7.2 Hz, 1H), 5.99 (s, 1H), 5.49 (s, 2H), 4.58 (q, J=7.1 Hz, 2H), 4.02 (s, 3H), 3.83 (s, 3H), 3.63-3.48 (m, 5H), 2.07 (s, 3H), 1.41 (t, J=7.1 Hz, 3H).

236

Example 24I

Synthesis of Quinone 9

Quinone 9 was prepared according to the following reaction scheme:

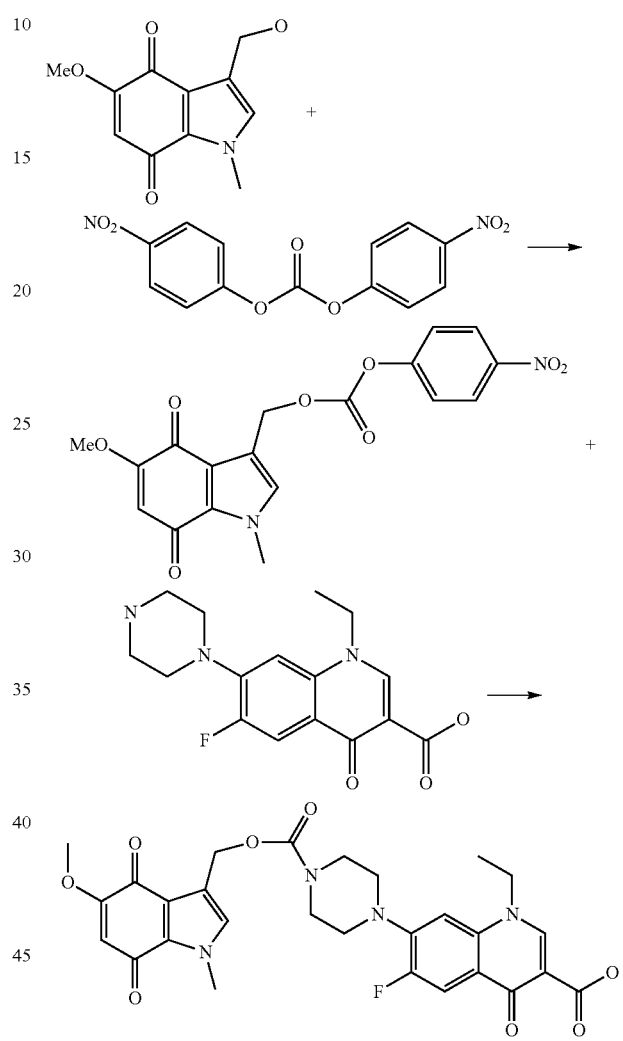

The alcohol (200 mg, 0.9 mmol) was dissolved in DMF (4 mL). p-nitrophenylcarbonate (284 mg, 1 mmol, 1.1 eq.) was added, followed by DIPEA (0.3 mL, 1.7 mmol, 2 eq.) and the reaction was stirred for 19 h at rt. The reaction was concentrated and carried on crude.

Norfloxacin (290 mg, 0.9 mmol, 1 eq.) was added to a vial, followed by the starting carbonate (350 mg, 0.9 mmol), followed by DMF (4 mL). HOBt (25 mg, 0.18 mmol, 0.2 eq.), then pyridine (0.74 mL, 9 mmol, 10 eq.) added and the reaction was stirred at rt for 24 h. The reaction was purified by HPLC to give 103 mg of the product (20% over two steps).

1H NMR (400 MHz, DMSO-d6) δ 8.99 (s, 1H), 7.98 (d, J=12.8 Hz, 1H), 7.31 (s, 1H), 7.24 (d, J=7.0 Hz, 1H), 5.86 (s, 1H), 5.19 (s, 2H), 4.61 (d, J=9.9 Hz, 4H), 3.92 (s, 3H), 3.80 (s, 3H), 3.63 (s, 6H), 1.58-1.33 (m, 3H).

Example 24J

Synthesis of Quinone 10

Quinone 10 was prepared according to the following reaction scheme:

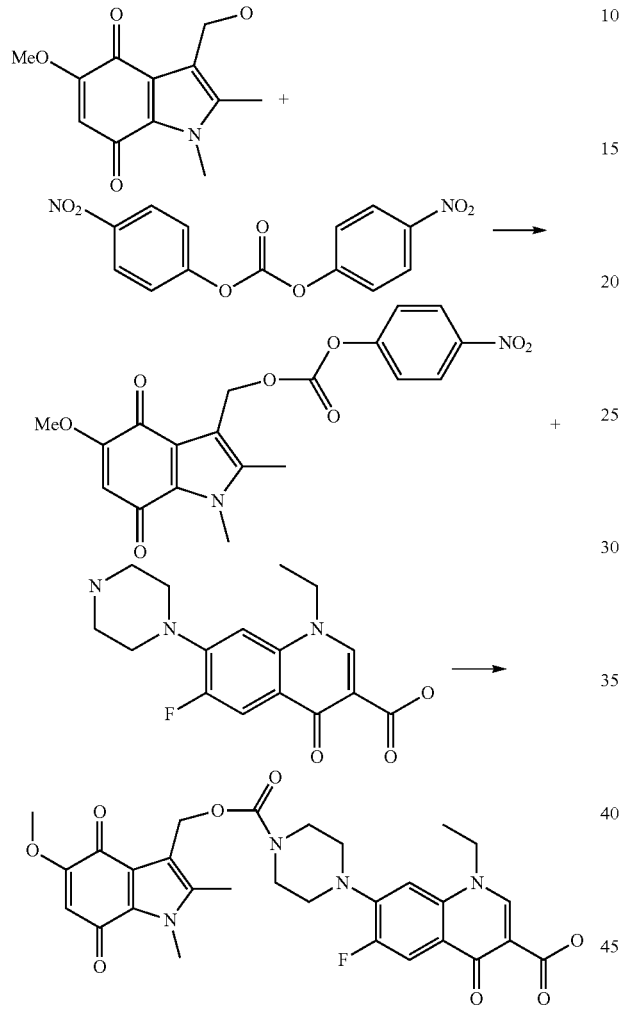

The alcohol (100 mg, 0.43 mmol) was dissolved in DMF (2 mL). p-nitrophenylcarbonate (142 mg, 0.47 mmol, 1.1 eq.) was added, followed by DIPEA (0.15 mL, 0.85 mmol, 2 eq.) and the reaction was stirred for 19 h at rt. The reaction was concentrated and carried on crude.

Norfloxacin (136 mg, 0.43 mmol, 1 eq.) was added to a vial, followed by the starting carbonate (170 mg, 0.43 mmol), followed by DMF (7 mL). HOBt (12 mg, 0.09 mmol, 0.2 eq.), then pyridine (0.35 mL, 4.3 mmol, 10 eq.) added and the reaction was stirred at rt for 24 h. The reaction was purified by HPLC to give 18 mg of the product (7% over two steps).

1H NMR (400 MHz, DMSO-d6) δ 8.95 (s, 1H), 8.48 (s, 1H), 7.94 (d, J=13.0 Hz, 1H), 7.20 (d, J=7.1 Hz, 1H), 6.80 (s, 1H), 5.78 (s, 1H), 5.17 (s, 2H), 4.58 (d, J=7.7 Hz, 2H), 3.86 (s, 3H), 3.76 (s, 4H), 3.53 (s, 5H), 2.28 (s, 3H), 1.40 (t, J=7.0 Hz, 3H).

Example 24K

Synthesis of Quinone 11

Quinone 11 was prepared according to the following reaction scheme:

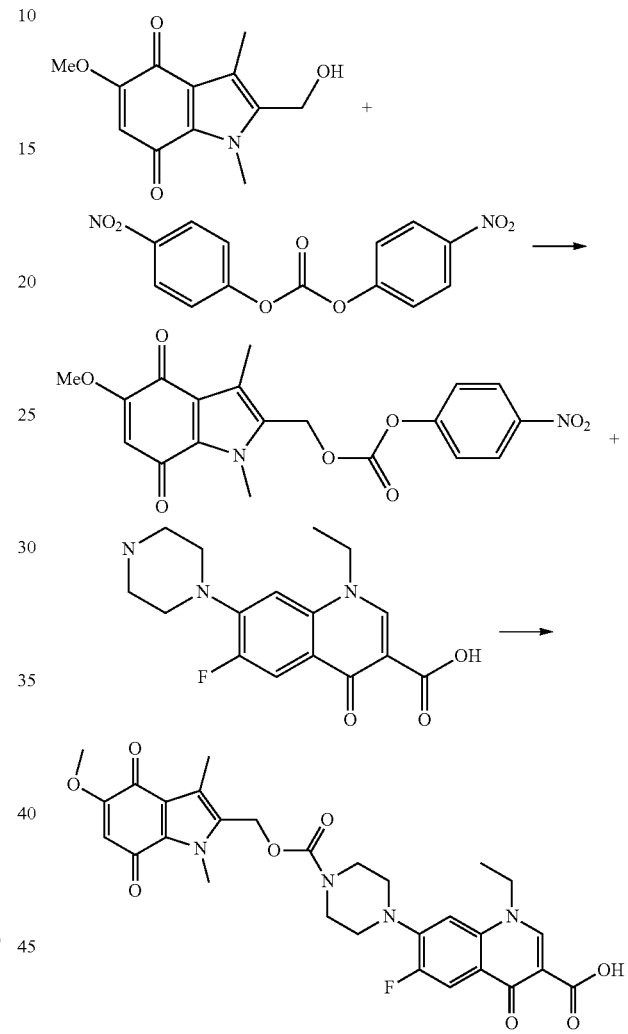

The alcohol (100 mg, 0.43 mmol) was dissolved in DMF (2 mL). p-nitrophenylcarbonate (142 mg, 0.47 mmol, 1.1 eq.) was added, followed by DIPEA (0.15 mL, 0.85 mmol, 2 eq.) and the reaction was stirred for 19 h at rt. The reaction was concentrated and carried on crude.

Norfloxacin (136 mg, 0.43 mmol, 1 eq.) was added to a vial, followed by the starting carbonate (170 mg, 0.43 mmol), followed by DMF (7 mL). HOBt (12 mg, 0.09 mmol, 0.2 eq.), then pyridine (0.35 mL, 4.3 mmol, 10 eq.) added and the reaction was stirred at rt for 24 h. The reaction was purified by HPLC to give 31 mg of the product (12% over two steps).

1H NMR (400 MHz, DMSO-d6) δ 8.95 (s, 1H), 8.49 (s, 2H), 7.94 (d, J=13.1 Hz, 1H), 6.76 (s, 2H), 5.19 (s, 2H), 4.58 (d, J=7.5 Hz, 2H), 3.96 (s, 3H), 3.83-3.69 (m, 5H), 3.58 (t, J=5.1 Hz, 4H), 2.30 (s, 3H), 1.40 (t, J=7.1 Hz, 3H).

Example 24L

Synthesis of Quinone 12

Quinone 12 was prepared according to the following reaction scheme:

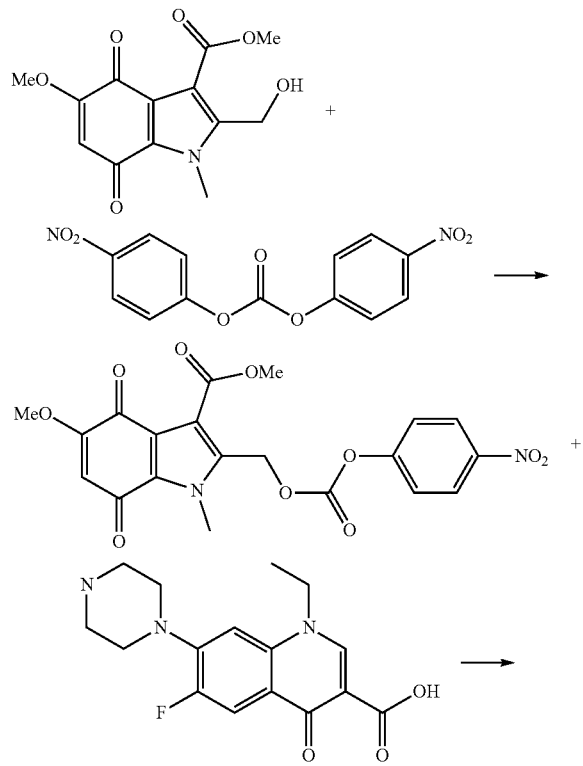

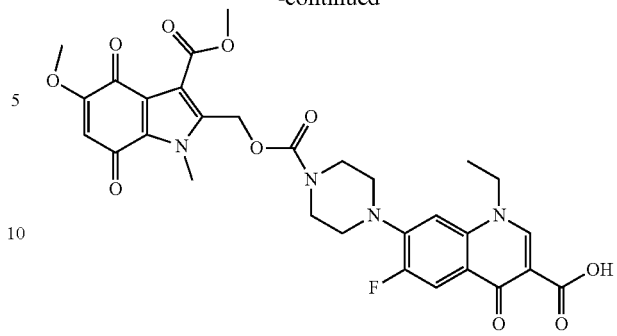

The alcohol (100 mg, 0.36 mmol) was dissolved in DMF (2 mL). p-nitrophenylcarbonate (545 mg, 1.8 mmol, 5 eq.) was added, followed by DIPEA (0.31 mL, 1.8 mmol, 5 eq.) and the reaction was stirred for 3 h at rt. The reaction was concentrated and carried on crude.

Norfloxacin (110 mg, 0.36 mmol, 1 eq.) was added to a vial, followed by the starting carbonate (160 mg, 0.36 mmol), followed by DMF (3 mL). HOBt (10 mg, 0.07 mmol, 0.2 eq.), then pyridine (0.29 mL, 3.6 mmol, 10 eq.) added and the reaction was stirred at rt for 19 h. Add more norfloxacin (110 mg, 0.36 mmol, 1 eq.) and the reaction was stirred for 2.5 days. The reaction was purified by HPLC to give 89 mg of the product (40% over two steps).

1H NMR (400 MHz, DMSO-d6) δ 8.96 (s, 1H), 7.94 (d, J=13.1 Hz, 1H), 7.20 (d, J=7.2 Hz, 1H), 5.93 (s, 1H), 5.32 (s, 2H), 4.58 (q, J=7.1 Hz, 2H), 4.00 (s, 3H), 3.80 (d, J=3.3 Hz, 6H), 3.64-3.49 (m, 8H), 1.41 (t, J=7.1 Hz, 3H).

Example 25

Synthesis of PBD Dimer Diaphorase Prodrug 1 Comprising a Linker for Conjugation to an Antibody PBD dimer diaphorase prodrug 1 comprising a linker was prepared according to the following reaction scheme:

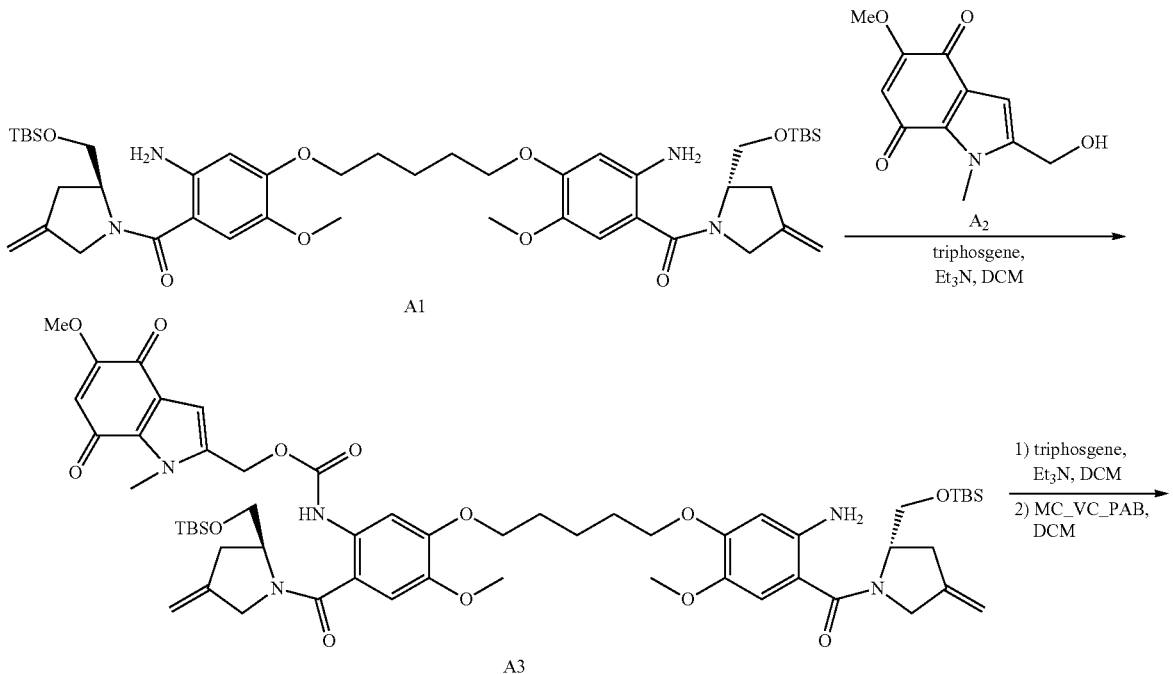

241                                                                                   242
-continued
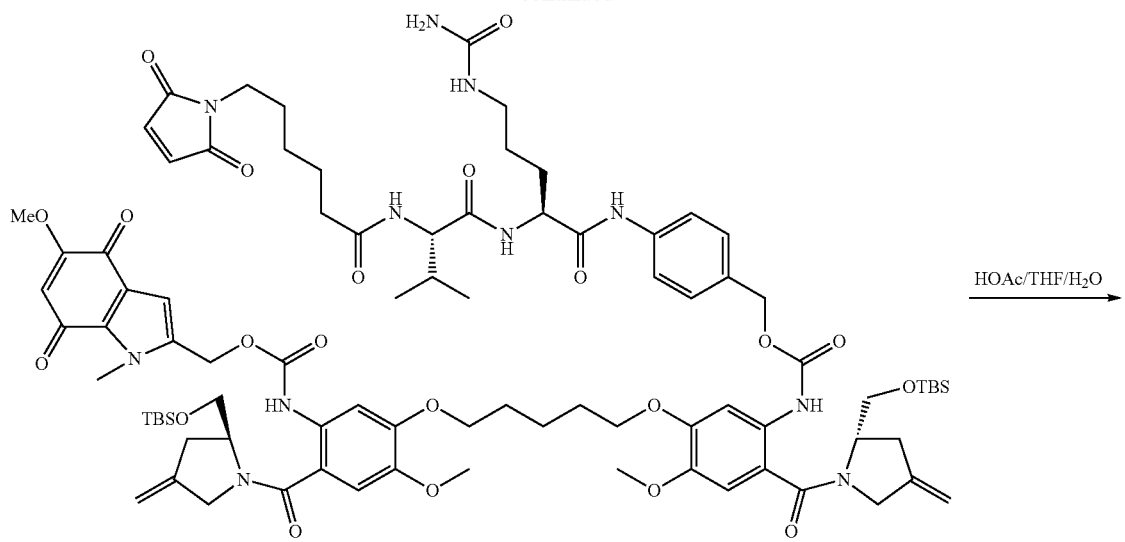
A4
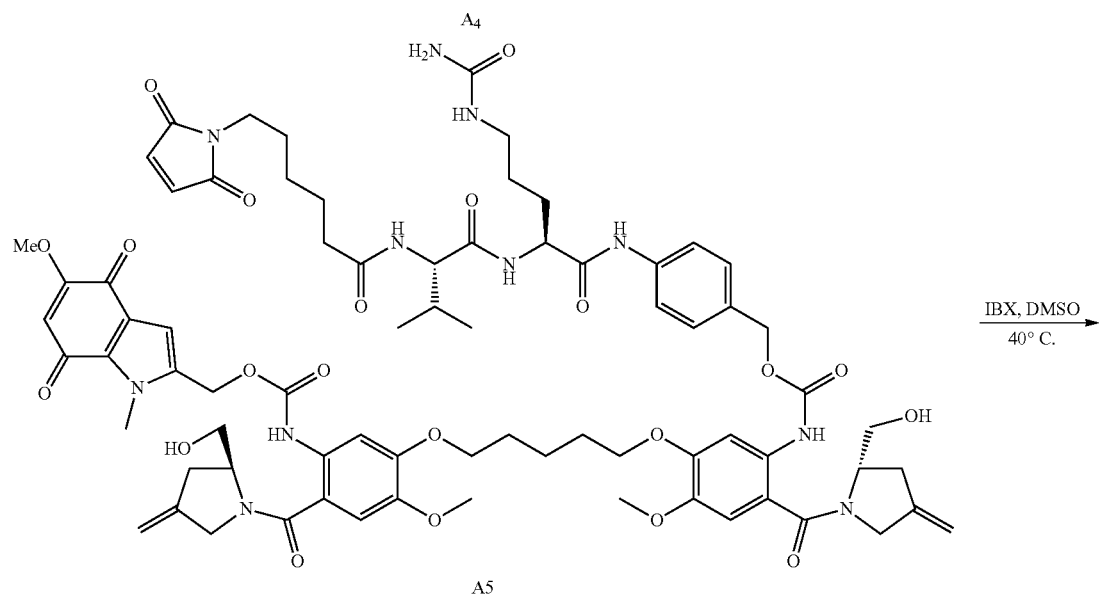
A5
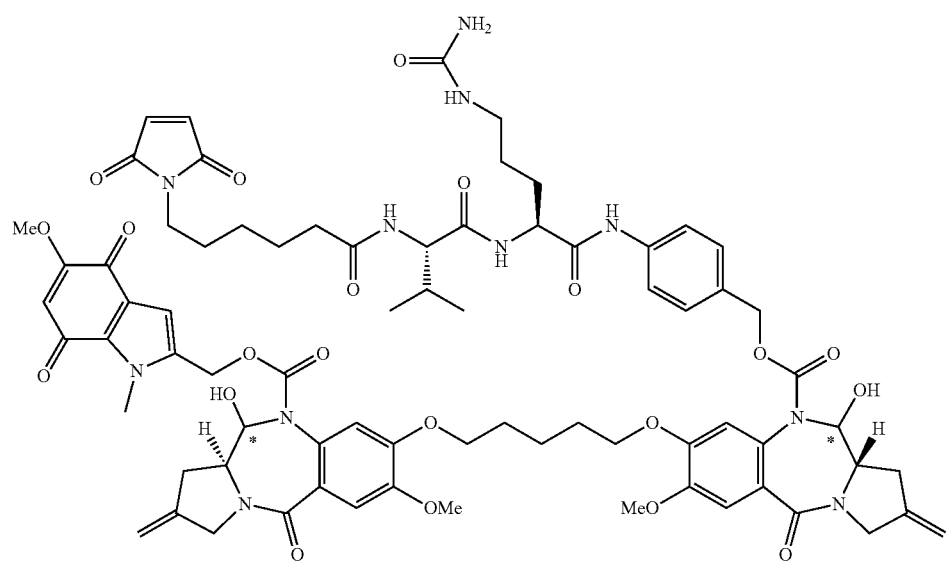

Each asterisk in the above structure, and elsewhere depicted in Example 25, represents a chiral center.

To a solution of compound A1 (1.00 g, 1.17 mmol) in DCM (30 mL) was added a solution of triphosgene (347 mg, 1.17 mmol) and Et$_3$N (356 mg, 3.52 mmol) in DCM (10 mL) at 30° C. After the mixture was stirred at 30° C. for 30 min, it was concentrated, and dibutyltin diacetate (0.32 mL, 1.22 mmol) was added, followed by a solution of Compound A2 (215 mg, 0.97 mmol) and Et$_3$N (369 mg, 3.65 mmol) in DMF (15 mL). The mixture was stirred at 25° C. for 1 h. The mixture was diluted with water (10 mL) and stirred for 20 min. Then the mixture was concentrated and purified by flash column chromatography (0-5% MeOH in DCM) to give Compound A3 (800 mg, 26.9%) as a yellow solid. LCMS (5-95, AB, 1.5 min): RT=1.032 min, m/z=1100.5 [M+1]+.

To a solution of triphosgene (97.1 mg, 0.33 mmol) in DCM (15 mL) was added a solution of Compound A3 (800.0 mg, 0.33 mmol) and Et$_3$N (99.31 mg, 0.98 mmol) in DCM (5.0 mL). After the mixture was stirred at 30° C. for 30 min, it was concentrated. To above residue was added a solution of MC_VC_PAB (368.0 mg, 0.33 mmol) and Et$_3$N (0.14 mL, 0.98 mmol) in DMF (15 mL). The mixture was stirred at 25° C. for 12 h. The mixture was concentrated and purified by flash column chromatography (5-10% MeOH in DCM) to give A4 (300 mg, 37%) as a yellow solid. LCMS (5-95, AB, 1.5 min): RT=1.023 min, m/z=850.5 [M/2+1]+.

To a solution of Compound A4 (300.0 mg, 0.18 mmol) in THF (1.0 mL) was added water (1.0 mL) and HOAc (1.5 mL), and stirred at 25° C. for 12 h. The mixture was diluted with EtOAc (80 mL), washed with sat. NaHCO$_3$ (3×40 mL), and concentrated to give Compound A5 (160 mg, 61.7%) as a red solid.

To a solution of Compound A5 (140.0 mg, 0.10 mmol) in DMSO (5.0 mL) was added IBX (266 mg, 0.95 mmol). After the mixture was stirred at 38° C. for 12 h, it was purified by prep-HPLC (ACN 37-67%/0.225% FA in water), followed by prep-TLC (10% MeOH in DCM, Rf=0.5) to give PBD dimer diaphorase prodrug 1 comprising a linker (15 mg, 10.5%) as a yellow solid. LCMS (5-95, AB, 1.5 min): RT=0.712 min, m/z=734.2 [M/2+1]+.

Example 26

Synthesis of PBD Dimer Prodrug Antibody-Drug Conjugates (ADC)

ADC 1A and 1B were prepared by conjugation of an antibody and the PBD dimer ADC disulfide prodrug linker-drug intermediate of Example 21D, and have the structure:

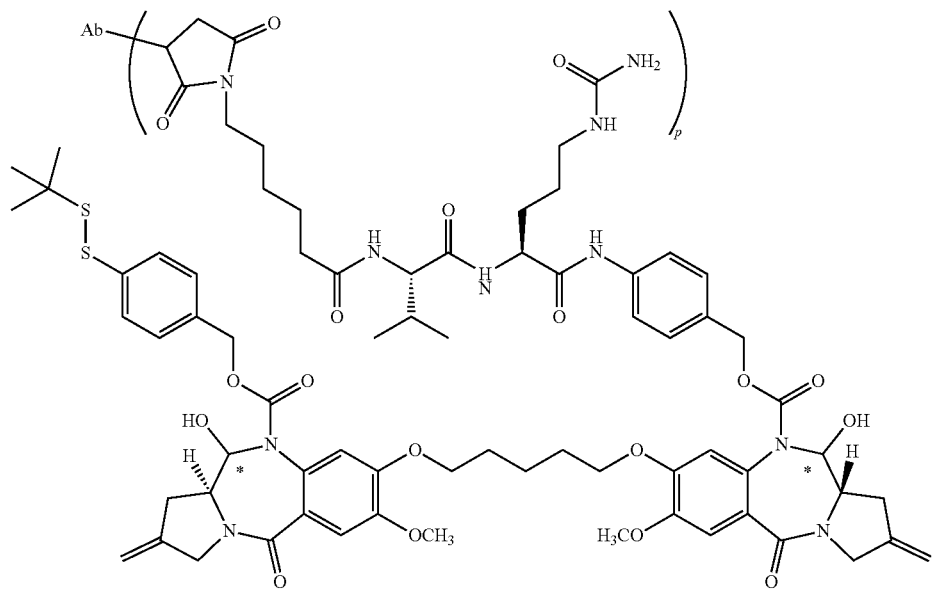

ADC 2A and 2B were prepared by conjugation of an antibody and the PBD dimer ADC disulfide prodrug linker-drug intermediate of Example 21B, and have the structure:
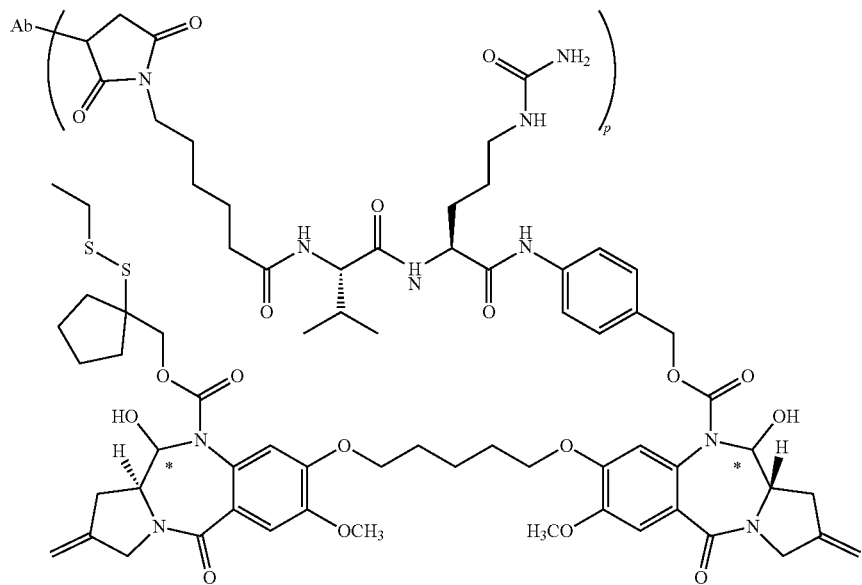
ADC 3 were prepared by conjugation of an antibody and the PBD dimer ADC disulfide prodrug linker-drug intermediate of Example 21A, and have the structure:
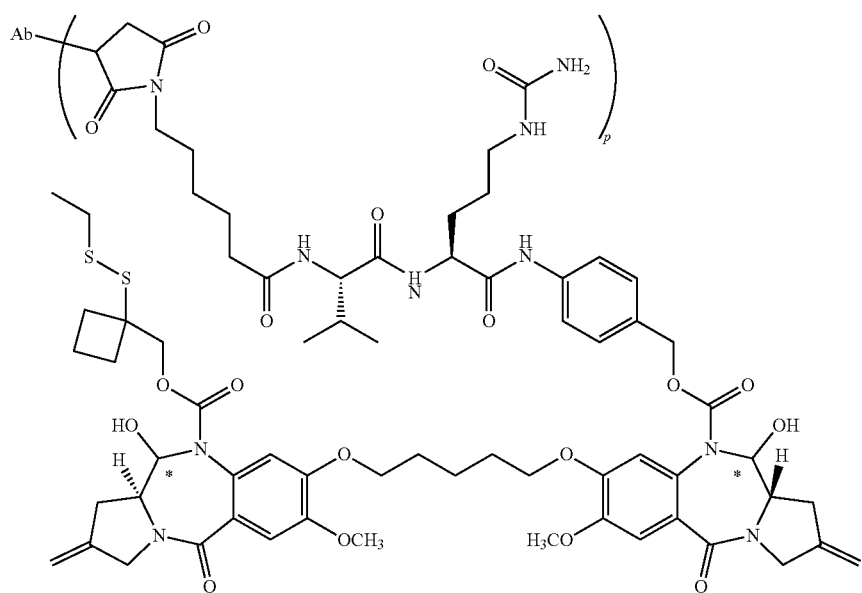

ADC 4 were prepared by conjugation of an antibody and the PBD dimer ADC disulfide prodrug linker-drug intermediate of Example 21C, and have the structure:
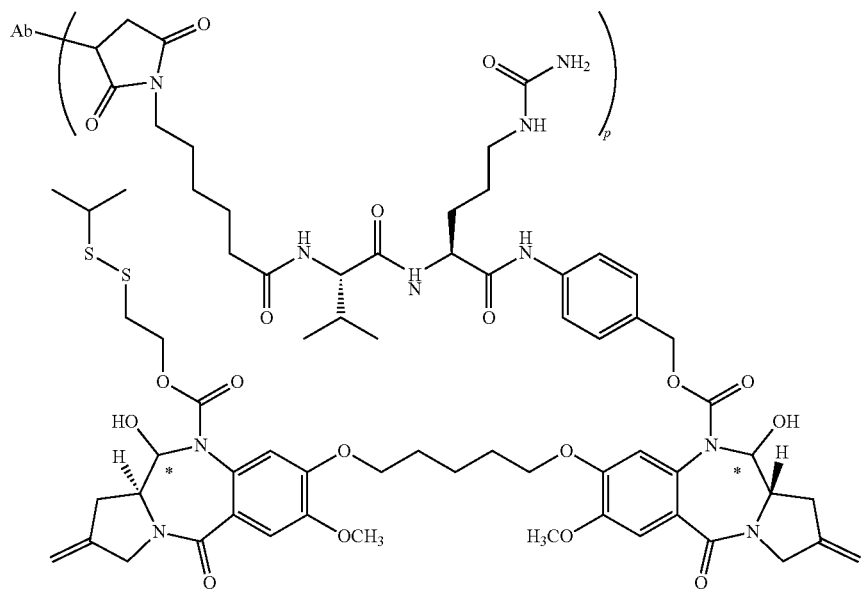
ADC 5 were prepared by conjugation of an antibody and the PBD dimer ADC disulfide prodrug linker-drug intermediate of Example 21E, and have the structure:
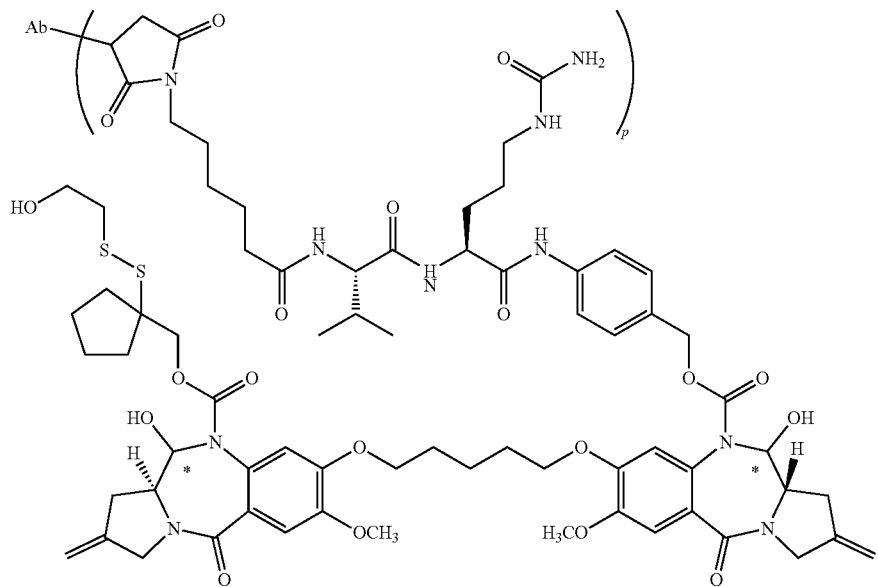

PBD Dimer ADC boronic acid prodrug 1A and 1B are prepared by conjugation of an antibody and the PBD dimer ADC boronic acid prodrug linker-drug intermediate of Example 22A, and have the structure:

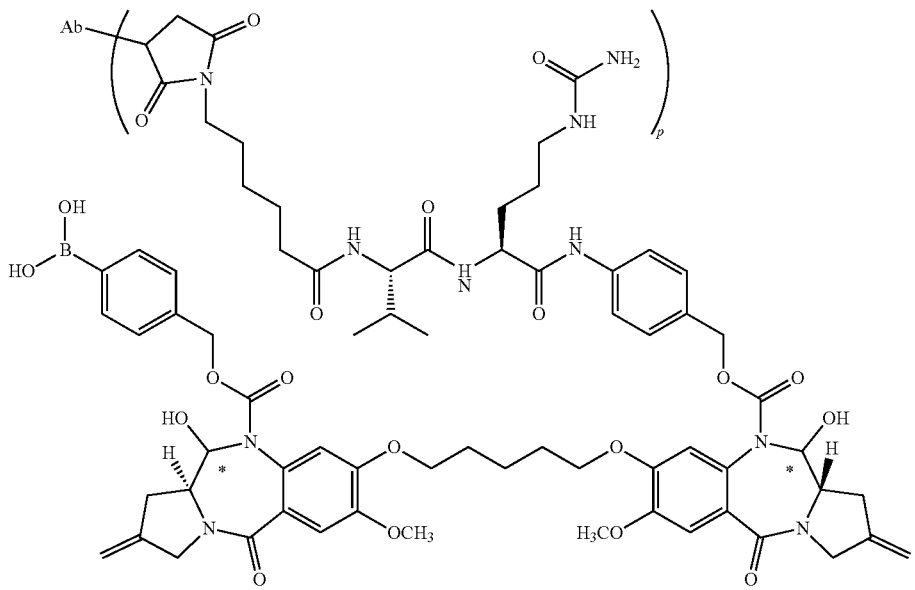

PBD Dimer ADC diaphorase prodrug 1A and 1B are prepared by conjugation of an antibody and the PBD dimer ADC diaphorase prodrug linker-drug intermediate of Example 25, and have the structure:

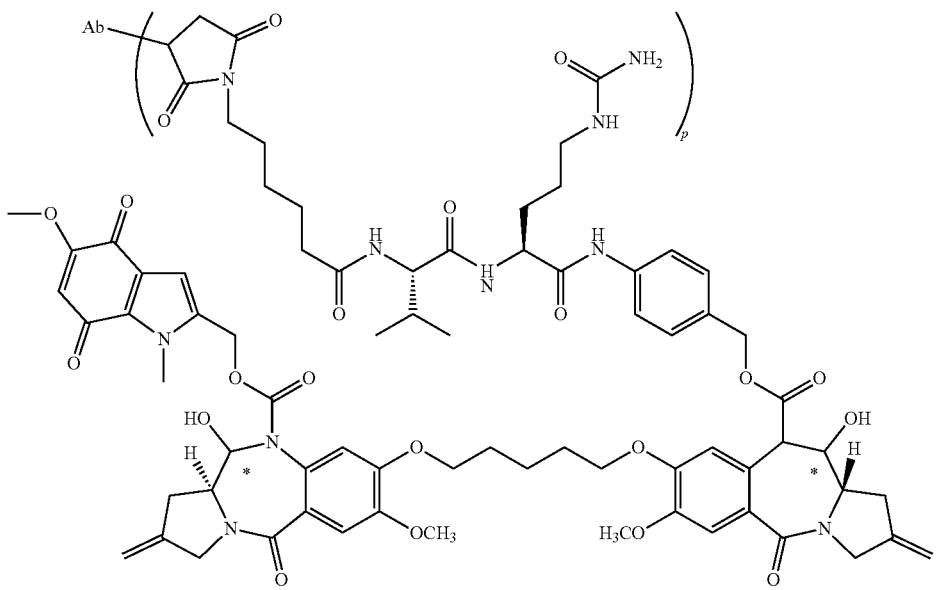

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A pyrrolobenzodiazepine prodrug dimer compound comprising a first pyrrolobenzodiazepine prodrug monomer M1 and a second pyrrolobenzodiazepine monomer M2, and having the formula:

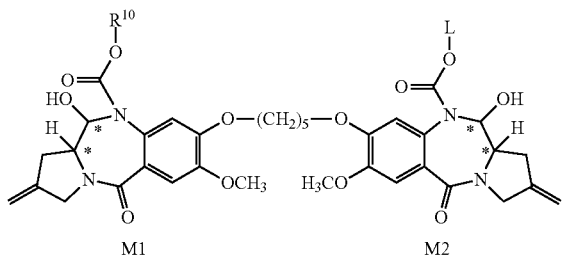

wherein $R^{10}$ is a prodrug moiety comprising a glutathione-activated disulfide of formula (V);

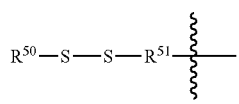

$R^{50}$ is selected from $CH_3CH_2$—, $HOCH_2CH_2$—, $(CH_3)_2CH$— and $(CH_3)_3C$—; and $R^{51}$ is selected from formulae (Vb) to (Vf):

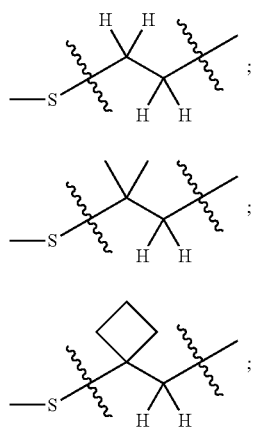

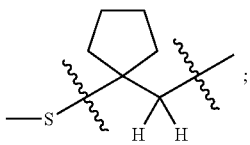

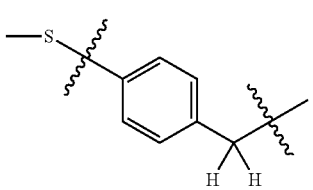

and

L is a self-immolative linker comprising at least one of a disulfide moiety, a peptide moiety and a peptidomimetic moiety, and a reactive group suitable for covalent conjugation to an antibody;

where each asterisk independently represents a chiral center of racemic or undefined stereochemistry.

2. The pyrrolobenzodiazepine prodrug dimer compound of claim 1 wherein L comprises p-aminobenzyloxycarbonyl.

3. The pyrrolobenzodiazepine prodrug dimer compound of claim 1 wherein the reactive group suitable for covalent conjugation to an antibody is selected from a pyridyl disulfide, maleimide, a bromacetamide, an iodoacetamide, or an alkene.

4. The pyrrolobenzodiazepine prodrug dimer compound of claim 3 wherein the reactive group suitable for covalent conjugation to an antibody is maleimide.

5. The pyrrolobenzodiazepine prodrug dimer compound of claim 1 wherein L comprises a peptide moiety selected from one or more of valine-citrulline, alanine-phenylalanine, valine-alanine, phenylalanine-lysine, phenylalanine-homolysine, N-methyl-valine-citrulline, glycine-valine-citrulline, and glycine-glycine-glycine.

6. The pyrrolobenzodiazepine prodrug dimer compound of claim 5 wherein the peptide moiety is valine-citrulline.

7. The pyrrolobenzodiazepine prodrug dimer compound of claim 5 wherein L further comprises p-aminobenzyloxycarbonyl.

8. The pyrrolobenzodiazepine prodrug dimer compound of claim 1 wherein L comprises a peptidomimetic moiety selected from one or more of triazoles, cyclobutane-1-1-dicarbaldehyde, cyclobutane-1-1-dicarbaldehyde-citrulline, alkenes, haloalkenes, and isoxazoles.

9. The pyrrolobenzodiazepine prodrug dimer compound of claim 8 wherein L further comprises p-aminobenzyloxycarbonyl.

10. A pyrrolobenzodiazepine prodrug dimer compound selected from:

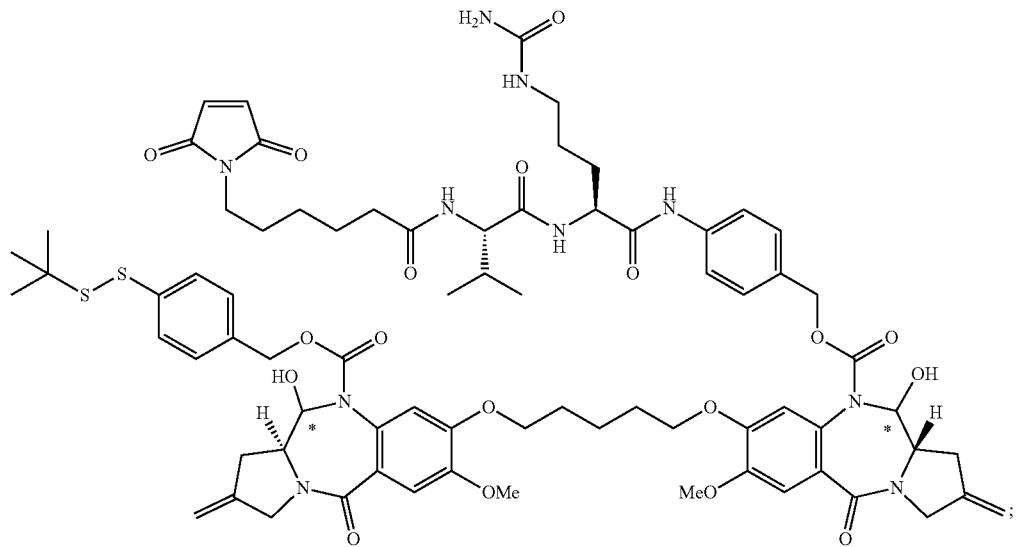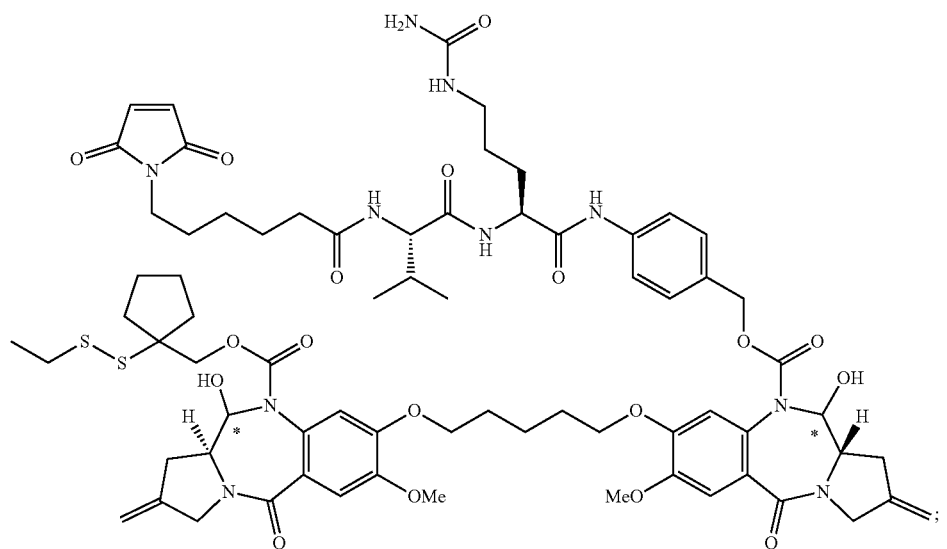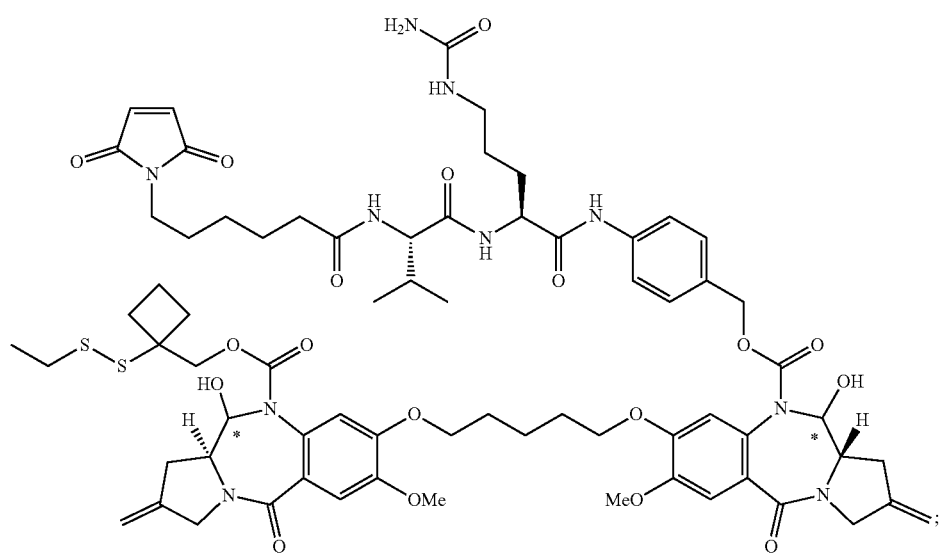

-continued
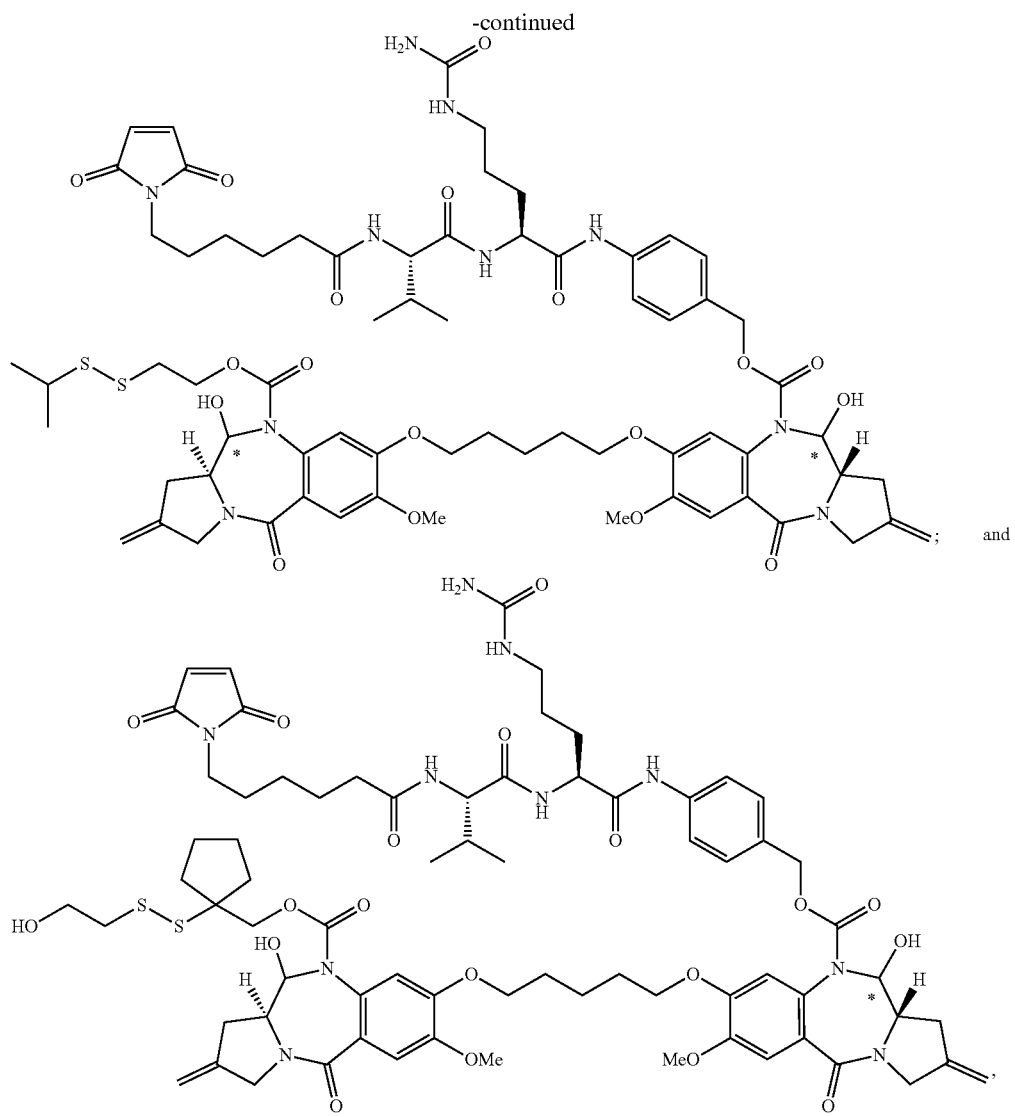
where each asterisk independently represents a chiral center of racemic or undefined stereochemistry.
* * * * *